(12) United States Patent
Bangera et al.

(10) Patent No.: US 8,753,677 B2
(45) Date of Patent: *Jun. 17, 2014

(54) EX VIVO MODIFIABLE MULTIPLE MEDICAMENT FINAL DOSAGE FORM

(75) Inventors: Mahalaxmi Gita Bangera, Renton, WA (US); Edward S. Boyden, Cambridge, MA (US); Roderick A. Hyde, Redmond, WA (US); Muriel Y. Ishikawa, Livermore, CA (US); Dennis J. Rivet, Portsmouth, VA (US); Elizabeth A. Sweeney, Seattle, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 678 days.

This patent is subject to a terminal disclaimer.

(21) Appl. No.: 12/387,325

(22) Filed: Apr. 29, 2009

(65) Prior Publication Data

US 2010/0068277 A1 Mar. 18, 2010

Related U.S. Application Data

(63) Continuation-in-part of application No. 12/284,015, filed on Sep. 16, 2008, and a continuation-in-part of application No. 12/284,014, filed on Sep. 16, 2008, and a continuation-in-part of application No. 12/284,013, filed on Sep. 16, 2008, and a continuation-in-part of application No. 12/322,877, filed on Feb. 5, 2009, and a continuation-in-part of application No. 12/322,874, filed on Feb. 5, 2009, and a continuation-in-part of application No. 12/322,878, filed on Feb. 5, 2009, and a continuation-in-part of application No. 12/387,312, filed on Apr. 29, 2009, and a continuation-in-part of application No. 12/387,326, filed on Apr. 29, 2009, and a continuation-in-part of application No. 12/387,329, filed on Apr. 29, 2009, and a continuation-in-part of application No. 12/387,324, filed on Apr. 29, 2009, and a continuation-in-part of application No. 12/387,323, filed on Apr. 29, 2009, and a continuation-in-part of application No. 12/387,328, filed on Apr. 29, 2009, and a continuation-in-part of application No. 12/387,311, filed on Apr. 29, 2009.

(51) Int. Cl.
*A61K 9/48* (2006.01)
*A61K 9/52* (2006.01)

(52) U.S. Cl.
CPC .................................. *A61K 9/4891* (2013.01)
USPC ............ 424/451; 424/452; 424/454; 424/457

(58) Field of Classification Search
CPC ................................................... A61K 9/4891
See application file for complete search history.

(56) References Cited

U.S. PATENT DOCUMENTS

| | | |
|---|---|---|
| 4,466,941 A | 8/1984 | Cerami et al. |
| 4,507,115 A | 3/1985 | Kambara et al. |
| 4,600,645 A | 7/1986 | Ghebre-Sellassie et al. |
| 4,728,512 A | 3/1988 | Mehta et al. |
| 4,743,398 A | 5/1988 | Brown et al. |
| 4,795,714 A | 1/1989 | Shafer |
| 4,801,459 A | 1/1989 | Liburdy |
| 4,801,559 A | 1/1989 | Imaoka |
| 4,939,194 A | 7/1990 | Scott et al. |
| 5,066,494 A * | 11/1991 | Becher .......................... 424/448 |
| 5,114,851 A | 5/1992 | Porter et al. |
| 5,190,766 A | 3/1993 | Ishihara |
| 5,252,646 A | 10/1993 | Iovine et al. |
| 5,271,940 A * | 12/1993 | Cleary et al. .................. 424/448 |
| 5,274,019 A | 12/1993 | Poyner et al. |
| 5,312,850 A | 5/1994 | Iovine et al. |
| 5,321,065 A | 6/1994 | Bono et al. |
| 5,410,290 A | 4/1995 | Cho |

(Continued)

FOREIGN PATENT DOCUMENTS

| | | |
|---|---|---|
| EP | 1064937 A1 | 1/2001 |
| WO | WO 00/55359 | 9/2000 |
| WO | WO 01/05941 A3 | 1/2001 |
| WO | WO 2006/084912 A1 | 8/2006 |

OTHER PUBLICATIONS

Birchard, Katherine R. et al.; "Suspected Pancreatic Cancer: Evaluation by Dynamic Gadolinium-Enhanced 3D Gradient-Echo MRI"; AJR; bearing a date of Sep. 2005; pp. 700-703; vol. 185; American Roentgen Ray Society.

(Continued)

*Primary Examiner* — Susan Tran

(74) *Attorney, Agent, or Firm* — Dorsey & Whitney LLP

(57) ABSTRACT

Described embodiments include a final dosage form for administering a medicament to an animal, an article of manufacture, and method. A described final dosage form includes a dosage portion having a medicament and a release element in a first medicament-release state. The medicament has a first bioavailability to the animal. The release element is modifiable ex vivo to a second medicament-release state by an exposure to a stimulus, wherein the medicament has a second bioavailability to the animal. The final dosage form includes another dosage portion having another medicament and another release element in another first medicament-release state. In the another first medicament-release state, the another medicament has another first bioavailability to the animal. The another release element is modifiable ex vivo to another second medicament-release state by an exposure to another stimulus, wherein the another medicament has another second bioavailability to the animal.

16 Claims, 67 Drawing Sheets

(56) References Cited

U.S. PATENT DOCUMENTS

| | | |
|---|---|---|
| 5,422,120 A | 6/1995 | Kim |
| 5,465,625 A | 11/1995 | Fujimoto et al. |
| 5,466,722 A | 11/1995 | Stoffer et al. |
| 5,482,719 A | 1/1996 | Guillet et al. |
| 5,565,132 A | 10/1996 | Salyer |
| 5,656,296 A | 8/1997 | Khan et al. |
| 5,679,442 A | 10/1997 | Haindl |
| 5,686,105 A | 11/1997 | Kelm et al. |
| 5,686,106 A | 11/1997 | Kelm et al. |
| 5,718,921 A | 2/1998 | Mathiowitz et al. |
| 5,753,724 A | 5/1998 | Edgington et al. |
| 5,797,898 A | 8/1998 | Santini, Jr. et al. |
| 5,840,329 A | 11/1998 | Bai |
| 5,973,024 A | 10/1999 | Imashiro et al. |
| 5,976,571 A | 11/1999 | Crison et al. |
| 5,990,193 A | 11/1999 | Russell et al. |
| 6,001,090 A | 12/1999 | Lenhart |
| 6,041,252 A | 3/2000 | Walker et al. |
| 6,051,576 A | 4/2000 | Ashton et al. |
| 6,056,734 A * | 5/2000 | Jacobsen et al. ........... 604/891.1 |
| 6,060,170 A | 5/2000 | Burgoyne, Jr. |
| 6,077,698 A | 6/2000 | Swan et al. |
| 6,099,864 A | 8/2000 | Morrison et al. |
| 6,258,789 B1 | 7/2001 | German et al. |
| 6,366,206 B1 | 4/2002 | Ishikawa et al. |
| 6,372,254 B1 | 4/2002 | Ting et al. |
| 6,416,740 B1 | 7/2002 | Unger |
| 6,471,968 B1 | 10/2002 | Baker, Jr. et al. |
| 6,475,521 B1 | 11/2002 | Timmins et al. |
| 6,491,666 B1 | 12/2002 | Santini, Jr. et al. |
| 6,527,759 B1 | 3/2003 | Tachibana et al. |
| 6,576,257 B1 | 6/2003 | Yarmut |
| 6,599,284 B2 | 7/2003 | Faour |
| 6,605,302 B2 | 8/2003 | Faour et al. |
| 6,623,430 B1 | 9/2003 | Slayton et al. |
| 6,624,915 B1 | 9/2003 | Kirkpatrick et al. |
| 6,656,162 B2 * | 12/2003 | Santini et al. ................. 604/191 |
| 6,682,758 B1 | 1/2004 | Tabibi et al. |
| 6,682,872 B2 | 1/2004 | Sachdev et al. |
| 6,719,989 B1 | 4/2004 | Matsushima et al. |
| 6,771,369 B2 | 8/2004 | Rzasa et al. |
| 6,774,116 B2 | 8/2004 | Gilbert et al. |
| 6,821,531 B2 | 11/2004 | Kumar |
| 6,859,304 B2 | 2/2005 | Miller et al. |
| 6,887,492 B2 | 5/2005 | Kay et al. |
| 6,897,205 B2 | 5/2005 | Beckert et al. |
| 6,962,691 B1 | 11/2005 | Lulla et al. |
| 6,984,393 B2 | 1/2006 | Amsden |
| 6,985,770 B2 | 1/2006 | Nyhart, Jr. |
| 6,989,196 B2 | 1/2006 | Chatterjee et al. |
| 7,017,412 B2 | 3/2006 | Thomas et al. |
| 7,019,043 B2 | 3/2006 | Maehara |
| 7,060,419 B2 | 6/2006 | Bentsen et al. |
| 7,073,667 B2 | 7/2006 | Burns et al. |
| 7,078,461 B2 | 7/2006 | Tomalia et al. |
| 7,083,572 B2 | 8/2006 | Unger et al. |
| 7,091,255 B2 | 8/2006 | DeVoe |
| 7,101,567 B1 | 9/2006 | Sano et al. |
| 7,104,517 B1 | 9/2006 | Derand et al. |
| 7,125,561 B2 | 10/2006 | Sackler |
| 7,138,143 B1 | 11/2006 | Mukai et al. |
| 7,163,693 B1 | 1/2007 | Clarke et al. |
| 7,175,961 B2 | 2/2007 | Beck et al. |
| 7,182,956 B2 | 2/2007 | Perricone et al. |
| 7,191,698 B2 | 3/2007 | Bond et al. |
| 7,226,442 B2 | 6/2007 | Sheppard, Jr. et al. |
| 7,229,973 B2 | 6/2007 | Bae et al. |
| 7,253,716 B2 | 8/2007 | Lovoi et al. |
| 7,255,874 B1 | 8/2007 | Bobo et al. |
| 7,256,446 B2 | 8/2007 | Hu et al. |
| 7,264,822 B2 | 9/2007 | Shalaby et al. |
| 7,265,161 B2 | 9/2007 | Leatherdale et al. |
| 7,270,808 B2 | 9/2007 | Cheng et al. |
| 7,279,174 B2 | 10/2007 | Pacetti et al. |
| 7,279,457 B2 | 10/2007 | Pohl et al. |
| 7,287,485 B2 | 10/2007 | Petrakis |
| 7,291,664 B2 | 11/2007 | Hao |
| 7,336,474 B2 | 2/2008 | Lerche et al. |
| 7,341,757 B2 | 3/2008 | Yadav |
| 7,351,768 B2 | 4/2008 | Rachita et al. |
| 7,364,754 B2 | 4/2008 | Prasad et al. |
| 7,537,590 B2 | 5/2009 | Santini, Jr. et al. |
| 2002/0072735 A1 * | 6/2002 | Kupperblatt et al. ...... 604/892.1 |
| 2003/0012815 A1 | 1/2003 | Ishibashi et al. |
| 2004/0096499 A1 | 5/2004 | Vaya et al. |
| 2004/0121010 A1 * | 6/2004 | Hirsh et al. ................... 424/468 |
| 2004/0236268 A1 | 11/2004 | Mitragotri et al. |
| 2004/0258750 A1 | 12/2004 | Alaux et al. |
| 2005/0025801 A1 | 2/2005 | Richard et al. |
| 2005/0076904 A1 | 4/2005 | Jones et al. |
| 2005/0112195 A1 | 5/2005 | Cruz et al. |
| 2005/0166913 A1 | 8/2005 | Sexton et al. |
| 2005/0191708 A1 | 9/2005 | Saul et al. |
| 2006/0024359 A1 | 2/2006 | Walker et al. |
| 2006/0078621 A1 | 4/2006 | Wedinger et al. |
| 2006/0078897 A1 | 4/2006 | Wedinger et al. |
| 2006/0105978 A1 | 5/2006 | Chu et al. |
| 2006/0140999 A1 | 6/2006 | Lendlein et al. |
| 2006/0269511 A1 | 11/2006 | Cantrell et al. |
| 2006/0292211 A1 | 12/2006 | Hood et al. |
| 2007/0026068 A1 | 2/2007 | Sackler |
| 2007/0159594 A9 | 7/2007 | Jani et al. |
| 2007/0172520 A1 | 7/2007 | VanAuker et al. |
| 2008/0050445 A1 | 2/2008 | Alcantar et al. |
| 2008/0132532 A1 | 6/2008 | Wright et al. |
| 2008/0139624 A1 | 6/2008 | Re |
| 2008/0181946 A1 | 7/2008 | Lohray et al. |
| 2008/0283439 A1 | 11/2008 | Sullivan et al. |
| 2009/0196903 A1 * | 8/2009 | Kliman ......................... 424/423 |
| 2010/0068152 A1 | 3/2010 | Bangera et al. |
| 2010/0068153 A1 | 3/2010 | Bangera et al. |
| 2010/0068233 A1 | 3/2010 | Bangera et al. |
| 2010/0068235 A1 | 3/2010 | Bangera et al. |
| 2010/0068254 A1 | 3/2010 | Bangera et al. |
| 2010/0068256 A1 | 3/2010 | Bangera et al. |
| 2010/0068266 A1 | 3/2010 | Bangera et al. |
| 2010/0068275 A1 | 3/2010 | Bangera et al. |
| 2010/0068278 A1 | 3/2010 | Bangera et al. |
| 2010/0068283 A1 | 3/2010 | Bangera et al. |
| 2010/0069821 A1 | 3/2010 | Bangera et al. |
| 2010/0069822 A1 | 3/2010 | Bangera et al. |
| 2010/0069887 A1 | 3/2010 | Bangera et al. |
| 2010/0233254 A1 * | 9/2010 | Miller ........................... 424/451 |
| 2011/0105864 A1 | 5/2011 | Robertson et al. |

OTHER PUBLICATIONS

Henderson, B. et al.; "A quantitative study of the effects of different grades of polyvinyl alcohol on the activities of certain enzymes in unfixed tissue sections"; Histochemical Journal; bearing a date of 1978; pp. 453-463; vol. 10; Chapman and Hall Ltd.

"Medicament"; TheFreeDictionary; printed on Mar. 10, 2011; pp. 1-3; located at http://www.thefreedictionary.com/medicament.

"Modifiable"; TheFreeDictionary; printed on Mar. 10, 2011; pp. 1-2; located at http://www.thefreedictionary.com/modifiable.

Salama, Rania et al.; "Preparation and characterisation of controlled release co-spray dried drug-polymer microparticles for inhalation 1: Influence of polymer concentration on physical and in vitro characteristics"; European Journal of Pharmaceutics and Biopharmaceutics; bearing a date of 2008; pp. 486-495; vol. 69; Elsevier B.V.

Gómez-Hens, Augustina et al.;"The role of liposomes in analytical processes"; Trends in Analytical Chemistry; bearing a date of 2005; pp. 9-19; vol. 24, No. 1; Elsevier Ltd.

Pascual-Reguera, M$^a$ Isabel et al.; "A single spectroscopic flow-through sensing device for determination of ciprofloxacin"; Journal of Pharmaceutical and Biomedical Analysis; bearing a date of 2004; pp. 689-695; vol. 35; Elsevier B.V.

Aguilar, M.R. et al.; "Smart Polymers and Their Applications as Biomaterials"; Biomaterials Chapter 6; bearing a date of 2007; pp. 1-27; CSIC.

(56) References Cited

OTHER PUBLICATIONS

Bei, Jian Zhong et al.; "Photodegradation Behavior of Polycaprolactone-Poly(ethylene glycol) Block Copolymer"; Chinese Chemical Letters; 1999; pp. 327-330; vol. 10, No. 4; printed on May 12, 2008; located at www.imm.ac.cn/journal/cc/1004/1004.html.

Berger, Michael; "Smart magnetic hydrogels for drug release"; nonowerk; May 18, 2006; pp. 1-3; printed on Nov. 18, 2008; located at http://www.nanowerk.com/spotlight/spotid=507.php.

"Celsion Presents Heat Activated Liposomes at CaP Cure Annual Retreat"; Business Wire; Sep. 20, 2002; pp. 1-2; printed on May 13, 2008; located at http://findarticles.com/p/articles/mi_m0EIN/is_2002_Sept_20/ai_91809594.

Chang, Jeong Ho, et al.; "Sustained Drug Release on Temperature-responsive Polymer Hybrid Nanoporous Silica Composites"; Bull. Korean Chem. Soc.; 2004; pp. 1257-1260; vol. 25, No. 8.

Deshmukh, Diwakar S. et al.; "Can Intact Liposomes be Absorbed in the Gut?"; Life Sciences; 1981; pp. 239-242; vol. 28, No. 3; Pergamon Press Ltd.; USA.

Druzhko, A.B. et al.; "4-Keto-bacteriorhodopsin films as a promising photochromic and electrochromic biological material"; Biosystems; 1995; pp. 129-132; 35(2-3); Elsevier.

Estrada R.F. et al.; "Smart polymeric membranes with adjustable pore size"; ISSN 0091-4037; 2003; vol. 52; pp. 833-843 (Abstract only provided pp. 1-2); bearing a date of 2008; INIST-CNRS; printed on Dec. 4, 2008; located at http://cat.inist.fr/?aModele=afficheN&cpsidt=15192602.

Gerasimov, Oleg V. et al.; "Cytosolic drug delivery using pH- and light-sensitive liposomes"; Advanced Drug Delivery Reviews; 1999; pp. 317-338; 38; Elsevier.

Giovannardi, Stefano et al.; "Flash Photolysis of Caged Compounds: Casting Light on Physiological Processes"; News Physiol. Sci.; Oct. 1998; pp. 251-255; vol. 13; Am. Physiol. Soc.

Henry, Celia M. et al.; "Drug Delivery"; CENEAR; Aug. 26, 2002; pp. 39-47 (13 pages total); vol. 80, No. 34; American Chemical Society.

Ho, Mae-Wan et al.; "Bioelectrodynamics and Biocommunication"; 1994; ISBN-10: 9810216653; pp. 1-436 (pp. 1-3 provided); World Scientific Publishing Company.

"How to Use FORADIL"; www.foradil.us/; 2008; pp. 1-4; printed on Sep. 2, 2008Schering Corporation; located at http://www.foradil.us/frdl/application?namespace=main&event=content_display&event_input=how_to_use_foradil.

Kaparissides, Costas et al.; "Recent Advances in Novel Drug Delivery Systems"; Journal of Nanotechnology Online; dated Jul. 1, 2005 and Mar. 25, 2006; pp. 1-13; printed on Nov. 18, 2008; located at http://www.azonano.com/details.asp?ArticleID=1538.

Kost, J. et al.; "Ultrasound-enhanced polymer degradation and release of incorporated substances"; Proc. Natl. Acad. Sci.; Oct. 1989; pp. 7663-7666; vol. 86; Applied Biological Sciences.

Lee, Jae Kyoo et al.; "Photo-Triggering of the Membrane Gates in Photo-Responsive Polymer for Drug Release"; Proceedings of the 2005 IEEE; Sep. 1-4, 2005; pp. 5069-5072; IEEE.

"Light Activated Drug Nanotransporters"; Medgadget.com; Apr. 1, 2008; pp. 1-4; printed on May 2, 2008; located at http://www.medgadget.com/archives/2008/04/light_activated_drug_nanotransporter.html; Medgadget LLC.

Lin, Chien-Chi et al.; "Hydrogels in controlled release formulations: Network design and mathematical modeling"; Advanced Drug Delivery Reviews; 2006; pp. 1379-1408; vol. 58; Elsevier B.V.

Marin, Alexander, M.D. et al.; "Acoustic activation of drug delivery from polymeric micelles: effect of pulsed ultrasound"; Journal of Controlled Release; bearing dates of Apr. 28, 2001, Oct. 16, 2000, Jan. 5, 2001, and Apr. 2, 2001; pp. 239-249 (Abstract only provided pp. 1-3); vol. 71, Issue 3; Elsevier Science; located at http://www.sciencedirect.com/science?_ob=ArticleURL&_udi=B6T3D-42R0RVT-3&_user=10&rdoc=1&_fmt=&_orig=search&_sort=d&view=c&_acct=&_C000050221&_version=1&_urlVersion=0&_userid=10&md5=298d9e0efff47080072e912621729774; printed on Dec. 4, 2008.

Masteikova, Ruta et al.; "Stimuli-sensitive hydrogels in controlled and sustained drug delivery"; Medicina; bearing dates of Jun. 19, 2003, Jun. 26, 3002, and Nov. 18, 2008; pp. 19-24; 39 tomas, 2 priedas.

McConville, Jason T.; "Recent Trends in Oral Drug Delivery"; Drug Delivery Report; Autumn/Winter 2005; pp. 24-27.

Nurjaya, S. et al.; "Effects of microwave on drug release properties of matrices of pectin"; Carbohydrate Polymers; 2005; pp. 245-257; vol. 62; Elsevier Ltd.

Ostro, Marc J.; "Liposomes From Biophysics to Therapeutics"; Apr. 27, 1987; pp. 1-418; Informa Healthcare; ISBN 082477762X (not provided).

Patel, Dr. Rakesh P.; "Niosome: An Unique Drug Delivery System"; Pharmainfo.net; bearing a date of Sep. 22, 2008; pp. 1-15; printed on Sep. 22, 2008; located at http://www.pharmainfo.net/reviews/niosome-unique-drug-delivery-system.

Qiu, Yong et al.; "Environment-sensitive hydrogels for drug delivery"; Advanced Drug Delivery Reviews; Dec. 31, 2001; pp. 321-339; vol. 53, Issue 3; printed on May 20, 2008; located at http://www.sciencedirect.com/science?_ob=ArticleURL&_udi=B6T3R-44420X2-2&_user=10&_coverDate=12%2F31%2F2001&_alid=742662573&_rdoc=1&_fmt=high&_orig=search&_cdi=4953&_sort=d&_docanchor=&view=c&_ct=1&_acct=C000050221&_version=1&_urlVersion=0&_userid=10&md5=f0073f411c6856def956dc0703954d94; (abstract only; pp. 1-3).

Rao, G.V. Rama et al.; "Synthesis of Smart Mesoporous"; Materials Research Society; bearing a date of 1995-2008; pp. 1-2; printed on Dec. 4, 2008; located at http://www.mrs.org/s_mrs/sec_subscribe.asp?CID=2605&DID=110382&action=detail.

Rolland, Alain; "Pharmaceutical Particulate Carriers"; Jul. 19, 1993; pp. 1-448 (particularly p. 92); Informa Healthcare; ISBN 0824790162 (not provided).

Skwarczynski, Mariusz et al.; "Development of first photoresponsive prodrug of paclitaxel"; Bioorganic & Medicinal Chemistry Letters; Sep. 1, 2006; pp. 4492-4496; vol. 16, Issue 17; printed on May 2, 2008; located at http://www.sciencedirect.com/science?_ob=ArticleURL&_udi=B6TF9-4K8S5NP-4&_user=10&_coverDate=09%2F01%2F2006&_alid=742665056&_rdoc=1&_fmt=high&_orig=search&_cdi=5221&_sort=d&_docanchor=&view=c&_ct=1&_acct=C000050221&_version=1&_urlVersion=0&_userid=10&md5=8253617a1196a18970e32670b2cd6259; (abstract only; pp. 1-2).

Teng, C.D. et al.; "Microwave Thermal Denaturation of Protein Matrices as Controlled Release Devices"; Journal of Controlled Release; 1990; pp. 43-49; 13; Elsevier Science Publishers B.V.; Amsterdam.

Utada, A.S. et al.; "Monodisperse Double Emulsions Generated from a Microcapillary Device"; Science Magazine; Apr. 22, 2005; pp. 537-541 (pp. 1-11 included); vol. 308, No. 5721; Sciencemag.org; printed on Dec. 1, 2008; located at http://www.sciencemag.org/cgi/content/full/308/5721/537.

Vandelli, Maria Angela et al.; "Microwave-treated gelatin microspheres as drug delivery system"; Journal of Controlled Release; 2004; pp. 67-84; vol. 96; Elsevier B.V.

Wong, Tin Wui et al.; "Design of controlled-release solid dosage forms of alginate and chitosan using microwave"; Journal of Controlled Release; 2002; pp. 99-114; 84; Elsevier.

Wong, T.W. et al.; "Use of Microwave in Processing of Drug Delivery Systems"; Current Drug Delivery; 2008; pp. 77-84; 5; Bentham Science Publishers Ltd.

"Handbook of Pharmaceutical Excipients"; Oct. 13, 1988; Cover Sheet and p. 369, total of 2 pages; American Pharmaceutical Association, Washington DC.

Provenzale, James M.; "Molecular Imaging: Facing the Future;" American Journal of Roentgenology; bearing a date of Feb. 2006; pp. 287-288; vol. 186, No. 2; American Roentgen Ray Society.

Clarke, R. N.; "2.6.5 Dielectric properties of materials"; Kaye & Laby Tables of Physical & Chemical Constants. Chapter 2 General

(56) References Cited

OTHER PUBLICATIONS

Physics, Section 2.6 Electricity and magnetism; bearing a date of 2011; 8 pages; Version 1.0; located at: http://www.kayelaby.npl.co.uk/general_physics/2_6/2_6_5.html; National Physical Laboratory, United Kingdom.

Physical Property; Thesaurus Entry, TheFreeDictionary.com; bearing a date of 2012; 2 pages located at www.thefreedictionary.com/physical+property; Farlex, Inc.

Siliconfareast.com; "Dielectric Constant, k"; bearing a date of 2005; 2 pages.

Ankareddi, Induvadana et al.; "Temperature Controlled Grafted Polymer Network Incorporated With Magnetic Nano Particles To Control Drug Release Induced By An external Magnetothermal Trigger"; NSTI-Nanotech; 2007 and Created on Jan. 14, 2014; pp. 431-434; vol. 2.

Aziz, A. W. et al.; "Ultrasonic Detection of Segmental Relaxations in Thermoplastic Polyurethanes; Journal of Applied Polymer Science"; 1986 and Created on Jan. 14, 2014; pp. 1585-1594; vol. 31; John Wiley & Sons, Inc.

Bonina, P. et al.; "pH-Sensitive Hydogels Composed of Chitosan and Polyacrylamide—Preparation and Properties": Journal of Bioactive and Compatible Polymers; Mar. 2004; pp. 101-116; vol. 19; Sage Publications.

Cho, Seong Min et al.; "pH-dependent release property of dioleoylphosphatidyl ethanolamine liposomes"; Korean J. Chem. Eng.; Accepted Jul. 25, 2007; pp. 390-393; vol. 25, No. 2.

Hafez, Ismail M. et al.; "Tunable pH-Sensitive Liposomes Composed of Mixtures of Cationic and Anionic Lipids"; Biophysical Journal; Sep. 2000; pp. 1438-1446; vol. 79; Biophysical Society.

Hoet, Peter HM et al.; "Nanoparticles—known and unknown health risks"; Journal of Nanobiotechnology; Published on Dec. 8, 2004; pp. 1-15; vol. 2, No. 12; BioMed Central Ltd.

Kheirolomoom, Azadeh et al.; "Acoustically-active microbubbles conjugated to liposomes: Characterization of a proposed drug delivery vehicle"; Journal of Control Release; Accepted Dec. 14, 2006; pp. 275-284; vol. 118; Elsevier B.V.

Kost, J. et al.; "Ultrasonically Controlled Polymeric Drug Delivery"; Makromol. Chem., Macromol. Symp.; 1988 and Created on Jan. 15, 2014; pp. 275-285; vol. 19.

Liburdy, R.P. et al.; "Microwave-Triggered Liposomal Drug Delivery: Investigation of a Model Drug Delivery System"; IEEE Engineering in Medicine & Biology Society 11th Annual International Conference; Created on Jan. 15, 2014; pp. 1163-1164.

Morton, Susan L. et al.; "Ultrasonic Cure Monitoring of Photoresist During Pre-Exposure Bake Process"; IEEE Ultrasonics Symposium; 1997 and Created on Jan. 15, 2014; pp. 837-840.

Sari, Ahmet et al.; "Polymer-stearic acid blends as form-stable phase change material for thermal energy storage"; Journal of Scientific & Industrial Research; Dec. 2005; pp. 991-996; vol. 64.

Skwarczynski, Mariusz et al.; "Development of first photoresponsive prodrug of paclitaxel"; Bioorganic & Medicinal Chemistry Letters; Accepted Jun. 9, 2006; pp. 4492-4496; vol. 16; Elsevier Ltd.

Tsaih, Min Larng et al.; "Effect of Degree of Deacetylation of Chitosan on the Kinetics of Ultrasonic Degradation of Chitosan"; Journal of Applied Polymer Science; Accepted Apr. 11, 2003; pp. 3526-3531; vol. 90; Wiley Periodicals, Inc.

Vijayalakshmi, S. P. et al.; "Photodegradation of Poly(vinyl alcohol) Under UV and Pulsed-Laser Irradiation in Aqueous Solution"; Journal of Applied Polymer Science; Accepted Nov. 9, 2005; pp. 958-966; vol. 102; Wiley Periodicals, Inc.

Wang, Yong et al.; "pH Sensitive polypropylene porous membrane prepared by grafting acrylic acid in supercritical carbon dioxide"; Polymer; Accepted Nov. 29, 2003; pp. 855-860; vol. 45; Elsevier Ltd.

Yoshizawa, Toru et al.; "pH- and temperature-sensitive permeation through polyelectrolyte complex films composed of chitosan and polyalkyleneoxide—maleic acid copolymer"; Journal of Membrane Science; Accepted Jun. 2, 2004; pp. 347-354; vol. 241; Elsevier B.V.

\* cited by examiner

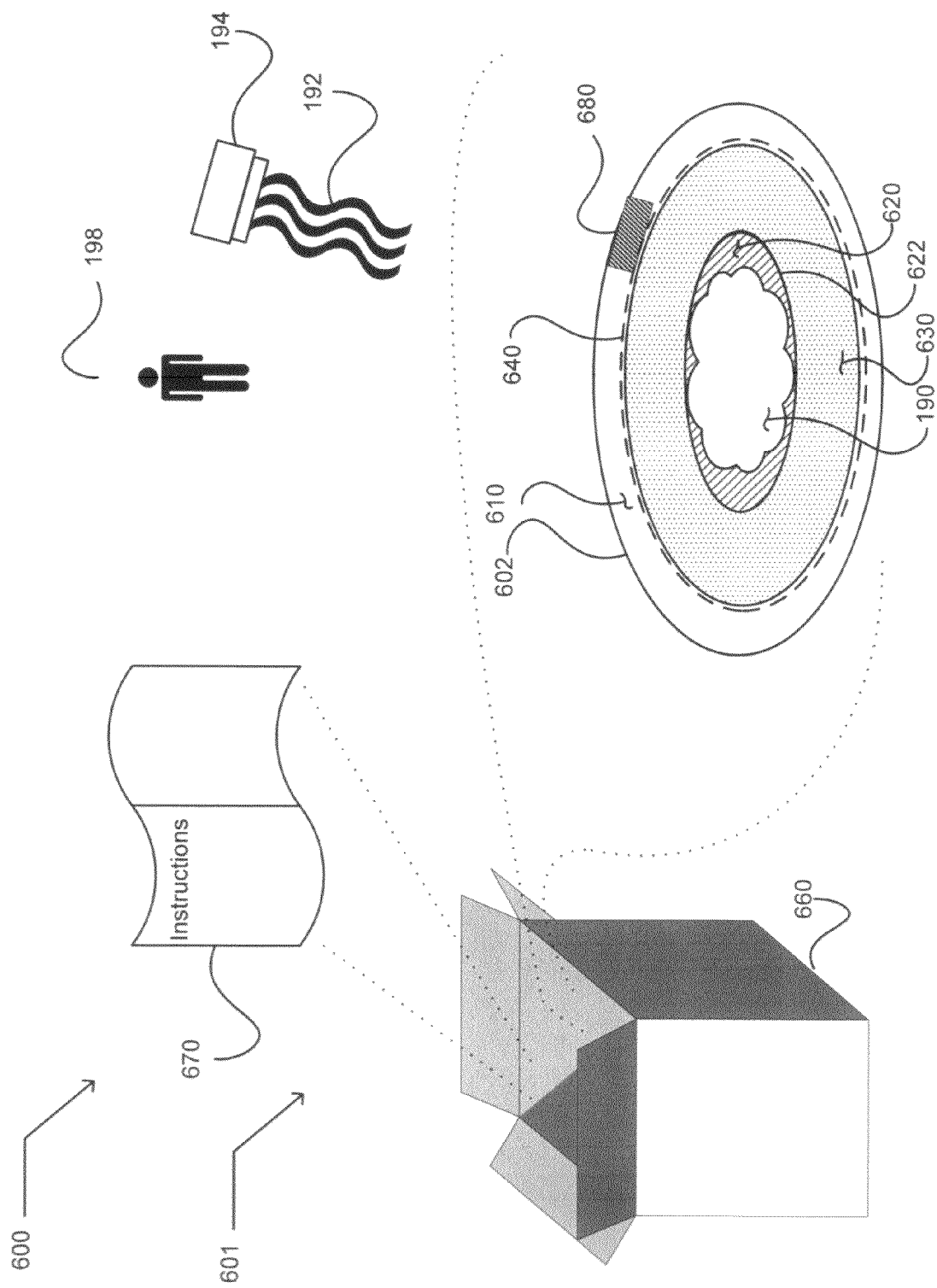

In an environment that includes a final dosage form, wherein the final dosage form includes a medicament; an outer layer; a release element configured in a first medicament-release state and modifiable to a second medicament-release state upon an *ex vivo* exposure to a stimulus; and a chamber at least substantially within the outer layer and configured to carry the medicament.

> 707 The final dosage form includes a containment element configured to retain the medicament within the final dosage form before introduction of the final dosage form into the animal.

Start

710

Irradiating the release element of the final dosage form *ex vivo* with a stimulus, the non-ionizing radiation selected to transform the release element from the first medicament-release state to the second medicament-release state.

End

Irradiating a release element of the final dosage form *ex vivo* with a stimulus, the non-ionizing radiation selected to transform the release element from the first medicament-release state to the second medicament-release state.

712 Irradiating in response to a human-initiated activation a release element of the final dosage form *ex vivo* with a stimulus.

714 Automatically initiating an *ex vivo* irradiation of a release element of the final dosage with a stimulus.

716 Irradiating a first release element of the final dosage form *ex vivo* with a stimulus without significantly irradiating a second release element of the final dosage form with the stimulus.

718 Irradiating a first release element of the final dosage form *ex vivo* with a stimulus without irradiating a second release element of the final dosage form with the stimulus, the first release element associated with a first chamber carrying a first instance of the medicament, and the second release element associated with a second chamber carrying a second instance of the medicament.

722 Irradiating a first release element of the final dosage form *ex vivo* with a stimulus without irradiating a second release element of the final dosage form with the stimulus, the first release element associated with a first chamber carrying a first medicament, and the second release element associated with a second chamber carrying a second medicament.

In an environment that includes a final dosage form, wherein the final dosage form includes a medicament; an outer layer; a release element configured in a first medicament-release state and modifiable to a second medicament-release state upon an *ex vivo* exposure to a stimulus; and a chamber at least substantially within the outer layer and configured to carry the medicament.

> 807 The final dosage form includes a containment element configured to retain the medicament within the final dosage form before introduction of the final dosage form into the animal.

Start

↓

810

Choosing pursuant to a request specifying a dose of a medicament for an individual animal an instance of a final dosage form that includes the medicament.

↓

830

Selecting a stimulus effective to change a medicament-release state of a release element of the final dosage form.

↓

850

Initiating an *ex vivo* exposure of the release element of the chosen instance of the final dosage form to the selected modification stimulus.

↓

End

810 Choosing pursuant to a request an instance of a final dosage form that includes the medicament.

812 Choosing pursuant to at least one of an order or a prescription an instance of a final dosage form that includes the medicament.

814 At least one of physically or manually choosing pursuant to the request an instance of a final dosage form that includes the medicament.

Selecting a stimulus effective to change a medicament-release state of a release element of the final dosage form.

832 Selecting a stimulus having an attribute indicated by at least one of a manufacturer of the final dosage form, an instruction packaged with the dosage form, an electronically published content, and a printed publication as effective to change a medicament-release state of a release element of the final dosage form.

834 Selecting a stimulus configured by at least one of a type, amount, level, wavelength, spectrum, waveform, duration, and/or pulse attribute to change a medicament-release state of a release element of the final dosage form.

836 Selecting a stimulus configured to change a medicament-release state of a release element of the final dosage form and to make the request-specified dose of medicament dose bioavailable by the final dosage form.

FIG. 13

Verifying the *ex vivo* exposure of the release element of the chosen instance of the final dosage form to the selected stimulus. ⎯ 870

> 872 Visually verifying the *ex vivo* exposure of the release element of the chosen instance of the final dosage form to the selected stimulus.

> 874 Electronically verifying the *ex vivo* exposure of the release element of the chosen instance of the final dosage form to the selected stimulus.

> 876 Quantifying the *ex vivo* exposure of the release element of the chosen instance of the final dosage form to the selected stimulus.

> 878 Initiating another *ex vivo* exposure of the release element of the chosen instance of the final dosage form to the selected stimulus in response to the quantifying the *ex vivo* exposure of the release element of the chosen instance of the final dosage form to the selected stimulus.

> 882 Terminating the *ex vivo* exposure of the release element of the chosen instance of the final dosage form to the selected stimulus in response to the quantifying the *ex vivo* exposure of the release element of the chosen instance of the final dosage form to the selected stimulus.

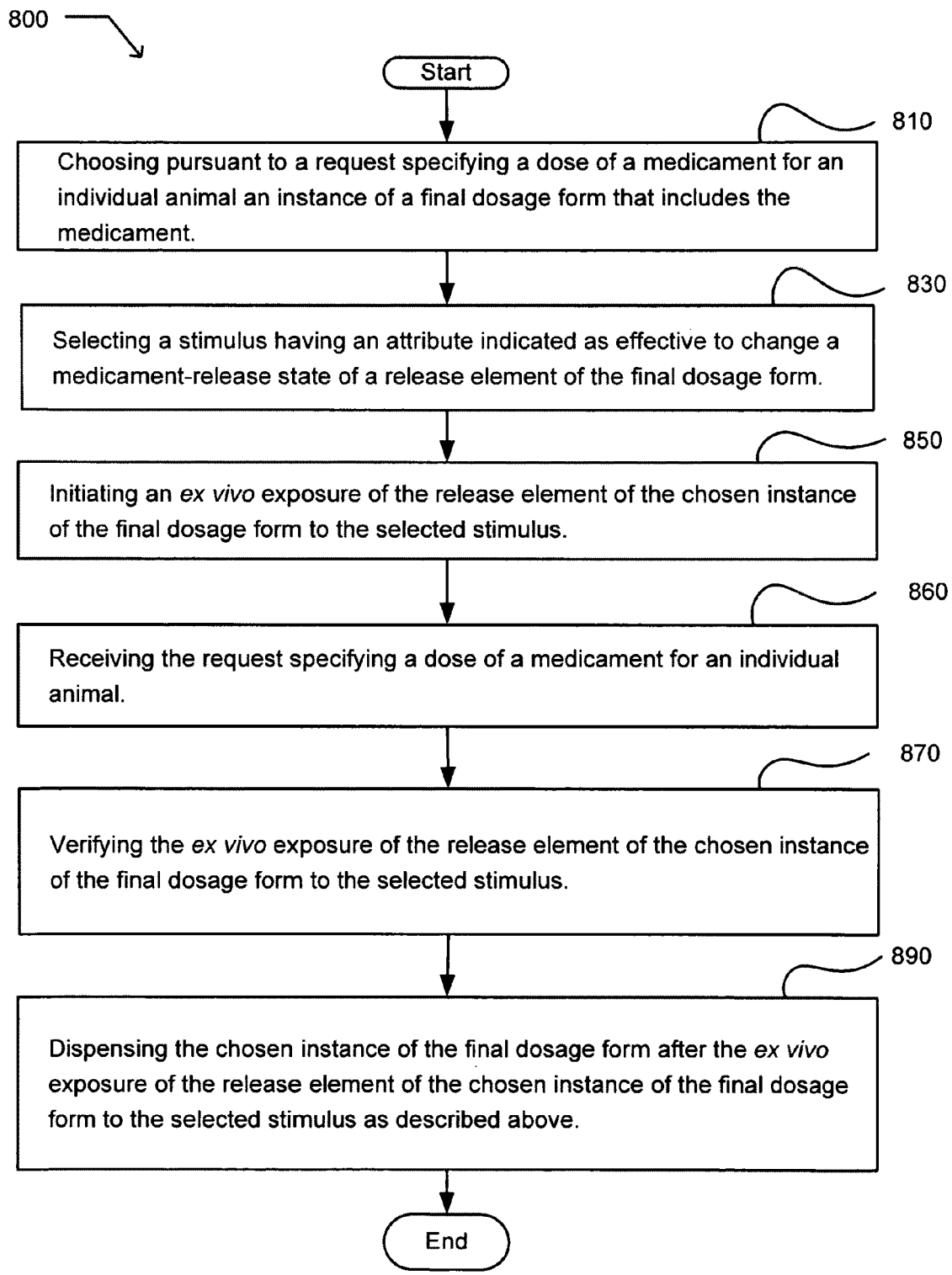

In an environment that includes a final dosage form, wherein the final dosage form includes a medicament; an outer layer; a release element configured in a medicament-holding state wherein a medicament is at least substantially not bioavailable to the animal and modifiable to a medicament-discharge state upon an *ex vivo* exposure to the stimulus wherein the medicament is at least substantially bioavailable to the animal; and a site configured to carry the medicament.

| 1307 The final dosage form further comprises a containment element configured to retain the medicament within the final dosage form until the final dosage form is introduced into the animal. | 1309 The final dosage form further comprises an indicator element configured to indicate an exposure of the release element to the stimulus. |

Start

1310

Initiating an *ex vivo* exposure of a release element of the final dosage form to a stimulus, the initiated stimulus selected to transform the release element from a medicament-holding state to a medicament-discharge state.

End

A final dosage form for administering a medicament to an animal.

1410 Means for protecting the final dosage form from an ex vivo environment.

1420 Means for releasing the medicament, configured in a medicament-holding state, and modifiable to a medicament-discharge state upon an ex vivo exposure to a stimulus.

1430 The medicament.

1440 Means for means for carrying the medicament.

1450 Means for indicating an exposure of the means for releasing the medicament to the stimulus.

1460 Means for containing the medicament within the final dosage form until the final dosage form is introduced into the animal.

FIG. 24
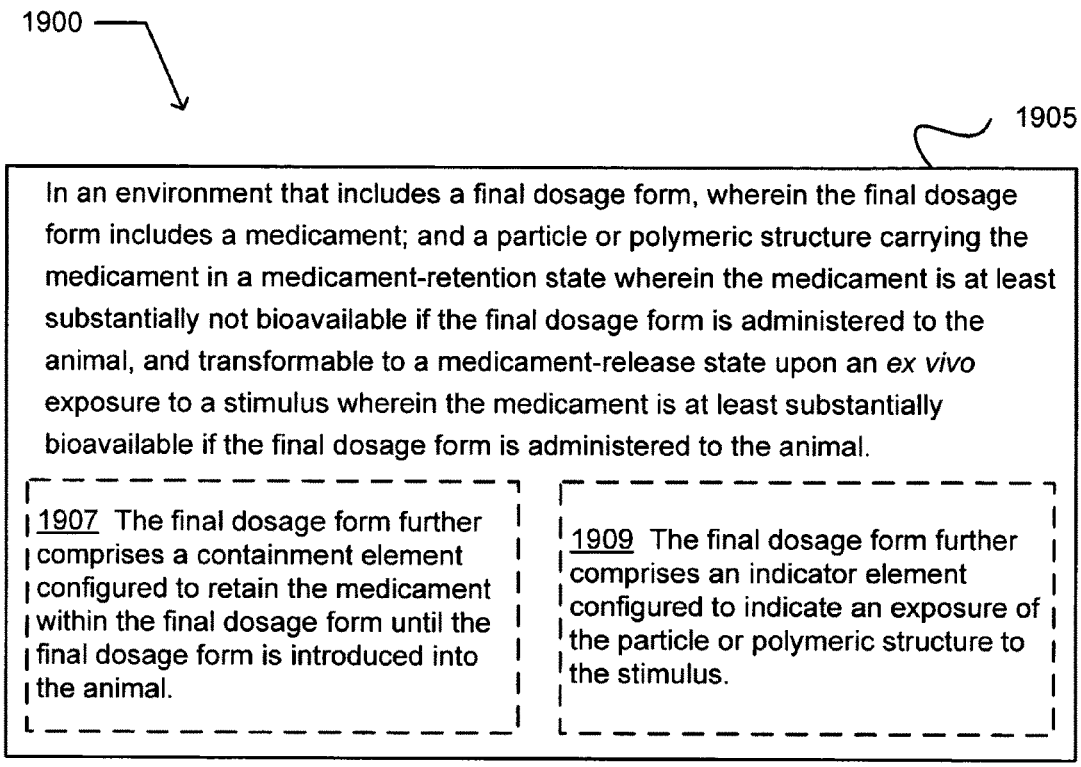
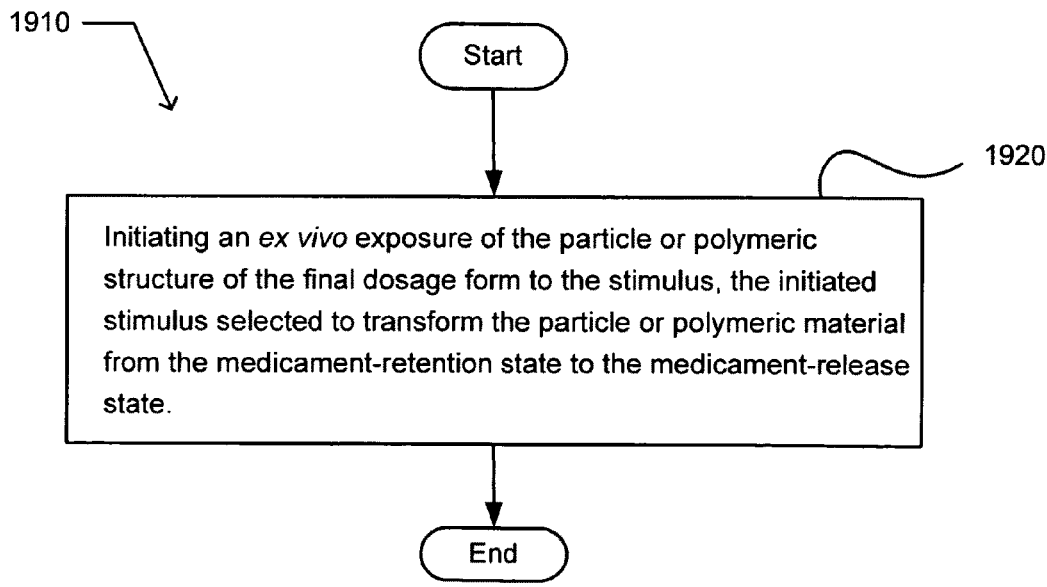

FIG. 25

1920 Initiating an *ex vivo* exposure of a particle or polymeric material of the final dosage form to a stimulus, the initiated stimulus selected to transform the particle or polymeric material from a medicament-retention state to a medicament-release state.

1922 The initiated stimulus having a parameter selected to transform the particle or polymeric material from a medicament-retention state to a medicament-release state.

1924 The initiated stimulus having at least one of a stimulation characteristic or a spatial characteristic selected to transform the particle or polymeric material from a medicament-retention state to a medicament-release state.

1926 Initiating a first *ex vivo* exposure of a particle or polymeric material of the final dosage form to a stimulus, the first initiated stimulus selected to transform the particle or polymeric material from a medicament-retention state to a medicament-release state;

receiving an indication of the first *ex vivo* exposure of the release element of the final dosage form to the stimulus, the indication generated in response to an indicator element of the final dosage form configured to indicate an exposure of the release element to the stimulus; and initiating a second *ex vivo* exposure of the release element of the final dosage form to the stimulus, the initiated second *ex vivo* exposure stimulus selected to further transform the release element from the medicament-holding state to the medicament-discharge state.

FIG. 26

2002 → A final dosage form for administering a medicament to an animal.

2010 Means for entrapping at least one molecule of the medicament.

2030 Means for protecting the means for entrapping at least one molecule of the medicament from an ex vivo environment of the final dosage form.

2040 The medicament.

2020 Means for controlling an availability of the entrapped at least one molecule of medicament, wherein the entrapped at least one molecule of medicament is initially at least substantially not bioavailable if the final dosage form is administered to the animal, and wherein the availability of the entrapped medicament is modifiable upon an ex vivo exposure to a stimulus to be at least substantially bioavailable if the final dosage form is administered to the animal.

2022 Means for controlling an availability of the entrapped at least one molecule of medicament and having a premodification characteristic resulting in an insignificant uptake in the gastrointestinal tract of the animal.

2050 Means for indicating an exposure to the stimulus to the means for controlling an availability of the entrapped at least one molecule of medicament.

2060 Means for containing the medicament within the final dosage form before the final dosage form is administered to the animal.

2070 Means for carrying the final dosage form into the animal.

FIG. 30
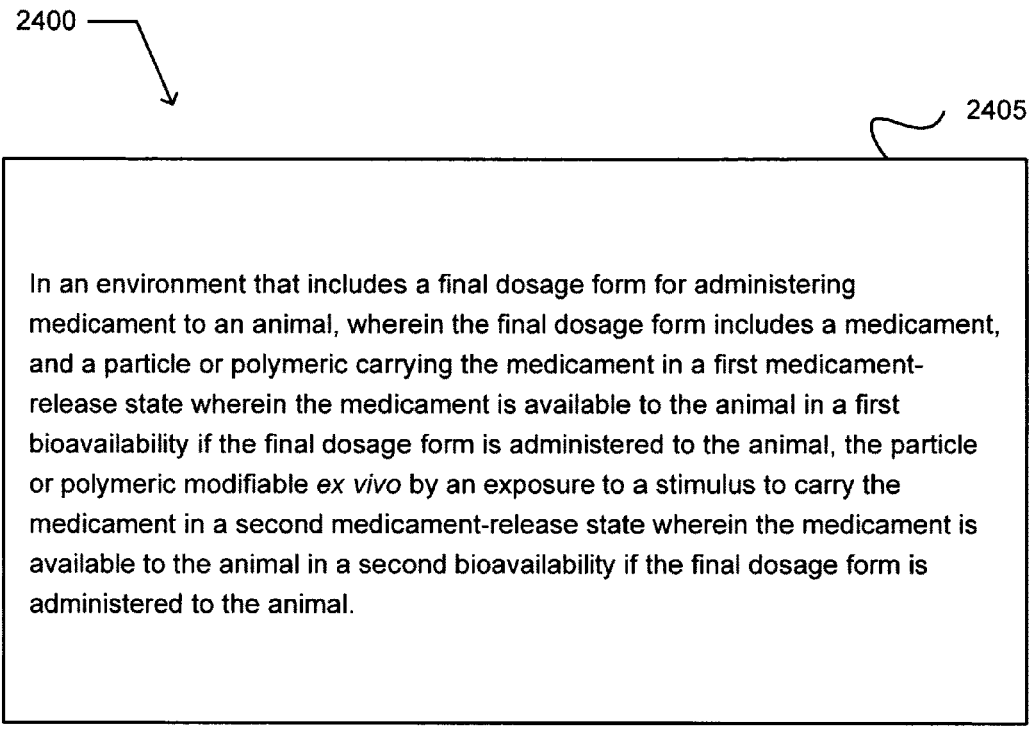
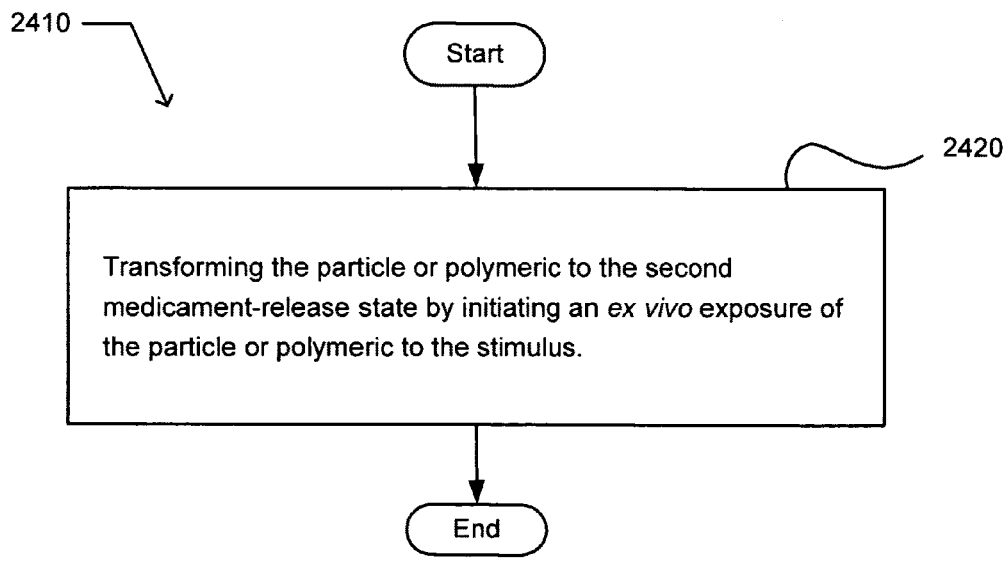

FIG. 31

An article of manufacture for administering medicament to an animal.

2510 Means for releasably encompassing a medicament in a first state wherein the medicament is available to the animal in a first bioavailability if the final dosage form is administered to the animal, the means for releasably encompassing the medicament in a first state modifiable ex vivo by an exposure to a stimulus to releasably encompass the medicament in a second state wherein the medicament is available to the animal in a second bioavailability if the final dosage form is administered to the animal.

2530 Means for protecting the means for releasably encompassing the medicament in a first state.

190 The medicament.

2550 Means for indicating an exposure to the stimulus of the means for releasably encompassing the medicament in a first state.

2560 Means for containing the medicament within the final dosage form before the final dosage form is administered to the animal.

2570 Means for carrying the final dosage form into the animal.

2502

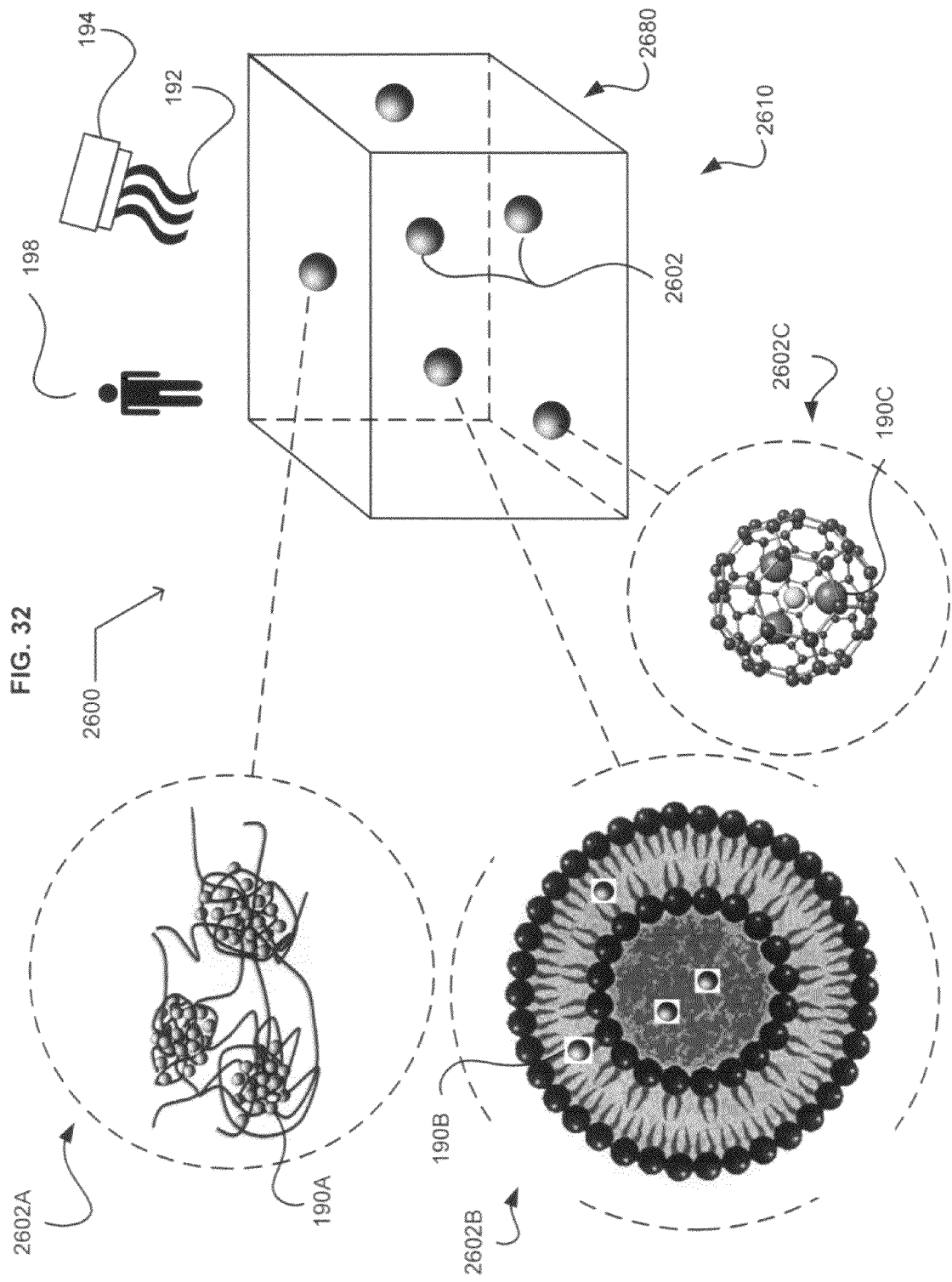

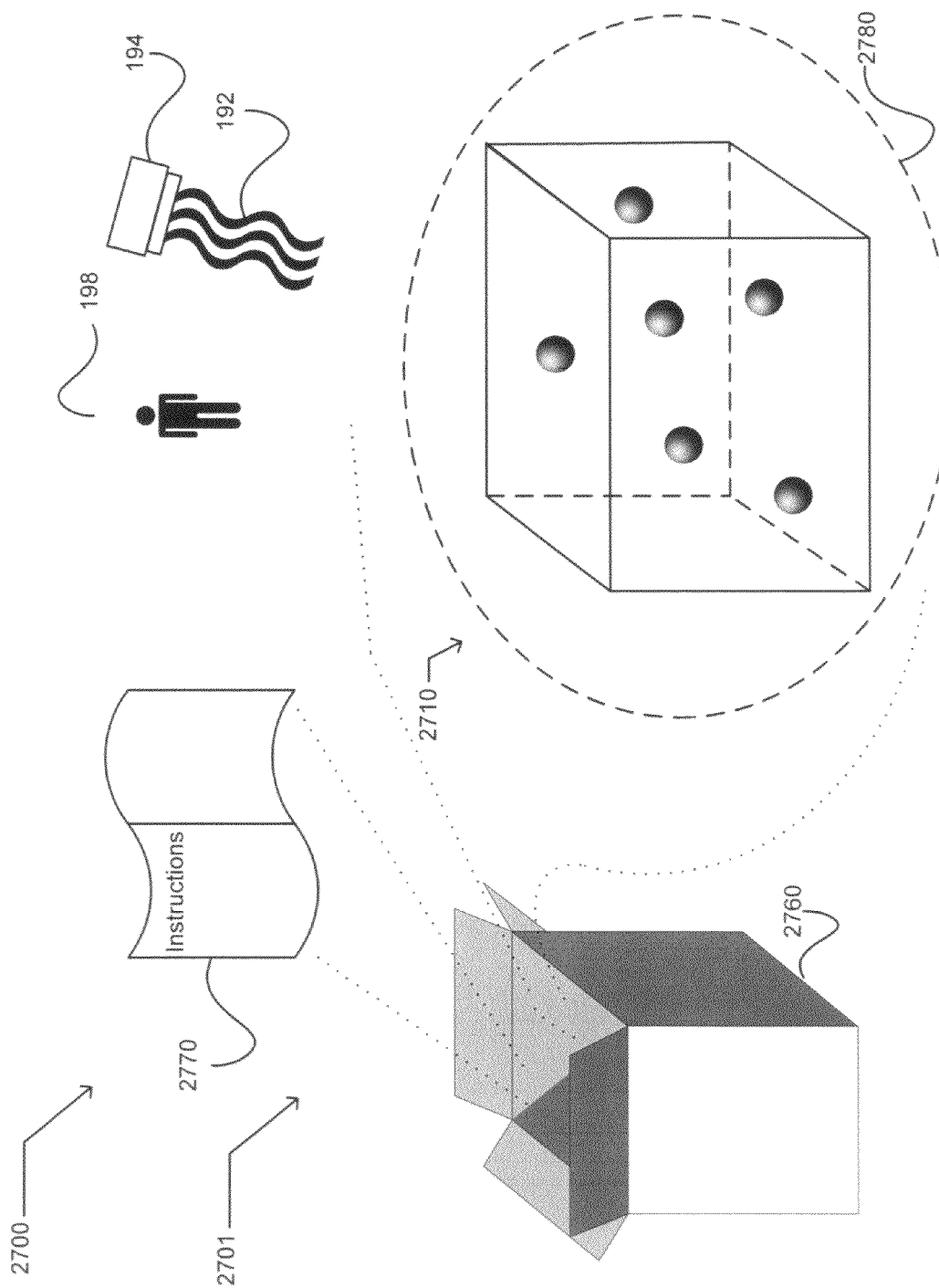

In an environment that includes a final dosage form for administering medicament to an animal, wherein the final dosage form includes a medicament, and a release-control substance carrying the medicament in a first medicament-release state wherein the medicament has a first bioavailability to the animal if the final dosage form is administered to the animal, the release-control substance modifiable *ex vivo* by an exposure to a first stimulus to carry the medicament in a second medicament-release state wherein the medicament has a second bioavailability to the animal if the final dosage form is administered to the animal, and the release-control substance modifiable *ex vivo* by an exposure to second stimulus to carry the medicament in a third medicament-release state wherein the medicament has a third bioavailability to the animal if the final dosage form is administered to the animal.

2810 ⟶

Start

2820

Transforming the medicament release state of the release-control substance to the second medicament-release state or the third medicament-release state by initiating an *ex vivo* exposure of the release-control substance respectively to the first stimulus or the second stimulus.

End

FIG. 35

2820 Transforming the medicament release state of the release-control substance to the second medicament-release state or the third medicament-release state by initiating an *ex vivo* exposure of the release-control substance respectively to the first stimulus or the second stimulus.

2822 Modifying the medicament release state of the release-control substance to the second medicament-release state or the third medicament-release state by initiating an *ex vivo* exposure of the release-control substance respectively to the first stimulus or the second stimulus.

2824 Transforming the medicament release state of the release-control substance to the second medicament-release state or the third medicament-release state by initiating an *ex vivo* exposure of the release-control substance to a stimulus selected respectively from the first stimulus or the second stimulus.

FIG. 36

2820 Initiating an ex vivo exposure of the release-control substance respectively to the first stimulus or the second stimulus.

2832 Initiating an ex vivo exposure of the release-control substance respectively to a modification stimulus selected from the first stimulus or the second stimulus, the selected modification stimulus having a parameter operative to transform the release-control substance carrying the medicament from the first medicament-release state to the second medicament-release state or to the third medicament-release state.

2834 Initiating an ex vivo exposure of the release-control substance to a modification stimulus selected from the first stimulus or the second stimulus, the selected modification stimulus operative to transform the release-control substance carrying the medicament from the first medicament-release state to the second medicament-release state or from the first medicament-release state to the third medicament-release state.

2836 Initiating an ex vivo exposure of the release-control substance respectively to a modification stimulus selected from the first stimulus or the second stimulus, the selected modification stimulus having at least one of a stimulation characteristic or a spatial characteristic operable to transform the release-control substance carrying the medicament from the first medicament-release state to the second medicament-release state or to the third medicament-release state.

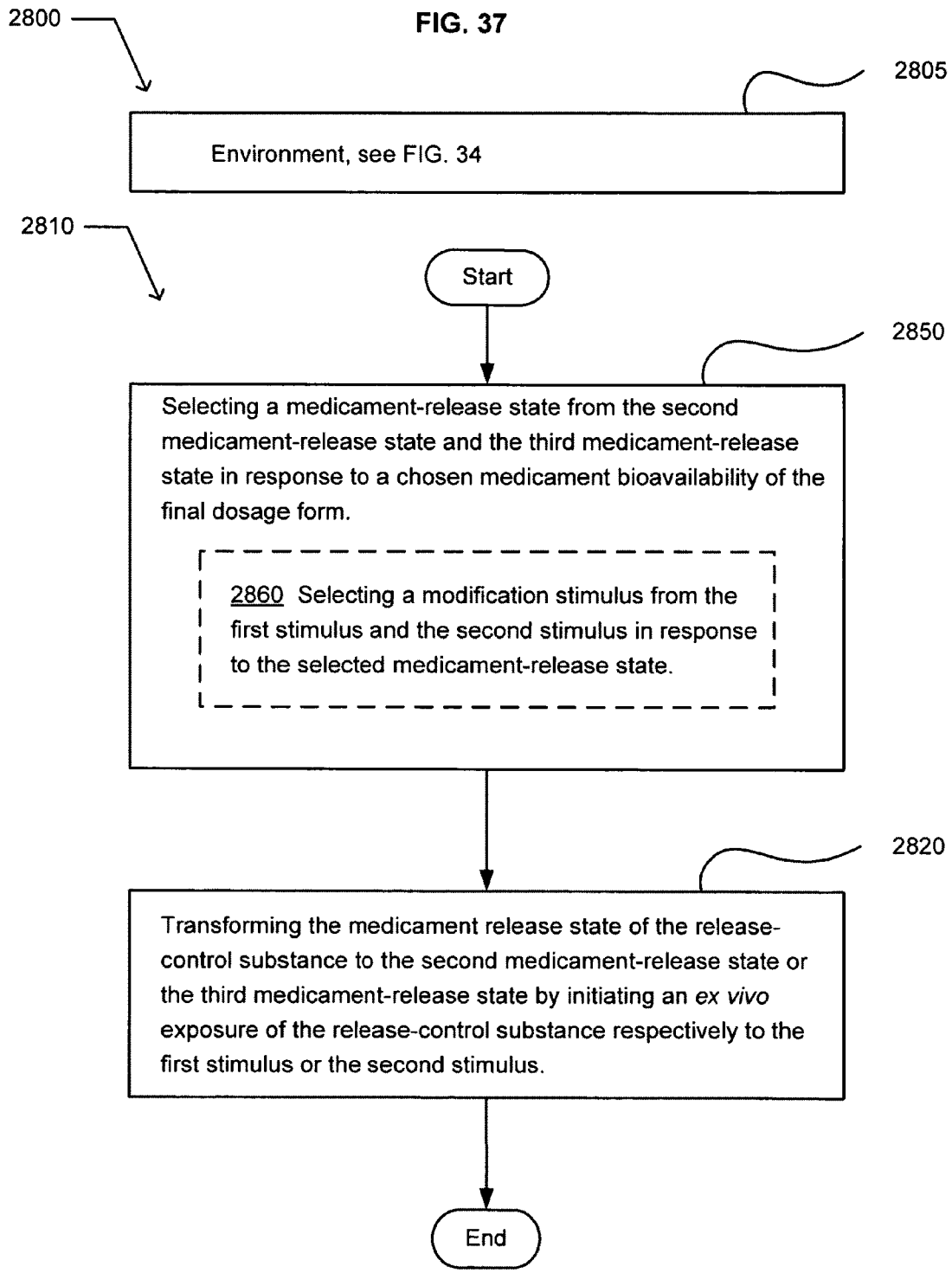

In an environment that includes a final dosage form for administering medicament to an animal, wherein the final dosage form includes
the medicament, and
a release-control substance carrying the medicament in a medicament-retention state wherein the medicament is substantially not bioavailable to the animal if the final dosage form is administered to the animal, >the release-control substance modifiable *ex vivo* by an exposure to a first stimulus to carry the medicament in a first medicament-release state wherein the medicament has a first bioavailability to the animal if the final dosage form is administered to the animal, and >the release-control substance modifiable *ex vivo* by an exposure to a second stimulus to carry the medicament in a second medicament-release state wherein the medicament has a second bioavailability to the animal if the final dosage form is administered to the animal.

2910

( Start )

2920

Automatically selecting a medicament-release state from the first medicament-release state and the second medicament-release state based on a specified medicament bioavailability of the final dosage form.

2930

Automatically selecting a modification stimulus from the first stimulus and the second stimulus in response to the selected medicament-release state.

2940

Transforming the medicament release state of the release-control substance by initiating an *ex vivo* exposure of the release-control substance to the selected modification stimulus.

( End )

FIG. 39

A vehicle for administering medicament to an animal.

3010 Means for releasably encompassing the medicament in a first medicament-release state wherein the medicament has a first bioavailability to the animal if the vehicle is administered to the animal, the means for releasably encompassing the medicament in a first medicament-release state being modifiable to a second medicament-release state upon an ex vivo exposure to a first stimulus, the medicament in the second medicament-release state having a second bioavailability to the animal if the vehicle is administered to the animal, and the means for releasably encompassing the medicament in a first medicament-release state being modifiable to a third medicament-release state upon an ex vivo exposure to a second stimulus, the medicament in the third medicament-release state having a third bioavailability to the animal if the vehicle is administered to the animal.

3030 Means for protecting the means for releasably encompassing the medicament against an ex vivo environment.

190 The medicament.

3050 Means for indicating an exposure of the means for releasably encompassing the medicament to the first stimulus or the second stimulus.

3060 Means for containing the medicament within the vehicle before the final dosage form is administered to the animal.

3070 Means for carrying the vehicle into the animal.

A system. 3102

3110 Means for persistently storing computer-readable information indicative of a stimulus operable to modify *ex vivo* a bioavailability of a medicament carried by a final dosage form for administration of the medicament to an animal.

3112 Means for persistently storing computer-readable information indicative of a stimulus to modify *ex vivo* a bioavailability of a medicament carried by a final dosage form for administration of the medicament to an animal, the computer-readable information indicative of a stimulus based upon a selected medicament bioavailability of the final dosage form.

3120 Means for establishing *ex vivo* of the animal a location of the final dosage form to receive the indicated stimulus from a stimulus source.

3130 Means for providing the indicated stimulus.

3140 Means for regulating an *ex vivo* exposure of the final dosage form to the indicated stimulus.

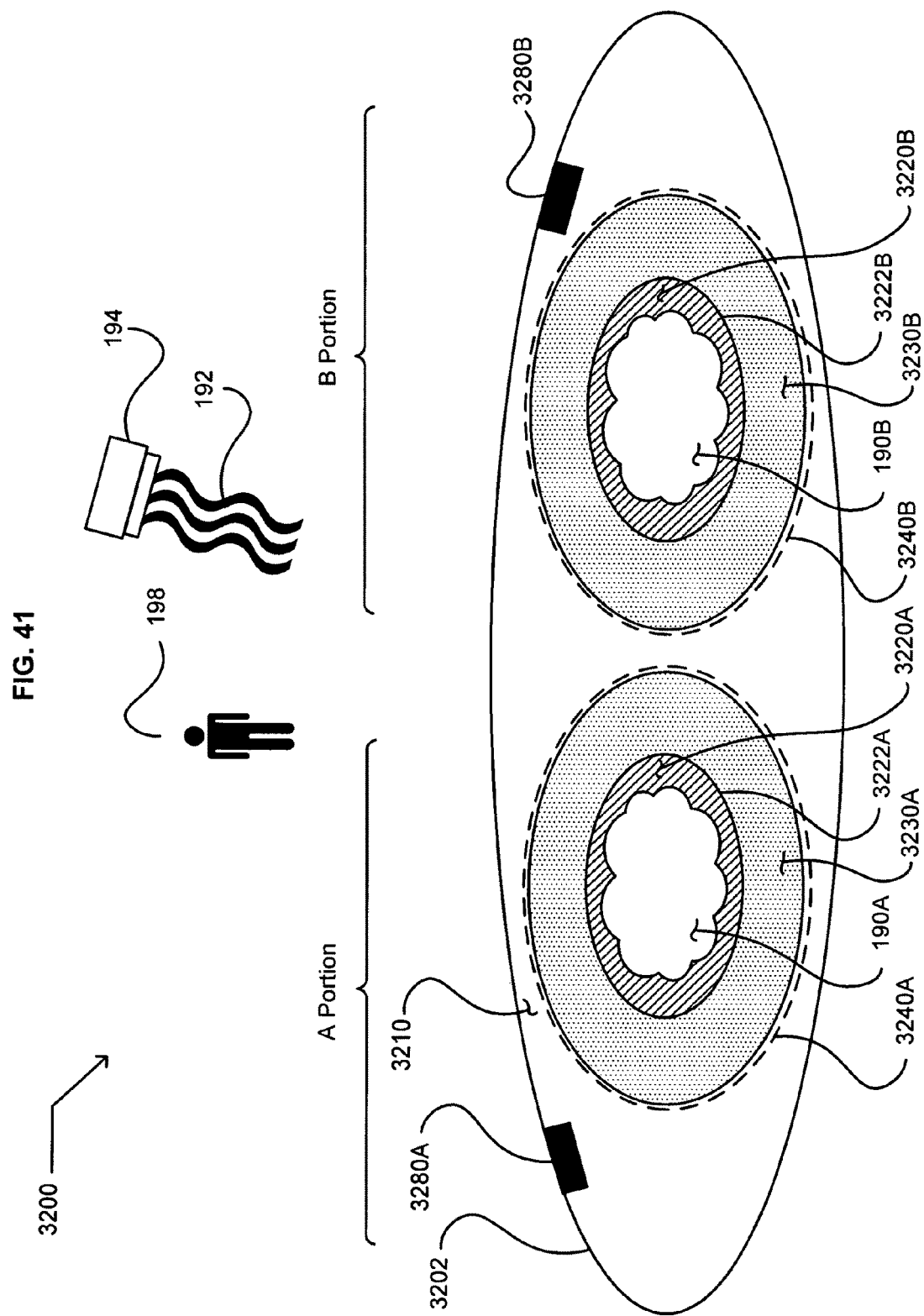

In an environment that includes a final dosage form for administering medicament to an animal, wherein the final dosage form includes
a dosage portion having a chamber carrying a medicament;

a release element in a first medicament-release state wherein the medicament has a first bioavailability to the animal if the final dosage form is administered to the animal in the first medicament-release state, the release element modifiable ex vivo to a second medicament-release state by an exposure to a stimulus, wherein the medicament has a second bioavailability to the animal if the final dosage form is administered to the animal in the second medicament-release state;

another dosage portion having another chamber carrying another medicament; and another release element in another first medicament-release state wherein the another medicament has another first bioavailability to the animal if the final dosage form is administered to the animal in the another first medicament-release state, the another release element modifiable *ex vivo* to another second medicament-release state by an exposure to another stimulus, wherein the another medicament has another second bioavailability to the animal if the final dosage form is administered to the animal in the another second medicament-release state.

3410

Start

3420

Transforming the final dosage form into a selected medicament-release profile by initiating an *ex vivo* exposure of the release element or the another release element to a modification stimulus respectfully selected from the stimulus and the another stimulus.

End

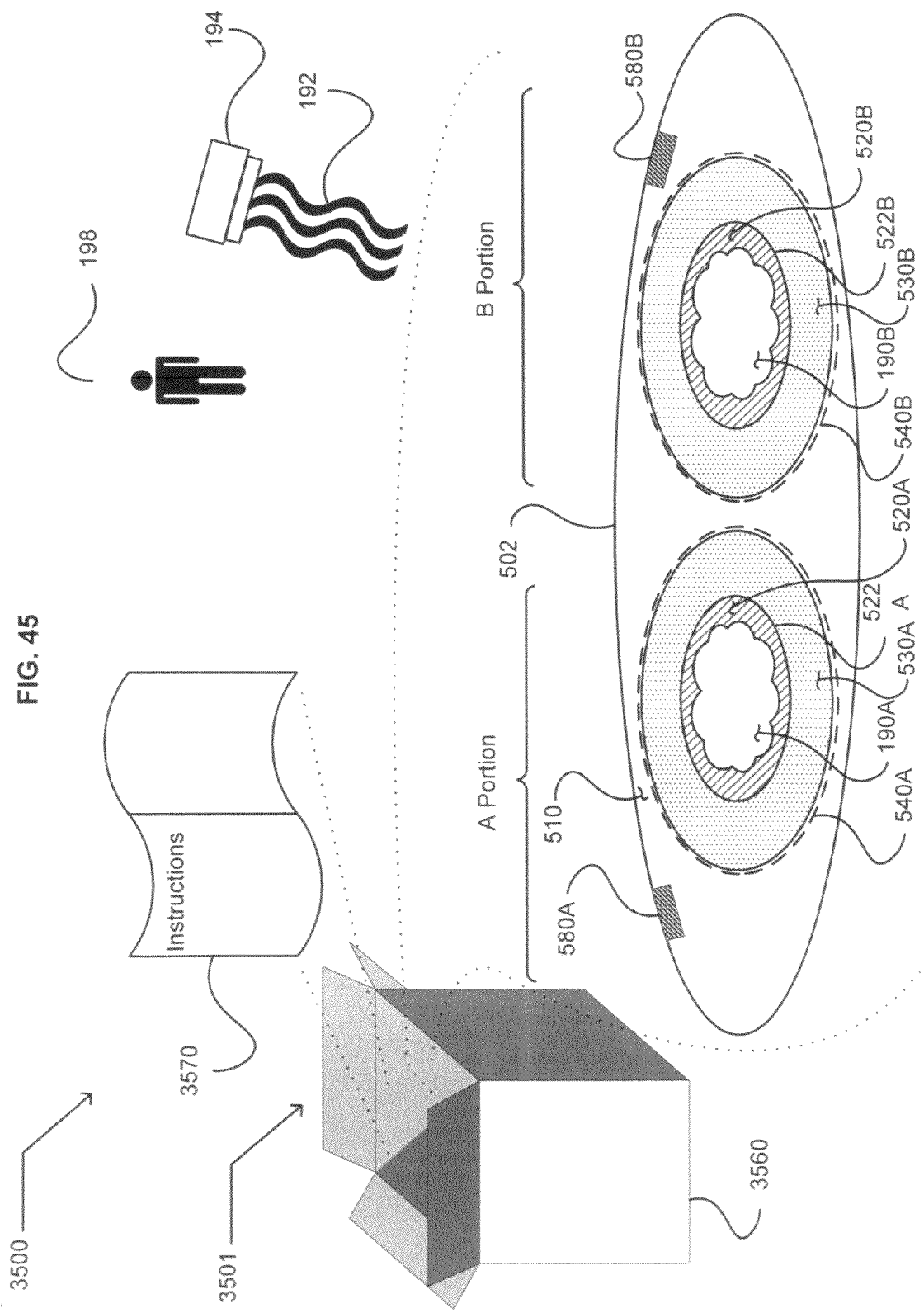

FIG. 46

An article of manufacture for administering medicament to an animal.

3610 A first portion.

3620 Means for carrying a medicament.

3624 Means for medicament release control in a first state wherein the medicament has a first bioavailability to the animal if the article of manufacture is administered to the animal, the means for medicament release control modifiable *ex vivo* to a second state by an exposure to a stimulus, wherein the medicament has a second bioavailability to the animal if the article of manufacture is administered to the animal.

190A The medicament.

3628 Means for indicating an exposure of the means for medicament release control to the stimulus.

3650 A second portion.

3660 Another means for carrying another medicament.

3664 Another means for medicament release control in another first state wherein the another medicament has another first bioavailability to the animal if the article of manufacture is administered to the animal, the another means for medicament release control modifiable *ex vivo* to another second state by an exposure to another stimulus, wherein the another medicament has another second bioavailability to the animal if the article of manufacture is administered to the animal.

190B The another medicament.

3668 Another means for indicating an exposure of the another means for medicament release control to the another stimulus.

3602

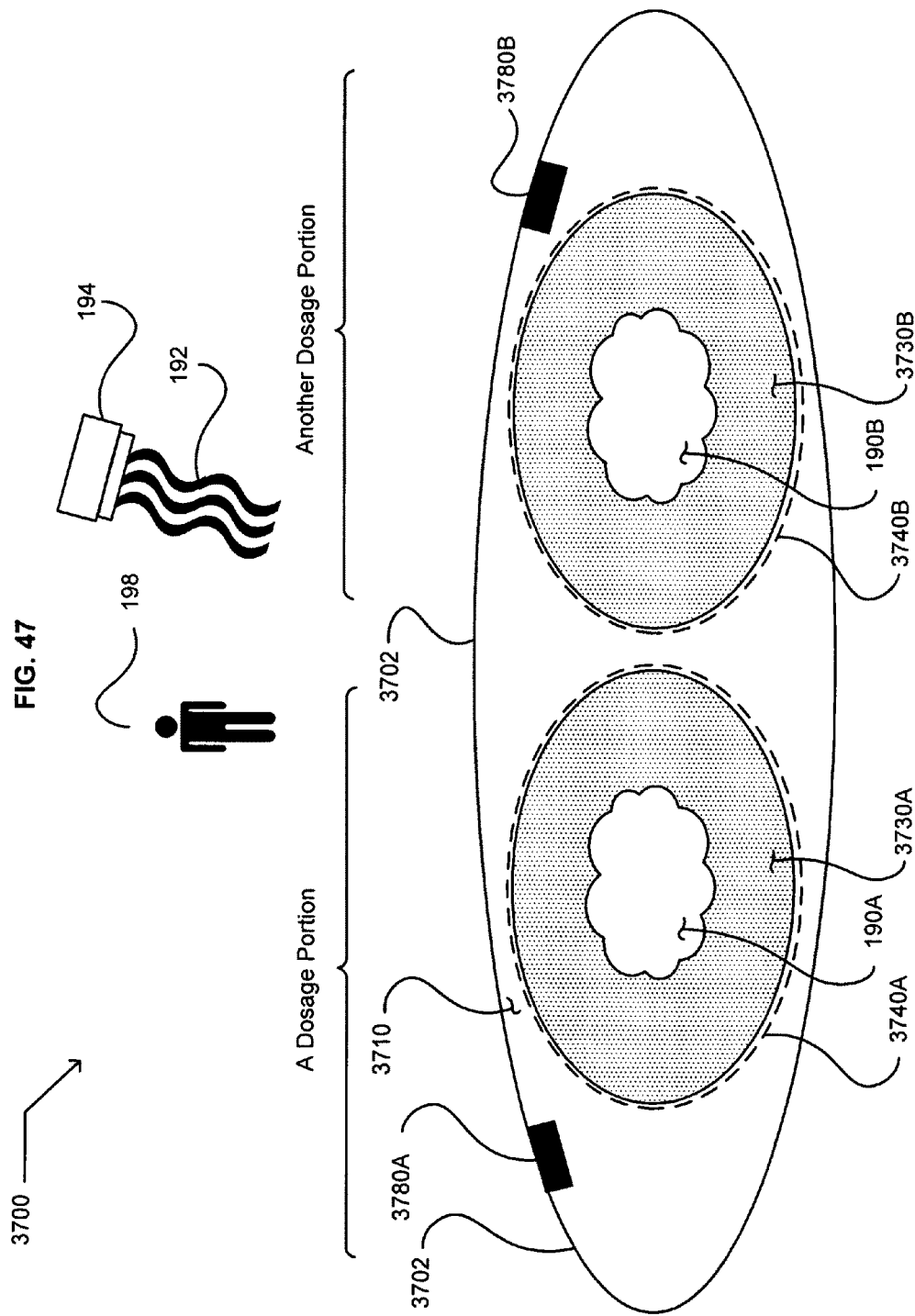

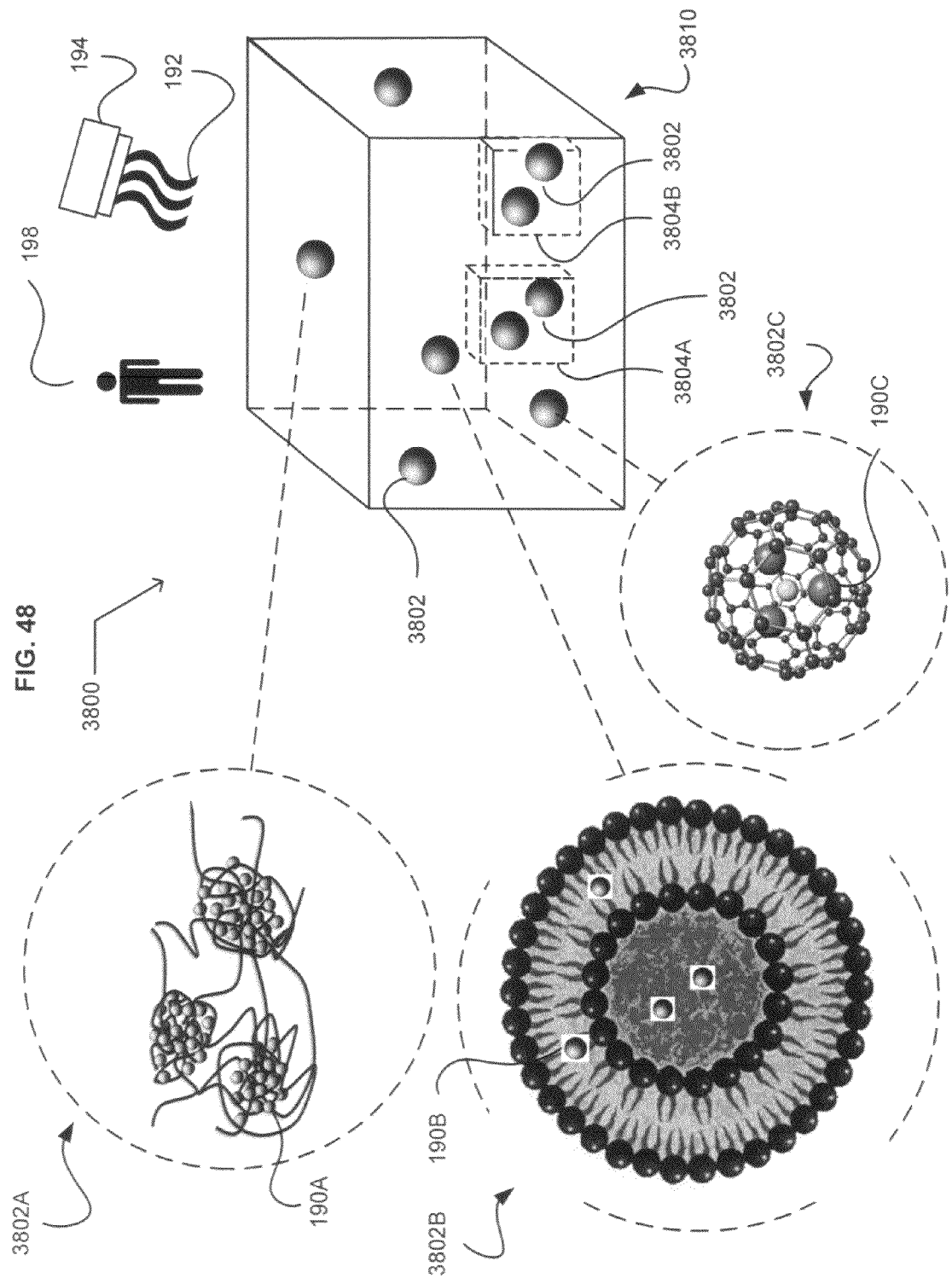

In an environment that includes a final dosage form for administering medicament to an animal, wherein the final dosage form includes a dosage portion having a medicament; and a release element in a first medicament-release state wherein the medicament has a first bioavailability to the animal if the final dosage form is administered to the animal in the first medicament-release state, the release element modifiable *ex vivo* to a second medicament-release state by an exposure to a stimulus, wherein the medicament has a second bioavailability to the animal if the final dosage form is administered to the animal in the second medicament-release state; and another dosage portion having another medicament another release element in another first medicament-release state wherein the another medicament has another first bioavailability to the animal if the final dosage form is administered to the animal in the another first medicament-release state, the another release element modifiable *ex vivo* to another second medicament-release state by an exposure to another stimulus, wherein the another medicament has another second bioavailability to the animal if the final dosage form is administered to the animal in the another second medicament-release state.

3910 ↘

( Start )

3920

Transforming the final dosage form into a selected medicament release profile by initiating an *ex vivo* exposure of the release element or the another release element to a modification stimulus respectfully selected from the stimulus or the another stimulus.

| 3922 Transforming the final dosage form into a selected medicament release profile by initiating an *ex vivo* exposure of the release element and the another release element to the stimulus and the another stimulus.

( End )

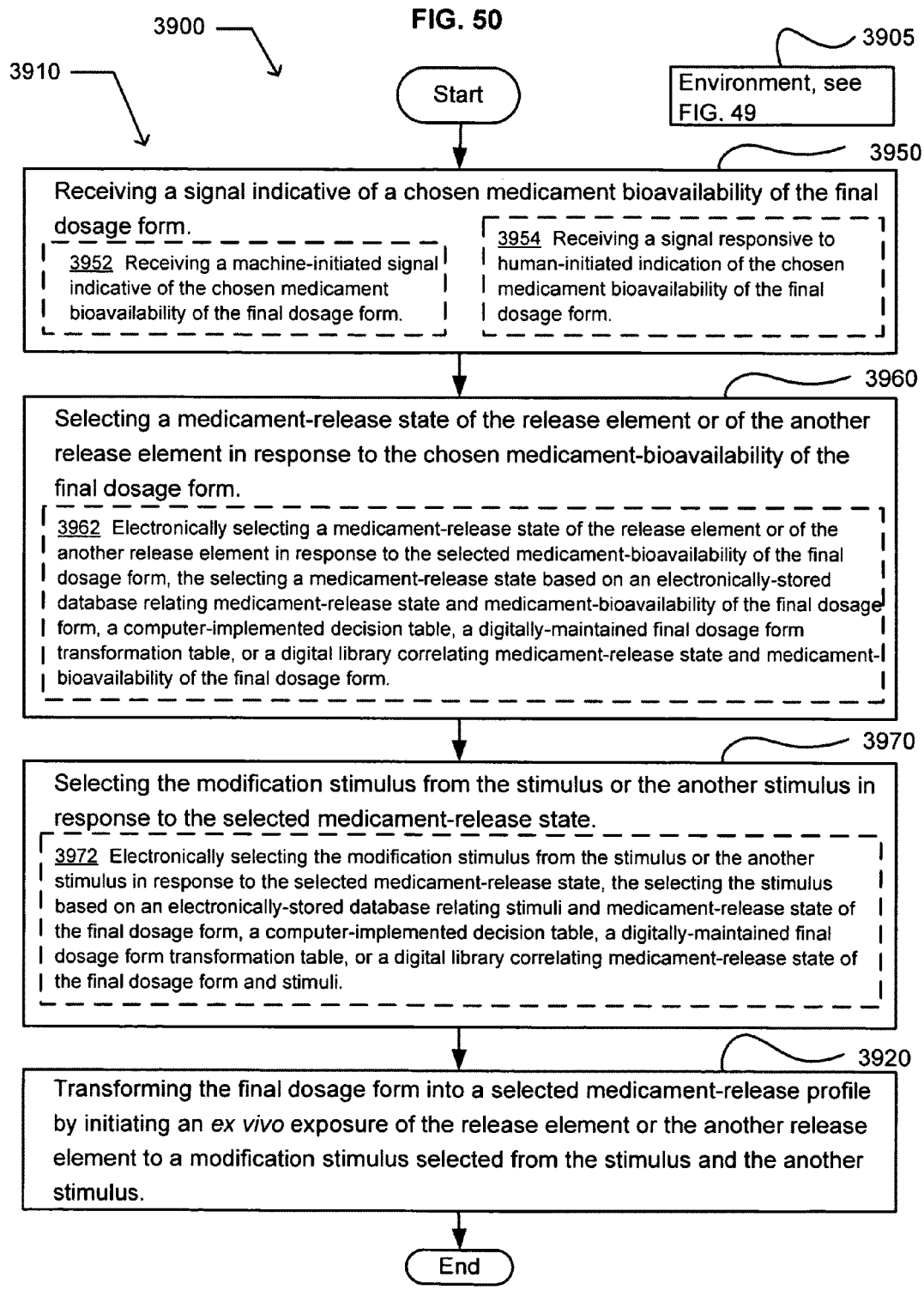

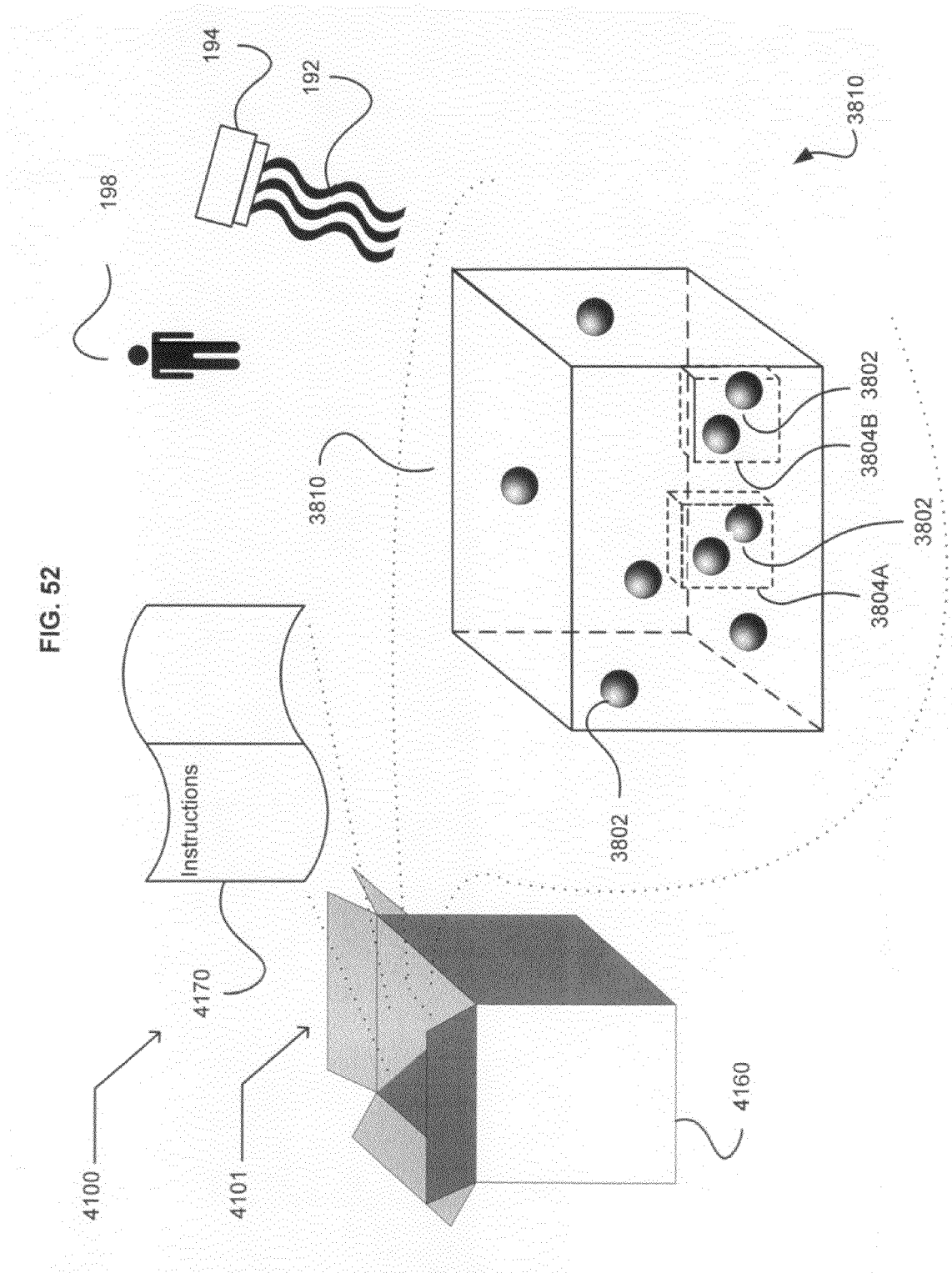

FIG. 53

An article of manufacture for administering medicament to an animal.

4224 Means for medicament release control in a first state wherein the medicament has a first bioavailability to the animal if the article of manufacture is administered to the animal, the means for medicament release control modifiable *ex vivo* to a second state by an exposure to a stimulus, wherein the medicament has a second bioavailability to the animal if the article of manufacture is administered to the animal.

190A A medicament.

4228 Means for indicating an exposure of the means for medicament release control to the stimulus.

4280 Means for protecting the article of manufacture against an *ex vivo* environment.

4264 Another means for medicament release control in another first state wherein the another medicament has another first bioavailability to the animal if the article of manufacture is administered to the animal, the another means for medicament release control modifiable *ex vivo* to another second state by an exposure to another stimulus, wherein the another medicament has another second bioavailability to the animal if the article of manufacture is administered to the animal.

190B Another medicament.

4268 Another means for indicating an exposure of the another means for medicament release control to the another stimulus.

4290 Means for carrying the article of manufacture into the animal.

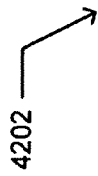

In an environment that includes a final dosage form for administering medicament to an animal, wherein the final dosage form includes a dosage portion having a medicament;

a site and the medicament in a first association wherein the medicament is substantially not bioavailable to the animal if the final dosage form is administered to the animal, the first association of the site and the medicament modifiable *ex vivo* to a second association by an exposure to a stimulus, wherein the medicament is substantially bioavailable to the animal if the final dosage form is administered to the animal; and another dosage portion having another medicament;

another site and the another medicament in another first association wherein the another medicament is substantially not bioavailable to the animal if the final dosage form is administered to the animal, the another first association of the site and the another medicament modifiable *ex vivo* to another second association by an exposure to another stimulus, wherein the another medicament is substantially bioavailable to the animal if the final dosage form is administered to the animal.

4410 ↘

Start

4420

Transforming the final dosage form into a selected medicament release profile by initiating an *ex vivo* exposure of the first association of the site and the medicament or the another first association of the another site and the another medicament to a modification stimulus respectfully selected from the stimulus or the another stimulus.

| 4422 Transforming the final dosage form into a selected medicament release profile by initiating an *ex vivo* exposure of the first association of the site and the medicament and the another first association of the another site and the another medicament to the stimulus and the another stimulus.

End

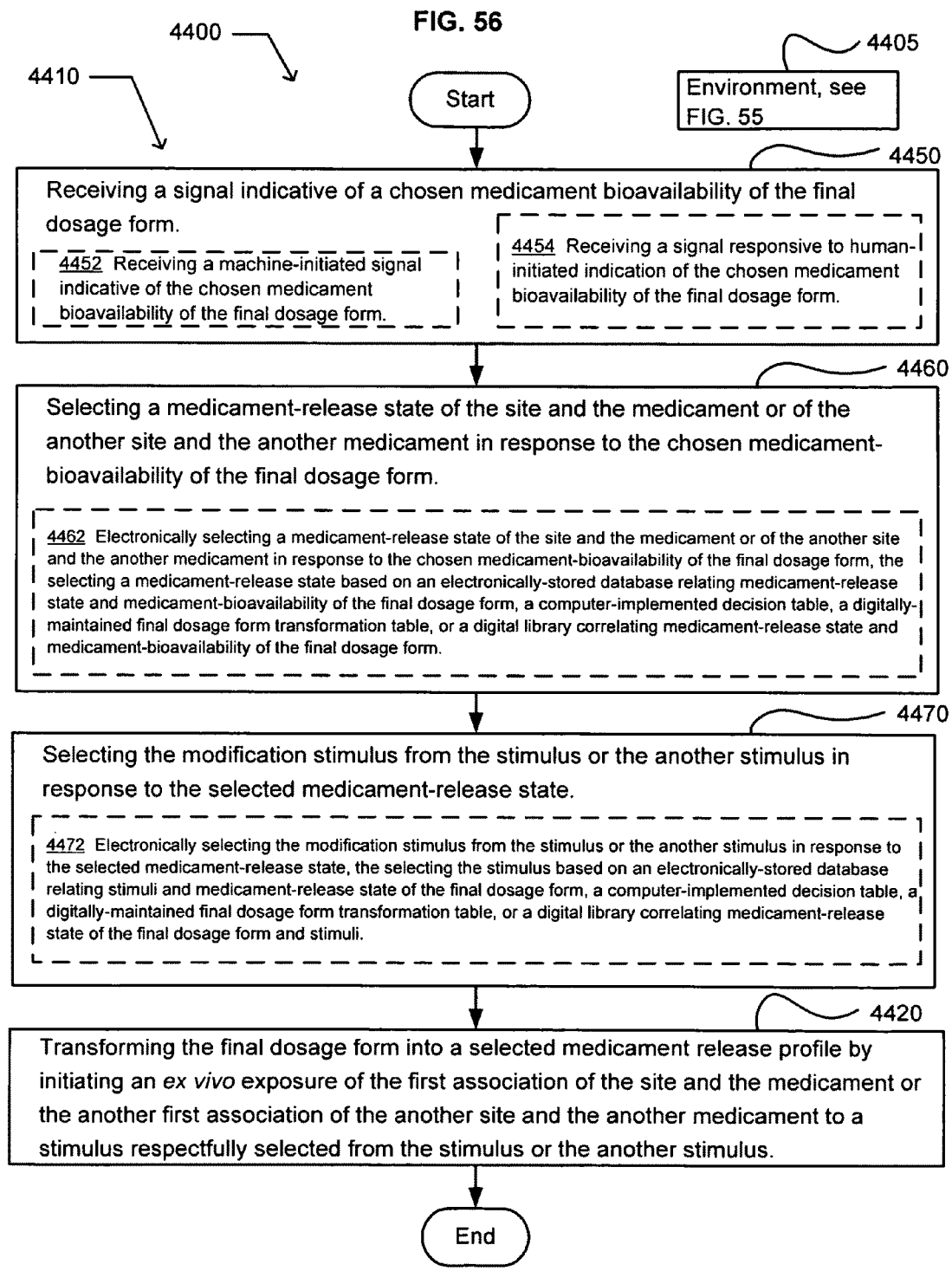

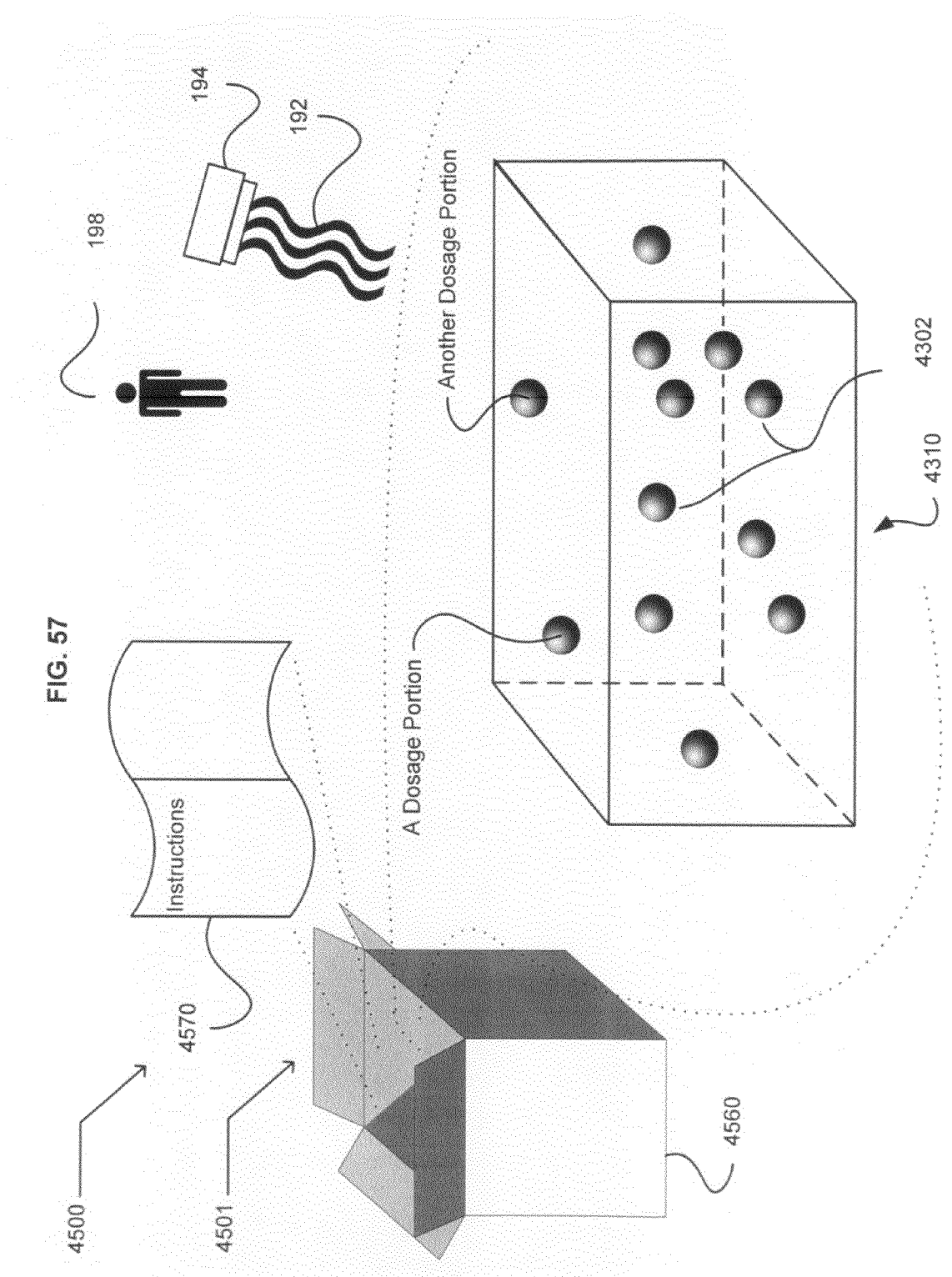

An article of manufacture for administering medicament to an animal.

4624 Means for encapsulating a medicament in a first medicament-release state, wherein the medicament has a first bioavailability to the animal if the article of manufacture is administered to the animal in the first medicament-release state, the means for encapsulating a medicament in a first medicament-release state modifiable ex vivo to a second medicament-release state by an exposure to a stimulus, wherein the medicament has a second bioavailability to the animal if the article of manufacture is administered to the animal in the second medicament-release state.

4664 Another means for encapsulating another medicament in another first medicament-release state, wherein the another medicament has another first bioavailability to the animal if the article of manufacture is administered to the animal in the another first medicament-release state, the another means for encapsulating another medicament in another first medicament-release state modifiable ex vivo to another second medicament-release state by an exposure to another stimulus, wherein the another medicament has another second bioavailability to the animal if the article of manufacture is administered to the animal in the another second medicament-release state.

190A The medicament.

190B The another medicament.

4628 Means for indicating an exposure of the means for encapsulating a medicament in a first medicament-release state to the stimulus.

4668 Another means for indicating an exposure of the another means for encapsulating another medicament in another first medicament-release state to the another stimulus.

4680 Means for protecting the article of manufacture against an ex vivo environment.

4690 Means for carrying the article of manufacture into the animal.

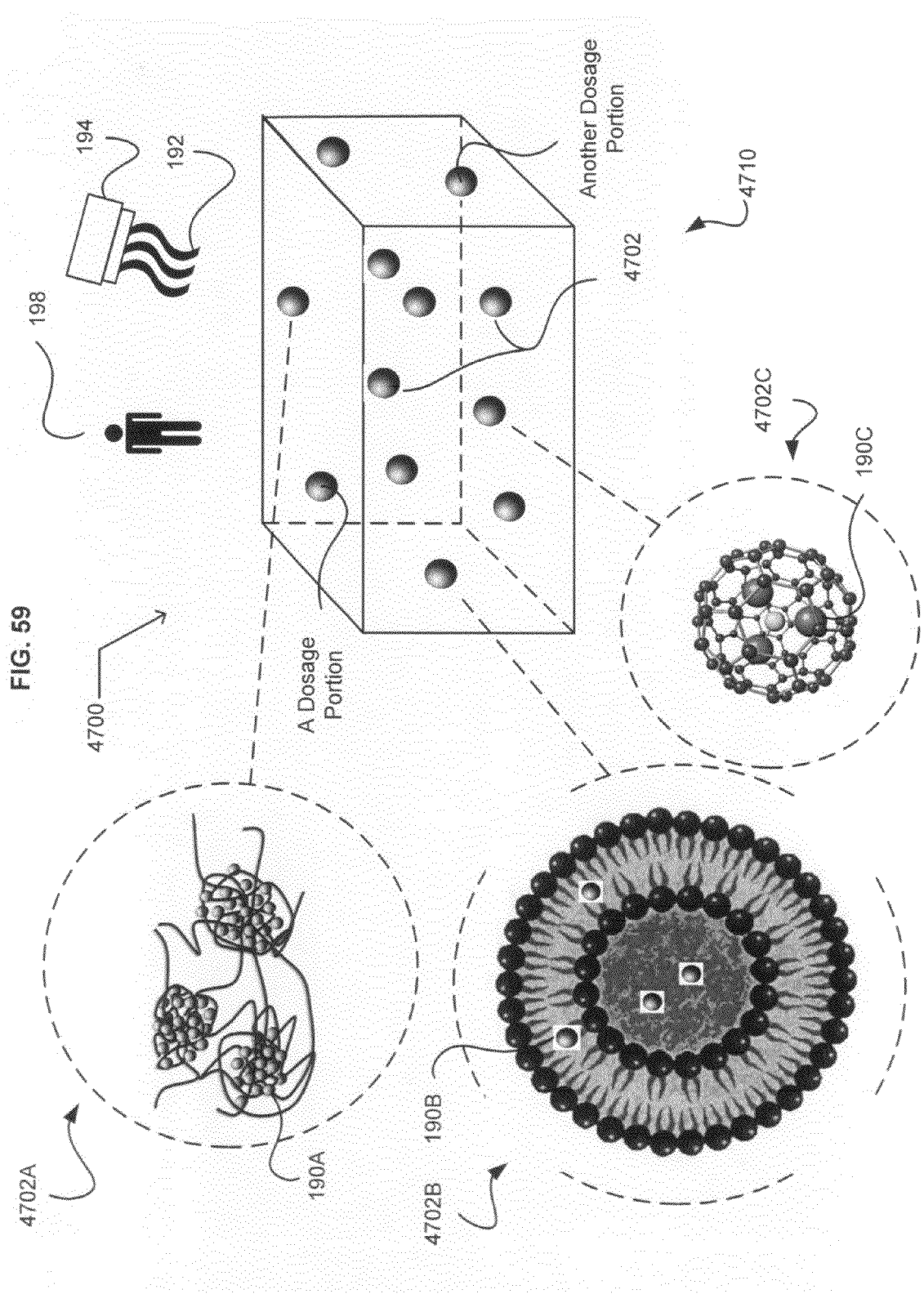

In an environment that includes a final dosage form for administering medicament to an animal, wherein the final dosage form includes a medicament;

a substance associated with the medicament in a first release-control state, wherein the medicament has a first bioavailability to the animal if the final dosage form is administered to the animal, the substance modifiable *ex vivo* by an exposure to a stimulus to associate with the medicament in a second release-control state, wherein the medicament has a second bioavailability to the animal if the final dosage form is administered to the animal;

another medicament; and another substance associated with the another medicament in another first release-control state, wherein the another medicament has another first bioavailability to the animal if the final dosage form is administered to the animal, the another substance modifiable *ex vivo* by an exposure to another stimulus to associate with the another medicament in another second release-control state, wherein the another medicament has another second bioavailability to the animal if the final dosage form is administered to the animal.

4810

Start

4820

Transforming the final dosage form into a selected medicament release state by initiating an *ex vivo* exposure of the substance associated with the medicament in a first release-control state or an *ex vivo* exposure of the another substance associated with the another medicament in another first release-control state to a modification stimulus respectfully selected from the stimulus or the another stimulus.

4822 Transforming the final dosage form into a selected medicament release state by initiating an *ex vivo* exposure of the substance associated with the medicament in a first release-control state and an *ex vivo* exposure of the another substance associated with the another medicament in another first release-control state to the stimulus and the another stimulus.

End

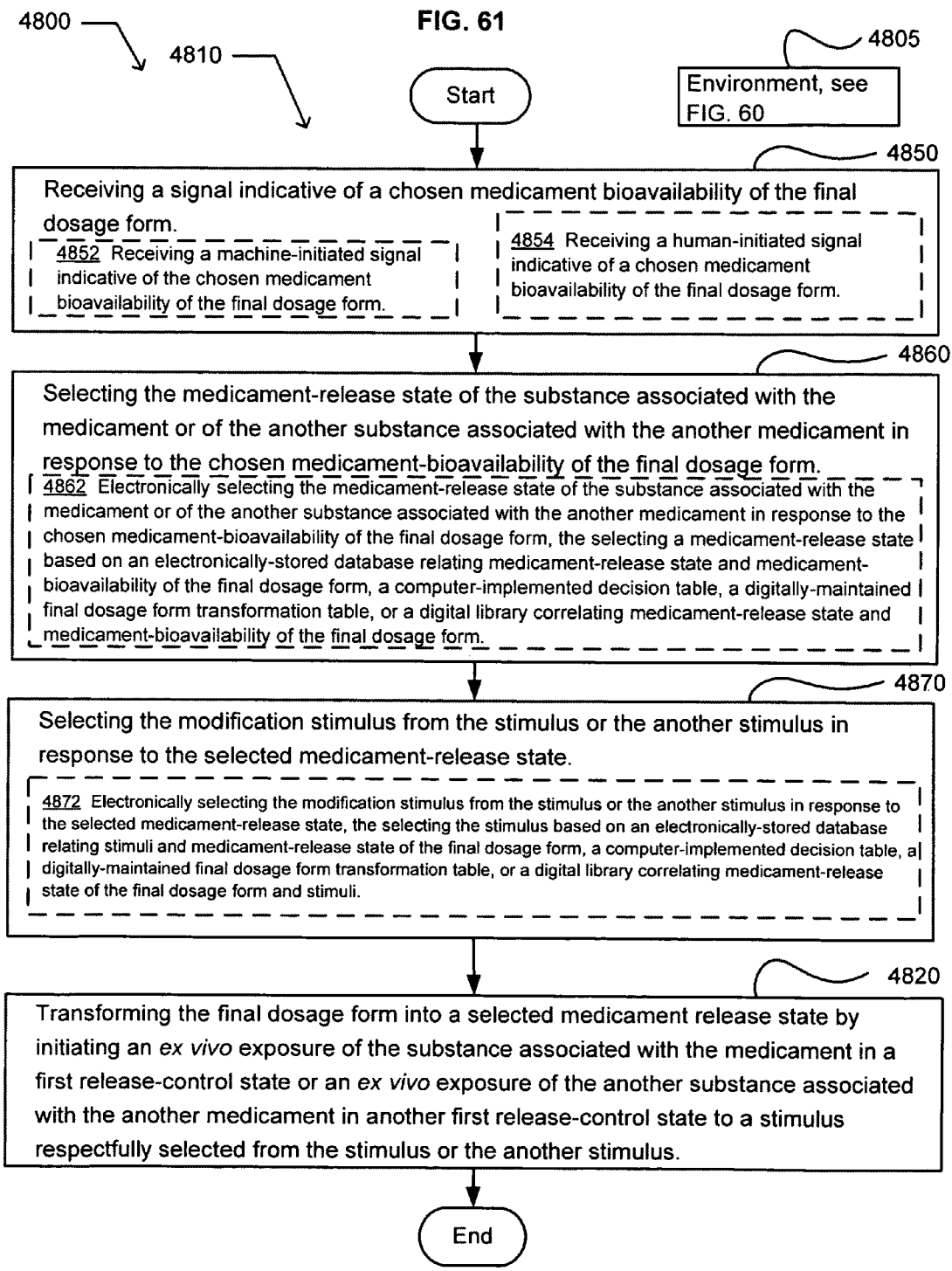

FIG. 62

An article of manufacture for administering medicament to an animal.

4924 An intelligent molecular means associated with the medicament in a first release-control state, wherein the medicament has a first bioavailability to the animal if the article of manufacture is administered to the animal, the intelligent molecular means modifiable *ex vivo* by an exposure to a stimulus to associate with the medicament in a second release-control state, wherein the medicament has a second bioavailability to the animal if the article of manufacture is administered to the animal.

4964 Another intelligent molecular means associated with the another medicament in another first release-control state, wherein the another medicament has another first bioavailability to the animal if the article of manufacture is administered to the animal, the another intelligent molecular means modifiable *ex vivo* by an exposure to another stimulus to associate with the another medicament in another second release-control state, wherein the another medicament has another second bioavailability to the animal if the article of manufacture is administered to the animal.

190A  A medicament.

4928 Means for indicating an exposure to the stimulus of the intelligent molecular means associated with a medicament in a first medicament-release state.

4980 Means for protecting the article of manufacture against an *ex vivo* environment.

190B  Another medicament.

4968 Another means for indicating an exposure to the another stimulus of the another intelligent molecular means associated with another medicament in another first medicament-release state.

4990 Means for carrying the article of manufacture into the animal.

4902

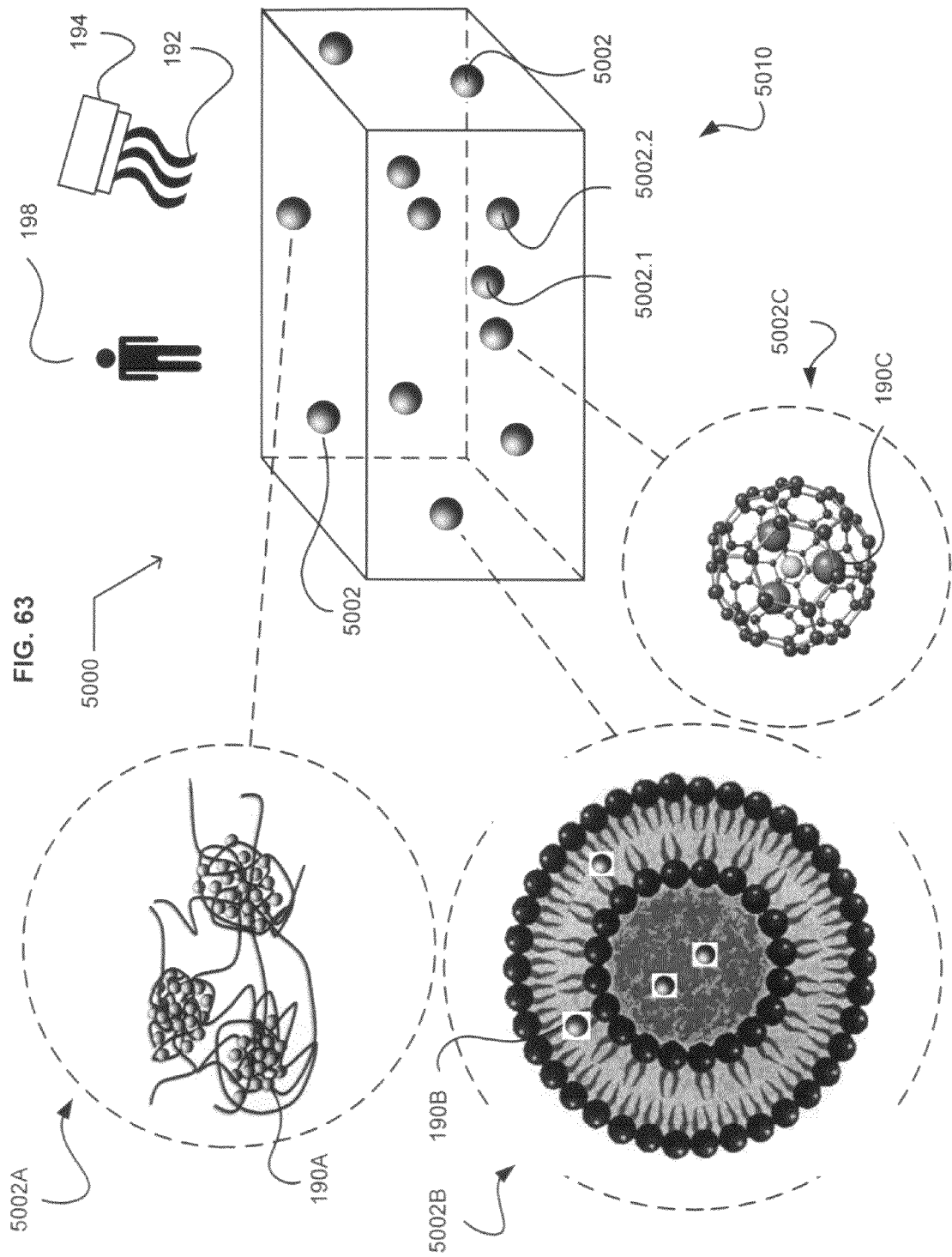

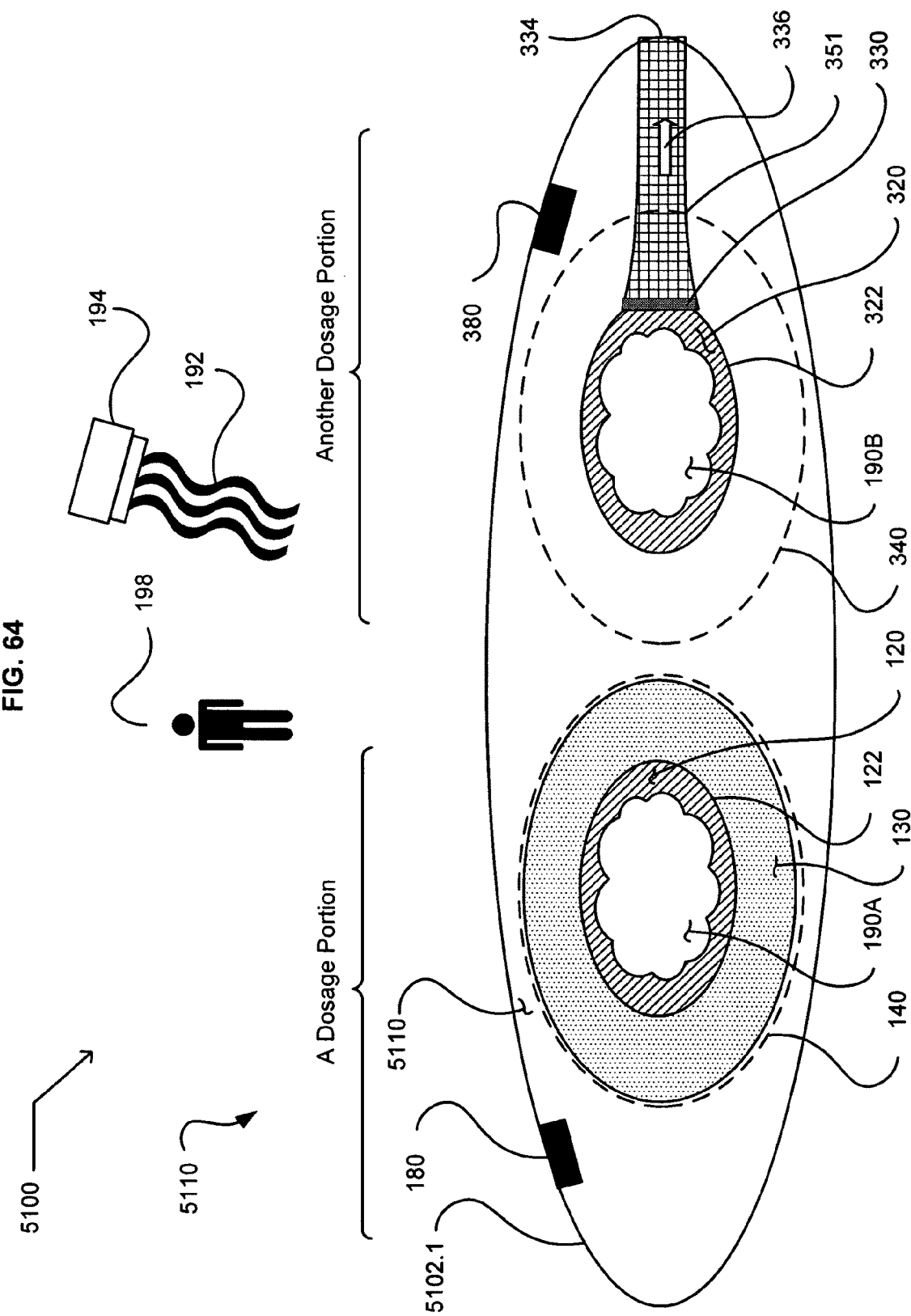

In an environment that includes a final dosage form for administering medicament to an animal, wherein the final dosage form includes a medicament;

a substance carrying the medicament in a first medicament-release state wherein the medicament has a first bioavailability to the animal if the final dosage form is administered to the animal, the substance modifiable ex vivo by an exposure to a first stimulus to carry the medicament in a second medicament-release state wherein the medicament has a second bioavailability to the animal if the final dosage form is administered to the animal, and the substance modifiable ex vivo by an exposure to a second stimulus to carry the medicament in a third medicament-release state, wherein the medicament has a third bioavailability to the animal if the final dosage form is administered to the animal;

another medicament; and another substance carrying the another medicament in another first medicament-release state wherein the another medicament has another first bioavailability to the animal if the final dosage form is administered to the animal, the another substance modifiable ex vivo by an exposure to another first stimulus to carry the another medicament in another second medicament-release state wherein the another medicament has another second bioavailability to the animal if the final dosage form is administered to the animal, and the another substance modifiable ex vivo by an exposure to another second stimulus to carry the another medicament in another third medicament-release state, wherein the another medicament has another third bioavailability to the animal if the final dosage form is administered to the animal.

5210 ↘

( Start )

5220

Transforming the final dosage form into a selected medicament-release state by initiating an *ex vivo* exposure to a modification stimulus of the substance carrying the medicament in a first medicament-release state or the another substance carrying the another medicament in another first medicament-release state, the modification stimulus respectfully selected from the first stimulus or the second stimulus for the substance, or from the another first stimulus or the another second stimulus for the another substance.

5222 Transforming the final dosage form into a selected medicament-release state by initiating an *ex vivo* exposure to a modification stimulus of the substance carrying the medicament in a first medicament-release state and the another substance carrying the another medicament in another first medicament-release state, the modification stimulus including a stimulus selected from the first stimulus or the second stimulus for the substance, and another stimulus selected from the another first stimulus or the another second stimulus for the another substance.

( End )

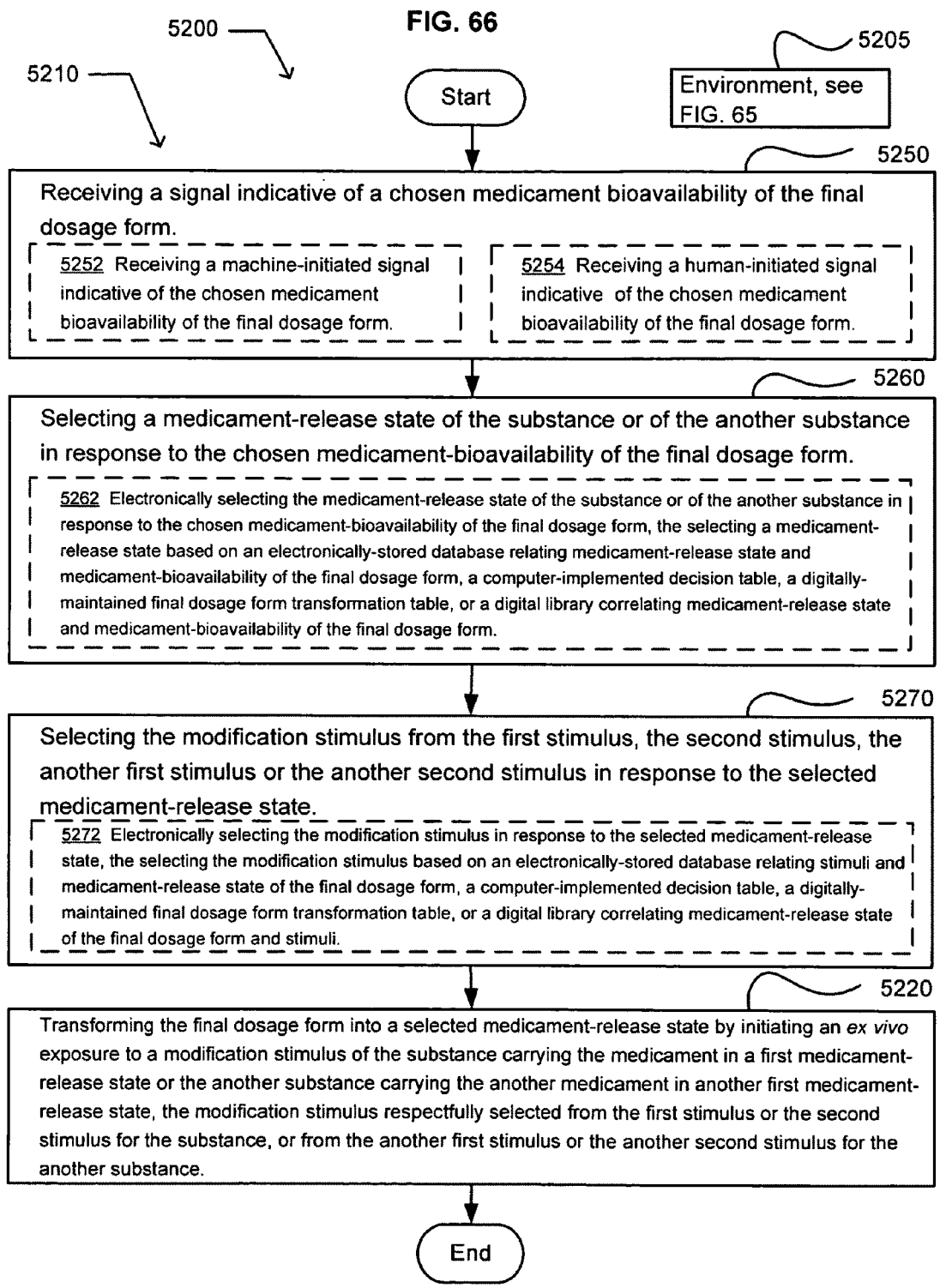

An article of manufacture for administering medicament to an animal.

5724 Intelligent molecular means associated with the medicament in a first medicament-release state wherein the medicament has a first bioavailability to the animal if the article of manufacture is administered to the animal, the intelligent molecular means modifiable ex vivo by an exposure to a first stimulus to carry the medicament in a second medicament-release state wherein the medicament has a second bioavailability to the animal if the article of manufacture is administered to the animal, and the intelligent molecular means modifiable ex vivo by an exposure to a second stimulus to carry the medicament in a third medicament-release state wherein the medicament has a third bioavailability to the animal if the article of manufacture is administered to the animal.

5764 Another intelligent molecular means associated with the another medicament in another first medicament-release state wherein the another medicament has another first bioavailability to the animal if the article of manufacture is administered to the animal, the another intelligent molecular means modifiable ex vivo by an exposure to another first stimulus to carry the another medicament in another second medicament-release state wherein the another medicament has another second bioavailability to the animal if the article of manufacture is administered to the animal, and the another intelligent molecular means modifiable ex vivo by an exposure to another second stimulus to carry the another medicament in another third medicament-release state wherein the another medicament has another third bioavailability to the animal if the article of manufacture is administered to the animal.

190A The medicament.

190B Another medicament.

EX VIVO MODIFIABLE MULTIPLE MEDICAMENT FINAL DOSAGE FORM

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

Related Applications

For purposes of the USPTO extra-statutory requirements, the present application constitutes a continuation-in-part of U.S. patent application Ser. No. 12/284,015, titled INDIVIDUALIZABLE DOSAGE FORM, naming Mahalaxmi Gita Bangera, Edward S. Boyden, Roderick A. Hyde, Muriel Y. Ishikawa, Dennis J. Rivet, Elizabeth A. Sweeney, Lowell L. Wood, Jr., and Victoria Y. H. Wood as inventors, filed Sep. 16, 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/284,014, titled PERSONALIZABLE DOSAGE FORM, naming Mahalaxmi Gita Bangera, Edward S. Boyden, Roderick A. Hyde, Muriel Y. Ishikawa, Dennis J. Rivet, Elizabeth A. Sweeney, Lowell L. Wood, Jr., and Victoria Y. H. Wood as inventors, filed Sep. 16, 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/284,013, titled MODIFIABLE DOSAGE FORM, naming Mahalaxmi Gita Bangera, Edward S. Boyden, Roderick A. Hyde, Muriel Y. Ishikawa, Dennis J. Rivet, Elizabeth A. Sweeney, Lowell L. Wood, Jr., and Victoria Y. H. Wood as inventors, filed Sep. 16, 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/322,877, titled EX VIVO-MODIFIABLE PARTICLE OR POLYMERIC BASED FINAL DOSAGE FORM, naming Mahalaxmi Gita Bangera, Edward S. Boyden, Roderick A. Hyde, Muriel Y. Ishikawa, Dennis J. Rivet, Elizabeth A. Sweeney, Lowell L. Wood, Jr., and Victoria Y. H. Wood as inventors, filed Feb. 5, 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/322,874, titled MODIFYING A MEDICAMENT AVAILABLLITY STATE OF A FINAL DOSAGE FORM, naming Mahalaxmi Gita Bangera, Edward S. Boyden, Roderick A. Hyde, Muriel Y. Ishikawa, Dennis J. Rivet, Elizabeth A. Sweeney, Lowell L. Wood, Jr., and Victoria Y. H. Wood as inventors, filed Feb. 5, 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/322,878, titled EX VIVO ACTIVATABLE FINAL DOSAGE FORM, naming Mahalaxmi Gita Bangera, Edward S. Boyden, Roderick A. Hyde, Muriel Y. Ishikawa, Dennis J. Rivet, Elizabeth A. Sweeney, Lowell L. Wood, Jr., and Victoria Y.H. Wood as inventors, filed Feb. 5, 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/387,312, titled EX VIVO MODIFIABLE PARTICLE OR POLYMERIC MATERIAL MEDICAMENT CARRIER, naming Mahalaxmi Gita Bangera, Edward S. Boyden, Roderick A. Hyde, Muriel Y. Ishikawa, Dennis J. Rivet, Elizabeth A. Sweeney, Lowell L. Wood, Jr., and Victoria Y.H. Wood as inventors, filed Apr. 29, 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/387,326, titled EX VIVO-MODIFIABLE MULTIPLE-RELEASE STATE FINAL DOSAGE FORM, naming Mahalaxmi Gita Bangera, Edward S. Boyden, Roderick A. Hyde, Muriel Y. Ishikawa, Dennis J. Rivet, Elizabeth A. Sweeney, Lowell L. Wood, Jr., and Victoria Y.H. Wood as inventors, filed Apr. 29, 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/387,329, titled SYSTEM FOR EX VIVO MODIFICATION OF MEDICAMENT RELEASE STATE, naming Mahalaxmi Gita Bangera, Edward S. Boyden, Roderick A. Hyde, Muriel Y. Ishikawa, Dennis J. Rivet, Elizabeth A. Sweeney, Lowell L. Wood, Jr., and Victoria Y.H. Wood as inventors, filed Apr. 29, 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/387,324, titled MULTIPLE CHAMBER EX VIVO ADJUSTABLE-RELEASE FINAL DOSAGE FORM, naming Mahalaxmi Gita Bangera, Edward S. Boyden, Roderick A. Hyde, Muriel Y. Ishikawa, Dennis J. Rivet, Elizabeth A. Sweeney, Lowell L. Wood, Jr., and Victoria Y.H. Wood as inventors, filed Apr. 29, 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/387,323, titled EX VIVO MODIFIABLE MEDICAMENT RELEASE-SITES FINAL DOSAGE FORM, naming Mahalaxmi Gita Bangera, Edward S. Boyden, Roderick A. Hyde, Muriel Y. Ishikawa, Dennis J. Rivet, Elizabeth A. Sweeney, Lowell L. Wood, Jr., and Victoria Y.H. Wood as inventors, filed Apr. 29, 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/387,328, titled EX VIVO MODIFIABLE MEDICAMENT RELEASE-ASSOCIATIONS, naming Mahalaxmi Gita Bangera, Edward S. Boyden, Roderick A. Hyde, Muriel Y. Ishikawa, Dennis J. Rivet, Elizabeth A. Sweeney, Lowell L. Wood, Jr., and Victoria Y.H. Wood as inventors, filed Apr. 29, 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/387,311, titled EX VIVO MODIFIABLE MEDICAMENT RELEASE-SUBSTANCE, naming Mahalaxmi Gita Bangera, Edward S. Boyden, Roderick A. Hyde, Muriel Y. Ishikawa, Dennis J. Rivet, Elizabeth A. Sweeney, Lowell L. Wood, Jr., and Victoria Y.H. Wood as inventors, filed Apr. 29, 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s)from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

An embodiment of the subject matter described herein describes a final dosage form for administering medicament to an animal. The final dosage form includes a dosage portion having a medicament and a release element in a first medicament-release state. In the first medicament-release state, the medicament has a first bioavailability to the animal if the final dosage form is administered to the animal in the first medicament-release state. The release element is modifiable ex vivo to a second medicament-release state by an exposure to a stimulus, wherein the medicament has a second bioavailability to the animal if the final dosage form is administered to the animal in the second medicament-release state. The final dosage form includes another dosage portion having another medicament and another release element in another first medicament-release state. In the another first medicament-release state, the another medicament has another first bioavailability to the animal if the final dosage form is administered to the animal in the another first medicament-release state. The another release element is modifiable ex vivo to another second medicament-release state by an exposure to another stimulus, wherein the another medicament has another second bioavailability to the animal if the final dosage form is administered to the animal in the another second medicament-release state.

An embodiment of the subject matter described herein describes a final dosage form for administering medicament to an animal. The final dosage form includes a dosage portion having a medicament and a release element in a medicament-holding state. In the medicament-holding state, the medicament is substantially not bioavailable to the animal if the final dosage form is administered to the animal in the medicament-holding state. The release element is modifiable ex vivo to a medicament-discharging state by an exposure to a stimulus wherein the medicament is bioavailable to the animal if the final dosage form is administered to the animal in the medicament-discharging state. The final dosage form includes another dosage portion having another medicament and another release element in another medicament-holding state. In the another medicament-holding state, the another medicament is substantially not bioavailable to the animal if the final dosage form is administered to the animal in the another medicament-holding state. The another release element is modifiable ex vivo to another medicament-discharge state by an exposure to another stimulus wherein the another medicament is bioavailable to the animal if the final dosage form is administered to the animal in the another medicament-discharge state. In an embodiment, the final dosage form may include an outer layer carrying the dosage portion and the another dosage portion.

An embodiment of the subject matter described herein describes a method of modifying medicament bioavailability of a final dosage form for administering medicament to an animal. The final dosage form includes a dosage portion having a medicament and a release element in a first medicament-release state. In the first medicament-release state, the medicament has a first bioavailability to the animal if the final dosage form is administered to the animal in the first medicament-release state. The release element is modifiable ex vivo to a second medicament-release state by an exposure to a stimulus, wherein the medicament has a second bioavailability to the animal if the final dosage form is administered to the animal in the second medicament-release state. The final dosage form includes another dosage portion having another medicament and another release element in another first medicament-release state. In another first medicament-release state, the another medicament has another first bioavailability to the animal if the final dosage form is administered to the animal in the another first medicament-release state. The another release element is modifiable ex vivo to another second medicament-release state by an exposure to another stimulus, wherein the another medicament has another second bioavailability to the animal if the final dosage form is administered to the animal in the another second medicament-release state. The method includes transforming the final dosage form into a selected medicament release profile by initiating an ex vivo exposure of the release element or the another release element to a modification stimulus respectfully selected from the stimulus or the another stimulus. In an embodiment, the method may include receiving a signal indicative of a chosen medicament bioavailability of the final dosage form. In an embodiment, the method may include selecting a medicament-release state of the release element or of the another release element in response to the chosen medicament-bioavailability of the final dosage form. In an embodiment, the method may include selecting the stimulus for initiation from the stimulus or the another stimulus in response to the selected medicament-release state.

An embodiment of the subject matter described herein describes an article of manufacture. The article of manufacture includes a final dosage form for administering medicament to an animal. The final dosage form includes a dosage portion having a medicament and a release element in a first medicament-release state. In the first medicament-release state, the medicament has a first bioavailability to the animal if the final dosage form is administered to the animal in the first medicament-release state. The release element is modifiable ex vivo to a second medicament-release state by an exposure to a stimulus, wherein the medicament has a second bioavailability to the animal if the final dosage form is administered to the animal in the second medicament-release state. The final dosage form includes another dosage portion having another medicament and another release element in another first medicament-release state. In another first medicament-release state, the another medicament has another first bioavailability to the animal if the final dosage form is administered to the animal in the another first medicament-release state. The another release element is modifiable ex vivo to another second medicament-release state by an exposure to another stimulus, wherein the another medicament has another second bioavailability to the animal if the final dosage form is administered to the animal in the another second medicament-release state. The article of manufacture includes instructions specifying an ex vivo exposure of the release element to the stimulus or an ex vivo exposure of the another release element to the another stimulus which when implemented respectfully transform the release element to the second medicament-release state or the another release element to the another second medicament-release state.

An embodiment of the subject matter described herein describes an article of manufacture for administering medicament to an animal. The article includes a medicament. The article also includes means for medicament release control in a first state wherein the medicament has a first bioavailability to the animal if the article of manufacture is administered to the animal. The means for medicament release control is modifiable ex vivo to a second state by an exposure to a stimulus, wherein the medicament has a second bioavailability to the animal if the article of manufacture is administered to the animal. The article includes another medicament. The article also includes another means for medicament release control in another first state wherein the another medicament has another first bioavailability to the animal if the article of manufacture is administered to the animal. The another means for medicament release control is modifiable ex vivo to another second state by an exposure to another stimulus, wherein the another medicament has another second bioavailability to the animal if the article of manufacture is administered to the animal.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 6 illustrates an example environment that includes an article of manufacture;

FIG. 7 illustrates an example operational flow modulating a medicament-release characteristic of a final dosage form;

FIG. 8 illustrates an alternative embodiment of the operational flow of FIG. 7;

FIG. 9 illustrates an example operational flow fulfilling a request specifying a dose of a medicament for an individual animal;

FIG. 11 illustrates another alternative embodiment of the example operational flow of FIG. 9

FIG. 13 illustrates another embodiment of the example operational flow of FIG. 9;

FIG. 14 illustrates a further embodiment of the example operational flow of FIG. 9.

FIG. 18 illustrates an example operational flow modifying a medicament availability characteristic of a final dosage form;

FIG. 19 illustrates an example final dosage form for administering a medicament to an animal;

FIG. 24 illustrates an example environment that includes a final dosage form and an operational flow;

FIG. 25 illustrates alternative embodiments of the activation operation of FIG. 24;

FIG. 26 illustrates an example embodiment of a final dosage form for administering a medicament;

FIG. 30 illustrates an example environment that includes a final dosage form and an operational flow;

FIG. 31 illustrates an example article of manufacture for administering medicament to an animal;

FIG. 32 illustrates an example environment that includes a final dosage form for administering medicament to an animal;

FIG. 33 illustrates an example environment that includes an article of manufacture;

FIG. 34 illustrates an example environment that includes a final dosage form and an operational flow;

FIG. 35 illustrates an alternative embodiment of the individualization operation of FIG. 34;

FIG. 36 illustrates an alternative embodiment of the individualization operation of FIG. 34;

FIG. 37 illustrates an alternative embodiment of the operational flow of FIG. 34;

FIG. 38 illustrates an example environment that includes a final dosage form and an operational flow;

FIG. 39 illustrates an example vehicle for administering a medicament to an animal;

FIG. 40 illustrates an example system;

FIG. 41 illustrates an example environment;

FIG. 43 illustrates an example environment that includes a final dosage form and an operational flow;

FIG. 45 illustrates an example environment that includes an article of manufacture;

FIG. 46 illustrates an example article of manufacture for administering medicament to an animal;

FIG. 47 illustrates an environment that includes a final dosage form for administering medicament to an animal;

FIG. 48 illustrates an example environment that includes a final dosage form for administering medicament to an animal;

FIG. 49 illustrates an example environment that includes a final dosage form and an operational flow;

FIG. 50 illustrates an example alternative embodiment of the operational flow of FIG. 49;

FIG. 52 illustrates an example environment that includes an article of manufacture;

FIG. 53 illustrates an example article of manufacture for administering medicament to an animal;

FIG. 55 illustrates an example environment that includes a final dosage form and an operational flow;

FIG. 56 illustrates an alternative embodiment of the operational flow described in FIG. 55;

FIG. 57 illustrates an example environment;

FIG. 58 illustrates an example article of manufacture for administering medicament to an animal;

FIG. 59 illustrates an example environment that includes a final dosage form for administering medicament to an animal;

FIG. 60 illustrates an example environment that includes a final dosage form for administering medicament to an animal and an operational flow;

FIG. 61 illustrates an alternative embodiment of the operational flow described in conjunction with FIG. 60;

FIG. 62 illustrates an example article of manufacture for administering medicament to an animal;

FIG. 63 illustrates an example environment that includes a final dosage form for administering medicament to an animal;

FIG. 64 illustrates an example environment that includes a final dosage form for administering medicament to an animal;

FIG. 65 illustrates an example environment that includes a final dosage form and an operational flow;

FIG. 66 illustrates an alternative embodiment of the operational flow described in conjunction with FIG. 65; and FIG. 67 illustrates an example article of manufacture for administering medicament to an animal.

DETAILED DESCRIPTION

Figure 1:
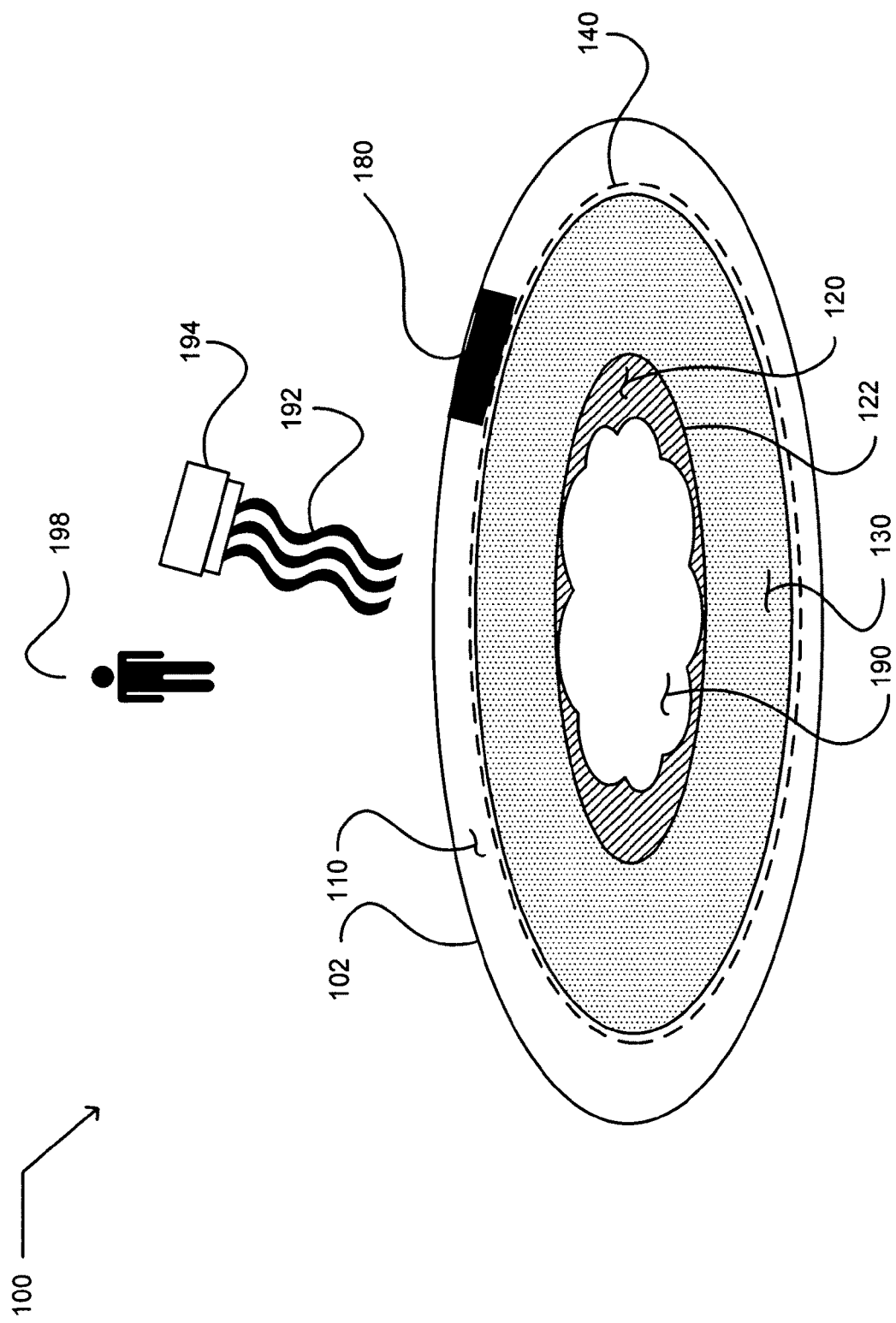
FIG. 1 illustrates an example environment that includes an animal, a cross-sectional view of an example final dosage form for administering a medicament to the animal, and an example stimulation source operable to emit a stimulus.

In the following detailed description, reference is made to the accompanying drawings, which form a part hereof. In the drawings, similar symbols typically identify similar components, unless context dictates otherwise. The illustrated embodiments described in the detailed description, drawings, and claims are not meant to be limiting. Other embodiments may be utilized, and other changes may be made, without departing from the spirit or scope of the subject matter presented here.

FIG. 1 illustrates an environment 100 that includes an animal 198, a cross-sectional view of an example final dosage form 102 for administering the medicament 190 to an animal, such as the animal 198, and an example stimulus source 194 configured to emit a stimulus 192. In an embodiment, the final dosage form includes a dosage form having completed a manufacturing or production process. In an embodiment, the final dosage form includes a product, finished tablet, or capsule ready for distribution to a hospital, pharmacy, or retail store for individualizing to a particular animal, such as the animal 198. In an embodiment, the final dosage form includes a tablet shape, a spherical shape, or an ellipsoidal shape. In an embodiment, the final dosage form includes a structure or a particle carryable or transportable by a liquid or other fluid carrier.

In an embodiment, the animal 198 includes any living being capable of voluntary movement and possessing specialized sense organs. In an embodiment, the animal includes a human. In an embodiment, the animal includes a mammal. In an embodiment, administering, administration, or administer the medicament to the animal includes give or apply the medicament 190 to the animal. In an embodiment, administering the medicament to the animal includes dispensing the medicament to the animal. In an embodiment, administering the medicament to the animal includes delivering the medicament to the animal. In an embodiment, administering the medicament to the animal includes directly or indirectly injecting the medicament to the animal. In an embodiment, administering the medicament to the animal includes applying the medicament to the animal. In an embodiment, administering the medicament to the animal includes providing the medicament to the animal.

The final dosage form 102 includes an outer layer 110, a release element 130, and a chamber 120. The release element 130 is configured in a first medicament-release state and modifiable ex vivo to a second medicament-release state by an exposure to a stimulus. For example, the stimulus may include the stimulus 192. The chamber 120 includes a chamber wall 122, which is substantially within the outer layer 110, and is configured to carry the medicament 190. In an embodiment, the final dosage form 102 includes an intermediate outer layer (not shown) with the release element interposed between the outer layer and the intermediate outer layer, and the chamber is substantially within the intermediate outer layer (not shown).

In an embodiment, the outer layer 110 of the final dosage form 102 includes an outer layer of at least one of a tablet, capsule, particle, or solid final dosage form. In an embodiment, the outer layer 110 includes an outer peripheral layer. FIG. 1 illustrates an example embodiment where the outer layer 110 includes an outer layer around the chamber wall 122 and the release element 130. In an embodiment, the outer layer 110 is configured for administration to the animal 198 by at least one of an oral, enteral, inhalation, or implant route. In an embodiment, an enteral route includes a rectal route, or a vaginal route, such as by a suppository. In an embodiment, the outer layer is configured for administration to the animal by at least one of parenteral, nasal, auditory canal, pulmonary, topical, or subdermal route.

In an embodiment, the outer layer 110 includes an outer layer configured to release the medicament in an in vivo environment of the animal. In an embodiment, the outer layer 110 includes an outer surface. In an embodiment, the outer layer includes an outer surface of a biocompatible medicament administration vehicle or transport.

In an embodiment, the outer layer 110 of the final dosage form 102 includes an erodible outer layer. Formulations of erodible dosage forms are known in the art. In an embodiment, the erodible outer layer includes an erodible outer layer that is at least one of soluble, permeable, or disintegrable within the animal 198. In an embodiment, the erodible outer layer includes an erodible outer layer having at least a portion that is at least one of soluble, permeable, or disintegrable in response to an acidic environment within the animal. In an embodiment, the erodible outer layer includes an erodible outer layer having at least a portion that is at least one of soluble, permeable, or disintegrable in response to a pH neutral or a basic environment within the animal.

In an embodiment, the outer layer 110 of the final dosage form 102 includes an outer portion of a plurality of particles. Examples of such a particle include one or more of hydrogels, microspheres, polymeric microspheres, and nanoparticles as described in Lin et al., *Hydrogels in controlled release formulations: Network design and mathematical modeling*, ADVANCED DRUG DELIVERY REVIEWS 58 (2006) (1379-1408). In an embodiment, the outer layer 110 of the final dosage form 102 includes an outer portion of an aggregation of molecules. An embodiment includes an outer layer 110 configured to allow an in vivo discharge of at least a portion of the medicament 190 from the chamber 120 after an exposure of the release element 130 to the stimulus 192. An embodiment includes an outer layer 110 configured in cooperation with the release element 130 to allow an in vivo discharge of at least a portion of the medicament 190 from the chamber 120 after an exposure of the release element 130 to the stimulus. In an embodiment, the outer layer 110 includes an outer layer of at least a portion of the release element. In an embodiment, the release element forms the outer layer. An embodiment includes an outer layer configured to contain the medicament until the final dosage form is administered into the animal.

In an embodiment of the release element 130, the first medicament-release state is configured to retard medicament release in vivo and the second medicament-release state is configured to allow medicament release in vivo. In an embodiment of the release element 130, the first medicament-release state is configured to allow medicament release in vivo and the second medicament-release state is configured to retard medicament release in vivo.

Figure 2:
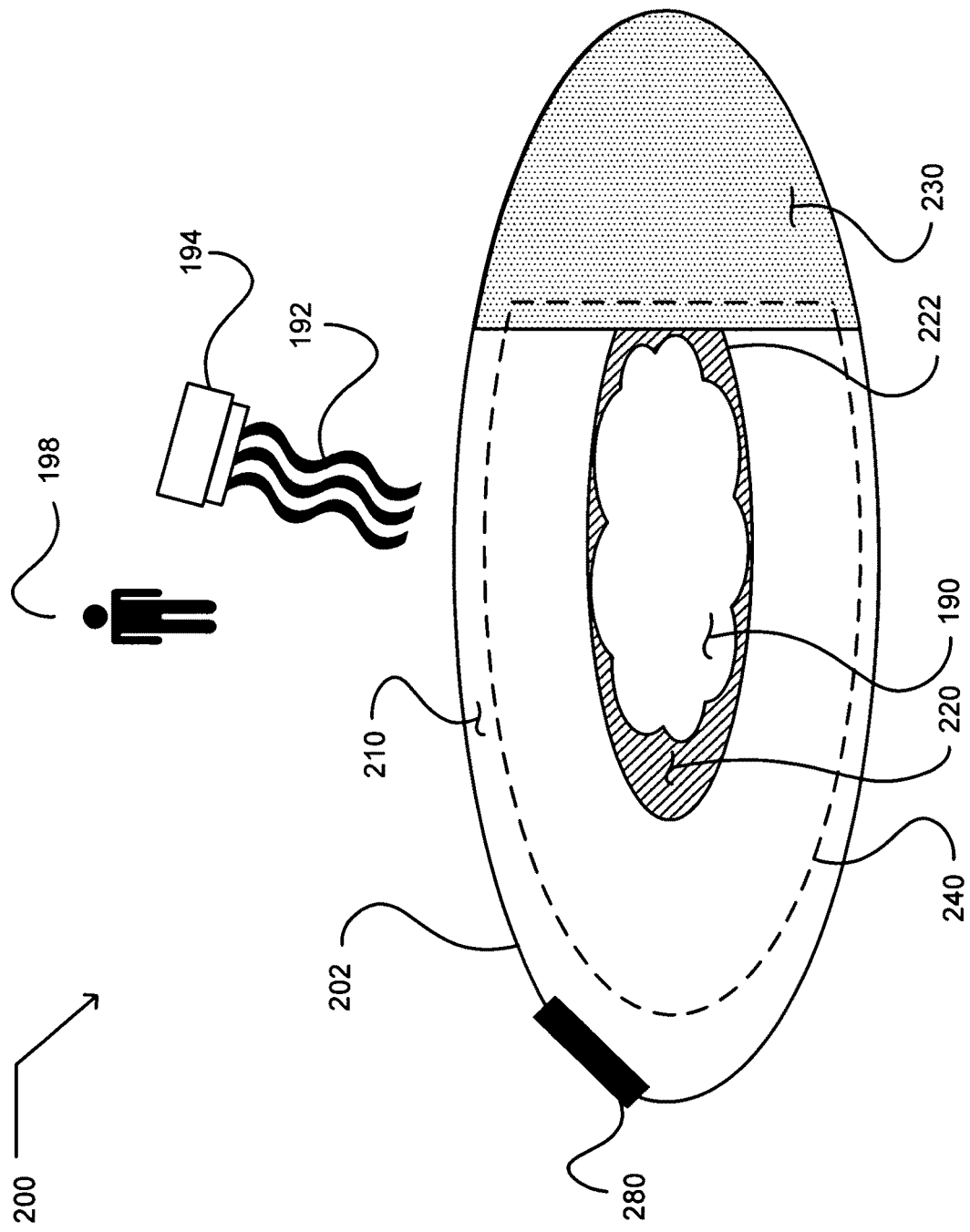
FIG. 2 illustrates another example environment that includes the animal, a cross-sectional view of an example final dosage form for administering a medicament to the animal, and the example stimulation source operable to emit the stimulus.
Figure 3:
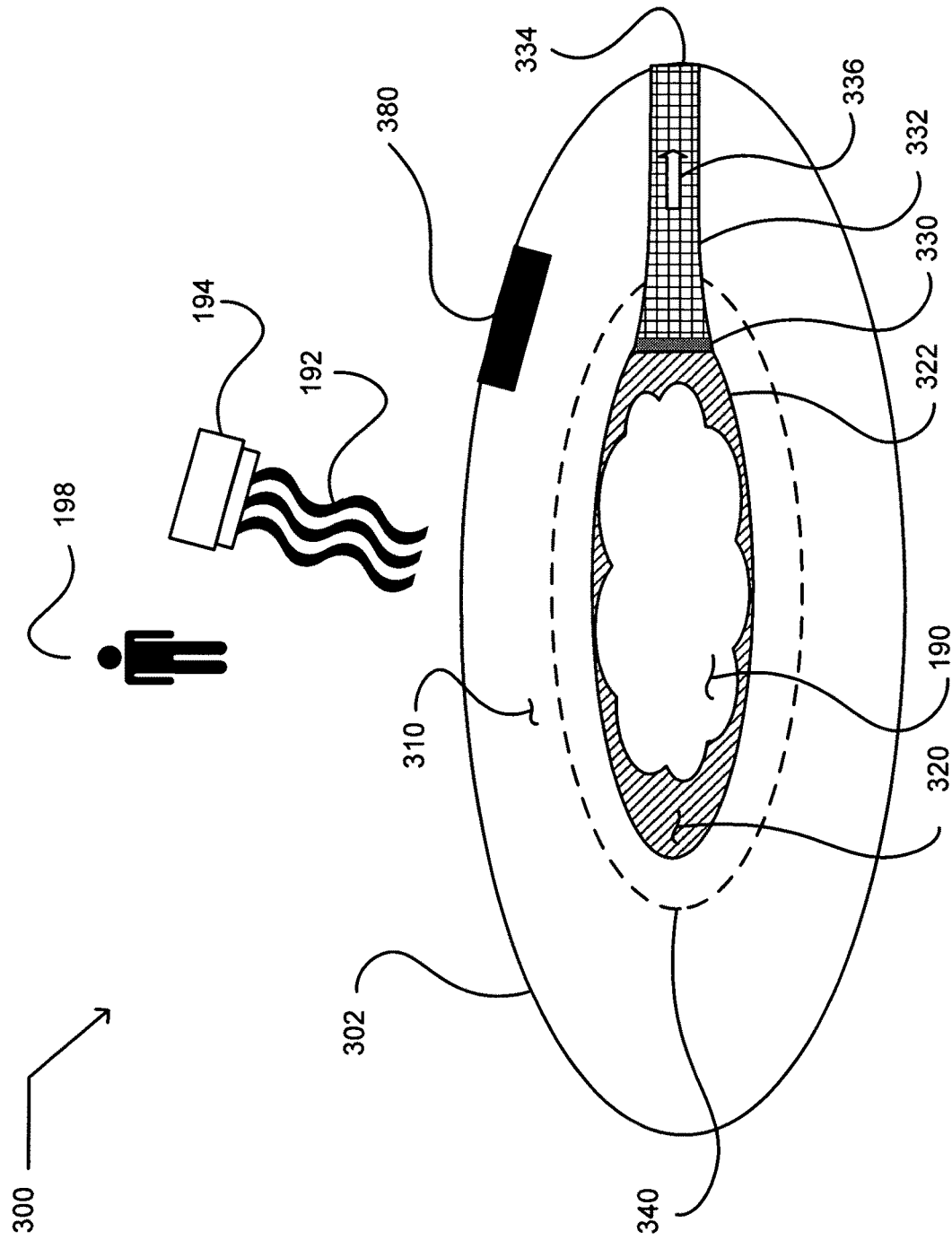
FIG. 3 illustrates a further example environment that includes the animal, a cross-sectional view of an example final dosage form for administering a medicament to the animal, and the example stimulation source operable to emit the stimulus.

FIG. 1 illustrates a release element 130 disposed within the outer layer 110. In an embodiment, the release element includes a release element that is at least partially disposed within the outer layer, or a release element that is not disposed within the outer layer. For example, FIG. 2 infra, illustrates an example of a final dosage form 202 that includes a release element 230 that is not disposed within the outer layer 210. FIG. 3, infra, illustrates an example of a final dosage form 302 that includes a release element 330 disposed at least partially within the outer layer 310.

Returning to FIG. 1, in an embodiment, a release element 130 may be configured in a first medicament-release state and modifiable ex vivo to a second medicament-release state by an exposure to the stimulus 192. An embodiment includes a release element configured in a first medicament-release state and reconfigurable to a second medicament-release state by an exposure to the stimulus.

In an embodiment, the release element 130 includes a release element configured in a first medicament-release state and modifiable ex vivo to a second medicament-release state by an exposure to a non-ionizing radiation, illustrated as the stimulus 192. In an embodiment, the release element 130 is configured in a first medicament-release state and modifiable ex vivo to a second medicament-release state by an exposure to an electromagnetic radiation, illustrated as the stimulus 192. In an embodiment, the release element 130 is configured in a first medicament-release state and modifiable ex vivo to a second medicament-release state by an exposure to a light radiation, also illustrated as the stimulus 192. For example, light radiation may include at least one of the spectrum of ultraviolet (UV), visible light, /or infrared (IR).

In an embodiment, the release element 130 includes, but is not limited to, at least one of a poly(vinyl alcohol), gel, gel matrix, hydrogel, or azopolymer membrane. For example, a poly(vinyl alcohol) is described in (S. P. Vijayalakshmi, et al., *Photodegradation of poly(vinyl alcohol) under UV and pulsed-laser irradiation in aqueous solution*, JOURNAL OF APPLIED POLYMER SCIENCE, Vol. 102, No. 2, 958-966, 2006). For example, photo responsive polymers, including using an azopolymer with laser holography to generate the gated layer, are described in (J. Kyoo Lee, et. al., *Photo-Triggering of the Membrane Gates in Photo-Responsive Polymer for Drug Release*, ENGINEERING IN MEDICINE AND BIOLOGY SOCIETY, (27th Annual International Conference) 2005 Pages: 5069-5072 (2005). In an embodiment, the release element includes a photo-labile bond between a molecule of the medicament 190 and a bioactivity inhibiting molecule that is configured in a first medicament-release state and modifiable ex vivo to a second medicament-release state by an exposure of the labile bond to the stimulus. Examples of such a photo-labile bond are described in M. Scwarcznski, et al., *Development of first photo responsive prodrug of paclitaxel,* 16 BIOORGANIC & MEDICAL CHEMISTRY LETTERS, Issue 17 4492-4496 (September 2006): Epub 27 Jun. 2006. Scwarcznski, et al., describe synthesization of a prodrug of paclitaxel which has a coumarin derivative conjugated to the amino acid moiety of isotaxel (O-acyl isoform of paclitaxel). The prodrug was selectively converted to isotaxel by visible light irradiation (430 nm) with the cleavage of coumarin. Finally, paclitaxel was released by subsequent spontaneous O—N intramolecular acyl migration.

In addition, the release element may include at least one of an additional appropriate photodegradable /or biocompatible barrier forming material.

In an embodiment, the release element 130 includes a release element configured in a first medicament-release state and modifiable ex vivo to a second medicament-release state by an exposure to an energetic stimulus, also illustrated as stimulus 192. In an embodiment, an energetic stimulus may include at least one of a mechanical stimulus, a non-ionizing radiation stimulus, an ionizing radiation stimulus, a chemical stimulus, an acoustic stimulus, an ultrasound stimulus, a radio wave stimulus, a microwave stimulus, a light wave stimulus, or a thermal stimulus.

In an embodiment, the release element 130 is configured in a first medicament-release state and modifiable ex vivo to a second medicament-release state by an exposure to at least one of terahertz radiation, microwave radiation, and radio wave radiation, also illustrated as the stimulus 192. For example, radio wave radiation may include, for example, at least one of ultra-high frequency radio waves (UHF), very high frequency radio waves (VHF), radio frequency (RF), or extremely low frequency (ELF) radio waves. In an embodiment, the release element 130 includes at least one of a foil, gold foil, a liposome, wax, dielectric/wax composite. An example of a microwave responsive liposome is described in U.S. Pat. No. 4,801,459 to R. Liburdy. An example of a microwave responsive material, including a wax and a wax/dielectric composite, is described in United States Patent Application Publication No. 2005/0191708 to R. Saul, et al. In an embodiment, the release element is configured in a first medicament-release state and modifiable ex vivo to a second medicament-release state by an exposure to a magnetic stimulus. In an embodiment, the release element is configured in a first medicament-release state and modifiable ex vivo to a second medicament-release state by an exposure to an electric field stimulus.

In an embodiment, the release element is configured in a first medicament-release state and modifiable ex vivo to a second medicament-release state by an exposure to a chemical stimulus (not shown). For example, a chemical stimulus may include at least one of a stimulus based on pH change, enzymatic exposure or catalysis. In an embodiment, a chemical stimulus may include a stimulus operable to release or reverse a cooperative or a reversible molecular binding, or a stimulus operable to form an irreversible binding.

In an embodiment, the release element 130 is configured in a first medicament-release state and modifiable ex vivo to a second medicament-release state by an exposure to a mechanical agitation stimulus (not shown). For example, a mechanical agitation stimulus may include a shaking or spinning to rupture a membrane or a seal or a foil. In an embodiment, a release element is configured in a first medicament-release state and modifiable ex vivo to a second medicament-release state by an ex vivo exposure to a mechanical stimulus (not shown). For example, a mechanical stimulus may include shaking a piercing member against a foil release element. In an embodiment, the release element is configured in a first medicament-release state and modifiable ex vivo to a second medicament-release state by an ex vivo exposure to the stimulus, the release element including a mechanically activatable structure (not shown). For example, the mechanically activatable structure may include a foil or a pressure-rupturable membrane, or a heat-activatable structure.

In an embodiment, the release element 130 is permeated, dissolved, or disintegrated in response to the stimulus. In an embodiment, a release element is changed such that it is permeated, dissolved, or disintegrated in response to an in vivo environment of the animal 198 where it would not have been so before exposure to the stimulus. In an embodiment, a release element is changed such that it forms a barrier, or is impermeable, solid, or integral in response to the exposure to the stimulus where it would not have been so before the exposure to the stimulus.

In an embodiment, the release element 130 is configured in a first medicament-release state and modifiable ex vivo to a second medicament-release state by an exposure to at least one of a thermal, acoustic stimulus and ultrasound. Examples of an acoustically active release element formed by conjugating liposomes and microbubbles are described in A. Kheirolomoom, et al., *Acoustically-active microbubbles conjugated to liposomes: Characterization of a proposed drug delivery vehicle,* 118 J CONTROL RELEASE, Issue 3, April 23; 118(3):275-284. Epub Dec. 23, 2006.

In an embodiment, the release element 130 includes a release element configured in a first medicament-release state and modifiable ex vivo to a second medicament-release state by an ex vivo exposure to at least one of an activation stimulus, or an actuation stimulus. In an embodiment, the release element is configured in a first medicament-release state and modifiable ex vivo to a second medicament-release state by an exposure to a de-activation stimulus.

In an embodiment, the release element 130 includes a release element configured in a first medicament-release state and modifiable ex vivo to a second medicament-release state by an exposure to an ultrasound stimulus. For example, the release element may include at least one of liposomes, lipid microspheres, microbubbles, liposheres, or liposomes responsive to an ultrasound stimulus, which are described in U.S. Pat. No. 6,416,740 to Unger. In an embodiment, the release element includes at least one of polyanhidrides, polyglycolides, polyactides, poly(vinyl acetate), poly(glycolic acid), poly(ethylene), poly(lactic acid), or chitosan. An example of ultrasound-responsive polymer is described in J. Kost, et al., *Ultrasound-enhanced polymer degradation and release of incorporated substances,* 86 PROCEEDINGS OF THE NATIONAL ACADEMY OF SCIENCES OF THE USA, 7663-7666 (1989). In this article, Kost describes up to a 5-fold reversible increase in degradation rate and up to 20-fold reversible increase in release rate of incorporated molecules were observed with biodegradable polyanhydrides, polyglycolides, and polylactides. This article also describes up to a 10-fold reversible increase in release rate of incorporated molecules within non-erodible ethylene/vinyl acetate copolymer were also observed. The release rate increased in proportion to the intensity of ultrasound. Temperature and mixing were relatively unimportant in effecting enhanced polymer degradation, whereas cavitation appeared to play a significant role. Another example of ultrasound-responsive polymer is described in J. Kost, et al., *Ultrasonically controlled polymeric drug delivery,* Makromolekulare Chemie 19 MACROMOLECULAR SYMPOSIA 275-285 (1988). In this article, Kost describes investigation of polymers that include lactic acid polymer, glycolic acid polymer, ethylene copolymer, vinyl acetate copolymer. An example of ultrasound-responsive chitosan is described in M. Tsaih, et al., *Effect of the degree of deacetylation of chitosan on the kinetics of ultrasonic degradation of chitosan;* 90 JOURNAL OF APPLIED POLYMER SCIENCE 3526-3531 (2003).

In an embodiment, the release element 130 includes at least one of polymeric micelle, liposome, lipid microsome, polymeric microsphere, nanoparticle, clathrate compound, cyclodextrin, gel, gel matrix, hydrogel, or cellulose. Examples of polymeric micelles are described in U.S. Pat. No. 7,229,973 to Bae, et al. Bae describes polymeric micelles including mixed micelles containing poly(L-histidine)-poly(ethylene glycol) block copolymer and poly(L-lactic acid)-poly(ethylene glycol) block copolymer. Examples of polymer microspheres are described in U.S. Pat. No. 5,718,921 to Mathiowitz, et al. Mathiowitz describes polymer microspheres built using polyanhydrides, polyorthoesters, polylactic acid polymers, and combinations thereof. Examples of cyclodextrin are described in U.S. Pat. No. 7,270,808 to Cheng, et al., titled "Cyclodextrin-based polymers for therapeutics delivery." Examples of hydrogels are described in Lin et al., *Hydrogels in controlled release formulations: Network design and mathematical modeling*, ADVANCED DRUG DELIVERY REVIEWS 58 (2006) 1379-1408). Examples of cellulose are described in U.S. Pat. No. 6,821,531 to Kumar.

In an embodiment, the release element 130 includes a release element enclosing the chamber 120, configured in a first medicament-release state, and modifiable ex vivo to a second medicament-release state by an exposure to a stimulus, illustrated as the stimulus 192. For example, FIG. 1 illustrates an embodiment where the outer layer 110 has a spherical shape, the chamber may have similar nested spherical shape, and the release element having a spherical shape and surrounding the chamber. However, nothing in this document expresses or implies a required similarity of shape among one or more of the chamber, the release element, or the outer layer. For example, an embodiment may include a liposome forming the release element and functionally defining a chamber.

In an embodiment, the release element 130 includes or defines a release element encapsulating the chamber. In an embodiment, the release element includes a release element encapsulating the medicament 190 in cooperation with the chamber wall 122, configured in a first medicament-release state, and modifiable ex vivo to a second medicament-release state by an exposure to the stimulus. For example, FIG. 2, infra, illustrates a release element 230 encapsulating the medicament 190 in cooperation with a chamber 220 as expressed or defined by a chamber wall 222. In an embodiment, the release element includes a release element obstructing an aperture of the chamber. For example, FIG. 3, infra, illustrates a release element 330 in cooperation with a chamber 320 as expressed by a chamber wall 322 obstructing an aperture 332 of the chamber and preventing a discharge of the medicament 190 along a fluid communication path 336 In an embodiment, the release element includes at least two particles each collectively or respectively forming a chamber carrying a respective instance of the medicament. For example, FIG. 4, infra, illustrates a release element 430 that includes a particle 432 forming a chamber carrying an instance of the medicament 190. An example of the particle 432 is additionally described in conjunction with FIGS. 16, 20, and 23, and respective corresponding particle or polymeric material 1180, 1580, and 1680. The particle is configured in a first medicament-release state, and modifiable ex vivo to a second medicament-release state by an exposure of the at least two particles to the stimulus. For example, the particle may include a clathrate compound forming a host/guest relationship with molecules of a medicament. For example, the particle may include at least one of hydrogels, liposomes, or dendrimers configured to carry the medicament in an association with their pores, interstitial cavities, structural interstices, bonds, or amorphous cavities.

In an embodiment, the release element includes a labile bond between a molecule of the medicament and a bioactivity inhibiting molecule configured in a first medicament-release state and modifiable ex vivo to a second medicament-release state by an exposure of the labile bond to the stimulus (not shown).

Referring again to FIG. 1, in an embodiment, the release element 130 is configured in a first medicament-release state and modifiable ex vivo to a second medicament-release state by an exposure to the stimulus, and configured to contain the medicament 190 at least until the final dosage form 102 is administered into the animal 198.

FIG. 1 illustrates an embodiment having the chamber 120 formed within the outer layer 110 and configured to carry the medicament 190. In an embodiment, the chamber 120 is substantially defined within the outer layer and configured to carry the medicament until released by the release element. For example, FIG. 2 illustrates an embodiment that includes the chamber 220 substantially defined within the outer layer 210 and configured to carry the medicament 190 until released by the release element 230. FIG. 3 illustrates an embodiment that includes the chamber 320 substantially defined within the outer layer 310 and configured to carry the medicament 190 until released by the release element 330.

In an embodiment (not shown), the release element and chamber both may be formed by a particle, such as a liposome, or a hydrogel. In such embodiment, the chamber includes at least one chamber substantially within the outer layer of the particle and configured to carry the medicament.

In an embodiment, the chamber 120 includes a chamber configured to confine the medicament 190 in cooperation with the release element 130. In an embodiment (not shown), the chamber includes at least one chamber configured to confine the medicament in a structural cooperation with the release element. In an embodiment (not shown), the chamber is configured to initially carry the medicament. The chamber is also configured to release at least a portion of the medicament upon at least one of a reconfiguration, bursting, puncture, permeation, dissolution, and disintegration of the release element 130.

In an embodiment (not shown), the chamber 120 includes a first chamber configured to carry a first medicament and a second chamber configured to carry a second medicament. An example of the first chamber configured to carry a first medicament and the second chamber configured to carry a second medicament is described in conjunction with FIG. 5 and chamber 520A and chamber 520B. In an embodiment (not shown), the chamber includes a first chamber configured to carry a first constituent of the medicament and a second chamber configured to carry a second constituent of the medicament. In an embodiment (not shown), the chamber includes a first chamber configured to carry a first reactant of the medicament and a second chamber configured to carry a second reactant of the medicament. In an embodiment (not shown), a combination of the first reactant and the second reactant in response to an ex vivo exposure of the release element initiates a chemical activation or a synthesis of the medicament and a physical releasability of the medicament. In an embodiment (not shown), a combination of the first reactant and the second reactant in response to an ex vivo exposure of the release element initiates a chemical activation or a synthesis of the medicament but does not provide a physical releasability of the medicament. In an embodiment, the resulting medicament product can be released in vivo through the release characteristics of the outer layer. Alternatively, the physical releasability of the medicament may occur by another ex vivo exposure of the dosage form to a stimulus, such as the stimulus 192.

In an embodiment shown in FIG. 1, the final dosage form 102 includes a containment element 140 retaining the medicament 190 within the final dosage form until the dosage form is administered to the animal 198. The containment element can be used in situations where the medicament is a liquid or other material that is prone to seepage or discharge through the outer layer. In embodiment, the containment element may include a separate structure, such as a film or coating, retaining the medicament. Such a containment element 140 may form an exterior layer over the outer layer 110, or may form a layer interposed between the outer layer 110 and the chamber 120. In an embodiment, the containment element 140 may inhibit a discharge of the medicament 190 from the final dosage form 102 prior to its introduction into the animal 198, without regard to whether the release element is in its first medicament-release state or its second medicament-release state. In an embodiment, the containment element 140 includes a containment element 140 retaining the medicament 190 within the final dosage form 102 until the final dosage form 102 is exposed to an in vivo environment in the animal 198, and to modulate a release of at least a portion of the medicament 190 in vivo upon administration of the final dosage form 102 to the animal 198. In an embodiment, the containment element may be formed by a combination of the outer layer 110 and the release element 130.

In an embodiment, the containment element 140 includes a containment layer configured to encompass the medicament 190 within the final dosage form 102 until the final dosage form is administered to the animal 198. For example, the containment element 140 may include a coating covering the outer layer 110 of the final dosage form 102, such as an enteric coating configured to prevent a release of the medicament from the final dosage form until the final dosage form is administered to the animal. In another example, the containment element 140 may include a coating covering the release element 130 of the final dosage form 102. In an embodiment, the containment element includes a containment envelope retaining the medicament within the final dosage form until the dosage form is administered to the animal.

In an embodiment, the containment element 140 includes an enteric coating. The enteric coating may include gelatin or cellulose encapsulation. In an embodiment, the containment element includes a hydroxypropyl methylcellulose acetate succinate (HPMCAS) based coating or a methacrylic acid copolymer based coating, for example such as described in U.S. Pat. No. 7,138,143 to Mukai, et al. In an embodiment, the containment element includes a polymer coating, such as an acidic group-containing (meth)acrylate copolymer, shellac, HPMCP (hydroxypropylmethylcellulose phthalate), CAP (cellulose acetate phthalate), HIPMC-AS (hydroxypropylm-ethylcellulose acetate succinate) or polyvinyl acetate phthalate, for example such as described in U.S. Pat. No. 6,887,492 to Kay, et al. In an embodiment, the containment element includes a polymer coating of a (meth)acrylate copolymer comprising free-radical polymerized C.sub.1- to C.sub.4-alkyl esters of acrylic or methacrylic acid and (meth)acrylate monomers with a quaternary anunonium group in the alkyl radical, a (meth)acrylate copolymer of 20 to 40% by weight of polymerized ethyl acrylate and 60 to 80% by weight of polymerized methyl methacrylate, ethylcellulose or polyvinyl acetate. For example, as described in U.S. Pat. No. 6,897,205 to Beckert et al. In an embodiment, the containment element includes a cellulose acetate phthalate polymer coating material, for example, as described in U.S. Pat. No. 5,686,106 to Kelm, et al. In an embodiment, the containment element includes a cellulose acetate phthalate; cellulose acetate trimellitate; hydroxypropyl methylcellulose phthalate; hydroxypropyl methylcellulose acetate succinate; polyvinyl acetate phthalate; poly(methacrylic acid, methyl methacrylate) 1:1; or poly(methacrylic acid, ethyl acrylate) 1:1; and compatible mixtures thereof. In another embodiment, the containment element includes a poly(methacrylic acid, methyl methacrylate) 1:2, or a mixture of poly(methacrylic acid, methyl methacrylate) 1:1 and poly(methacrylic acid, methyl methacrylate) 1:2 in a ratio of about 1:10 to about 1:2. For example, as described in U.S. Pat. No. 5,686,105 to Kelm, et al.

In an embodiment illustrated in FIG. 2 infra, the containment element 240 includes a containment element 240 configured to prevent a release of the medicament 190 from the final dosage form 202 until the final dosage form 202 is introduced into the animal 198.

Returning to FIG. 1, in an embodiment, the medicament 190 includes at least one of an agent, treatment agent, drug, prodrug, therapeutic, nutraceutical, medication, vitamin, nutritional supplement, medicine, remedy, medicinal substance, or cosmetic. In an embodiment, the medicament includes a first reactant of the medicament and a second reactant of the medicament. In an embodiment, the medicament includes at least one prodrug and optionally an activating-enzyme of the prodrug. In an embodiment, the chamber includes a first chamber configured to carry a prodrug, and a second chamber configured to carry an activating enzyme of the prodrug.

In an embodiment, the final dosage form 102 may further include a indicator element 180 configured to indicate an exposure of the release element 130 to the stimulus 192. In an embodiment, the indicator element 180 includes an indicator element 180 configured to optically indicate an exposure of the release element to the stimulus 192 by at least one of dielectric, a conductivity, or ultrasonic profile responsive to an exposure of the release element to the stimulus. The indicator element 180 including, for example, at least one of 4-keto-bacteriorhodopsin films, cinnamylidene acetyl chloride, α-methylcinnamylidene acetyl chloride, α,γ-dimethyl-cinnamylidene acetyl chloride, α-phenylcinnamylidene acetyl chloride, α-phenoxycinnamylidene acetyl chloride, and cyanocinnamylidene acetyl chloride, leuco dye-serum albumin albumin complexes, azo dyes, or poly(ethylene glycol). Examples of bacteriorhodopsin films are described in A. Druzhko, et al., 4-*Keto-bacteriorhodopsin films as a promising photochromic and electrochromic biological material*, BIOSYSTEMS. 1995; 35(2-3): 129-32. Examples of hydrophilic photosensitive polymers are described in U.S. Pat. No. 5,990,193 to Russell, et al. Examples of photosensitive compositions for detection of radiation in the ultraviolet wavelength, including leuco dye-serum albumin complexes, are described in U.S. Pat. No. 4,466,941 to Cerami, et al. Examples of using azo dye for an indicator is described in U.S. Pat. No. 5,679,442. Examples of poly(ethylene glycol) are described in U.S. Pat. No. 5,990,193 to Russell, et al., and in Zhong, et al., *Photodegradation Behavior of Polycaprolactone-Poly(ethylene glycol) Block Copolymer*, Vol. 10, No. 4 CHINESE CHEMICAL LETTERS 327-330 (1999).

In an embodiment depicted in FIG. 1, the indicator element 180 includes an electronically-detectable indicator element 180 configured to indicate an exposure of the release element 130 to the stimulus 192. For example, the electronically-detectable indicator element 180 may include a substance, material, or device having a conductive property that makes an electronically-detectable change in response to an exposure to the stimulus 192. An example of such substance, material, or device includes a shape memory alloy switch that responds to heat described in U.S. Pat. No. 5,410,290 to Cho. Other examples of such substances, materials, or devices include a material that polymerizes in the presence of an ultrasound and changes a conductive property in response, such as the ultrasonic polymerization of methyl methacrylate described in U.S. Pat. No. 5,466,722 to Stoffer, et al., the heat or UV radiation triggered polymerization of acrylamide, or the microwave triggered polymerization of trimethylene carbonate. Another example of such substances, materials, or devices include the use of bistable compounds whose conductivity changes based upon exposure to electromagnetic radiation as described in U.S. Pat. No. 7,175,961 to Beck, et al. Another example includes a metal film or foil degradable by microwaves to release the medication whose state can degradation detected electrically.

In an embodiment, the indicator element 180 includes an electronically-detectable indicator element 180 configured to indicate an exposure of the release element 130 to the stimulus 192. For example, the electronically-detectable indicator element 180 may include a dielectric element having a property that makes an electronically-detectable change in response to an exposure to the stimulus 192. An example of such a dielectric element may include a one-time programmable memory cell described in U.S. Pat. No. 7,256,446, to Hu, et al., or a switch comprising microelectromechanical elements described in U.S. Pat. No. 7,336,474 to Lerche, et al.

In an example, the electronically-detectable indicator element 180 may include an element having a permittivity that makes an electronically-detectable change in response to an exposure of the release element to the stimulus 192. An example of such an element having a permittivity may include photonic crystals whose permittivity changes through the addition of photonic and/or electrical energy as described in U.S. Pat. No. 6,859,304 to Miller, et al.

In another example, the electronically-detectable indicator element 180 may include an element having an ultrasonic profile that makes an ultrasound-discernable change in response to an exposure of the release element to the stimulus 192. An example of an element having an ultrasonic profile that includes a polymer monitorable using the continuous wave ultrasonic process monitor is described in U.S. Pat. No. 7,017,412 to Thomas, et al. Another example of an element having an ultrasonic profile that includes a polymer monitorable using the apparatus for degree on doneness is described in U.S. Pat. No. 7,191,698 to Bond, et al. A further example of an element having an ultrasonic profile that includes a degradable metal film or metal foil.

In another example, the electronically-detectable indicator element 180 may include a carrier, admixture, diluent, or excipient having a property that makes an ultrasound-discernable change in response to an exposure of the release element to the stimulus 192. For example, an admixture may include a phase change material (PCM) as an inert filler and having a property that makes an ultrasound-discernable change in response to an exposure of the release element to ultrasound. Examples of such PCMs include polyvinyl alcohol (PVA)-stearic acid (SA) and polyvinyl chloride (PVC)-stearic acid (SA). An example of Polymer-stearic acid blend is described in Ahmet Sari, et al., *Polymer-stearic acid blends as form-stable phase change material for thermal energy storage*, 64 JOURNAL OF SCIENTIFIC & INDUSTRIAL RESEARCH, at pp. 991-996 (December 2005). Other examples are described in United States Patent Application No. 2007/0249753 to Lin, et al. (polyether fatty-acid ester(polyethylene glycol or polytetramethylene glycol base polymer), and U.S. Pat. No. 5,565,132 to Salyer (Addition of microwave absorber to make PCM materials sensitive to microwaves). Ultrasonic detection or discernment of phase changes in a PCM may be implemented using techniques described by A. W. Aziz, & S. N. Lawandy, *Ultrasonic detection of segmental relaxations in thermoplas-* *tic polyurethanes*, 31 JOURNAL OF APPLIED POLYMER SCIENCE 1585 (Issue 6, 2003) or S. L. Morton, *Ultrasonic cure monitoring of photoresist during pre-exposure bake process*, ULTRASONICS SYMPOSIUM, 1997. PROCEEDINGS., 1997 IEEE Volume 1, at 837-840 (October 1997).

The indicator element 180 (as enumerated in FIG. 1) can be made biocompatible so as to not cause an adverse reaction in the animal. Biocompatibility can be achieved through the use of a biocompatible material or through the use of a minimal amount of material so that any adverse reaction to the indicator element 180 is minimized.

FIG. 2 illustrates an environment 200 that includes the animal 198, a cross-sectional view of an example final dosage form 202 for administering the medicament 190 to the animal, and the example stimulation source 194 operable to emit the stimulus 192. In an embodiment, the final dosage form includes a dosage form having completed a manufacturing or production process. In an embodiment, the final dosage form includes a product, finished tablet, or capsule ready for distribution to a hospital, pharmacy, or retail store for individualizing to a particular animal, such as the animal 198. In an embodiment, the final dosage form may include a tablet shape, a spherical shape, or an ellipsoidal shape. In an embodiment, the final dosage form may include a structure or a particle carryable or transportable by a liquid or other fluid carrier.

The final dosage form 202 includes an outer layer 210, the release element 230, and the chamber 220 as expressed or defined by the chamber wall 222. The release element is configured in a first medicament-release state and modifiable ex vivo to a second medicament-release state by an exposure to a stimulus. For example, the stimulus may include the stimulus 192. The chamber includes a chamber wall 222, is substantially within the outer layer, and is configured to carry the medicament 190. In an embodiment, the final dosage form may include an indicator element 280. In an embodiment, the final dosage form may include a containment element 240.

The environment 200 illustrates an embodiment where the release element 230 encompasses the medicament 190 in cooperation with the chamber 220 as expressed or defined by the chamber wall 222. The outer layer 210 and the release element 230 are cooperatively retaining the medicament 190 if the release-element is in a first medicament-release state and allow an in vivo discharge of at least a portion of the medicament from the chamber if the release-element is in a second medicament release state. In an embodiment, the release element may include at least one of a poly(vinyl alcohol), gel, gel matrix, hydrogel, and azopolymer photo or light modifiable substance as described above. In an embodiment, the release element may include at least one of a polyanhidride, polyglycolide, polyactide, poly(vinyl acetate), poly(glycolic acid), poly(ethylene), poly(lactic acid), chitosan, or an acoustic or ultrasound-modifiable substance as described above. For example, when the first medicament-release state is configured to retard medicament release and the second medicament-release state is configured to allow medicament release in vivo, the release element when configured in the first medicament-release state will retard medicament release from the final dosage form upon administration of the final dosage form into the animal. For example, in a first medicament release state, the release element is impermeable to the environment outside the final dosage form, and impermeable to the medicament in the chamber. Following exposure to an appropriately configured stimulus, the release element achieves a second medicament release state that is, for example, permeable to the medicament. The second medicament release state may include, for example, a state where the release element changes shape or size (e.g., expands, shrinks), dissolves, or dissipates upon exposure to an aqueous environment, gastric juices or a certain pH environment.

FIG. 3 illustrates a non-limiting environment 300 that includes the animal 198, a cross-sectional view of an example final dosage form 302 for administering the medicament 190 to the animal, and the example stimulation source 194 operable to emit the stimulus 192. In an embodiment, the final dosage form includes a dosage form having completed a manufacturing or production process. In an embodiment, the final dosage form includes a product, finished tablet, or capsule ready for distribution to a hospital, pharmacy, or retail store for individualizing to a particular animal, such as the animal 198. In an embodiment, the final dosage form may include a tablet shape, a spherical shape, or an ellipsoidal shape. In an embodiment, the final dosage form may include a structure or a particle carryable or transportable by a liquid or other fluid carrier.

The final dosage form 302 includes an outer layer 310, a chamber 320, and a release element 330. The final dosage form also includes a release passageway 332 configured to provide a medicament communication pathway between the chamber and the environment through an aperture 334 in the outer layer. The release element is configured in a first medicament-release state and modifiable ex vivo to a second medicament-release state by an exposure to a stimulus. For example, the stimulus may include the stimulus 192. The chamber includes a chamber wall 322, is substantially within the outer layer, and is configured to carry the medicament 190. In an embodiment, the final dosage form may include an indicator element 380. In an embodiment, the final dosage form may include a containment element 340.

FIG. 3 illustrates a non-limiting embodiment wherein an embodiment of the final dosage form 302 includes the release element 330 retaining the medicament 190 in cooperation with the chamber 320 as expressed by the chamber wall 322. The outer layer 310 and the release-element 330 are cooperatively retaining the medicament 190 if the release-element is in one medicament-release state and allowing an in vivo discharge of at least a portion of the medicament from the chamber if the release-element is in another medicament release state. When the release-element is in a state that releases the medicament, the medicament may discharge or flow along the fluid communication path 336 expressed or defined at least in part by the release passageway 332.

In an embodiment, the release element may include at least one of a poly(vinyl alcohol), gel, gel matrix, hydrogel, and azopolymer photo or light modifiable substance as described above. In an embodiment, the release element may include at least one of a foil, gold foil, wax, or dielectric/wax composite microwave modifiable substance. In an embodiment of this example, the release element may include at least one of a polyanhidride, polyglycolide, polyactide, poly(vinyl acetate), poly(glycolic acid), poly(ethylene), poly(lactic acid), chitosan, or an acoustic or ultrasound-modifiable substance as described above. For example, when the first medicament-release state is configured to retard medicament release and the second medicament-release state is configured to allow medicament release in vivo, the release element when configured in the first medicament-release state will retard medicament release from the release passageway 332 and the aperture 334 of the final dosage form upon administration of the final dosage form into the animal.

Figure 4:
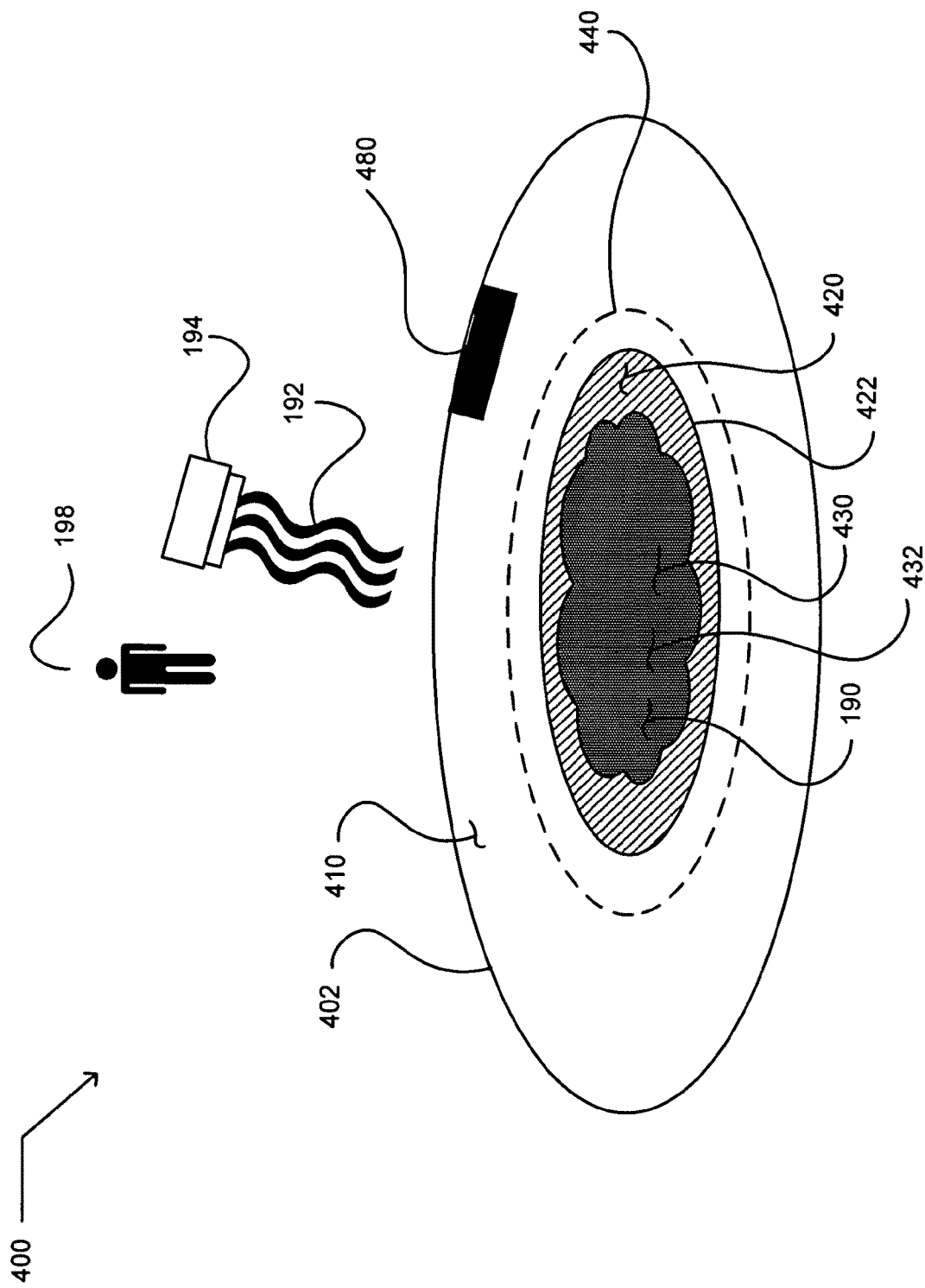
FIG. 4 illustrates another example environment that includes the animal, a cross-sectional view of an example final dosage form for administering a medicament to the animal, and the example stimulation source operable to emit the stimulus.

FIG. 4 illustrates an environment 400 that includes the animal 198, a cross-sectional view of an example final dosage form 402 for administering the medicament 190 to the animal, and the example stimulation source 194 operable to emit the stimulus 192. In an embodiment, the final dosage form 402 includes a dosage form having completed a manufacturing or production process. In an embodiment, the final dosage form 402 includes a product, finished tablet, or capsule ready for distribution to a hospital, pharmacy, or retail store for individualizing to a particular animal, such as the animal 198. In an embodiment, the final dosage form 402 may include a tablet shape, a spherical shape, or an ellipsoidal shape. In an embodiment, the final dosage form 402 may include a structure or a particle carryable or transportable by a liquid or other fluid carrier.

The final dosage form 402 includes an outer layer 410, a chamber 420, and a release element 430. The release element is configured in a first medicament-release state and modifiable ex vivo to a second medicament-release state by an exposure to a stimulus. For example, the stimulus may include the stimulus 192. The chamber includes a chamber wall 422, is substantially within the outer layer, and is configured to carry the medicament 190. In an embodiment, the final dosage form 402 may include an indicator element 480. In an embodiment, the final dosage form 402 may include a containment element 440.

In an embodiment, the chamber 420 includes a chamber substantially within the outer layer 410 and configured to carry the medicament 190. In an embodiment, the chamber encloses at least two structures within the chamber having respective subchambers configured to carry the medicament. For example, such at least two structures may include at least two pores, molecular structures having interstitial cavities, smaller chambers, molecular structure having interstices, or molecular structure having amorphous cavities. In an embodiment, the chamber may contain at least one of an absorbent, liposome, or hydrogel molecular structure which define respective chambers therein. For example, at least two particles may be located in a cavity, such as the chamber 120, and in themselves define a distributed chamber by an aggregation of their pores, interstitial cavities, smaller chambers, interstices of a molecular structure, or amorphous cavities. In another example, at least two microparticles may be throughout a carrier having an outer layer, each microparticle having an effective chamber. In an embodiment, the chamber is located substantially within the release element 430. In an embodiment, the distributed chamber is located substantially within the outer layer 410.

The final dosage form 402 may include a release element 430 that is associated with the medicament 190 in the chamber 420. In an embodiment, the release element 430 may include a carrier, admixture, diluent, or excipient configured in a first medicament-release state and modifiable ex vivo to a second medicament-release state by an ex vivo exposure to the stimulus 192. Particles of such a carrier, admixture, diluent, or excipient may be configured to retain or bind to particles of the medicament 190 and reduce its bioavailability if the release-element 430 is in a first medicament-release state, and release from or unbind particles of the medicament 190 and allow an in vivo discharge of at least a portion of the medicament 190 from the chamber 420 if the release-element 430 is in a second medicament release state.

In an embodiment, an instance of the final dosage form 402 may carry at least two particles, small particles, or microparticles that each include a portion that forms a release element 430 modifiable ex vivo by exposure to the stimulus 192, and a chamber (not shown). The chambers of the at least two particles, small particles, or microparticles each configured to carry a respective instance of the medicament, and collectively forming a distributed chamber. For example, the at least two particles, small particles, or microparticles may include hydrogels, liposomes, or dendrimers having pores, interstitial cavities, structural interstices, bonds, or amorphous cavities configurable to carry molecules of the medicament. The at least two particles, small particles, or microparticles are configured in a first medicament-release state and modifiable ex vivo to a second medicament-release state by an exposure of the at least two particles, small particles, or microparticles to the stimulus. For example, photosensitive hydrogel particles may carry the medicament. In an embodiment, microwave sensitive liposomes may carry the medicament. In an embodiment, the release element includes a labile bond between a molecule of the medicament and molecule of a bioactivity inhibiting molecule configured in a first medicament-release state and modifiable ex vivo to a second medicament-release state by an exposure of the labile bond to the stimulus (not illustrated).

Figure 5:
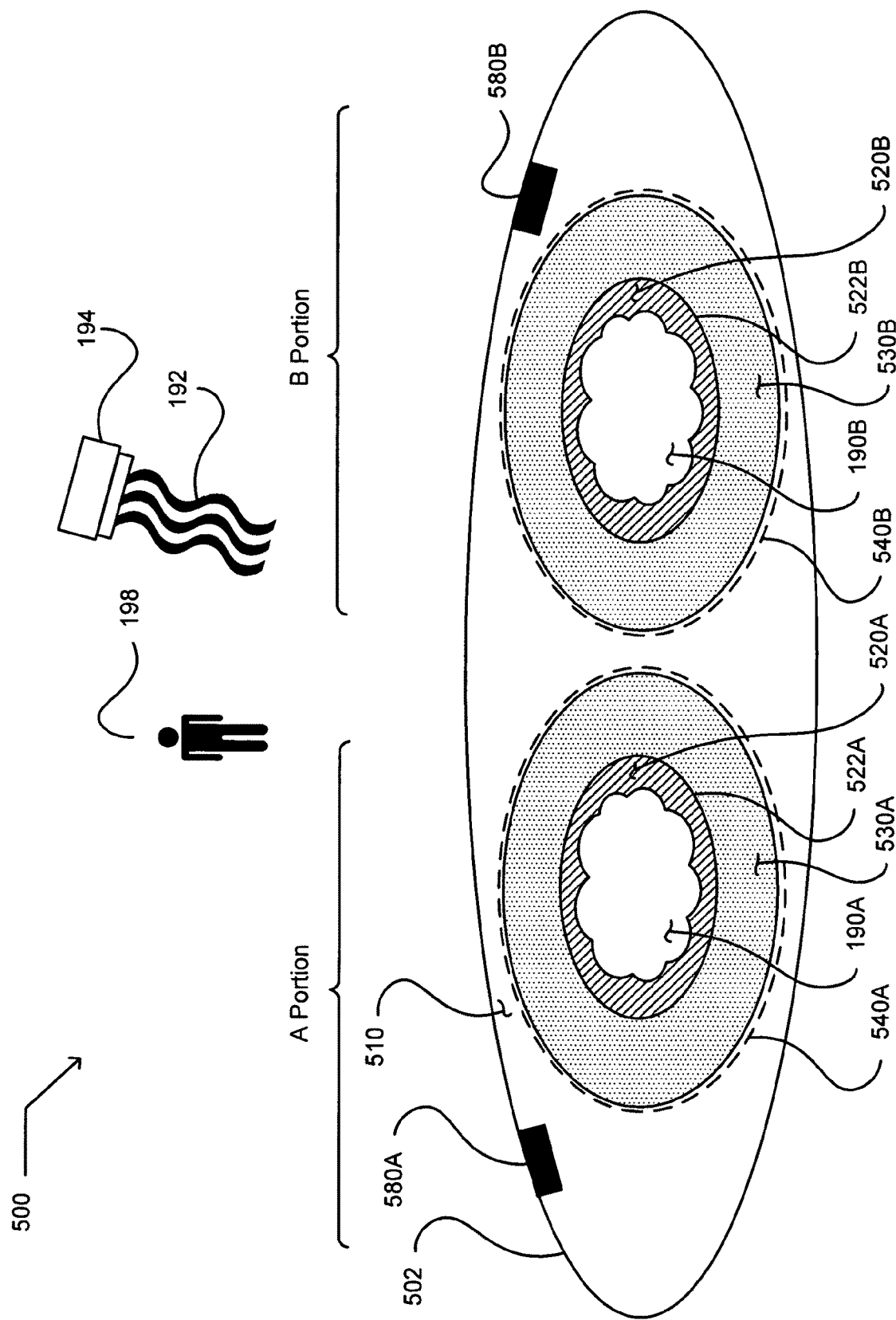
FIG. 5 illustrates a further example environment that includes an animal, a cross-sectional view of an example final dosage form for transporting medicament to the animal.

FIG. 5 illustrates an environment 500 that includes the animal 198, a cross-sectional view of a final dosage form 502 for transporting a medicament to the animal. The medicament is illustrated as a first medicament 190A and second medicament 190B. In an embodiment, the final dosage form includes a dosage form having completed a manufacturing or production process. In an embodiment, the final dosage form 502 includes a product, finished tablet, or capsule ready for distribution to a hospital, pharmacy, or retail store for individualizing to a particular animal, such as the animal 198. In an embodiment, the final dosage form 502 may include a tablet shape, a spherical shape, or an ellipsoidal shape. In an embodiment, the final dosage form 502 may include a structure or a particle carryable or transportable by a liquid or other fluid carrier.

The final dosage form 502 includes an outer layer 510, and at least two dosage elements. The at least two dosage elements are illustrated as A Portion and B Portion, and by "A" and "B" after certain reference numbers in FIG. 5. The A Portion includes a chamber 520A, a release element 530A, and a medicament 190A. In an embodiment, the A Portion includes a containment element 540A. In an embodiment, the A Portion includes an indicator element 580A. The B Portion includes a chamber 520B, a release element 530B, and a medicament 190B. In an embodiment, the B Portion includes a containment element 540B. In an embodiment, the B Portion includes an indicator element 580B.

In an embodiment, the A Portion of the final dosage form 502 may be substantially similar to the chamber 120, the release element 130, the containment element 140, and the indicator element 180 of FIG. 1. In an embodiment, the A Portion may be substantially similar to the chamber 220, the release element 230, the containment element 240, and the indicator element 280 of FIG. 2. In an embodiment, the A Portion may be substantially similar to the chamber 320, the release element 330, the containment element 340, and the indicator element 380 of FIG. 3. In an embodiment, the A Portion may be substantially similar to the chamber 420, the release element 430, the containment element 440, and the indicator element 480 of FIG. 4. Similarly, the B Portion of the final dosage form 502 may be substantially similar to that described in conjunction with at least one of FIG. 1, FIG. 2, FIG. 3, or FIG. 4.

In an embodiment, the first medicament 190A and the second medicament 190B may be substantially similar instances of the same medicament. In an embodiment, the first medicament 190A and the second medicament 190B may be substantially similar instances of the same medicament, but in substantially differing dosage amounts. For example, the first medicament 190A may be, for example, a 50-milligram dose of a medicament and the second medicament 190B may be, for example, a 100-milligram dose of the same medicament. In an embodiment, the first medicament 190A and the second medicament 190B may be substantially similar instances of the same medicament, but in substantially differing dosage characteristics, such as a regular release formulation and a sustained release formulation. In an embodiment, the first medicament 190A and the second medicament 190B may be different medicaments.

In use, the A Portion and the B Portion of the final dosage form 502 may be individually or collectively exposed ex vivo to a stimulus, illustrated as the stimulus 192. For example, the final dosage form 502 can be configured to provide any of three possible dosage levels of the medicament. For example, where the first medicament 190A is a 50-milligram dose of a medicament and the second medicament 190B is a 100-milligram dose of a same medicament, where the release element 530A and release element 530B are modifiable ex vivo by the same stimulus, such as microwave energy, and where the first medicament-release state is configured to retard medicament release in vivo and the second medicament-release state is configured to allow medicament release in vivo, irradiation of the A Portion with microwave energy will actuate the A Portion and make 50-milligrams of the medicament available upon administration of the final dosage form to the animal 198. Similarly, irradiation of the B Portion with microwave energy will actuate the B Portion and make 100-milligrams of the medicament available upon administration of the final dosage form to the animal. Further, irradiation of both the A Portion and the B Portion with microwave energy will actuate both Portions and make 150-milligrams of the medicament available upon administration of the final dosage form to the animal. In another example, the first medicament 190A is a 100-milligram dose of a first medicament and the second medicament 190B is a 100-milligram dose of a second medicament. Selective irradiation of the A Portion or the B Portion will make one or both of the medicaments bioavailable upon administration of the final dosage form to the animal. In a further example, the release element 530A is modifiable ex vivo by a first stimulus and the release element 530B is modifiable ex vivo by the second and different stimulus.

FIG. 6 illustrates an example environment 600 that includes an article of manufacture 601. The article of manufacture includes a package 660 containing a final dosage form 602 and providing an instruction 670. The final dosage form includes a medicament 190, an outer layer 610, a release element 630, and a chamber 620. The release element is configured in a first medicament-release state and modifiable ex vivo to a second medicament-release state by an exposure to an actuation-stimulus. The chamber lies substantially within the outer layer and is configured to carry the medicament. The instruction includes instruction for preparation of the final dosage form for an efficacious administration to an animal by an exposure of the release element of the final dosage form to the stimulus.

In an embodiment, the final dosage form 602 may be substantially similar to the final dosage form 102 of FIG. 1. In an embodiment, the final dosage form 602 may be substantially similar to the final dosage form 202 of FIG. 2. In an embodiment, the final dosage form 602 may be substantially similar to the final dosage form 302 of FIG. 3. In an embodiment, the final dosage form 602 may be substantially similar to the final dosage form 402 of FIG. 4. In an embodiment, the final dosage form 602 may be substantially similar to the final dosage form 502 of FIG. 5.

In an embodiment, the instruction 670 includes at least one of information indicating an actuation-stimulus type, an actuation-stimulus wavelength, an actuation-stimulus intensity, an actuation-stimulus duration, a spatial distribution of the stimulus relative to the final dosage form, a target-value for an exposure indicator, or a combination thereof. For example, the information indicating a spatial distribution of the stimulus relative to the final dosage form may include information corresponding to aiming the stimulus, such as toward a right hand portion, a center portion, or a left hand portion of the final dosage form. In an embodiment, the instruction includes an instruction presented by at least one of a label (not shown) on the package 660, an insert in the package, illustrated as the instruction 670, or an address to electronically published content (not shown). In an embodiment, the instruction includes instruction for preparation of the final dosage form for an efficacious administration to an animal by a human-initiated exposure of the release element of the final dosage form to the actuation-stimulus.

In an embodiment, the final dosage form 602 further includes a containment element 640 retaining the medicament within the final dosage form until the final dosage form is introduced into the animal. In an embodiment, the final dosage form includes an indicator element 680 configured to indicate an exposure of the release element to the stimulus. In an embodiment, the instruction 670 includes information indicating an expected value of the indicator element.

FIG. 7 illustrates an example operational flow 700 modulating a medicament-release characteristic of a final dosage form. A start operation occurs in an environment 705 that includes the final dosage form. The final dosage form includes a medicament, an outer layer, a release element configured in a first medicament-release state and modifiable ex vivo to a second medicament-release state by an exposure to the stimulus, and a chamber substantially within the outer layer and configured to carry the medicament. After the start operation, the operational flow includes an individualization operation 710. The individualization operation includes irradiating the release element of the final dosage form ex vivo with a non ionizing radiation, the non-ionizing radiation selected to transform the release element from the first medicament-release state to the second medicament-release state. For example, the irradiating the release element of the final dosage form ex vivo with the stimulus may occur in a hospital pharmacy, a retail pharmacy, a battlefield hospital, a veterinary facility, or other location dispensing medicaments. In another example, the irradiating a release element of the final dosage form ex vivo with the stimulus may occur in a persons home. The operational flow then proceeds to an end operation. In an alternative embodiment, the final dosage form further includes a containment element retaining the medicament within the final dosage form before introduction of the final dosage form into the animal.

FIG. 8 illustrates an alternative embodiment of the operational flow 700 of FIG. 7. The individualization operation 710 may include at least one additional operation. The at least one additional operation may include at least one of an operation 712, an operation 714, an operation 716, an operation 718, or an operation 722. The operation 712 includes irradiating in response to a human-initiated activation a release element of the final dosage form ex vivo with a non-ionizing radiation. The operation 714 includes automatically initiating an ex vivo irradiation with a non-ionizing radiation a release element of the final dosage. The operation 716 includes irradiating a first release element of the final dosage form ex vivo with a non-ionizing radiation without irradiating a second release element of the final dosage form with the stimulus. The operation 718 includes irradiating a first release element of the final dosage form ex vivo with a non-ionizing radiation without irradiating a second release element of the final dosage form with the non-ionizing radiation. The first release element is associated with a first chamber carrying a first instance of the medicament, and the second release element is associated with a second chamber carrying a second instance of the medicament. The operation 722 includes irradiating a first release element of the final dosage form ex vivo with a non-ionizing radiation without irradiating a second release element of the final dosage form with the stimulus. The first release element is associated with a first chamber carrying a first medicament, and the second release element is associated with a second chamber carrying a second medicament.

FIG. 9 illustrates an example operational flow 800 fulfilling a request specifying a dose of a medicament for an individual animal. A start operation occurs in an environment that includes a final dosage form. The final dosage form includes an outer layer, a release element configured in a first medicament-release state and changeable to a second medicament-release state by an exposure to the stimulus, a chamber substantially within the outer layer and configured to carry the medicament, and the medicament. In an alternative embodiment, the final dosage form further includes a containment element retaining the medicament within the final dosage form before introduction of the final dosage form into the animal. After the start operation, the operational flow includes a picking operation 810. The picking operation includes choosing pursuant to the request an instance of a final dosage form that includes the medicament. A decision operation 830 includes selecting a stimulus configured to change or transform a medicament-release state of a release element of the final dosage form. A customization operation 850 includes initiating an exposure of the release element of the chosen instance of the final dosage form to the selected stimulus. The operational flow then proceeds to an end operation.

In use of an embodiment, a person such as a pharmacist working in a pharmacy may receive a prescription specifying a dose of a medicament for a patient. A pharmacy typically may have available several different final dosage forms capable of administering the prescribed medicament dose. For example, the available different dosage forms may include at least one of the embodiments of final dosage forms illustrated in FIGS. 1-5. In a picking operation, the pharmacist chooses pursuant to the request an instance of a final dosage form that includes the medicament. In a decision operation, the pharmacist selects a stimulus effective to change a medicament-release state of a release element of the final dosage form. The pharmacist may select the stimulus after consulting with an instruction presented by at least one of a label on box containing the chosen instance of a final dosage form, a package insert in the box, or an address to electronically published content indicated on the label, or package insert. The pharmacist enters the selected stimulus setting for a stimulus emitter, such as the stimulus source 194 of FIG. 1. In a customization operation, the pharmacist initiates an exposure of the release element of the chosen instance of the final dosage form to the selected stimulus. The pharmacist may confirm exposure of the release element to the stimulus by referring to the indicator element. For example, the indicator element may change color in response to an exposure to the selected stimulus. If the prescription specifies multiple doses of the medicament for the patient, the pharmacist may repeat the above sequence until sufficient doses have customized. Alternatively, and if appropriate for the chosen final dosage forms, multiple instances of the final dosage form may be ex vivo exposed to the selected stimulus at one time.

Figure 10:
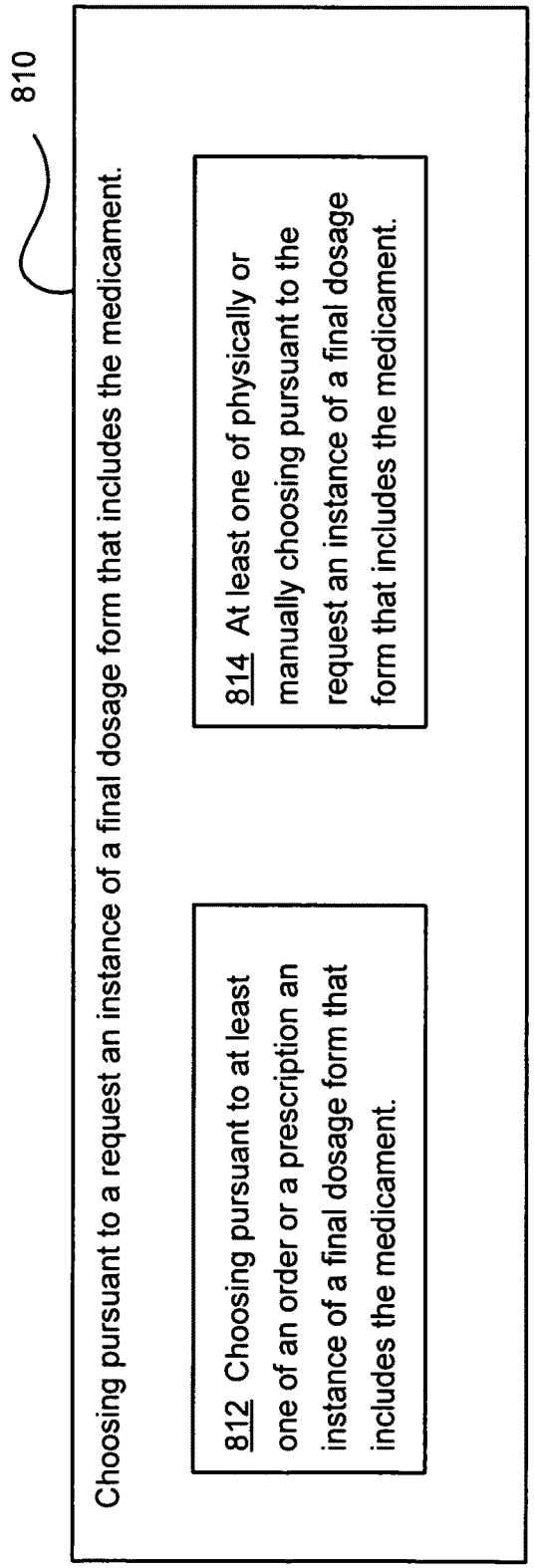
FIG. 10 illustrates an alternative embodiment of the example operational flow of FIG. 9.

FIG. 10 illustrates an alternative embodiment of the example operational flow 800 of FIG. 9. The picking operation 810 may include at least one additional operation. The at least one additional operation may include an operation 812, or an operation 814. The operation 812 includes choosing pursuant to at least one of an order or a prescription an instance of a final dosage form that includes the medicament. The operation 814 includes at least one of physically or manually choosing pursuant to the request an instance of a final dosage form that includes the medicament.

FIG. 11 illustrates another embodiment of the example operational flow 800 of FIG. 9. The decision operation 830 may include at least one additional operation. The at least one additional operation may include an operation 832, an operation 834, or an operation 836. The operation 832 includes selecting a stimulus having an attribute indicated by at least one of a manufacturer of the final dosage form, an instruction packaged with the dosage form, an electronically published content, and a printed publication as effective to change a medicament-release state of a release element of the final dosage form. For example, electronically published content may include a website maintained by the manufacturer of the final dosage form. In a further example, a printed publication may include a reference book, such as *Physician's Desk Reference*. The operation 834 includes selecting a stimulus configured by at least one of a type, amount, level, wavelength, spectrum, waveform, spatial distribution, duration, or pulse attribute to change a medicament-release state of a release element of the final dosage form. The operation 836 includes selecting a stimulus configured to change a medicament-release state of a release element of the final dosage form and to make the request-specified dose of medicament dose bioavailable by the final dosage form.

Figure 12:
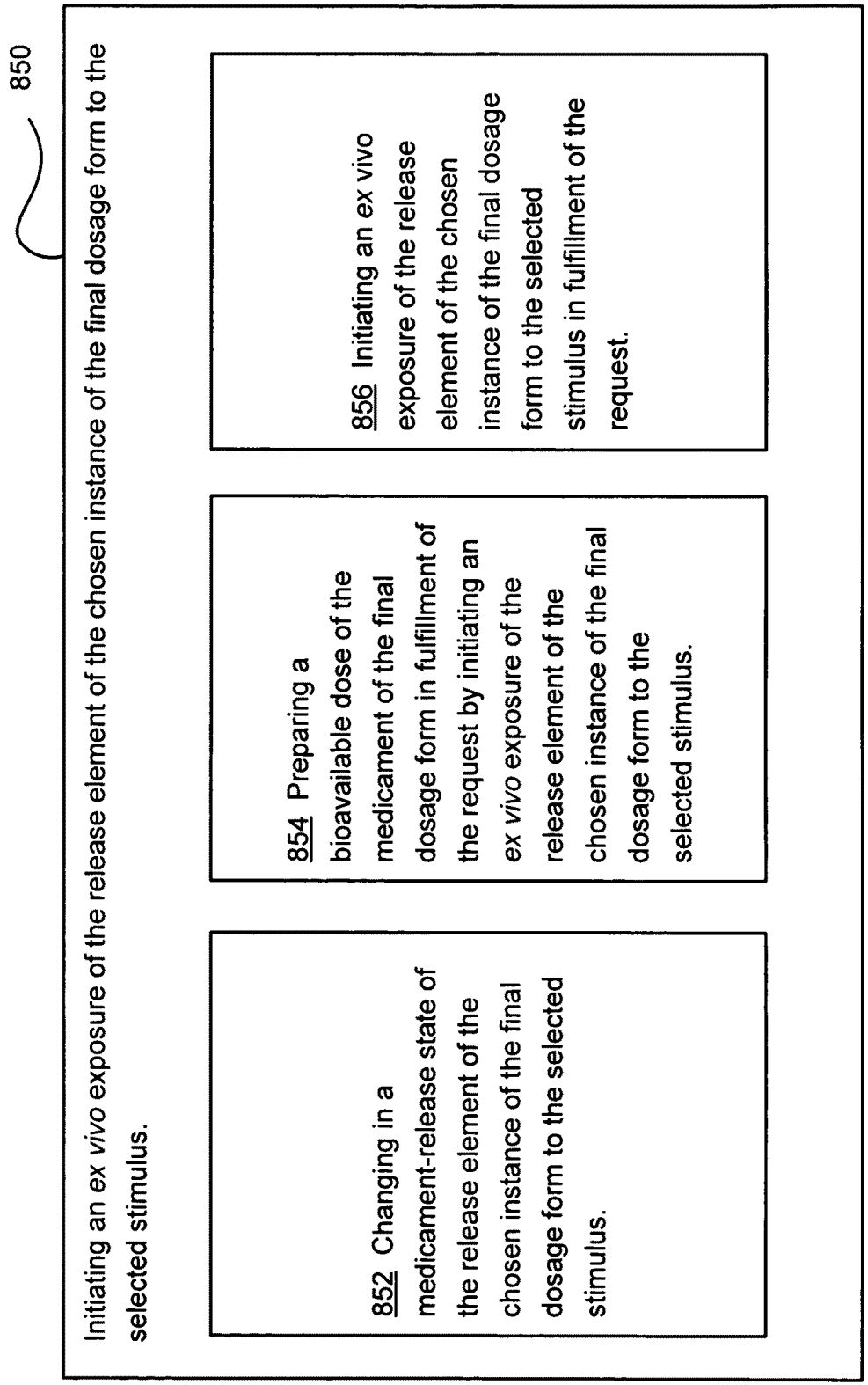
FIG. 12 illustrates a further embodiment of the example operation of FIG. 9.

FIG. 12 illustrates an embodiment of the example operation 800 of FIG. 9. The customization operation 850 may include at least one additional operation. The at least one additional operation may include an operation 852, an operation 854, or an operation 856. The operation 852 includes changing a medicament-release state of the release element of the chosen instance of the final dosage form by initiating an exposure of the release element of the chosen instance of the final dosage form to the selected stimulus. The operation 854 includes preparing a bioavailable dose of the medicament of the final dosage form in fulfillment of the request by initiating an exposure of the release element of the chosen instance of the final dosage form to the selected stimulus. The operation 856 includes initiating an exposure of the release element of the chosen instance of the final dosage form to the selected stimulus in fulfillment of the request.

FIG. 13 illustrates an embodiment of the example operational flow 800 of FIG. 9. The operation 870 may include at least one additional operation. The at least one additional operation may include an operation 872, an operation 874, or an operation 876. The operation 870 may include at least one additional operation. The at least one additional operation may include an operation 872, an operation 874, or an operation 876. The operation 872 includes optically verifying the exposure of the release element of the chosen instance of the final dosage form to the selected stimulus. For example, optically verifying the exposure may be implemented using human vision, machine vision, or ultrasound techniques. The operation 874 includes electronically verifying the exposure of the release element of the chosen instance of the final dosage form to the selected stimulus. For example, electronically verifying the exposure of the release element may be implemented using a dielectric element having a property that makes an electronically discernable change in response to an exposure to the stimulus. The operation 876 includes quantifying the exposure of the release element of the chosen instance of the final dosage form to the selected stimulus. The operation 876 may include at least one additional operation. The at least one additional operation may include an operation 878, or an operation 882. The operation 878 includes initiating another exposure of the release element of the chosen instance of the final dosage form to the selected stimulus in response to the quantifying the exposure of the release element of the chosen instance of the final dosage form to the selected stimulus. The operation 882 includes terminating the exposure of the release element of the chosen instance of the final dosage form to the selected stimulus in response to the quantifying the exposure of the release element of the chosen instance of the final dosage form to the selected stimulus.

FIG. 14 illustrates an embodiment of the example operational flow 800 of FIG. 9. The operational flow 800 may include at least one additional operation. The at least one additional operation may include an operation 860, an operation 870, or an operation 890. The operation 860 includes receiving the request specifying a dose of a medicament for an individual animal. The operation 860 may include at least one additional operation. The at least one additional operation may include an operation 862, or an operation 864. The operation 862 (not shown) includes receiving the request specifying an efficacious medicament dose for an individual animal. The operation 864 (not shown) includes receiving the request specifying the final dosage form that includes the medicament for an individual animal.

The operation 870 includes verifying the exposure of the release element of the chosen instance of the final dosage form to the selected stimulus. The operation 890 includes dispensing the chosen instance of the final dosage form after the exposure of the release element of the chosen instance of the final dosage form to the selected stimulus as described above. The operation 890 may include at least one additional operation, such as an operation 892. The operation 892 (not shown) includes dispensing the ex vivo exposed instance of the final dosage form in a package bearing an identifier of the individual animal. For example, the identifier may include a name, or identification number of the animal.

Figure 15:
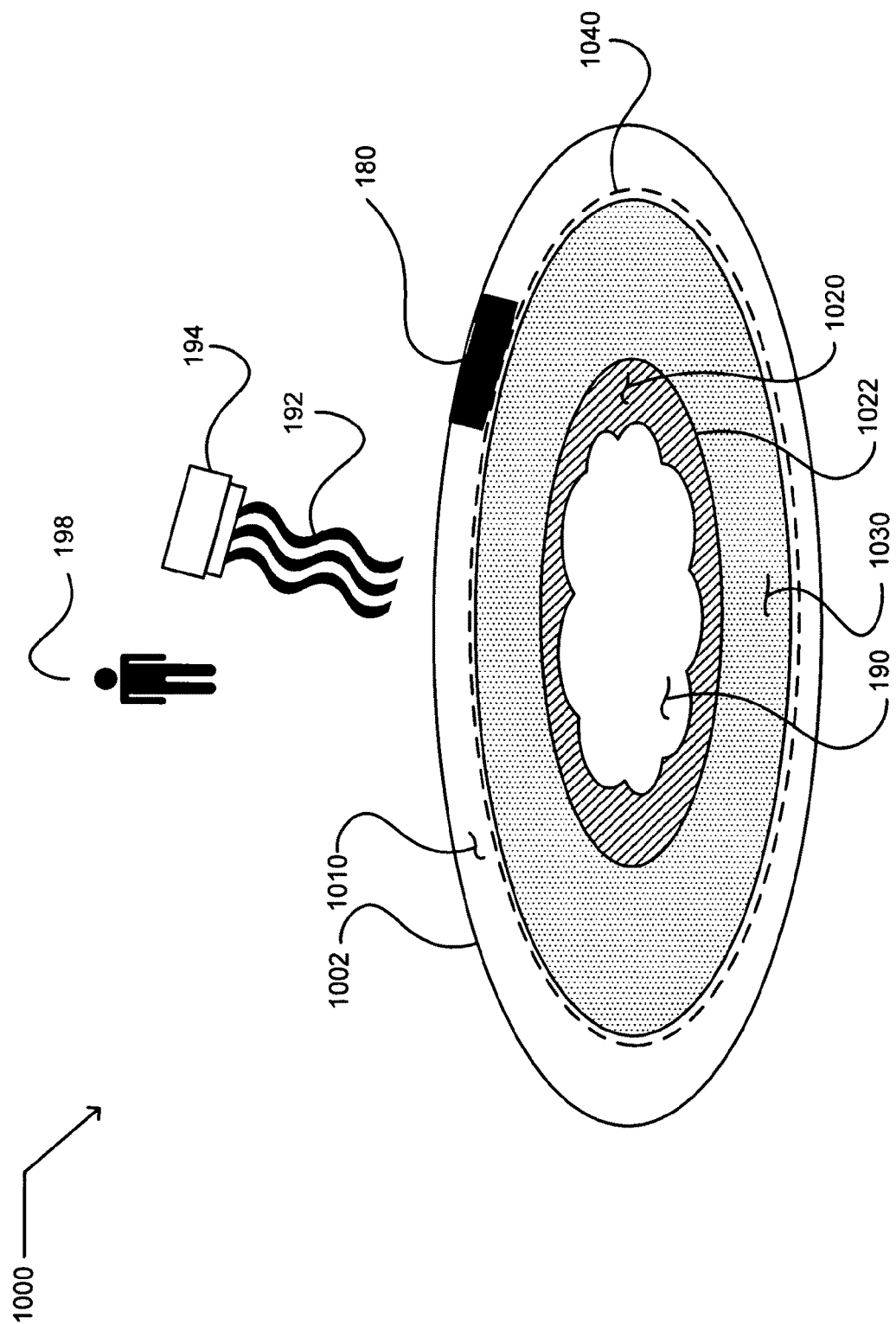
FIG. 15 illustrates an example environment that includes an animal, a cross-sectional view of an example final dosage form for administering the medicament to the animal, and the example stimulation source operable to emit a stimulus.

FIG. 15 illustrates an example environment 1000 that includes the animal 198, a cross-sectional view of an example final dosage form 1002 for administering the medicament 190 to the animal 198, and the example stimulus source 194 operable to emit a stimulus 192. In an embodiment, the final dosage form includes a dosage form having completed a manufacturing or production process. In an embodiment, the final dosage form includes a product, finished tablet, or capsule ready for distribution to a hospital, pharmacy, or retail store for individualizing for a particular animal. In an embodiment, the final dosage form includes a tablet shape, a spherical shape, or an ellipsoidal shape. In an embodiment, the final dosage form includes a structure, a particle, or a polymer that is carryable or transportable to the animal by a solid, cream, liquid, or fluid carrier.

The final dosage form 1002 includes an outer layer 1010, a release element 1030, and the medicament 190. The release element is configured in a medicament-holding state. The release element is modifiable ex vivo to a medicament-discharge state by an exposure to a stimulus, illustrated as the stimulus 192. In an embodiment, ex vivo includes outside the body of the animal. In an embodiment, ex vivo includes an environment outside or away from the body of the animal. In an embodiment, ex vivo includes outside a living organism, such as "in vitro." In an embodiment, ex vivo includes an external or ambient environment.

In an embodiment, the stimulus 192 includes at least one of a non-ionizing radiation, an electromagnetic radiation, a magnetic field, an electric field, an energetic stimulus, or a chemical stimulus. In an embodiment, the stimulus includes at least one of a light radiation, terahertz radiation, microwave radiation, or radio wave radiation. In an embodiment, the stimulus includes at least one of a mechanically activatable structure, heat activatable structure, or pressure activatable structure. In an embodiment, the stimulus includes at least one of a thermal, acoustic, or ultrasound stimulus. In an embodiment, the stimulus includes at least one of an activation stimulus, or an actuation stimulus.

In an embodiment, the release element 1030 includes a release element configured in a medicament-holding state. In the medicament-holding state, the medicament 190 is substantially not bioavailable to the animal 198 if the final dosage form 1002 is administered to the animal. The release element is modifiable ex vivo to a medicament-discharge state by an exposure to the stimulus 192. In the medicament-discharge state, the medicament is substantially bioavailable to the animal if the final dosage form is administered to the animal. In an embodiment, substantially not bioavailable to the animal includes having no substantial therapeutic or adverse effect on the animal. In an embodiment, bioavailable to the animal includes the medicament being physiologically available, absorbable, transportable, usable, or utilizable by the animal. In an embodiment, bioavailable to the animal indicates that a portion of an administered dose of medicament reaches the systemic circulation. In an embodiment, not bioavailable to the animal includes the medicament being physiologically not available, not absorbable, not transportable, not usable, or not utilizable by the animal.

In an embodiment, the release element 1030 includes a release element configured in a medicament-holding state. In the medicament-holding state, the medicament 190 is insubstantially bioavailable if the final dosage form 1002 is administered to the animal 198. The release element is modifiable ex vivo to a medicament-discharge state by an exposure to the stimulus 192. In the medicament-discharge state, the medicament is substantially bioavailable if the final dosage form is administered to the animal. In an embodiment, the release element includes a release element configured in a medicament-holding state. In the medicament-holding state, the medicament is substantially bio-unavailable if the final dosage form is administered to the animal. The release element is modifiable ex vivo to a medicament-discharge state by an exposure to the stimulus wherein the medicament is substantially bioavailable if the final dosage form is administered to the animal. In an embodiment, bio-unavailable includes present but not usable by the animal.

In an embodiment, the release element includes a release element 1030 configured in a medicament-holding state. In the medicament-holding state, the medicament 190 has a substantially insignificant effect on the animal 198 if the final dosage form 1002 is administered to the animal. The release element is modifiable ex vivo to a medicament-discharge state by an exposure to the stimulus. In the medicament-discharge state, the medicament has a substantially significant effect on the animal if the final dosage form is administered to the animal. In an embodiment, the release element includes a release element configured in a medicament-withholding state, and modifiable ex vivo to a medicament-supplying state by an exposure to the stimulus.

In an embodiment, the release element 1030 includes a release element configured in a medicament-holding state and field-modifiable ex vivo to a medicament-discharge state by an exposure to the stimulus 192. For example, the release element may be field modified at a point of administration of the final dosage form, such as clinic or hospital, at a pharmacy such as when a pharmacist is filling a prescription that includes the final dosage form, or at a residence by a caregiver or by a person for whom the final dosage form is prescribed. In an embodiment, the release element includes a release element configured in a medicament-holding state and modifiable ex vivo post-manufacture to a medicament-discharge state by an exposure to the stimulus. In an embodiment, the release element includes a release element forming an imperforate barrier in a medicament-holding state. The release element is modifiable ex vivo by an exposure to the stimulus to form a perforate barrier in a medicament-discharge state. In an alternative embodiment, the release element is modifiable ex vivo by an exposure to the stimulus to form a perforate barrier in a medicament-discharge state to form at least one discharge pathway.

In an embodiment, the release element 1030 includes a release element configured in a medicament-holding state. The release element is modifiable ex vivo to a medicament-discharge state by an exposure to the stimulus 192, the stimulus including at least one of light or radio waves.

In an embodiment, the final dosage form 1002 includes a particle or polymer implemented release element. In an embodiment, a polymer may include an intelligent polymer having a changeable property that in one state admits or discharges at least one molecule of medicament and in another state engages or retains the at least one molecule of medicament. An intelligent polymer includes a polymer structurally responsive to an externally applied energy or stimulus. In an embodiment, "applied energy" includes both positive and negative energy values, i.e. supplying and removing energy. Examples of intelligent polymers are described in U.S. Pat. No. 7,104,517 to Derand, et al. In an embodiment, a particle may include a microsphere, polymeric microsphere, or nanoparticle.

Figure 16:
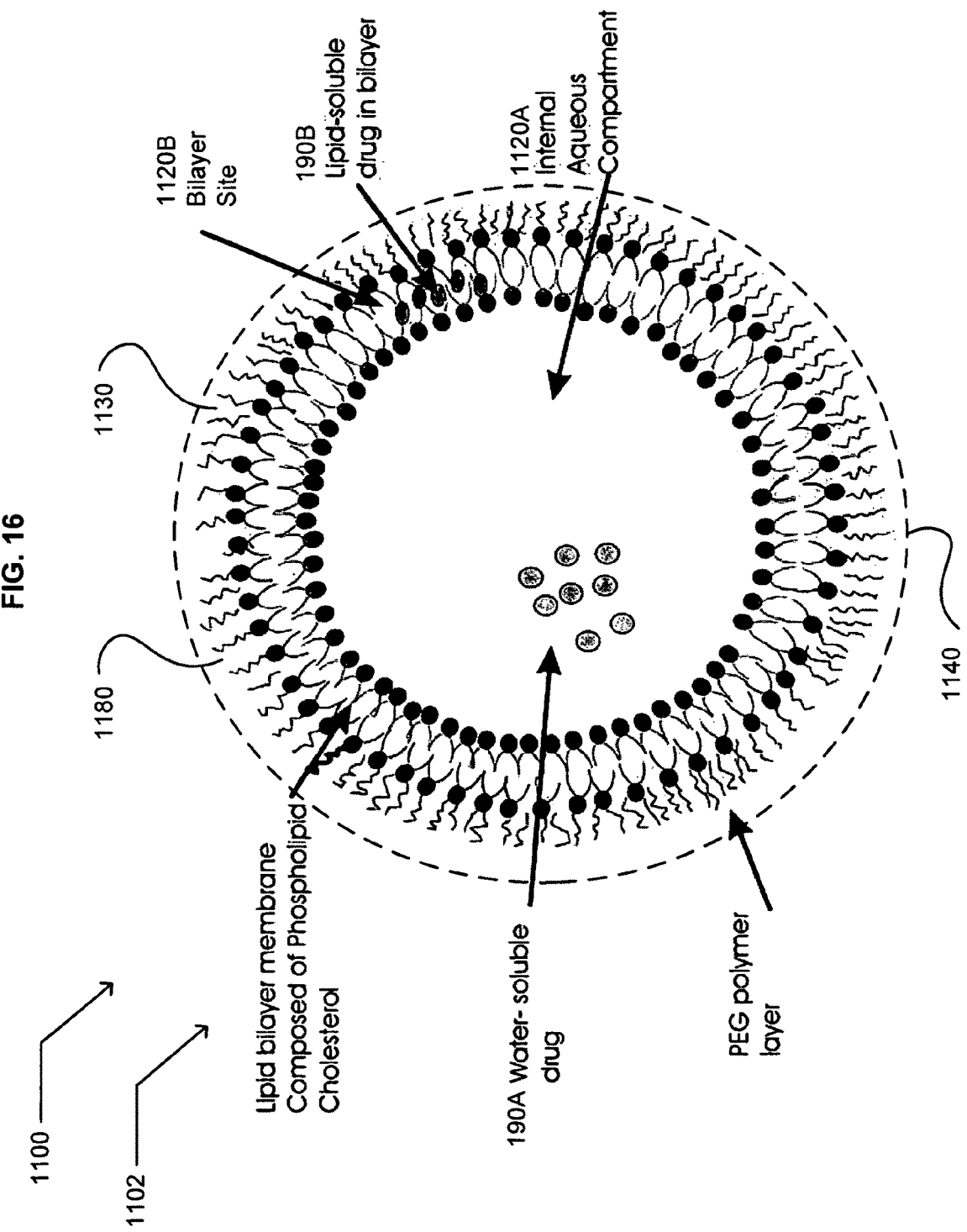
FIG. 16 illustrates an example environment that illustrates a final dosage form having a release element implemented by a characteristic response of a particle or a polymer to the stimulus.

FIG. 16 illustrates an example environment 1100 that illustrates a final dosage form 1102 having a release element 1130 implemented by a characteristic response of a particle or a polymeric material 1180 to a stimulus such as, the stimulus 192. An example of the particle or polymeric material is illustrated as a liposome. The final dosage form includes molecules of the medicament 190 carried by the particle or a polymeric material, again illustrated with respect to the liposome. Example water-soluble drug molecules 190A are illustrated as engaged, retained, or entrapped in an internal aqueous compartment site 1120A. Example lipid-soluble drug molecules 190B are illustrated as engaged, retained or entrapped in a bilayer site 1120B. The example environment 1100 illustrates the release element configured in a medicament-holding state with at least one molecule of the medicament engaged, retained or entrapped. In an embodiment, the release element has, for example by application of a stimulus, such as the stimulus 192, been changed into a state (not shown) that admits at least one molecule of the medicament, illustrated as the water-soluble drug molecules 190A or the lipid-soluble drug molecules 190B. The release element state is changed by withdrawal of the stimulus into a state (shown) that engages, retains or entraps the water-soluble drug molecules 190A or the lipid-soluble drug molecules 190B. Continuing this example, the release element is modifiable ex vivo to a medicament-discharge state by an exposure to a stimulus, such as the stimulus 192, which may be the same stimulus used to switch the release element and load the water-soluble drug molecules 190A or the lipid-soluble drug 190B into the liposome, or may be another stimulus 192. In an alternative of this example, a chemical stimulus may be used to load the at least one molecule in the liposome, and another stimulus, such as an electromagnetic wave used to modify the liposome to a medicament-discharge state.

The characteristic response of the particle or polymeric material to the stimulus 192 may include any characteristic response that releases an engaged, retained, or entrapped medicament 190 from the particle or polymeric material. For example, a characteristic response of a particular particle or polymeric material may include a releasing bursting, expanding, cleaving, or degradation of the particular particle or polymeric material in response to a microwave stimulus implements the release element 1130.

In an embodiment, the release element 1130 is configured in a medicament-holding state. The release element is modifiable ex vivo to a medicament-discharge state by an exposure to the stimulus 192. The release element including at least one of a gel, gel matrix, hydrogel fibrin, or a dendrimer. Examples hydrogels are described in Y. Qiu, et al, *Enivoronment-sensitive hydrogels for drug delivery*, SCIENCEDIRECT (October 2001), citing *Triggering in Drug Delivery Systems*, 53 ADVANCED DRUG DELIVERY REVIEWS 321-339 (Issue 3, December 2001). Examples polymers and dendrimers are described in C. Henry, *Drug Delivery*, 80 CHEMICAL & ENGINEERING NEWS 39-47 (No. 34, Aug. 26, 2002) (The drugs are conjugated to the dendrimers using photocleavable or labile linkers, which can be made to release the drug using light or through acid cleavage). Examples of photo-labile, radio-labile, and enzyme-labile dendrimers are described in U.S. Pat. No. 6,471,968 to Baker, et al.; and in U.S. Pat. No. 7,078,461 to Tomalia, et al. In an embodiment, a particle or polymeric material having a characteristic responsive to an exposure to the stimulus include an intelligent or environmentally sensitive particle or polymeric material.

In an embodiment, the release element 1130 includes a particle (not specifically shown) configured in a medicament-holding state. The particle is modifiable ex vivo to a medicament-discharge state by an exposure to the stimulus 192. Examples of environmentally sensitive particles such as microspheres have been described previously herein. In an embodiment, the release element includes a polymer substance configured in a medicament-holding state. The polymer substance is modifiable ex vivo to a medicament-discharge state by an exposure to the stimulus. Examples of environmentally sensitive polymer substances have been described previously herein.

Returning to FIG. 15, in an embodiment, the release element 1030 includes a non-shape-memory material configured in a medicament-holding state. The non-shape-memory material is modifiable ex vivo to a medicament-discharge state by an exposure to the stimulus 192. In an embodiment, the release element includes a release element disposed at least partially within the outer layer 1010 and configured in a medicament-holding state. The release element is modifiable ex vivo to a medicament-discharge state by an exposure to the stimulus. In the medicament-discharge state the medicament 190 is substantially available for an in vivo release into the animal 198 if the final dosage form is administered to the animal while the release element is configured in the medicament-discharge state.

In an embodiment, the final dosage form 1002 further includes a chamber 1020 located substantially within the outer layer 1010 and carrying the medicament 190. In an embodiment, the chamber 1020 is substantially similar to the chamber 120 described in conjunction with FIG. 1. In an embodiment, the final dosage form further includes the indicator element 180 configured to indicate an exposure of the release element 1030 to the stimulus 192.

Another embodiment provides a final dosage form 1002 for administering the medicament 190 to the animal 198. This embodiment of the final dosage may be illustrated by reference to FIG. 15 and/or by reference to FIG. 16. With reference to an embodiment illustrated by FIG. 15, the final dosage form 1002 includes a release element 1030, a site 1020 carrying the medicament, the medicament, and a containment element 1040. The release element 1030 is configured in a medicament-holding state and modifiable ex vivo to a medicament-discharge state by an exposure to the stimulus 192. The containment element retains the medicament within the final dosage form until the final dosage form is administered to the animal. In an embodiment, the containment element may be substantially similar to the containment element 140 described in conjunction with FIG. 1.

With reference to an embodiment illustrated by FIG. 16, an embodiment of the final dosage form includes the final dosage form 1102 having a release element 1130 formed by a particle or polymer 1180, a site carrying the medicament 190 (depicted as the internal aqueous compartment site 1120A or as the bilayer site 1120B), the medicament. The release element is configured in a medicament-holding state and modifiable ex vivo to a medicament-discharge state by an exposure to the stimulus.

In an embodiment, the final dosage form 1102 includes a containment element 1140. The containment element retains the medicament within the final dosage form until the final dosage form is administered to the animal. In an embodiment, the containment element 1140 includes a particle or polymeric substance retaining the medicament 190 within the final dosage form 1102 until the final dosage form is administered to the animal 198 (not shown). For example, the containment element may include a gel, hydrogel, liposome microsphere, polymeric microsphere, dendrimer, or nanoparticle. In an embodiment, the containment element may be another particle or polymer that engages, retains, or entraps the particle or polymer in a containing manner (not shown). In an embodiment, the containment element may be substantially similar to the containment element 140 of the final dosage from 102 described in conjunction with FIG. 1. In an embodiment, the containment element may be substantially similar to the erodible outer layer 110 of the final dosage form 102 described in conjunction with FIG. 1. In an embodiment, the release element 1130 and the containment element are at least a substantially same structure, for example a microsphere. In an embodiment, the release element and the containment element are substantially different structures, for example a microsphere containment element containing a dendrimer release element. In an embodiment, the containment element includes a carrier, excipient, diluent, or admixture retaining the medicament within the final dosage form until the final dosage form is administered to the animal.

In an embodiment, the site 1120 carrying the medicament 190 includes a chamber carrying the medicament. In an embodiment, the site carrying the medicament includes a region carrying the medicament. In an embodiment, the site carrying the medicament includes a binding site releasably carrying the medicament. In an embodiment, the site carrying the medicament includes the release element 1130 or a particle or polymeric material carrying the medicament. In an embodiment, the site carrying the medicament includes a binding site releasably carrying the medicament.

In an embodiment, the final dosage form includes an indicator element 180 configured to indicate an exposure of the release element to the stimulus. With reference to an embodiment illustrated by FIG. 15, the final dosage form 1002 includes an indicator element 180 configured to indicate an exposure of the release element 1030 to the stimulus 192. With reference to FIG. 16, the final dosage form 1102 includes an indicator element (not shown) configured to indicate an exposure of the release element 1130 to the stimulus 192.

Figure 17:
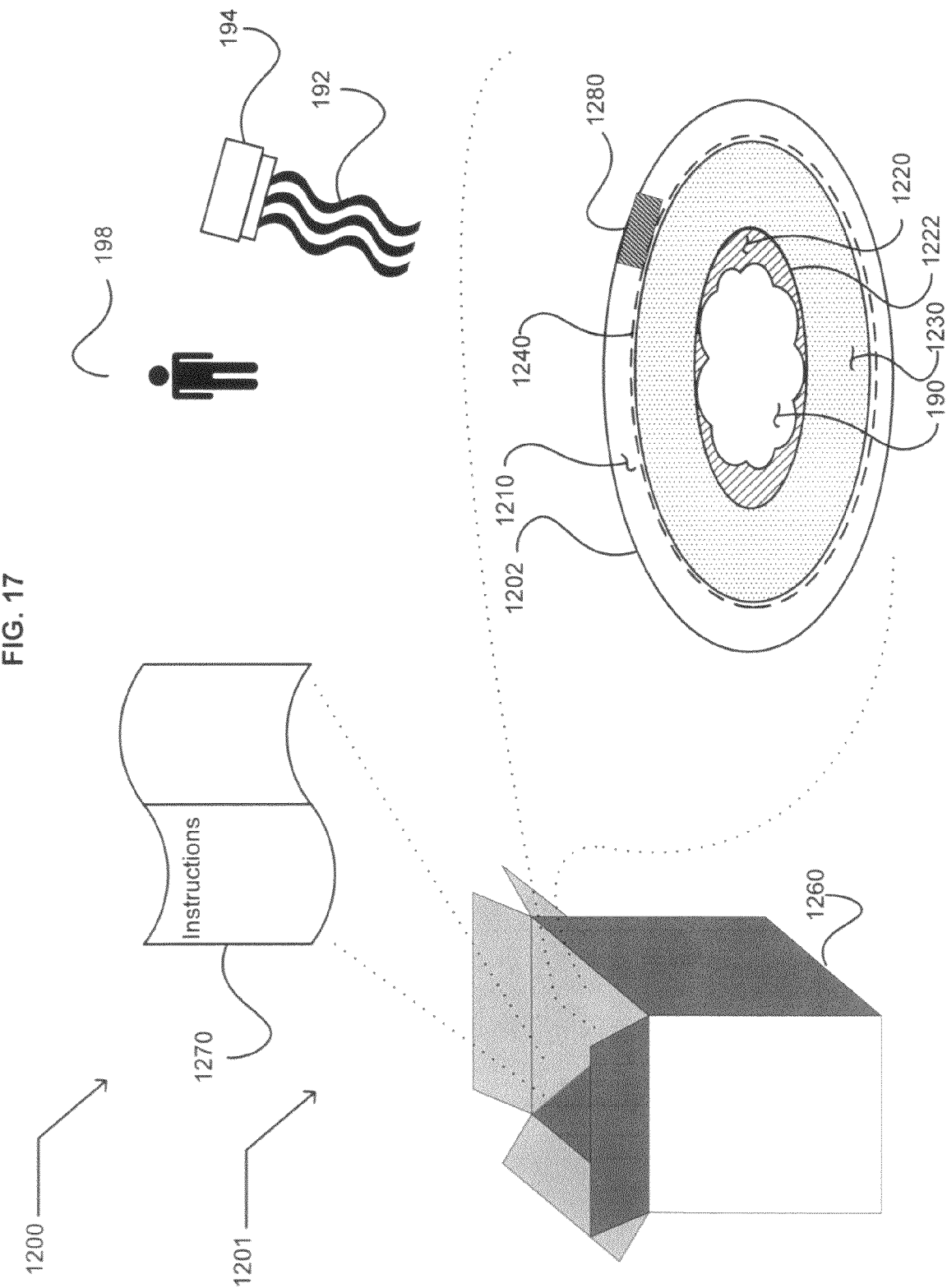
FIG. 17 illustrates an example environment that includes an article.

FIG. 17 illustrates an example environment 1200 that includes an article 1201. The article includes at least one final dosage form for administering a therapeutically effective amount of a medicament to an animal. In an embodiment, the final dosage form includes a final dosage 1202 that is substantially similar to the final dosage form 1002 described in conjunction with FIG. 15. In an embodiment, the final dosage form includes the final dosage form 1202 that is substantially similar to the final dosage form 1102 described in conjunction with FIG. 16 (not shown in FIG. 17). The final dosage form of FIG. 17 includes an outer layer 1210, a release element 1230, a site 1220 carrying the medicament 190. The release element includes a release element configured in a medicament-holding state. The release element is modifiable ex vivo to a medicament-discharge state by an exposure to the stimulus 192. The article also includes instructions 1270 for the exposure of the release element to the stimulus sufficient to modify the release element to the medicament-discharge state. In an embodiment, the instructions include instructions specifying the exposure of the release element to a human-initiated stimulus sufficient to modify the release element to the medicament-discharge state. In an embodiment, the instructions include instructions specifying the exposure of the release element to provide an automatically-initiated stimulus sufficient to modify the release element to the medicament-discharge state.

FIG. 18 illustrates an example operational flow 1300 modifying a medicament availability characteristic of a final dosage form. A start operation occurs in an environment 1305 that includes the final dosage form. The final dosage form includes an outer layer, a release element, a site carrying the medicament, and the medicament. The release element is configured in a medicament-holding state wherein a medicament is substantially not bioavailable to the animal, such as the animal 198. The release element is modifiable ex vivo to a medicament-discharge state by an exposure to the stimulus wherein the medicament is substantially bioavailable to the animal. In an embodiment, the final dosage form is substantially similar to the final dosage form 1002 described in conjunction with FIG. 15. In an embodiment, the final dosage form is substantially similar to the final dosage form 1102 described in conjunction with FIG. 16

After the start operation, the operational flow 1300 includes an activating operation 1310. The activating operation includes initiating an exposure of a release element of the final dosage form to a stimulus, such as the stimulus 192. The initiated stimulus is selected to transform the release element from a medicament-holding state to a medicament-discharge state. In an embodiment, the initiated stimulus includes an initiated stimulus having a parameter selected to transform the release element from a medicament-holding state to a medicament-discharge state. In an embodiment, the initiated stimulus includes an initiated stimulus having at least one of a stimulation characteristic or a spatial characteristic selected to transform the release element from a medicament-holding state to a medicament-discharge state. In an embodiment, the initiating an exposure of a release element of the final dosage form to a stimulus includes initiating a first exposure of a release element of the final dosage form to a stimulus. The initiated first stimulus is selected to transform the release element from a medicament-holding state to a medicament-discharge state. This embodiment further includes receiving an indication of the first exposure of the release element of the final dosage form to the stimulus, the indication generated in response to an indicator element of the final dosage form configured to indicate an exposure of the release element to the stimulus. This embodiment further includes initiating a second exposure of the release element of the final dosage form to the stimulus. The initiated second exposure stimulus is selected to further transform the release element from the medicament-holding state to the medicament-discharge state.

In an embodiment, the final dosage form includes a containment element retaining the medicament within the final dosage form until the final dosage form is introduced into the animal. In an embodiment, the final dosage form includes an indicator element configured to indicate an exposure of the release element to the stimulus.

FIG. 19 illustrates an example final dosage form 1400 for administering a medicament to an animal. The final dosage includes means 1410 for protecting the final dosage form from an ex vivo environment. The final dosage form includes means 1420 for releasing the medicament, configured in a medicament-holding state, and modifiable ex vivo to a medicament-discharge state by an exposure to a stimulus, such as the stimulus 192. The final dosage form includes the medicament 1430.

In an embodiment, the final dosage form includes means 1440 for carrying the medicament. In an embodiment, the means 1440 for carrying the medicament is positioned substantially within the means 1410 for protecting the final dosage form. In an embodiment, the final dosage form includes means 1450 for indicating an exposure of the means for releasing the medicament to the stimulus. In an embodiment, the final dosage form includes means 1460 for containing the medicament within the final dosage form until the final dosage form is introduced into the animal.

An embodiment provides a final dosage form for administering a medicament to an animal. In this embodiment, the final dosage form includes at least one particle or polymeric material respectively carrying at least one molecule of the medicament. The particle or polymeric material is configured in a medicament-retention state wherein the medicament is substantially not bioavailable to the animal if the final dosage form is administered to the animal. The particle or polymeric material is modifiable ex vivo by an exposure to the stimulus to a medicament-release state wherein the medicament is substantially bioavailable to the animal if the final dosage form is administered to the animal. This embodiment is described, for example, by reference to FIG. 16, FIG. 20, and/or FIG. 21. In an embodiment, the particle or polymeric material may include at least one of the particle or polymeric materials previously described. In an embodiment, the particle or polymeric material includes an intelligent particle or polymeric material. In an embodiment, the particle or polymeric material includes a polymer matrix structure responsive to the exposure to a stimulus. In an embodiment, the particle or polymeric material includes at least one of a microparticle, a gel or a dendrimer based microparticle responsive to the exposure to a stimulus. In an embodiment, the particle or polymeric material includes at least one of a noisome, fibrin, polymeric micelle, microsome, cyclodextrin, polymer-medicament conjugate, or cellulose responsive to the exposure to a stimulus. In an embodiment, the particle or polymeric material includes at least one of a gel, a gel matrix, a natural gel, a synthetic gel, a colloid gel, or a hydrogel structure covalently bonded to the medicament using a photo labile bond and responsive to the exposure to a stimulus. A synthetic gel may include cellulose or polymers. In an embodiment, the particle or polymeric material includes at least one of a dendrimer, dendrimsome, dendromsome, dendron (partial dendrimer), or dendriplex material. In an embodiment, the particle or polymeric material includes at least one of an emulsion, nano-emulsion, or double emulsion. In an embodiment, the particle or polymeric material includes at least one of a lipid, cationic lipid, lipid micelle, liposome, lipospheres, acoustically active lipospheres, acoustically-active microbubbles conjugated to liposomes, lipid-coated microbubbles, cerasomes, magnetic liposomes, metallosomes, or a mimetic. Acoustically-active microbubbles conjugated to liposomes are described in A. Kheirolomoom, et al., *Acoustically-active microbubbles conjugated to liposomes: characterization of a proposed drug delivery vehicle*, J. CONTROL RELEASE 118(3) (Apr. 23, 2007):275-84; Epub Dec. 23, 2006. A cerasomes may include liposomes with a silicate surface. A mimetic may include an artificial micelle or membrane.

Figure 20:
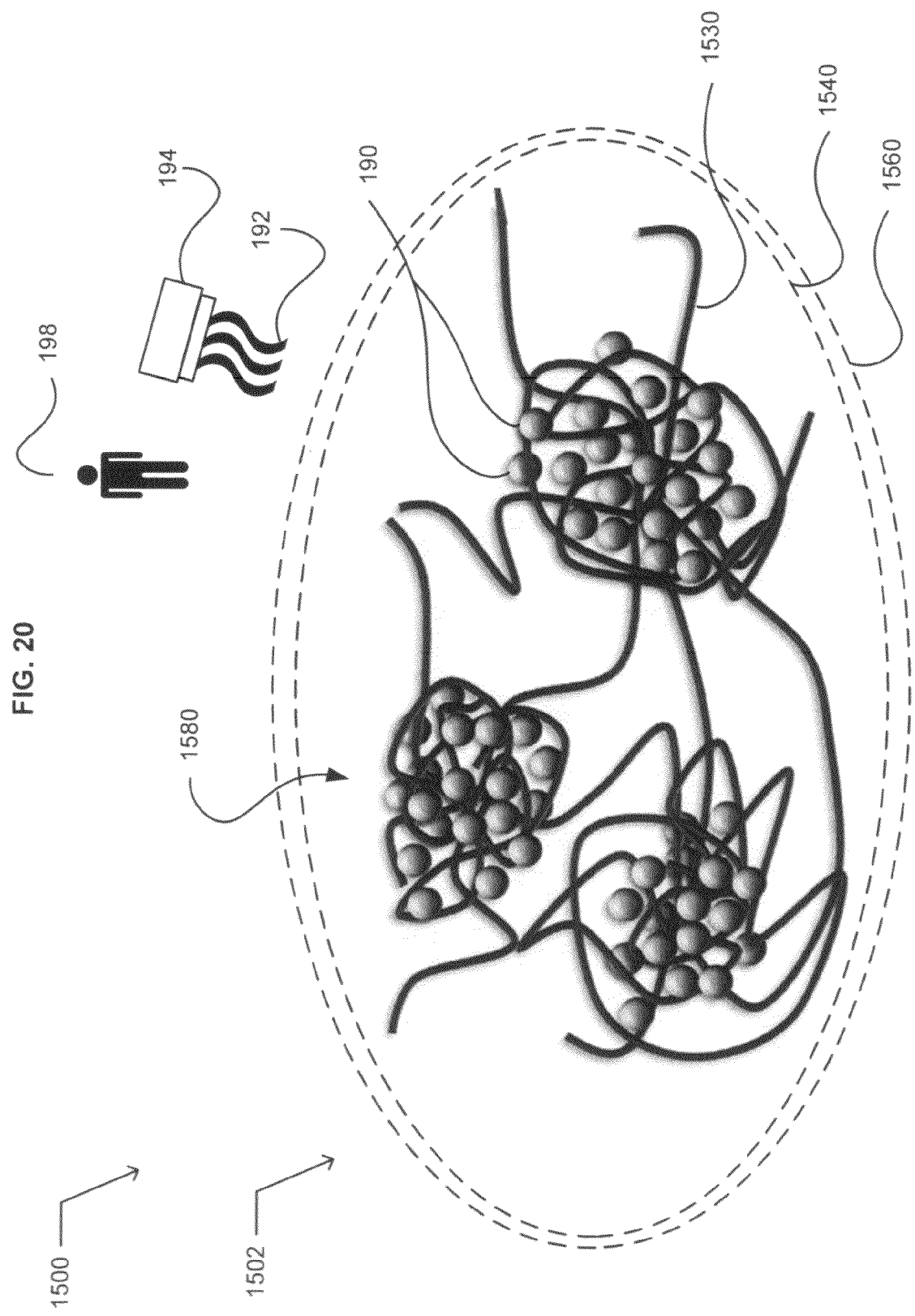
FIG. 20 illustrates an example environment that includes a final dosage form 1502 configurable to administer a medicament to an animal.

FIG. 20 illustrates an example environment 1500 that includes a final dosage form 1502 configurable to administer a medicament to the animal 198. The final dosage form includes at least one molecule of the medicament 190. The final dosage form also includes at least one of a particle or polymeric material 1580, which is depicted as a gel. The particle or polymeric material has a characteristic response 1530 to the stimulus 192 that releases an engaged, retained, or entrapped at least one molecule of the medicament 190 from the particle or polymeric material. For example, a characteristic response of a particular particle or polymeric material may include a releasing bursting, expanding, cleaving, or degradation of the particular particle or polymeric material in response to a microwave stimulus.

The at least one particle or polymeric material 1580 respectively carries the at least one molecule of the medicament 190. The particle or polymeric material is configured in a medicament-retention state wherein the medicament is substantially not bioavailable to the animal 198 if the final dosage form is administered to the animal. The particle or polymeric material being modifiable ex vivo by an exposure to the stimulus 192 to carry the medicament in a medicament-release state wherein the medicament is substantially bioavailable to the animal if the final dosage form is administered to the animal.

Figures 21, 21A, 21B:
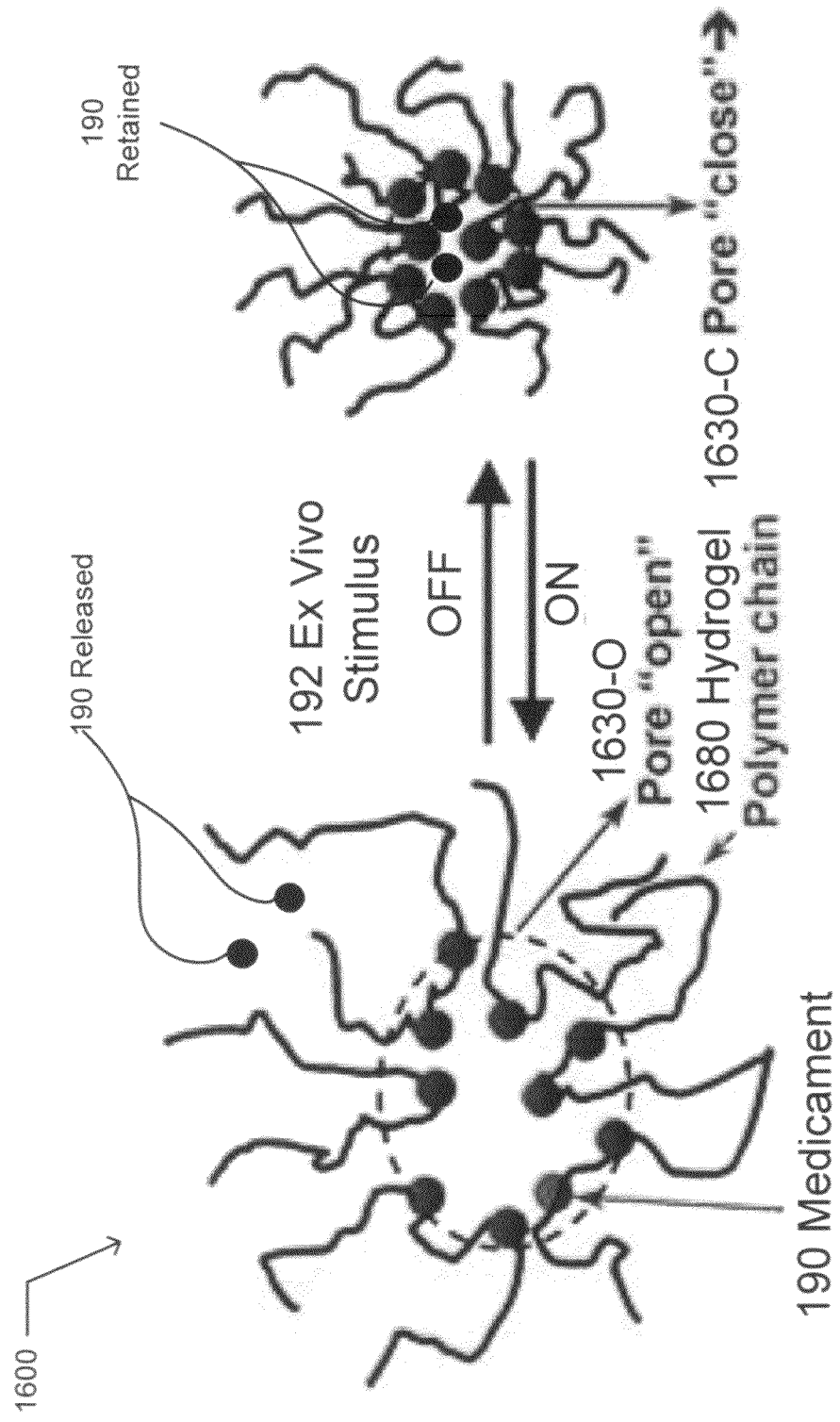
FIG. 21 illustrates an example environment depicting retention and release states of particle or polymeric material (depicted as a hydrogel) responsive to an ex vivo stimulus.

FIG. 21 illustrates an example environment 1600 depicting retention and release states of particle or polymeric material 1680 (depicted as a hydrogel) carrying the medicament 190 and responsive to an ex vivo stimulus 192. FIG. 21A illustrates a medicament-release state where two instances of the medicament, collectively labeled "190 Released," have been released from the particle or polymeric material in a medicament-release state. FIG. 21B illustrates a medicament-retention state where two instances of the medicament, collectively labeled "190 Retained" are carried by the particle or polymeric material in a medicament-retention state. Application of the stimulus ex vivo to the particle or polymeric material switches it from the medicament-retention state to the medicament-release state. For example, an ex vivo application of the stimulus to the hydrogel switches it from a pore "closed" state 1630-C to a pore "open" state 1630-O.

Returning to FIG. 16, FIG. 16 illustrates the particle or polymeric material 1180, which is depicted as a liposome. The particle or polymeric material carries the medicament 190. The particle or polymeric material is configured in a medicament-retention state wherein the medicament is substantially not bioavailable to the animal if the final dosage form is administered to the animal 198. The particle or polymeric material is modifiable ex vivo by an exposure to the stimulus 192 to carry the medicament in a medicament-release state wherein the medicament is substantially bioavailable to the animal if the final dosage form is administered to the animal.

Returning to FIG. 20, in an embodiment, the medicament 190 includes a pharmacologically-active agent. In an embodiment, the medicament includes at least one of an agent, treatment agent, drug, prodrug, therapeutic, nutraceutical, medication, vitamin, nutritional supplement, medicine, remedy, medicinal substance, or cosmetic.

In an embodiment, the particle or polymeric material 1580 carrying the medicament 190 includes a particle or polymeric material conjugated with the medicament. In an embodiment, the particle or polymeric material carrying the medicament includes a particle or polymeric material containing, intertwined, or bound with the medicament. In an embodiment, the particle or polymeric material carrying the medicament includes a particle or polymeric material entrapping the medicament.

In an embodiment, the particle or polymeric material 1180 carrying the medicament 190 includes a particle or polymeric material carrying the medicament 190 and configured in a medicament-withholding state. In the medicament-withholding state the medicament is substantially not bioavailable to the animal 198 if the final dosage form 1102 is administered to the animal 198. The particle or polymeric material is modifiable ex vivo by an exposure to the stimulus 192 to carry the medicament in a medicament-supplying state wherein the medicament is substantially bioavailable to the animal if the final dosage form is administered to the animal. In an embodiment, the particle or polymeric material includes a particle or polymeric material carrying the medicament and configured in a medicament-retention state. In the medicament-retention state the medicament is substantially not bioavailable to the animal if the final dosage form is administered to the animal. The particle or polymeric material is modifiable ex vivo upon at least one of a post-manufacture or a field exposure to the stimulus to a medicament-release state. In medicament-release state, the medicament is substantially bioavailable to the animal if the final dosage form is administered to the animal. In an embodiment, the particle or polymeric material includes a particle or polymeric material carrying the medicament and configured in a medicament-holding state. In the medicament-holding state the medicament is substantially not bioavailable to the animal if the final dosage form is administered to the animal. The particle or polymer material is modifiable ex vivo to an in vivo release-facilitation state by an exposure to the stimulus to a medicament-release state. In the in vivo release-facilitation state the medicament is substantially bioavailable to the animal if the final dosage form is administered to the animal.

In an embodiment, the particle or polymeric material 1580 includes a particle or polymeric material having a premodification characteristic that results in an insignificant uptake of the particle or polymeric material in the gastrointestinal tract of the animal 198. In an embodiment, the particle or polymeric material includes an intact particle or polymeric material having a premodification characteristic that results in an insignificant uptake of the particle or polymeric material in the gastrointestinal tract of the animal. In an embodiment, the particle or polymeric material includes at least one of a gel, gel matrix, or hydrogel structure covalently bonded to the medicament using a photo labile bond. An example of a medicament covalently bonded to a hydrogel using photo labile bonds, and the medicament is not be released unless the gel matrix is exposed to enough light to break the bonds is described in U.S. Pat. No. 6,985,770 to Nyhart, Jr. An example of a medicament conjugated to dendrimers using photocleavable or labile linkers, which can be made to release the drug using light or through acid cleavage is described in Y. Qiu, supra., and C. Henry, supra. In an embodiment, the particle or polymeric material includes at least one of a dendrimer, dendrimsome, or dendriplex material. Examples of photo-labile, radio-labile, and enzyme-labile dendrimers are described in U.S. Pat. No. 6,471,968 to Baker, et al.; and examples of photo labile biocompatible dendrimers made from poly(propyleneimine) (POPAM) interiors and poly(amidoamine) (PAMAM) are described in U.S. Pat. No. 7,078,461 to Tomalia, et al.

In an embodiment, the particle or polymeric material 1580 includes a liposome carrier entrapping the medicament and having an intact particle size resulting in an insignificant uptake in the gastrointestinal tract of the animal 198. In an embodiment, the particle or polymeric material includes a liposome carrier having a particle size of at least approximately three microns. An example of a liposome carrier having a particle size of at least approximately three microns resulting an insignificant uptake in the gastrointestinal tract of the animal is described in D. Deshmukh, *Can intact liposomes be absorbed in the gut?* LIFE SCI. Jan. 19, 1981;28(3): 239-42; See also, MARC J. OSTRO, LIPOSOMES: FROM BIOPHYSICS TO THERAPEUTICS 140 (1987); 42 J. PHARMACY AND PHARMACOLOGY 821-826 (1990); 86 INTER. J. PHARMACY 239-246 (1992); PHARMACEUTICAL PARTICULATE CARRIERS: THERAPEUTIC APPLICATIONS Ch. 4 (p. 65, and FIGS. 15 and 16 at page 92) (edited By Alain Rolland 1993). In an embodiment, the particle or polymeric material includes a liposome having a particle size of at least approximately four microns.

In an embodiment, the particle or polymeric material 1580 includes at least one of a nanoparticle, a microsphere, or a polymeric microsphere responsive to the exposure to the stimulus 192. In an embodiment, the particle or polymeric material includes a pharmaceutically-acceptable inert particle or polymeric material.

In an embodiment, the stimulus 192 includes a non-ionizing radiation stimulus. In an embodiment, the stimulus includes an electromagnetic radiation stimulus. In an embodiment, the stimulus includes at least one of a light radiation, terahertz radiation, microwave radiation, and radio wave radiation stimulus. In an embodiment, the stimulus includes a magnetic stimulus. In an embodiment, the stimulus includes an electric stimulus. In an embodiment, the stimulus includes an energetic stimulus. In an embodiment, the stimulus includes a chemical stimulus. In an embodiment, the stimulus includes at least one of a mechanical, heat, or pressure stimulus. In an embodiment, the stimulus includes at least one of an activation stimulus, or an actuation stimulus. In an embodiment, the stimulus includes at least one of at least one of a thermal, acoustic, or ultrasound stimulus. In an embodiment, the stimulus includes a stimulus facilitating a release of the medicament by at least one of an expansion of a gel, gel matrix, or hydrogel carrier. In an embodiment, the stimulus includes a stimulus facilitating a release of the medicament by at least one of an expansion of a gel, gel matrix, or hydrogel carrier to allow a diffusion and bioavailability of the medicament. In an embodiment, the stimulus includes a stimulus facilitating the release of the medicament from the particle or polymeric carrier by at least one of a bursting of a liposome material, formation of a pore in a liposome material, or an unpacking of the particle or polymeric material.

In an embodiment, the particle or polymeric material 1580 includes a particle or polymeric material carrying the medicament 190 and configured in a medicament-retention state wherein the medicament is substantially not bioavailable to the animal 198 if the final dosage form is administered to the animal. The particle or polymeric material modifiable ex vivo by an exposure to the stimulus 192 to carry the medicament in a medicament-release state allowing an in vivo release of the medicament if the final dosage form is administered to the animal.

In an embodiment, the particle or polymeric material 1580 includes a first particle or polymeric material carrying the medicament 190, and a second particle or polymeric material (not shown) carrying the first particle or polymeric material. The second particle or polymeric material is configured in a first particle or polymeric material-retention state wherein the first particle or polymeric material is substantially not bioavailable to the animal if the final dosage form is administered to the animal 198. The second particle or polymeric material is modifiable ex vivo by an exposure to the stimulus 192 to carry the medicament a first particle or polymeric material-release state wherein the first particle or polymeric material is substantially bioavailable to the animal if the final dosage form is administered to the animal.

In an embodiment, the final dosage form 1502 further includes a transport medium 1560 suitable for administering the particle or polymeric material 1580 carrying the medicament to the animal 198. For example, the transport medium may include a carrier, admixture, diluent, or excipient. In another example, the transport medium may include a polymer, such as a hydrogel. An example of a polymer transport medium is described in United States Patent Application Pub. 2008/0050445 by Alcantar. In an embodiment, the final dosage form further includes an indicator substance (not illustrated) configured to indicate an exposure of the particle or polymeric substance to the stimulus 192. In an embodiment, the final dosage form further includes an indicator substance (not illustrated) configured to visually indicate an exposure of the particle or polymeric substance to the stimulus 192.

An embodiment includes the final dosage form for administering the medicament 190 to the animal 198. In this embodiment, the final dosage form includes the medicament and a particle or polymeric material. The particle or polymeric material carries the medicament. The particle or polymeric material is configured in a medicament-retention state wherein the medicament is substantially not bioavailable to the animal if the final dosage form is administered to the animal. The particle or polymeric material is modifiable ex vivo by an exposure to a first stimulus to carry the medicament a first medicament-release state wherein the medicament has a first bioavailability to the animal if the final dosage form is administered to the animal. The particle or polymeric material is modifiable ex vivo by an exposure to a second stimulus to carry the medicament in a second medicament-release state wherein the medicament has a second bioavailability to the animal if the final dosage form is administered to the animal. Understanding of this embodiment may be facilitated by reference to the preceding description in conjunction with FIG. 16, FIG. 20, or FIG. 21.

In an embodiment, the first bioavailability includes a first delivery rate of the medicament and the second bioavailability includes a second delivery rate of the medicament. For example, the particle or polymeric material may have a characteristic that include an adjustable pore size responsive to a temperature of the particle or polymeric material attained in response to a heat stimulus. The heat stimulus may include a microwave or a light source. The first stimulus may include an exposure of the particle or polymeric material to a first temperature, or to a given temperature for a first period of time. The second stimulus may include an exposure of the particle or polymeric material to a second temperature, or to a given temperature for a second period of time. For example, selective control of temperature-modulatable materials is described in G. Rao, et al., *Synthesis of Smart Mesoporous Materials*, MRS BULLETIN P7.8 (Spring 2003). For example, an adjustable porosity of an organic polymer membrane is described in R. Estrada, et al., *Smart polymeric membranes with adjustable pore size*, 52 International journal of polymeric materials 833-843 (No. 9, 2003). For example, a thermosensitive grafted polymeric system which can be triggered to release the loaded drug with an increase in temperature, induced by a magnetic thermal heating event, is described in I. Ankareddi, et al., *Development of a Magnetically Triggered Drug Delivery System using Thermoresponsive Grafted Polymer Networks with Magnetic Nanoparticles*, 2 NANOTECH 431-434 (Vol. 2, 2007). See also, R. Liburdy, et al., *Microwave-triggered liposomal drug delivery: investigation of amodel drug delivery system*, Engineering in Medicine and Biology Society 1163-1164, (Vol. 4, November 1989) (Images of the Twenty-First Century, Proceedings of the Annual International Conference of the IEEE Engineering). In another example, the first stimulus may include a first ultrasound power density and the second stimulus may include a second ultrasound power density. For example, bioavailability of polymeric micelles as a variable function of ultrasound power density is at least suggested by A. Marin, et al., *Acoustic activation of drug delivery from polymeric micelles: effect of pulsed ultrasound*, 71 JOURNAL OF CONTROLLED RELEASE 239-249 (Issue 3, 28 Apr. 2001).

In an embodiment, the final dosage form 1502 configurable to administer a medicament to the animal 198 includes a containment element 1540. In an embodiment, the containment element 1540 may be substantially similar to the containment element 140 described in conjunction with FIG. 1. In an embodiment, the containment element 1540 includes a pH-sensitive component of a liposome. For example, S. Cho, et al, *pH-dependent release property of dioleoylphosphatidyl ethanolamine liposomes*, 25 KOREAN JOURNAL OF CHEMICAL ENGINEERING 390 (No. 2, 2008) describes a pH-sensitive liposome prepared by a detergent removal method that retains at neutral pH (6-8), and releases at pH 5. In an embodiment, the containment element includes tunable component of a liposome. For example, I. Hafez, et al., *Tunable pH-Sensitive Liposomes Composed of Mixtures of Cationic and Anionic Lipids*, 79 BIOPHYSICAL JOURNAL 1438 (Issue 3, 2000) describes a tunable liposome using cationic and anionic lipid mixtures (cholesteryl hemisuccinate (CHEMS) and N,N-dioleoyl-N, N-dimethylammonium chloride. In an embodiment, the containment element includes pH sensitive Chitosan and polyacrylamide copolymer hydrogels releasing contained substances upon pH changes. For example, as described in P. Bonina, et al., 19 JOURNAL OF BIOACTIVE AND COMPATIBLE POLYMERS 101 (No. 2, 2004). In an embodiment, the containment element includes a pH sensitive Chitosan and polyalkyleneoxide-maleic acid copolymer releasing substances on pH changes. For example, as described in T. Yoshizawa, et al., *pH- and temperature-sensitive permeation through polyelectrolyte complex films composed of chitosan and polyalkyleneoxide-maleic acid copolymer*, 241 JOURNAL OF MEMBRANE SCIENCE 347 (Issue 2, 2004). In an embodiment, the containment element includes an acrylic acid (AA) grafted onto porous polypropylene (PP) producing a pH sensitive membrane. For example, as described in Y. Wang, et al., *pH sensitive polypropylene porous membrane prepared by grafting acrylic acid in supercritical carbon dioxide*, 45 POLYMER 855 (No. 3, 2004).

Figure 22:
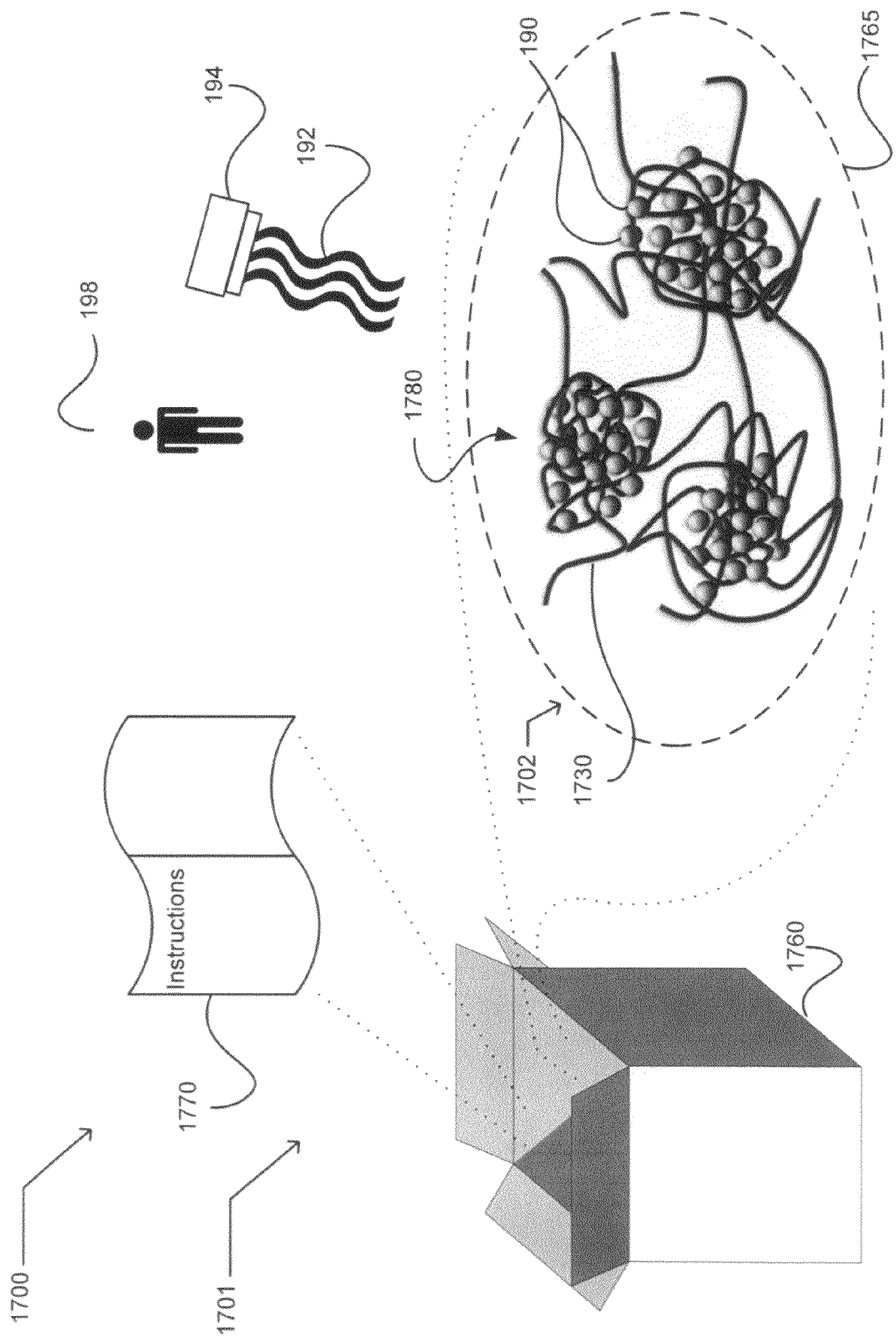
FIG. 22 illustrates an example environment that includes an article of manufacture.

FIG. 22 illustrates an example environment 1700 that includes an article of manufacture 1701. The article of manufacture includes at least one final dosage form 1702 for administering the medicament 190 to the animal 198. The final dosage form includes the medicament, a particle or polymeric material 1780 carrying the medicament, and an instruction 1770. In an embodiment, the particle or polymeric material carrying the medicament may include the particle or polymeric material described in conjunction with FIG. 20. In an embodiment, the particle or polymeric material carrying the medicament may include a particle or polymeric material described in this paper. An embodiment of the particle or polymeric material carrying the medicament is depicted in FIG. 22 as a gel material for illustrative purposes. The particle or polymeric material has a characteristic response 1730 to the stimulus 192 that releases an engaged, retained, or entrapped at least one molecule of the medicament 190 from the particle or polymeric material. For example, a characteristic response of a particular particle or microparticle may include a releasing bursting, expanding, cleaving, or degradation of the particular particle or microparticle in response to a microwave stimulus.

The particle or polymeric material 1780 is in a medicament-retention state wherein the medicament is substantially not bioavailable to the animal 198 after administration of the final dosage form. The particle or polymeric material is modifiable ex vivo to a medicament-release state by an exposure to the stimulus 192 wherein the medicament is substantially bioavailable to the animal after administration of the final dosage form.

The instruction 1770 includes an instruction for the exposure of the particle or polymeric material 1780 to a human-initiated stimulus 192 sufficient to transform the particle or polymeric material to allow a discharge of at least a portion of the therapeutically effective amount of the medicament from the particle or polymeric carrier.

In an embodiment, the article of manufacture 1701 further includes a label associated with the at least one final dosage form 1702 or an insert into a package 1760 containing the at least one final dosage form, the insert providing the instructions 1770. In an embodiment, the final dosage form further includes a transport medium 1765 suitable for administering the particle or polymeric material 1780 carrying the medicament 190 to the animal 195. In an embodiment, the final dosage form further includes an indicator substance (not shown) configured to indicate an exposure of the particle or polymeric material to the stimulus 192.

Figure 23:
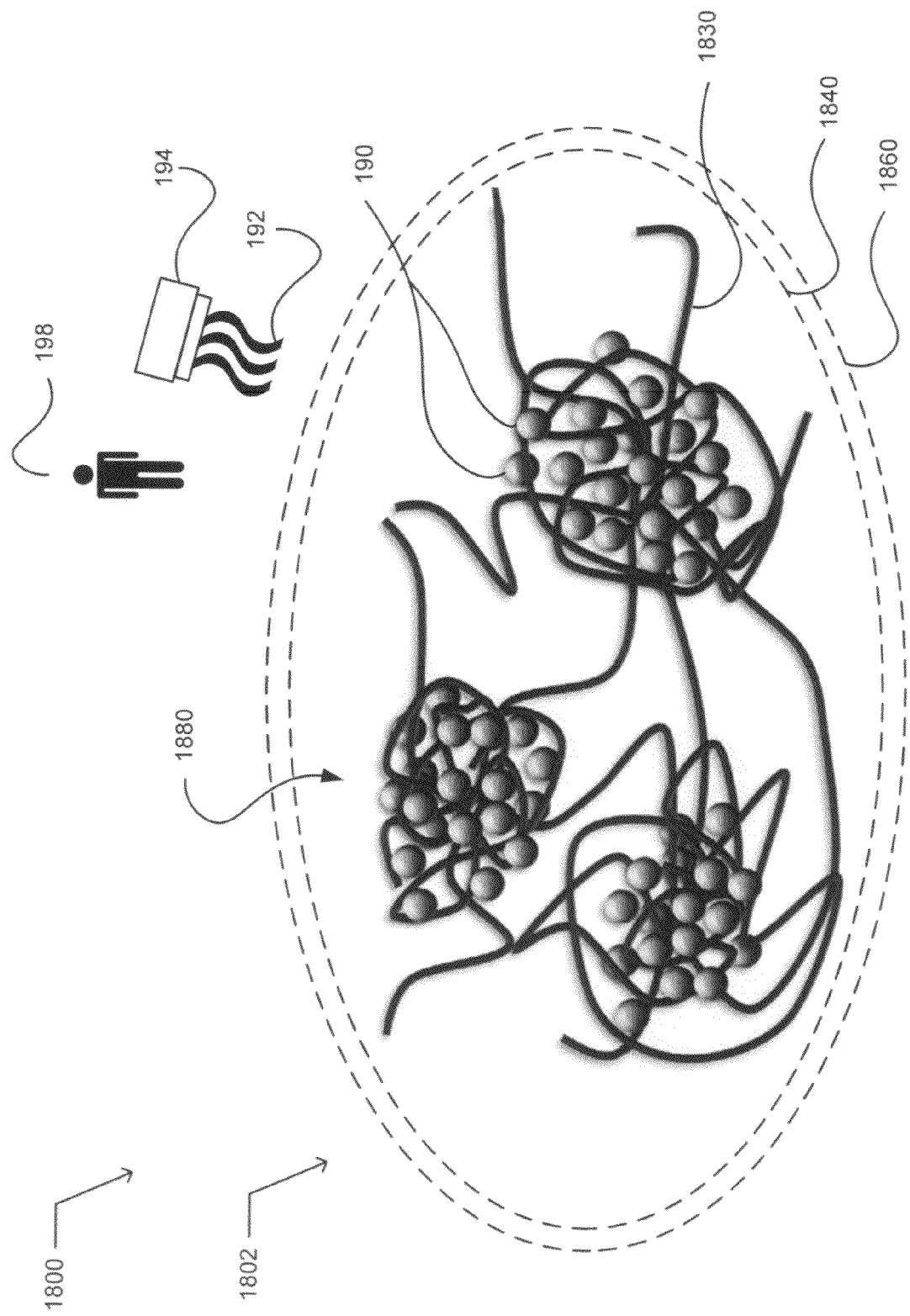
FIG. 23 illustrates an example environment that includes a final dosage form for administering the medicament to an animal.

FIG. 23 illustrates an example environment 1800 that includes a final dosage form 1802 for administering the medicament 190 to the animal 198. The final dosage form includes at least one molecule of the medicament and a particle or polymeric carrier 1880, is depicted as a gel, and which is operable to bind the at least one molecule of the medicament. The particle or polymeric carrier is configured in a first medicament-bioavailability state, and modifiable ex vivo to a second medicament-bioavailability state by an exposure to a stimulus, illustrated as the stimulus 192. In an embodiment, the particle or polymeric carrier operable to bind the at least one molecule of the medicament has a characteristic response 1830 to a stimulus, such as the stimulus 192, that releases the bound at least one molecule of the medicament 190 from the particle or polymeric carrier. An example of such characteristic response is described in conjunction with FIG. 21. In another embodiment, the particle or polymeric carrier operable to bind the at least one molecule of the medicament has a characteristic response 1830 to a stimulus, such as the stimulus 192, that unbinds or releases the at least one molecule of the medicament 190 from the particle or polymeric carrier.

In an embodiment, the particle or polymeric carrier 1880 includes a pharmaceutically-acceptable inert particle or polymeric carrier operable to bind the at least one molecule of the medicament 190. In an embodiment, the particle or polymeric carrier includes a particle or polymeric carrier operable to engage, retain, or entrap at least one molecule of the medicament.

In an embodiment, the first medicament-bioavailability state is configured to retard medicament release in vivo and the second medicament-bioavailability state is configured to allow medicament release in vivo. In an embodiment, the first medicament-bioavailability state is configured to allow medicament release in vivo and the second medicament-bioavailability state is configured to retard medicament release in vivo.

In an embodiment, the particle or polymeric carrier 1860 includes a liposome carrier operable to bind the at least one molecule of the medicament 190 and having an intact particle size resulting in an insignificant uptake in the gastrointestinal tract of the animal 198. In an embodiment, liposome carrier operable to bind the at least one molecule of the medicament and having an intact particle size resulting in an insignificant uptake in the gastrointestinal tract of the animal includes a liposome carrier operable to bind the at least one molecule of the medicament and having an intact particle size of at least approximately one micron. For a description of an example, see, P. Hoet, et al., *Nanoparticles—known and unknown health risks,* 2 JOURNAL OF NANOBIOTECHNOLOGY 12, at section 4 (2004). In an embodiment, the liposome carrier operable to bind the at least one molecule of the medicament and having an intact particle size resulting in an insignificant uptake in the gastrointestinal tract of the animal includes a liposome carrier operable to bind the at least one molecule of the medicament and having an intact particle size of at least approximately three microns. In an embodiment, the liposome carrier operable to bind the at least one molecule of the medicament and having an intact particle size resulting in an insignificant uptake in the gastrointestinal tract of the animal includes a liposome carrier operable to bind the at least one molecule of the medicament and having an intact particle size of at least approximately four microns.

In an embodiment, the final dosage form 1802 further includes a transport medium 1860 suitable for administering to the animal 198 the particle or polymeric carrier 1880 holding the at least one molecule of the medicament 190. In an embodiment, the final dosage form of claim further includes an indicator substance (not shown) configured to visually indicate an exposure of the particle or polymeric carrier holding the at least one molecule of the medicament to the stimulus 192.

In an embodiment, the final dosage form 1802 configurable to administer a medicament 190 to the animal 198 includes a containment element 1840. In an embodiment, the containment element 1840 may be substantially similar to the containment element 140 described in conjunction with FIG. 1. In an embodiment, the containment element 1840 may be substantially similar to the containment element 1540 described in conjunction with FIG. 20.

FIG. 24 illustrates an example environment 1900 that includes a final dosage form 1905 and an operational flow 1910. The final dosage form includes the medicament and a particle or polymeric material. The particle or polymeric material carries the medicament in the medicament-retention state wherein the medicament is substantially not bioavailable if the final dosage form is administered to the animal, such as the animal 198. The particle or polymeric material is transformable to the medicament-release state by the exposure to a stimulus, such as the stimulus 192, wherein the medicament is substantially bioavailable if the final dosage form is administered to the animal. In an embodiment, the final dosage form is at least similar to the final dosage form 1102 described in conjunction with FIG. 16. In an embodiment, the final dosage form is at least similar to the final dosage form 1502 described in conjunction with FIG. 20. In an embodiment, the final dosage form may is least similar to the final dosage form 1802 described in conjunction with FIG. 23. After a start operation, the operational flow includes an activation operation 1920. The activation operation includes initiating an exposure of the particle or polymeric material of the final dosage form to a stimulus, such as the stimulus 192 previously described. The initiated stimulus is selected to transform the particle or polymeric material from the medicament-retention state to the medicament-release state.

In an embodiment, the final dosage form 1905 further includes a containment element retaining the medicament within the final dosage form until the final dosage form is introduced into the animal. In an embodiment, the final dosage form further includes an indicator element configured to indicate an exposure of the particle or polymeric material to the stimulus.

FIG. 25 illustrates alternative embodiments of the activation operation 1920 of FIG. 24. The activation operation may include an operation 1922, an operation 1924, or an operation 1926. The operation 1922 includes an initiated stimulus having a parameter selected to transform the particle or polymeric material from a medicament-retention state to a medicament-release state. The operation 1924 includes an initiated stimulus having at least one of a stimulation characteristic or a spatial characteristic selected to transform the particle or polymeric material from a medicament-retention state to a medicament-release state. The operation 1926 includes initiating a first exposure of a particle or polymeric material of the final dosage form to a stimulus, the first initiated stimulus selected to transform the particle or polymeric material from a medicament-retention state to a medicament-release state. The operation 1926 also includes receiving an indication of the first exposure of the release element of the final dosage form to the stimulus, the indication generated in response to an indicator element of the final dosage form configured to indicate an exposure of the release element to the stimulus. The operation 1926 further includes initiating a second exposure of the release element of the final dosage form to the stimulus, the initiated second exposure stimulus selected to further transform the release element from the medicament-holding state to the medicament-discharge state.

FIG. 26 illustrates an example embodiment of a final dosage form 2002 for administering a medicament, such as the medicament 190 as previously described, to an animal, such as the animal 198 as previously described. The final dosage form includes means 2010 for entrapping at least one molecule of the medicament. The final dosage form also includes means 2020 for controlling an availability of the entrapped at least one molecule of medicament, wherein the entrapped at least one molecule of medicament is initially substantially not bioavailable if the final dosage form is administered to the animal. The availability of the entrapped medicament is modifiable ex vivo by an exposure to a stimulus, such as the stimulus 192 described above, to be substantially bioavailable if the final dosage form is administered to the animal. The final dosage form further includes means 2030 for protecting the means 2010 for entrapping at least one molecule of the medicament from an ex vivo environment of the final dosage form. The final dosage form also includes the medicament 190.

In an embodiment, the means 2020 for controlling an availability of the entrapped at least one molecule of medicament includes means 2022 for controlling an availability of the entrapped at least one molecule of medicament and having a premodification characteristic resulting in an insignificant uptake in the gastrointestinal tract of the animal. In an embodiment, the final dosage form further includes means 2050 for indicating an exposure to the stimulus by the means for controlling an availability of the entrapped at least one molecule of medicament. In an embodiment, the final dosage form further includes means 2060 for containing the medicament within the final dosage form before the final dosage form is administered to the animal. In an embodiment, the final dosage form further includes means 2070 for carrying the final dosage form into the animal.

Figure 27:
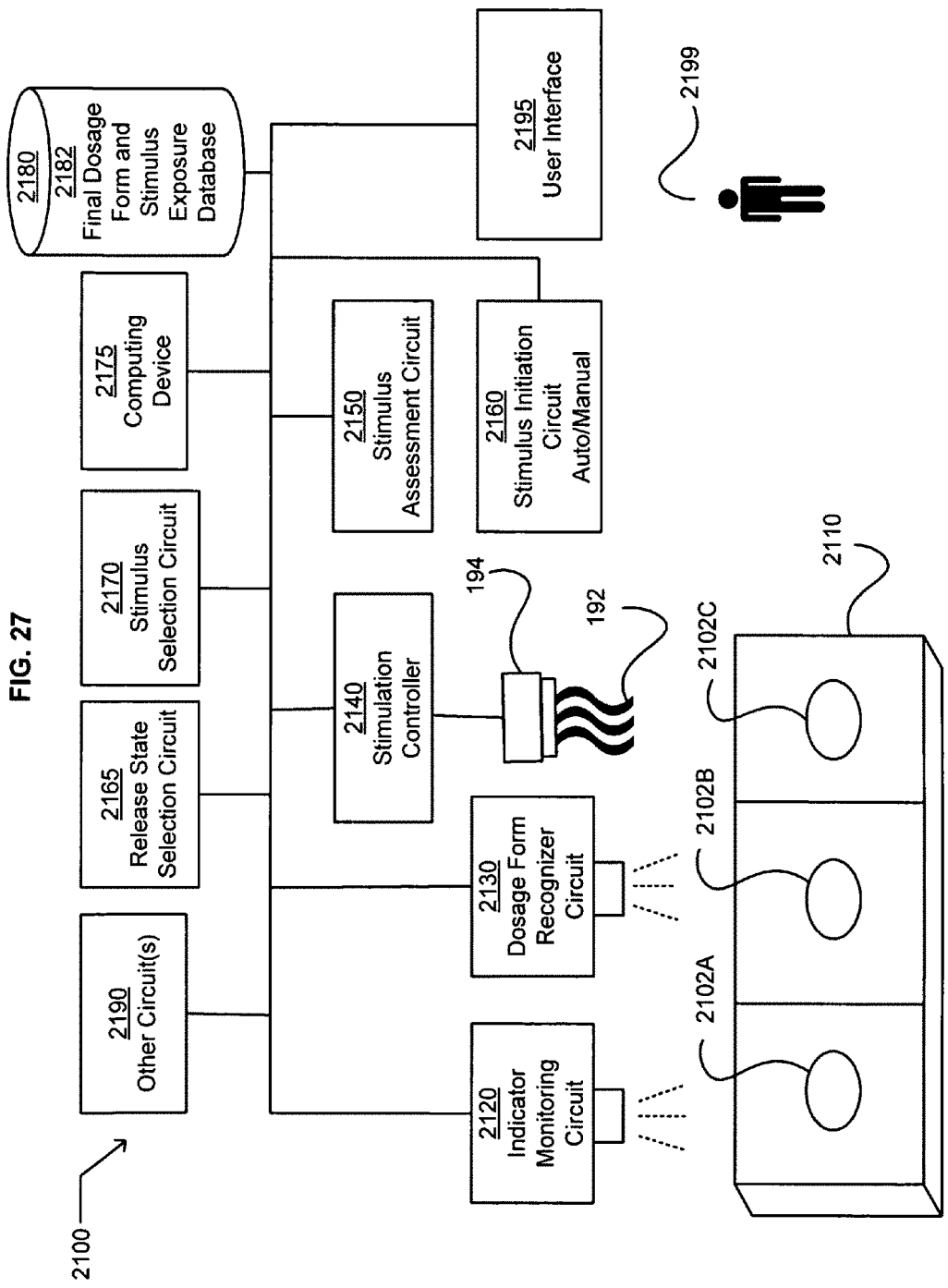
FIG. 27 illustrates an example system in which embodiments may be implemented.

FIG. 27 illustrates an example system 2100. The system includes a final dosage form holder 2110 configured to carry at least one instance of a final dosage form, illustrated as final dosage form holder portions 2102A-2102C. The system also includes the stimulus source 194 having at least one controllable stimulus parameter or characteristic, operable to generate the stimulus 192, and configured to direct the stimulus toward at least a portion of the final dosage form holder. In an embodiment, the stimulus generator is operable to direct the stimulus toward a selectable portion of the final dosage form holder, such as the portion 2102A, or a portion of the portion 2102A. The system further includes a stimulation controller 2140 operable to regulate a controllable parameter of the stimulus source. In an embodiment, the stimulation controller is operable to regulate the controllable stimulus parameter by regulating the stimulus source, by regulating a stimulus transmission pathway between the stimulus source and the final dosage form holder, or by regulating which spatial portion of the dosage form receives the stimulus.

The system 2100 also includes a stimulation initiation circuit 2160 operable to initiate a stimulus 192 having a selected stimulus parameter or characteristic in response to a received input. In an embodiment, the stimulation initiation circuit is configured to transmit using the user interface 2195 a human perceivable indication of an assessed quality or quantity of the stimulus received by a final dosage form. The stimulation initiation circuit may receive input from a human 2199, such as pharmacist or health care provider, or from a stimulus assessment circuit 2150. The stimulus assessment circuit is operable to monitor the stimulus received by a final dosage form in response to data received from an indicator monitoring circuit 2120. The indicator monitoring circuit is operable to monitor an indicator substance portion of the at least one instance of the final dosage form. In an embodiment, the stimulus assessment circuit is operable to generate a signal usable to provide a human perceivable indication of the assessed stimulus received by a final dosage form via the user interface.

In an embodiment, the system 2100 includes a final dosage form recognizer circuit 2130 operable to generate data usable in distinguishing a final dosage form. In an embodiment, the system includes a release-state selection circuit 2165. In an embodiment, the release-state selection circuit is responsive to signals indicative of a chosen medicament bioavailability of a final dosage form. In an embodiment, the release-state selection circuit is responsive to a human 2199 initiated input entered into the user interface 2195. In an embodiment, the system includes a stimulus selection circuit 2170. In an embodiment, the stimulus selection circuit is responsive to data generated by the final dosage form recognizer circuit. In an embodiment, the stimulus selection circuit is responsive to a human 2199 initiated input.

In an embodiment, the system 2100 includes a computer-readable storage medium 2180 configured by a final dosage form and stimulus exposure database 2182. The final dosage form and stimulus exposure database may include instructions for modification or state transformation of the final dosage form for an efficacious administration to an animal by an exposure of the final dosage form to a stimulus, such as the instructions 670 of FIG. 6, the instructions 1270 of FIG. 17, or the instructions 1770 of FIG. 22. The final dosage form and stimulus exposure database may include instructions for modification or state transformation of the final dosage form for an efficacious administration to an animal by an exposure of the final dosage form to the stimulus, such as electronically published instructions, or such as indicated by a reference book, such as *Physician's Desk Reference*. The final dosage form and stimulus exposure database may include an electronically-stored database relating stimuli and medicament-bioavailability of the final dosage form, a computer-implemented decision table, a digitally-maintained final dosage form transformation table, or a digital library correlating medicament-bioavailability of the final dosage form and stimuli.

In an embodiment, the system 2100 may be used to modify or transform a bioavailability of a medicament associated with a final dosage form described herein. For example, the system may be used to modify or transform a bioavailability of a medicament associated with the final dosage form 102 described in conjunction with FIG. 1; the final dosage form 202 described in conjunction with FIG. 2; with the final dosage form 302 described in conjunction with FIG. 3; with the final dosage form 402 described in conjunction with FIG. 4; with the final dosage form 502 described in conjunction with FIG. 5; with the final dosage form 602 described in conjunction with FIG. 6; with the final dosage form 1002 described in conjunction with FIG. 15; with the final dosage form 1102 described in conjunction with FIG. 16; with the final dosage form 1202 described in conjunction with FIG. 17; with the final dosage form 1502 described in conjunction with FIG. 20; with the final dosage form 1702 described in conjunction with FIG. 22; or with the final dosage form 1802 described in conjunction with FIG. 23.

In an embodiment, the system 2100 may be used to implement an operational flow modifying or transforming a bioavailability of a medicament associated with a final dosage form described herein. For example, the system may be used to implement the example operational flow 700 modulating a medicament-release characteristic of a final dosage form described in conjunction with FIG. 7; the example operational flow 800 fulfilling a request specifying a dose of a medicament for an individual animal described in conjunction with FIG. 9; the example operational flow 1300 modifying a medicament availability characteristic of a final dosage form described in conjunction with FIG. 18; or the example operation flow 1910 described in conjunction with FIG. 24.

Figure 28:
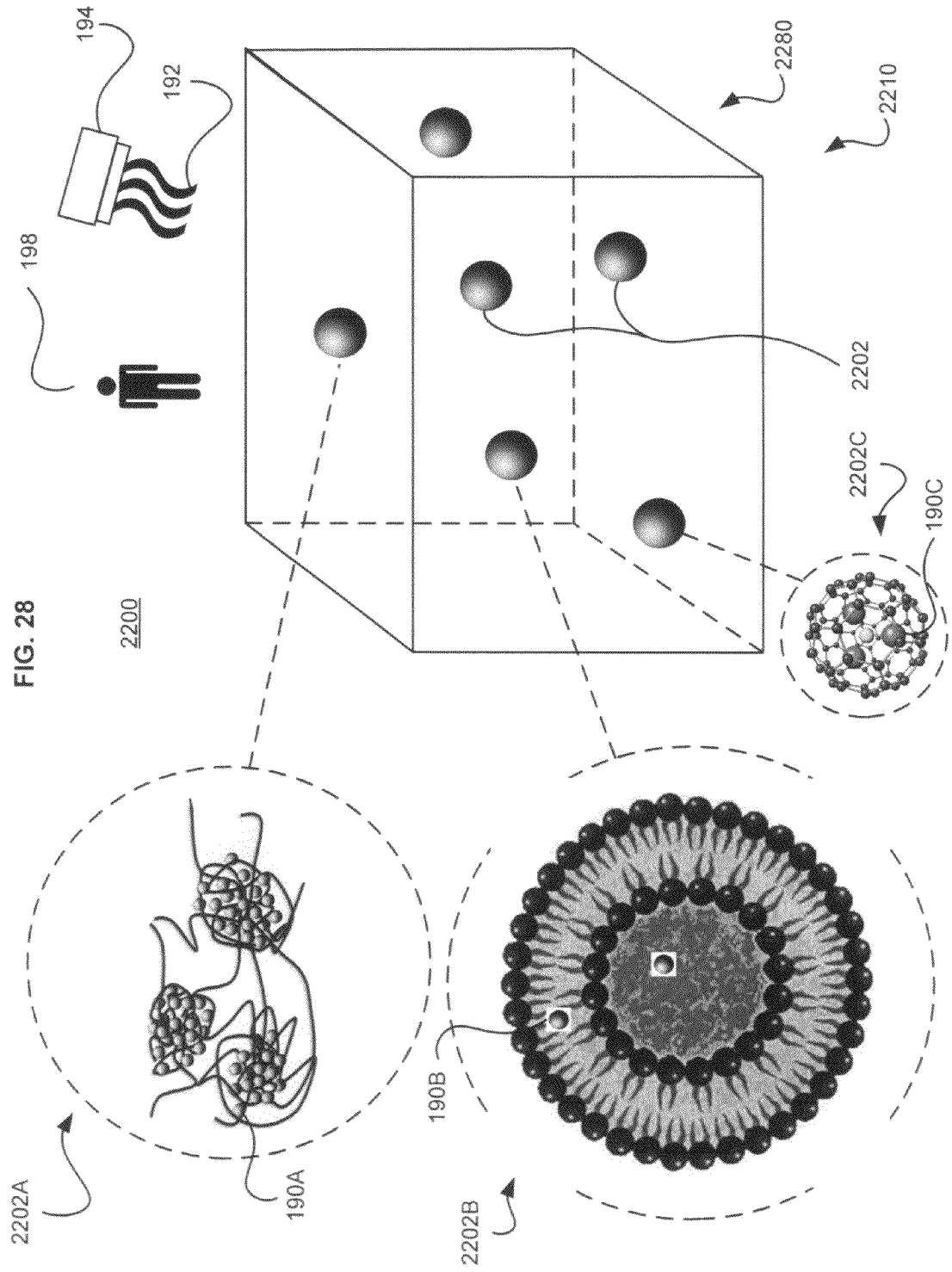
FIG. 28 illustrates an example environment that includes a final dosage form for administering the medicament to an animal.

FIG. 28 illustrates an example environment 2200. The environment includes a final dosage form 2210 for administering the medicament 190 to the animal 198. The final dosage form includes a particle or polymeric 2202 carrying the medicament in a first medicament-release state wherein the medicament is available to the animal in a first bioavailability if the final dosage form is administered to the animal. The particle or polymeric material is modifiable ex vivo by an exposure to a stimulus, such as the stimulus 192 to carry the medicament in a second medicament-release state wherein the medicament is available to the animal in a second bioavailability if the final dosage form is administered to the animal.

The particle or polymeric material may include a gel, illustrated as a hydrogel 2202A, carrying a medicament 190A in a first medicament-release state wherein the medicament is available to the animal in a first bioavailability if the final dosage form is administered to the animal. The particle or polymeric material may include a liposome, illustrated as a liposome 2202B, carrying a medicament 190B in a first medicament-release state wherein the medicament is available to the animal in a first bioavailability if the final dosage form is administered to the animal. The particle or polymeric material may include a nanoparticle, illustrated as a nanosphere 2202C, carrying a medicament 190C in a first medicament-release state wherein the medicament is available to the animal in a first bioavailability if the final dosage form is administered to the animal.

In an embodiment, the first bioavailability to the animal 198 includes a first bioavailability characteristic to the animal and the second bioavailability to the animal includes a second bioavailability characteristic. In an embodiment, the first bioavailability characteristic includes the medicament 190 having a bioavailability in the small intestine of the animal, and the second bioavailability characteristic includes the medicament having a bioavailability in the large intestine of the animal. In an embodiment, the first bioavailability characteristic includes the medicament having a first medicament quantity available to the animal, and the second bioavailability characteristic includes the medicament having a second medicament quantity available to the animal. For example, the first medicament quantity may be 100 mg and the second medicament quantity may be 200 mg. In an embodiment, the first bioavailability characteristic includes the medicament having an immediate release medicament quantity available to the animal, and the second bioavailability characteristic includes the medicament having a time-release medicament quantity available to the animal. In an embodiment, the first bioavailability characteristic includes the medicament having a first time-release rate, and the second bioavailability characteristic includes the medicament having a second time-release rate. In an embodiment, the first bioavailability characteristic includes the medicament having a first release-decay rate medicament release to the animal, and the second bioavailability characteristic includes the medicament having a second release-decay rate medicament release to the animal. In an embodiment, the first bioavailability characteristic includes the medicament having a first pH sensitivity, and the second bioavailability characteristic includes the medicament having a second pH sensitivity.

In an embodiment, the first bioavailability to the animal 198 includes a first bioavailability characteristic to the animal and the second bioavailability to the animal includes a second bioavailability characteristic. In this embodiment, the second bioavailability characteristic to the animal may include a substantially different bioavailability characteristic to the animal than the first bioavailability characteristic to the animal. In an alternative of this embodiment, the first bioavailability characteristic to the animal includes a first medicament dosage and the second bioavailability characteristic to the animal includes a second medicament dosage. In another alternative of this embodiment, the first bioavailability characteristic to the animal includes a first medicament release kinetic and the second bioavailability characteristic to the animal includes a second medicament release kinetic. In a further alternative of this embodiment, the first bioavailability characteristic to the animal includes a first medicament release profile and the second bioavailability characteristic to the animal includes a second medicament release profile. In an alternative of this embodiment, the first bioavailability characteristic to the animal includes a first medicament release rate and the second bioavailability characteristic to the animal includes a second medicament release rate. In another alternative of this embodiment, the first bioavailability characteristic to the animal includes a first medicament release delay time and the second bioavailability characteristic to the animal includes a second medicament release delay time. In a further alternative of this embodiment, the first bioavailability characteristic to the animal includes a first medicament release pH dependence and the second bioavailability characteristic to the animal includes a second medicament release pH dependence.

In an embodiment, the particle or polymeric material 2202 carrying the medicament 190 includes an inert particle or polymeric material carrying the medicament. In an embodiment, the particle or polymeric material carrying the medicament includes a particle or polymeric material carrying the medicament in an association. In an embodiment, the particle or polymeric material carrying the medicament includes a particle or polymeric material encapsulating the medicament. In an embodiment, the particle or polymeric material carrying the medicament includes a particle or polymeric material encompassing the medicament. In an embodiment, the particle or polymeric material carrying the medicament includes a particle or polymeric material at least one of engaging, retaining, or binding the medicament. In an embodiment, the particle or polymeric material carrying the medicament includes a particle or polymeric material carrier conjugated with the medicament. In an embodiment, the particle or polymeric material carrying the medicament includes the medicament taken-up by the particle or polymeric material.

In an embodiment, the final dosage form 2210 further includes a transport medium 2280 suitable for delivering the particle or polymeric material binding the medicament to the animal. In an embodiment, the transport medium may include a carrier, admixture, diluent, or excipient. In an embodiment, the final dosage form includes an indicator substance (not illustrated) associated with the particle or polymeric material and configured to indicate an exposure to the stimulus of the particle or polymeric material carrying the medicament.

Figure 29:
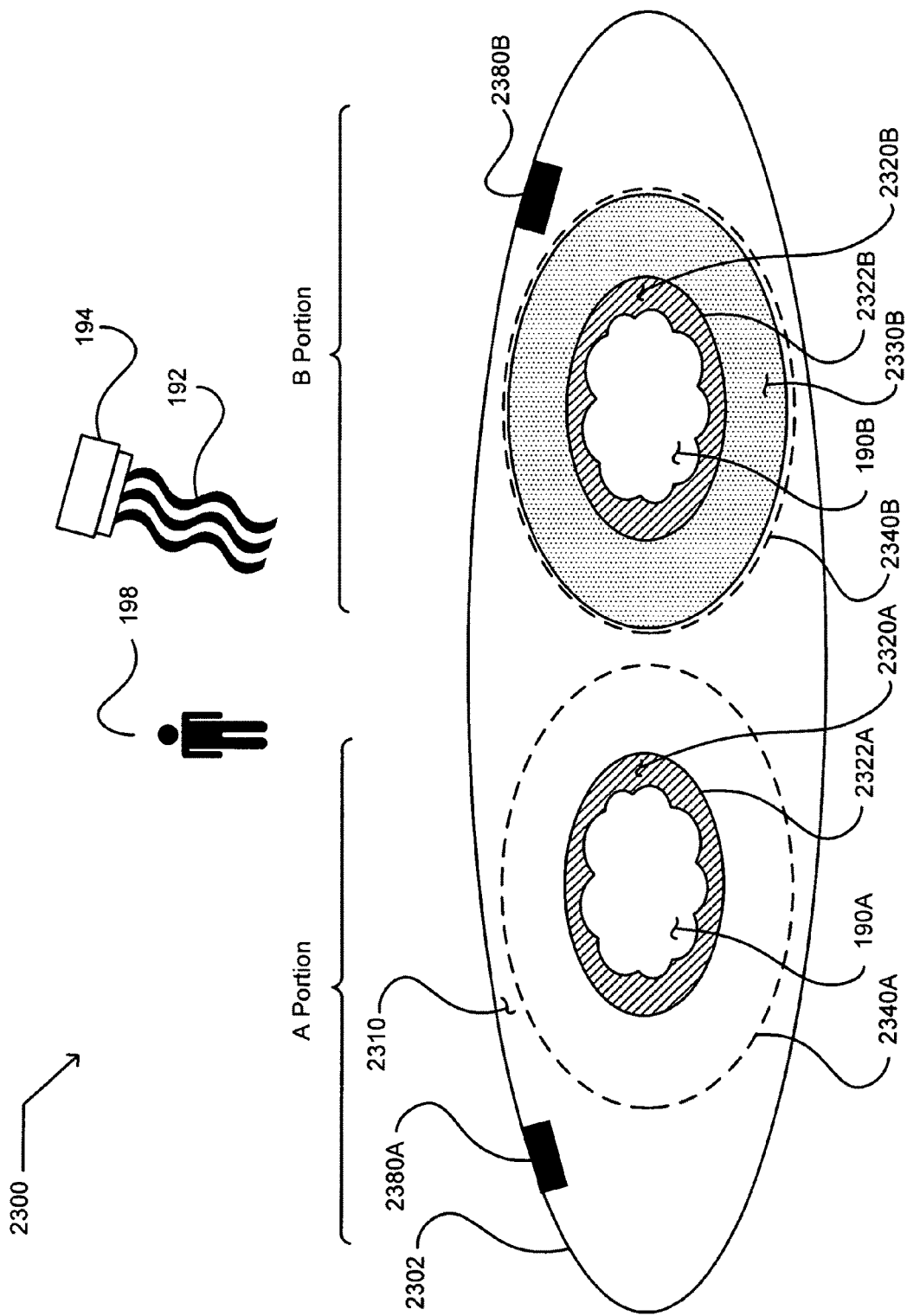
FIG. 29 illustrates an example environment that includes a final dosage form for administering the medicament to an animal.

FIG. 29 illustrates an example environment 2300. The example environment includes a final dosage form 2310 for administering the medicament 190 to the animal 198. The final dosage form includes a dosage portion labeled as "A Portion" carrying a medicament 190A in a first medicament-release state wherein the medicament is bioavailable to the animal if the final dosage form is administered to the animal. In an embodiment, the dosage portion "A" includes a chamber 2320A defining a chamber periphery 2322A. The final dosage portion includes another dosage portion labeled as "B Portion" carrying another medicament 190B and including a release element 2330B in a first medicament-release state wherein the another medicament has a first bioavailability to the animal if the final dosage form is administered to the animal in the first medicament-release state. The release element is modifiable ex vivo to second medicament-release state by an exposure to stimulus, wherein the another medicament has a second bioavailability to the animal if the final dosage form is administered to the animal in the second medicament-release state. In an embodiment, the dosage portion "B" includes a chamber 2320B defining a chamber periphery 2322B.

FIG. 30 illustrates an example environment 2400 that includes a final dosage form 2405 and an operational flow 2410. The final dosage form includes a medicament. The final dosage form also includes a particle or polymeric material carrying the medicament in a first medicament-release state wherein the medicament is available to the animal in a first bioavailability if the final dosage form is administered to the animal. The particle or polymeric material is modifiable ex vivo by an exposure to a stimulus to carry the medicament in a second medicament-release state wherein the medicament is available to the animal in a second bioavailability if the final dosage form is administered to the animal. In an embodiment, the final dosage form may be implemented using the final dosage form 2210 described in conjunction with FIG. 28.

The operational flow 2410 includes, after a start operation, a modification operation 2420. The modification operation includes transforming the particle or polymeric material to the second medicament-release state by initiating an ex vivo exposure of the particle or polymeric material to the stimulus. The operational flow includes an end operation. In an embodiment, the modification operation 2420 may be implemented using the system 2100 described in conjunction with FIG. 27.

FIG. 31 illustrates an example article of manufacture 2502 for administering medicament to an animal. The article includes means 2510 for releasably encompassing a medicament in a first state wherein the medicament is available to the animal in a first bioavailability if the final dosage form is administered to the animal. The means for releasably encompassing the medicament in a first state is modifiable ex vivo by an exposure to a stimulus to releasably encompass the medicament in a second state, wherein the medicament is available to the animal in a second bioavailability if the final dosage form is administered to the animal. The article also includes the medicament 190.

In an embodiment, the article 2502 includes means 2530 for protecting the means 2510 for releasably encompassing the medicament in a first state. In an embodiment, the article includes means 2550 for indicating an exposure to the stimulus of the means for releasably encompassing the medicament in a first state. In an embodiment, the article includes means 2560 for containing the medicament within the final dosage form before the final dosage form is administered to the animal. In an embodiment, the article includes means 2570 for carrying the final dosage form into the animal.

FIG. 32 illustrates an example environment 2600. The environment includes a final dosage form 2610 for administering medicament 190 to the animal 198. The final dosage form includes a release-control substance 2602 carrying the medicament in a first medicament-release state wherein the medicament has a first bioavailability to the animal if the final dosage form is administered to the animal. The release-control substance is modifiable ex vivo by an exposure to a first stimulus, such as a first stimulus 192A (not separately shown) of the stimulus 192, to carry the medicament in a second medicament-release state wherein the medicament has a second bioavailability to the animal if the final dosage form is administered to the animal. The release-control substance is modifiable ex vivo by an exposure to second stimulus, such as a second stimulus 190B (not shown) of the stimulus 192, to carry the medicament in a third medicament-release state wherein the medicament has a third bioavailability to the animal if the final dosage form is administered to the animal. The final dosage form also includes the medicament 190.

The release-control substance 2602 may include a gel, illustrated as a hydrogel 2602A carrying a medicament 190A in a first medicament-release state wherein the medicament is available to the animal in a first bioavailability if the final dosage form is administered to the animal. The release-control substance may include a liposome, illustrated as a liposome 2602B carrying a medicament 190B in a first medicament-release state wherein the medicament is available to the animal in a first bioavailability if the final dosage form is administered to the animal. The release-control substance may include a nanoparticle, illustrated as a nanosphere 2602C carrying a medicament 190C in a first medicament-release state wherein the medicament is available to the animal in a first bioavailability if the final dosage form is administered to the animal.

In an embodiment, the first bioavailability to the animal 198 includes the medicament 190 being substantially not bioavailable to the animal. In an embodiment, the first bioavailability to the animal includes the medicament being substantially bioavailable to the animal. In this embodiment, the second bioavailability to the animal may include the medicament being substantially bioavailable to the animal, wherein the second bioavailability to the animal is substantially different from the first bioavailability to the animal. In an embodiment, the second bioavailability to the animal includes the medicament being substantially not bioavailable to the animal. In an embodiment, the second bioavailability to the animal includes the medicament being substantially bioavailable to the animal. In an embodiment, the third bioavailability to the animal includes the medicament being substantially not bioavailable to the animal. In an embodiment, the third bioavailability to the animal includes the medicament being substantially bioavailable to the animal.

In an embodiment, the third bioavailability to the animal 198 includes the medicament 190 being substantially bioavailable to the animal, wherein the third bioavailability to the animal is substantially different from the second bioavailability to the animal. For example, the third bioavailability may be substantially different from the second bioavailability in dosage amount, dosage rate, or dosage profile. In an embodiment, the third bioavailability to the animal includes the medicament being substantially bioavailable to the animal, wherein the third bioavailability is substantially different from both the first bioavailability and the second bioavailability. In an embodiment, the first bioavailability includes a first bioavailability characteristic, the second bioavailability includes a second bioavailability characteristic, and the third bioavailability includes a third bioavailability characteristic.

In an embodiment, the release-control substance 2602 includes a biocompatible substance. In an embodiment, a biocompatible substance includes a substance having a quality of not having toxic or injurious effects on biological systems of the animal. In another embodiment, a biocompatible substance includes a substance that does not elicit any undesirable local or systemic effects in the animal. In an embodiment, the release-control substance includes a release-control substance having a modifiable medicament release characteristic. In an embodiment, the release-control substance includes a release-control substance carrying the medicament 190 in an initial medicament-retention state. In an embodiment, the release-control substance includes a particle. In an embodiment, the release-control substance includes a polymeric material. In an embodiment, the release-control substance includes a small molecule. In an embodiment, the release-control substance includes a capsule structure.

In an embodiment, the second stimulus 192B (not separately shown) includes a substantially different category of stimulus than the first stimulus 192A. In an embodiment, the second stimulus has at least a substantially different intensity than the first stimulus. In an embodiment, the second stimulus includes a substantially different duration than the first stimulus. In an embodiment, the second stimulus includes a substantially different waveform than the first stimulus.

In an embodiment, the release-control substance 2602 includes a release-control substance modifiable ex vivo by an exposure of a first portion of the release-control substance to the first stimulus 192A to carry the medicament in a second medicament-release state. In this embodiment, the release-control substance includes a release-control substance modifiable ex vivo by an exposure of a second portion of the release-control substance to the second stimulus 192B to carry the medicament in a third medicament-release state.

In an embodiment, the final dosage form 2610 includes a transport medium 2680 configured to facilitate administering the medicament and the release-control substance to the animal. In an embodiment, the final dosage form includes an indicator substance (not shown) configured to indicate an exposure of at least a portion of the release-control substance to at least one of the first stimulus or the second stimulus. In an embodiment, the final dosage form includes an in vivo degradable containment element (not shown) configured to retain the release-control substance until the final dosage form is administered to the animal.

The following table illustrates several states of an example of the final dosage form 2610:

TABLE 1

Example bioavailability configurations 1-3

| Release control substance state | Bioavailability of medicament in a final dosage form configuration #1 | Bioavailability of medicament in a final dosage form configuration #2 | Bioavailability of medicament in a final dosage form configuration #3 |
| --- | --- | --- | --- |
| First medicament-release state | 1 | 0 | 0 |
| Modified to second medicament-release state | 0 | 1 | 2 |
| Modified to third medicament-release state | 2 | 2 | 1 |

0 = the medicament is substantially not bioavailable
1 = the medicament is substantially bioavailable
2 = the medicament is substantially bioavailable in a characteristic substantially different that in 1

FIG. 33 illustrates an example environment 2700 that includes an article of manufacture 2701. The article of manufacture includes a final dosage form 2710 for administering medicament to the animal 198. The final dosage form includes the medicament 190 (not shown). The final dosage form also includes a release-control substance carrying the medicament in a first medicament-release state wherein the medicament has a first bioavailability to the animal if the final dosage form is administered to the animal. The release-control substance is modifiable ex vivo by an exposure to a first stimulus to carry the medicament in a second medicament-release state wherein the medicament has a second bioavailability to the animal if the final dosage form is administered to the animal. The release-control substance is modifiable ex vivo by an exposure to a second stimulus to carry the medicament in a third medicament-release state wherein the medicament has a third bioavailability to the animal if the final dosage form is administered to the animal. In an embodiment, the final dosage form includes a transport medium 2780 configured to facilitate administering the medicament and the release-control substance to the animal. In an embodiment, the final dosage form may be substantially similar to the final dosage form 2610 described in conjunction with FIG. 32. The article of manufacture also includes instructions 2770 specifying an ex vivo exposure of the release-control substance to the first stimulus or to the second stimulus to achieve a selected second medicament release state or a selected third medicament-release state.

In an embodiment, the instructions 2770 include instructions specifying an ex vivo exposure of the release-control substance to a selected first stimulus or to a selected second stimulus, such that when implemented transform the release-control substance to the selected second medicament-release state or the selected third medicament-release state.

FIG. 34 illustrates an example environment 2800 that includes a final dosage form 2805 and an operational flow 2810. The final dosage form includes a medicament. The final dosage form also includes a release-control substance carrying the medicament in a first medicament-release state wherein the medicament has a first bioavailability to the animal if the final dosage form is administered to the animal. The release-control substance is modifiable ex vivo by an exposure to a first stimulus to carry the medicament in a second medicament-release state wherein the medicament has a second bioavailability to the animal if the final dosage form is administered to the animal. The release-control substance is modifiable ex vivo by an exposure to second stimulus to carry the medicament in a third medicament-release state wherein the medicament has a third bioavailability to the animal if the final dosage form is administered to the animal. In an embodiment, the final dosage form 2805 is substantially similar to the final dosage form 2610 described in conjunction with FIG. 32.

After a start operation, the operational flow includes an individualization operation 2820. The individualization operation includes transforming the medicament release state of the release-control substance of the final dosage form 2805 to the second medicament-release state or the third medicament-release state by initiating an ex vivo exposure of the release-control substance respectively to the first stimulus or the second stimulus. The operational flow includes an end operation. In an embodiment, the operational flow 2810 may be implemented using the system 2100 described in conjunction with FIG. 27.

FIG. 35 illustrates an alternative embodiment of the individualization operation 2820 of FIG. 34. The individualization operation may include at least one additional operation. The at least one additional operation includes an operation 2822, or an operation 2824. The operation 2822 includes modifying the medicament release state of the release-control substance to the second medicament-release state or the third medicament-release state by initiating an ex vivo exposure of the release-control substance respectively to the first stimulus or the second stimulus. In an embodiment, the operational 2282 may be implemented using the system 2100 described in conjunction with FIG. 27. The operation 2824 includes transforming the medicament release state of the release-control substance to the second medicament-release state or the third medicament-release state by initiating an ex vivo exposure of the release-control substance to a stimulus selected respectively from the first stimulus or the second stimulus. In an embodiment, the operation 2822 may be implemented using the stimulus selection circuit 2165 described in conjunction with FIG. 21.

FIG. 36 illustrates an alternative embodiment of the individualization operation 2820 of FIG. 34. The individualization operation may include at least one additional operation. The at least one additional operation includes an operation 2832, an operation 2834, or an operation 2836. The operation 2832 includes initiating an ex vivo exposure of the release-control substance respectively to a modification stimulus selected from the first stimulus or the second stimulus. The selected modification stimulus having a parameter operative to transform the release-control substance carrying the medicament from the first medicament-release state to the second medicament-release state or to the third medicament-release state. The operation 2834 includes initiating an ex vivo exposure of the release-control substance to a modification stimulus selected from the first stimulus or the second stimulus, the selected modification stimulus operative to transform the release-control substance carrying the medicament from the first medicament-release state to the second medicament-release state or from the first medicament-release state to the third medicament-release state. The operation 2836 includes initiating an ex vivo exposure of the release-control substance respectively to a stimulus selected from the first stimulus or the second stimulus, the selected stimulus having at least one of a stimulation characteristic or a spatial characteristic operable to transform the release-control substance carrying the medicament from the first medicament-release state to the second medicament-release state or to the third medicament-release state. For example, a stimulation characteristic may include a waveform, duration, or intensity. A spatial characteristic may include initiating an ex vivo exposure of a portion of the release-control substance to the stimulus.

The operations 2832, 2834, or 2286 may be implemented using the stimulus selection circuit 2170 described in conjunction with FIG. 21. In another embodiment, the operation 3972 may be implemented using a combination of the stimulus selection circuit 2170, the computing device 2175, and/or the final dosage form and stimulus exposure database 2182 described in conjunction with FIG. 21.

FIG. 37 illustrates an alternative embodiment of the operational flow 2810 of FIG. 34. The operational flow 2810 may include at least one additional operation, such as a choosing operation 2850. The choosing operation includes selecting a medicament-release state from the second medicament-release state and the third medicament-release state in response to a chosen medicament bioavailability of the final dosage form. The choosing operation may be implemented using the release-state selection circuit 2165 described in conjunction with FIG. 27. In an embodiment, the stimulus selection circuit 2170, the computing device 2175, and/or the final dosage form and stimulus exposure database 2182 (saved on the computer-readable storage medium 2180) may cooperatively implement the choosing operation. The choosing operation may include at least one additional operation, such as an operation 2860. The operation 2860 includes selecting a modification stimulus from the first stimulus and the second stimulus in response to the selected medicament-release state. The operation 2860 may be implemented using the stimulus selection circuit 2170 described in conjunction with FIG. 27. In an embodiment, the stimulus selection circuit, the computing device 2175, and/or the final dosage form and stimulus exposure database 2182 may cooperatively implement the operation 2860.

FIG. 38 illustrates an example environment 2900 that includes a final dosage form 2905 and an operational flow 2910. The final dosage form includes a medicament. The final dosage form also includes a release-control substance carrying the medicament in a medicament-retention state wherein the medicament is substantially not bioavailable to the animal if the final dosage form is administered to the animal. The release-control substance is modifiable ex vivo by an exposure to a first stimulus to carry the medicament in a first medicament-release state wherein the medicament has a first bioavailability to the animal if the final dosage form is administered to the animal. The release-control substance is modifiable ex vivo by an exposure to a second stimulus to carry the medicament in a second medicament-release state wherein the medicament has a second bioavailability to the animal if the final dosage form is administered to the animal. In an embodiment, the final dosage form 2905 may be substantially similar to the final dosage form 2610 described in conjunction with FIG. 32.

After a start operation, the operational flow includes a release state choosing operation 2920. The release state choosing operation includes automatically selecting a medicament-release state from the first medicament-release state and the second medicament-release state based on a specified medicament bioavailability of the final dosage form. In an embodiment, the specified medicament bioavailable may be indicated by a physician's prescription, a request by a person to receive the final dosage form, or a table. In an embodiment, the release state choosing operation may be implemented using the system 2100 described in conjunction with FIG. 27. For example, the person 2199 may enter a prescription of 500 mg of penicillin into the user interface 2195. In response thereto, the release-state selection circuit 2165 of the system automatically selects a medicament-release state to achieve 500 mg of penicillin from the first medicament-release state and the second medicament-release state based on the specified medicament bioavailability of the final dosage form. In an embodiment, the selection may be facilitated using the computing device 2175 and information provided by the final dosage form, and stimulus exposure database 2182 described in conjunction with FIG. 27.

A stimulus choosing operation 2930 includes automatically selecting a stimulus from the first stimulus and the second stimulus in response to the selected medicament-release state. In an embodiment, the stimulus choosing operation may be implemented using the system 2100 described in conjunction with FIG. 27. For example, the stimulus selection circuit 2170 may implement the stimulus choosing operation. In an embodiment, the stimulus choosing operation may be implemented in part, in whole by, or in cooperation with the computing device 2175, and/or the final dosage form and stimulus exposure database 2182. A dosage configuration operation 2940 includes transforming the medicament release state of the release-control substance by initiating an ex vivo exposure of the release-control substance to the selected stimulus. In an embodiment, the dosage configuration operation may be implemented using the system 2100 described in conjunction with FIG. 27. For example, the stimulus initiation circuit 2160 may initiate the ex vivo exposure of the release-control substance to the selected stimulus 192 generated by the stimulus source 194. The operational flow includes an end operation.

FIG. 39 illustrates an example vehicle 3002 for administering a medicament to the animal 198. The vehicle including means 3010 for releasably encompassing the medicament in a first medicament-release state wherein the medicament has a first bioavailability to the animal if the vehicle is administered to the animal. The means for releasably encompassing the medicament in a first medicament-release state is modifiable to a second medicament-release state upon an ex vivo exposure to a first stimulus, the medicament in the second medicament-release state having a second bioavailability to the animal if the vehicle is administered to the animal. The means for releasably encompassing the medicament in a first medicament-release state is modifiable to a third medicament-release state upon an ex vivo exposure to a second stimulus, the medicament in the third medicament-release state having a third bioavailability to the animal if the vehicle is administered to the animal. The vehicle also includes the medicament 190.

In an embodiment, the vehicle includes means 3030 for protecting the means for releasably encompassing the medicament against an ex vivo environment. In an embodiment, the vehicle includes means 3050 for indicating an exposure of the means for releasably encompassing the medicament to the first stimulus or the second stimulus. In an embodiment, the vehicle includes means 3060 for containing the medicament within the vehicle before the final dosage form is administered to the animal. In an embodiment, the vehicle includes means 3070 for carrying the vehicle into the animal.

Returning to FIG. 27, FIG. 27 illustrates another example of system 2100. The system includes the computer-readable storage medium 2180 configured to indicate a stimulus to modify ex vivo a bioavailability of a medicament carried by a final dosage form based upon a selected medicament bioavailability of the final dosage form. The system also include a holder 2110 configured to establish ex vivo of the animal a location of a final dosage form to receive the indicated stimulus 192 from a stimulus source 194. The system further includes the stimulus source operable to provide the indicated stimulus. The system also includes a stimulation controller 2140 operable to regulate an ex vivo exposure of a final dosage form to the indicated stimulus.

In an embodiment, the computer-readable storage medium 2180 includes a computer-readable storage medium configured to indicate a stimulus to modify ex vivo a bioavailability of a medicament carried by a final dosage form based upon a selected medicament bioavailability of the final dosage form. The indicated stimulus includes at least one of a type, time, intensity, wave form, or pulse form characteristic of the stimulus. In an embodiment, the computer-readable storage medium includes a computer-readable storage medium configured to indicate a stimulus to modify ex vivo a bioavailability of a medicament carried by a final dosage form based upon a selected medicament bioavailability of the final dosage form. The computer-readable storage medium is also configured to indicate another stimulus to modify ex vivo a bioavailability of another medicament carried by another final dosage form based upon another selected medicament bioavailability of the another final dosage form. In an embodiment, the computer-readable storage medium includes a computer-readable storage medium configured to indicate a stimulus to modify ex vivo a bioavailability of a medicament carried by a final dosage form based upon a selected medicament bioavailability of the final dosage form. The computer-readable storage mediums is also configured to indicate another stimulus to modify ex vivo a bioavailability of the medicament carried by a final dosage form based upon the selected medicament bioavailability of the final dosage form. In an embodiment, the computer-readable storage medium includes a computer-readable storage medium configured to indicate a stimulus to that is at least one of sufficient, effective, or operable modify ex vivo a bioavailability of a medicament carried by a final dosage form based upon a selected medicament bioavailability of the final dosage form.

In an embodiment, the computer-readable storage medium 2180 includes a computer-readable storage medium configured to indicate a stimulus 192 operable to modify ex vivo a bioavailability of a medicament carried by a final dosage form based upon a selected medicament bioavailability of the final dosage form. In an embodiment, the computer-readable storage medium includes a computer-readable storage medium configured to indicate a stimulus to substantially modify ex vivo a bioavailability of a medicament carried by a final dosage form based upon a selected medicament bioavailability of the final dosage form. In an embodiment, the computer-readable storage medium includes a computer-readable storage medium configured to indicate a stimulus to modify ex vivo a bioavailability of a medicament carried by a final dosage form based upon a selected treatment using the final dosage form. In an embodiment, the computer-readable storage medium includes a computer-readable storage medium configured to indicate a stimulus to modify ex vivo a bioavailability of a medicament carried by a final dosage form based upon a selected efficacious treatment using the final dosage form.

In an embodiment, the holder 2110 includes a holder operable to locate a final dosage form in a position to receive the indicated stimulus 192 from a stimulus source 194 before an administration of the final dosage form to the animal 192. In an embodiment, the holder includes a holder operable to establish a location of a final dosage form to receive the indicated stimulus from a stimulus source and ex vivo of the animal. In an embodiment, the holder includes a holder operable to establish ex vivo of the animal a location of at least two instance of a final dosage form to receive the indicated stimulus from a stimulus source.

In an embodiment, the stimulus source 194 includes a stimulus device, circuit, module, or generator operable to provide the indicated stimulus 192 for a final dosage form. In an embodiment, the stimulus source includes a stimulus source operable to produce the indicated stimulus. In an embodiment, the stimulus source includes a stimulus source operable to generate the indicated stimulus. In an embodiment, the stimulus source includes a stimulus source operable to provide the indicated stimulus to at least two instances of the final dosage form. In an embodiment, the stimulus source includes a stimulus source operable to provide the indicated stimulus. The indicated stimulus includes at least one of a mechanical stimulus, a non-ionizing radiation stimulus, an ionizing radiation stimulus, a chemical stimulus, an acoustic stimulus, an ultrasound stimulus, a radio wave stimulus, a microwave stimulus, a light wave stimulus, or a thermal stimulus. In an embodiment, the stimulus source includes a stimulus source operable to provide an indicated stimulus having at least one controllable characteristic. In an embodiment, the stimulus source includes a stimulus source operable to provide the indicated stimulus and to direct the provided stimulus at a portion of the location of a final dosage form established by the holder. In an alternative of the this embodiment, the stimulus source is operable to provide the indicated stimulus and to direct the provided stimulus at a selectable portion of the location of a final dosage form established by the holder. In an embodiment, the stimulus source includes a stimulus source operable to provide the indicated stimulus for a final dosage form and for another final dosage form. In an embodiment, the stimulus source includes a stimulus source operable to provide the indicated stimulus for at least two instances of a final dosage form.

In an embodiment, the stimulation controller 2140 includes a stimulation controller operable to regulate the stimulus source 194 in response to a received human-initiated activation input. In an embodiment, the stimulation controller includes a stimulation controller operable to regulate the stimulus source in response to a received feedback device-initiated activation input. In an embodiment, the stimulation controller includes a stimulation controller operable to regulate the stimulus source in response to a received stimulus-selector initiated activation input. In an embodiment, the stimulation controller includes a stimulation controller operable to regulate the stimulus source in response to a received activation input indicating a selected stimulus. In an embodiment, the stimulation controller includes a stimulation controller operable to regulate the stimulus source in response to the indicated stimulus for a final dosage form and in response to a received activation input. In an embodiment, the stimulation controller includes a stimulation controller device, circuit, module, or programmed device operable to regulate an ex vivo exposure of a final dosage form to the indicated stimulus. In an embodiment, the stimulation controller includes a stimulation controller operable to regulate a stimulus transmission pathway between the stimulus source and the holder in response to the indicated stimulus for a final dosage form. In an embodiment, the stimulation controller includes a stimulation controller operable to regulate the stimulus source and direct the stimulus toward a selected portion of a final dosage form carried by the holder 2110 in response to the indicated stimulus for the final dosage form, and in response to a received activation input.

In an embodiment, the stimulation controller 2140 includes a stimulation controller operable to regulate a duration of the stimulus, a wave characteristic of the stimulus, an intensity of the stimulus, a density of the stimulus, or amplitude of the stimulus source in response to the indicated stimulus for a final dosage form. In an embodiment, the wave characteristic may include a pulse form or a dynamic waveform.

In an embodiment, the system 2100 further includes a stimulus assessment circuit 2150 operable to monitor an aspect of the indicated stimulus 192 provided by the stimulus source 194. In an embodiment, the stimulus assessment circuit includes a stimulus assessment circuit operable to monitor an aspect of the indicated stimulus received by a final dosage form. In an embodiment, the stimulus assessment circuit includes a stimulus assessment circuit operable to monitor at least one of a type, quantity, or a characteristic of the indicated stimulus received by a final dosage form. In an embodiment, the stimulus assessment circuit includes a stimulus assessment circuit operable to monitor an aspect of the indicated stimulus received by at least a portion of a final dosage form. In an embodiment, the stimulus assessment circuit includes a stimulus assessment circuit operable to monitor an aspect of an indicator substance portion of a final dosage form. In an embodiment, the stimulus assessment circuit includes a stimulus assessment circuit operable to sense a parameter of a final dosage form responsive to the indicated stimulus received by the final dosage form. In an embodiment, the stimulus assessment circuit includes a stimulus assessment circuit operable to monitor an aspect of the indicated stimulus received by a final dosage form, and to generate an output indicative of the monitored aspect of the indicated stimulus received by the final dosage form. In this embodiment, the stimulation controller 2140 includes a stimulation controller operable to regulate an ex vivo exposure of a final dosage form to the indicated stimulus in response to the generated output indicative of the monitored aspect of the indicated stimulus received by the final dosage form. In an alternative embodiment, the stimulus assessment circuit includes a stimulus assessment circuit operable to monitor an aspect of the indicated stimulus received by a final dosage form, and to generate an output signal indicative of the monitored aspect of the indicated stimulus received by the final dosage form and receivable by the stimulation controller 2140. In an embodiment, the stimulus assessment circuit includes a stimulus assessment circuit operable to generate a signal usable in providing a human perceivable indication of an aspect of the indicated stimulus received by a final dosage form.

In an embodiment, the system 2100 further includes an indicator monitoring circuit 2120 operable to generate a signal indicative of a status of an indicator substance associated with a final dosage form and configured to indicate an exposure to the indicated stimulus by the final dosage form. In an embodiment, the indicator monitoring circuit includes an indicator monitoring circuit operable to generate signal indicative of at least one of an exposed, exposed to an extent, or not exposed status of an indicator substance associated with a final dosage form and configured to indicate an exposure to the indicated stimulus by the final dosage form. In an embodiment, the indicator monitoring circuit includes an indicator monitoring circuit operable to generate a human perceivable indication of a status of an indicator substance associated with a final dosage form and configured to indicate an exposure to the indicated stimulus by the final dosage form. In an embodiment, the indicator monitoring circuit includes an indicator monitoring circuit operable to generate a machine readable signal indicative of a status of an indicator substance associated with a final dosage form and configured to indicate an exposure to the indicated stimulus by the final dosage form.

In an embodiment, the system 2100 further includes a stimulus initiation circuit 2160 operable to initiate the provision of the indicated stimulus by the stimulation source. In an embodiment, the stimulus initiation circuit includes a stimulus initiation circuit operable to initiate the provision of the indicated stimulus by the stimulation source in response to at least one of a received user input or an automatically generated instruction. In an embodiment, the stimulus initiation circuit includes a stimulus selection circuit operable to select the indicated stimulus for provision by the stimulus source. In an embodiment, the stimulus initiation circuit includes a stimulus selection circuit operable to select the indicated stimulus for provision by the stimulus source in response to at least one of a received user input or in response to an automatically generated input.

In an embodiment, the system 2100 further includes a final dosage form recognizer circuit 2130 operable to generate data indicative of an identifying characteristic of a final dosage form. The data indicative of an identifying characteristic of the final dosage form may be acquired in response to discernable aspect of the final dosage form, such as a bar code, shape, color, or marking.

FIG. 40 illustrates an example system 3100. The system includes means 3110 for persistently storing computer-readable information indicative of a stimulus operable to modify ex vivo a bioavailability of a medicament carried by a final dosage form for administration of the medicament to an animal. The system also includes means 3120 for establishing ex vivo of the animal a location of the final dosage form to receive the indicated stimulus from a stimulus source. The system further includes means 3130 for providing the indicated stimulus. The system also includes means 3140 for regulating an ex vivo exposure of the final dosage form to the indicated stimulus.

In an embodiment, the means 3110 for persistently storing computer-readable information includes means 3112 for persistently storing computer-readable information indicative of a stimulus to modify ex vivo a bioavailability of a medicament carried by a final dosage form for administration of the medicament to an animal. The computer-readable information indicative of a stimulus based upon a selected medicament bioavailability of the final dosage form.

FIG. 41 illustrates an example environment 3200. The environment includes a final dosage form 3202 for administering medicament to the animal 198. The final dosage form includes a dosage portion, illustrated as an "A" Portion. The dosage portion has a chamber 3220A carrying a medicament 190A. The dosage portion includes a release element 3230A in a first medicament-release state. In the first medicament state, the medicament has a first bioavailability to the animal if the final dosage form is administered to the animal in the first medicament-release state. The release element is modifiable ex vivo to a second medicament-release state by an exposure to a stimulus 192A (not illustrated). In the second medicament-release state, the medicament has a second bioavailability to the animal if the final dosage form is administered to the animal in the second medicament-release state. The final dosage form includes another dosage portion, illustrated as a "B" Portion. The another dosage portion has another chamber 3220B carrying another medicament 190B. The another dosage portion includes another release element 3230B in another first medicament-release state. In the another first medicament-release state, the another medicament has another first bioavailability to the animal if the final dosage form is administered to the animal in the another first medicament-release state. The another release element is modifiable ex vivo to another second medicament-release state by an exposure to another stimulus 192B (not illustrated). In the another second medicament-release state, the another medicament has another second bioavailability to the animal if the final dosage form is administered to the animal in the another second medicament-release state. The final dosage form includes an outer layer 3210 enclosing the dosage portion and the another dosage portion.

In an embodiment, the first medicament-release state includes a first medicament-release state wherein the medicament 190A is not bioavailable to the animal 198. In an embodiment, the first medicament-release state includes a first medicament-release state wherein the medicament is bioavailable to the animal. In an embodiment, the second medicament-release state includes a second medicament-release state wherein the medicament is not bioavailable to the animal. In an embodiment, the second medicament-release state includes a second medicament-release state wherein the medicament is bioavailable to the animal.

In an embodiment, the another first medicament-release state includes another first medicament-release state wherein the another medicament 190B is not bioavailable to the animal 198. In an embodiment, the another first medicament-release state includes another first medicament-release state wherein the another medicament is bioavailable to the animal. In an embodiment, the another second medicament-release state includes another second medicament-release state wherein the another medicament is not bioavailable to the animal. In an embodiment, the another second medicament-release state includes another second medicament-release state wherein the another medicament is bioavailable to the animal.

In an embodiment of the final dosage form 3202, if the first medicament-release state includes the medicament 190A being bioavailable to the animal and if the another first medicament-release state includes the another medicament 190B being bioavailable to the animal 198, a first ratio exists between the bioavailability of the medicament and the bioavailability of the another medicament. In this embodiment of the final dosage form, if the second medicament-release state includes the medicament 190A being bioavailable to the animal and if the another second medicament-release state includes the another medicament 190B being bioavailable to the animal, a second ratio exists between the bioavailability of the medicament and the bioavailability of the another medicament. In an embodiment, the first ratio is equal to or greater than the second ratio. In an embodiment, the first ratio is less than the second ratio.

In an embodiment of the final dosage form 3202, if the second medicament-release state includes the medicament 190A being bioavailable to the animal 198 and if the another second medicament-release state includes the another medicament 190B being bioavailable to the animal, a second ratio exists between the bioavailability of the medicament and the bioavailability of the another medicament.

In an embodiment, the medicament 190A and the another medicament 190B are at least substantially similar instances of one medicament. In an embodiment, the medicament and the another medicament are at least substantially different medicaments. In an embodiment, the first bioavailability to the animal includes a first bioavailability characteristic and the second bioavailability to the animal includes a second bioavailability characteristic.

In an embodiment, the release element 3230A is at least substantially similar to the another release element 3230B. In an embodiment, the release element is at least substantially different from the another release element.

In an embodiment, the stimulus 190A is at least substantially similar to the another stimulus 190B. In an embodiment, the stimulus is at least substantially different from the another stimulus.

In an embodiment, the final dosage form 3202 further includes an indicator element 3280A configured to indicate an exposure of the release element 3230A to the stimulus 192A or the another stimulus 192B. In an embodiment, the final dosage form 3202 further includes another indicator element 3280B configured to indicate an exposure of the another release element to the stimulus or the another stimulus. In an embodiment, the final dosage form further includes an indicator element, for example, indicator element 3280A, configured to indicate an exposure of at least one of the release element or the another release element to the stimulus or the another stimulus.

In an embodiment, the final dosage form 3202 includes a containment element 3240A or a containment element 3240B configured to respectfully retain the medicament 190A or the another medicament 190B until the final dosage form is administered to the animal 198.

In an embodiment, the final dosage form 3202 further includes a further dosage portion (not illustrated). The further dosage portion includes a further chamber carrying a further medicament. The further dosage portion also includes a further release element in a further first medicament-release state. In the further first medicament-release state, the further medicament has a further first bioavailability to the animal 198 if the final dosage form is administered to the animal in the further first medicament-release state. The further release element is modifiable ex vivo to a further second medicament-release state by an exposure to a further stimulus. In the further second medicament-release state, the further medicament has a further second bioavailability to the animal if the final dosage form is administered to the animal in the further second medicament-release state.

The following table illustrates several states of an example of the final dosage form 3202:

TABLE 2

Example bioavailability configurations

| | Example Configuration #1 Bioavailability Profile | | Example Configuration #2 Bioavailability Profile | |
|---|---|---|---|---|
| State of release element (RE) | RE 1 (100 mg) | RE 2 (200 mg TR) | RE 1 (100 mg TR) | RE 2 (200 mg) |
| State 1 (initial) | 0 | 0 | 1 | 0 |
| State 2 (stimulus to RE of chamber 1) | 1 | 0 | 0 | 0 |
| State 3 (stimulus to RE of chamber 2) | 0 | 1 | 1 | 1 |
| State 4 (stimuli to REs of chambers 1 & 2) | 1 | 1 | 0 | 1 |

0 = medicament is substantially not bioavailable
1 = medicament is bioavailable

Figure 42:
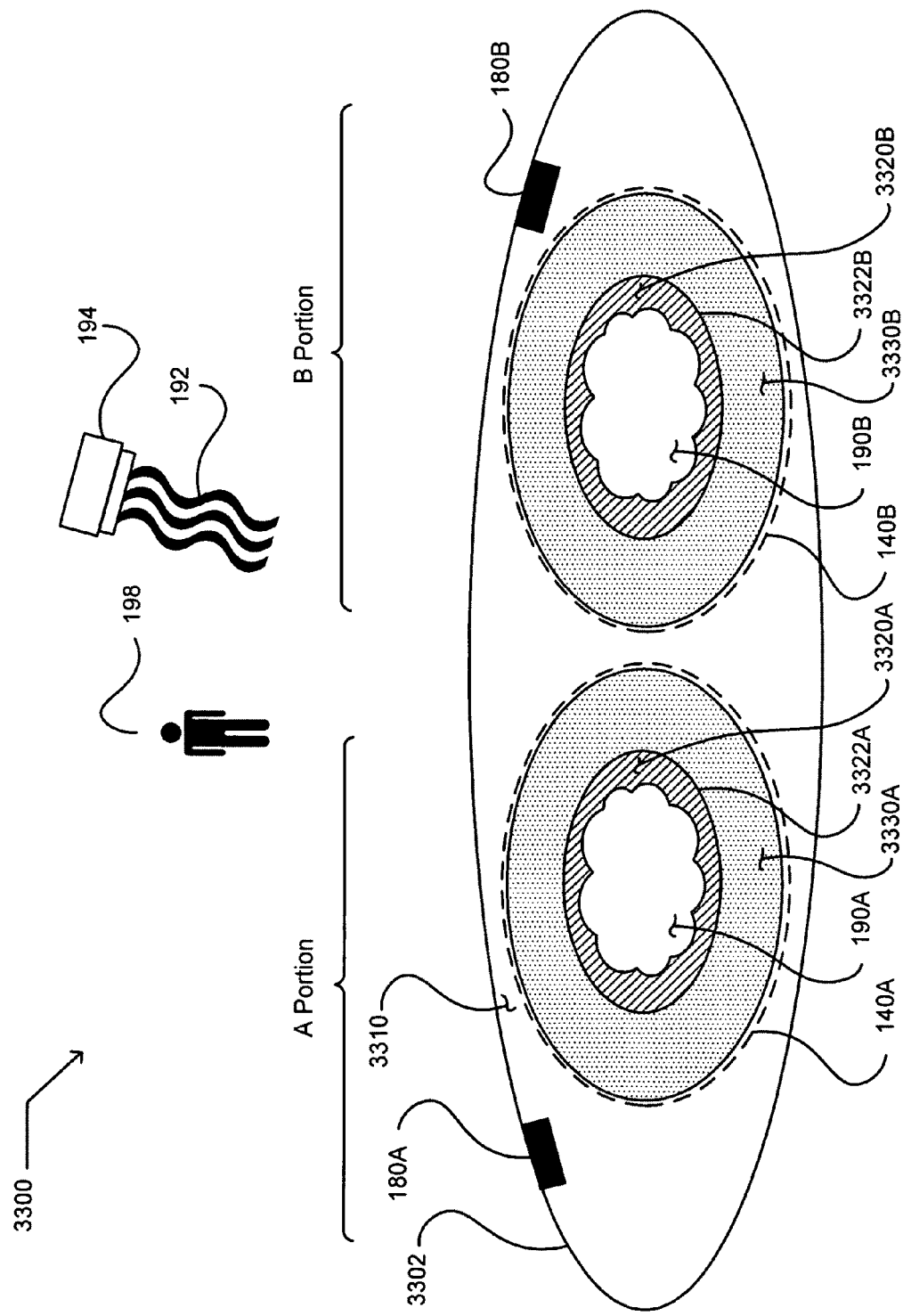
FIG. 42 illustrates an example environment that includes a final dosage form for administering medicament to an animal.

FIG. 42 illustrates an example environment 3300. The environment includes a final dosage form 3302 for administering medicament to the animal 198. The final dosage form includes a dosage portion, illustrated as "A" Portion, having a chamber 3320A carrying a medicament 190A. The dosage portion includes a release element 3330A in a medicament-retention state. The medicament is substantially not bioavailable to the animal if the final dosage form is administered to the animal in the first medicament-retention state. The release element is modifiable ex vivo to a medicament-release state by an exposure to a stimulus. The medicament is bioavailable to the animal if the final dosage form is administered to the animal in the medicament-release state. The final dosage form includes another dosage portion, illustrated as "B" Portion, having another chamber 3320B carrying another medicament 190B. The another dosage portion includes another release element 3330B in another medicament-retention state. The another medicament is substantially not bioavailable to the animal if the final dosage form is administered to the animal in the another medicament-retention state. The another release element is modifiable ex vivo to another medicament-release state by an exposure to another stimulus. The another medicament is bioavailable to the animal if the final dosage form is administered to the animal in the another medicament-release state.

FIG. 43 illustrates an example environment 3400 that includes a final dosage form 3405 and an operational flow 3410. The final dosage form includes a dosage portion having a chamber carrying a medicament. The dosage portion also includes a release element in a first medicament-release state. The medicament has a first bioavailability to the animal if the final dosage form is administered to the animal in the first medicament-release state. The release element modifiable ex vivo to a second medicament-release state by an exposure to a stimulus, wherein the medicament has a second bioavailability to the animal if the final dosage form is administered to the animal in the second medicament-release state. The final dosage form also includes another dosage portion having another chamber carrying another medicament. The another dosage portion also includes another release element in another first medicament-release state. The another medicament has another first bioavailability to the animal if the final dosage form is administered to the animal in the another first medicament-release state. The another release element modifiable ex vivo to another second medicament-release state by an exposure to another stimulus. The another medicament has another second bioavailability to the animal if the final dosage form is administered to the animal in the another second medicament-release state. In an embodiment, the final dosage form 3405 may be substantially similar to the final dosage form 3202 described in conjunction with FIG. 41.

After a start operation, the operational flow 3410 includes a modification operation 3420. The modification operation includes transforming the final dosage form 3405 into a selected medicament-release profile by initiating an ex vivo exposure of the release element or the another release element to a modification stimulus respectfully selected from the stimulus and the another stimulus. For example, the selected medicament-release profile may include a configuration of bioavailabilities of the medicament and the another medicament to achieve a prescribed medicament dosage. The operational flow includes an end operation. In an embodiment, the operational flow may be implemented using the system 2100 described in conjunction with FIG. 27.

Figure 44:
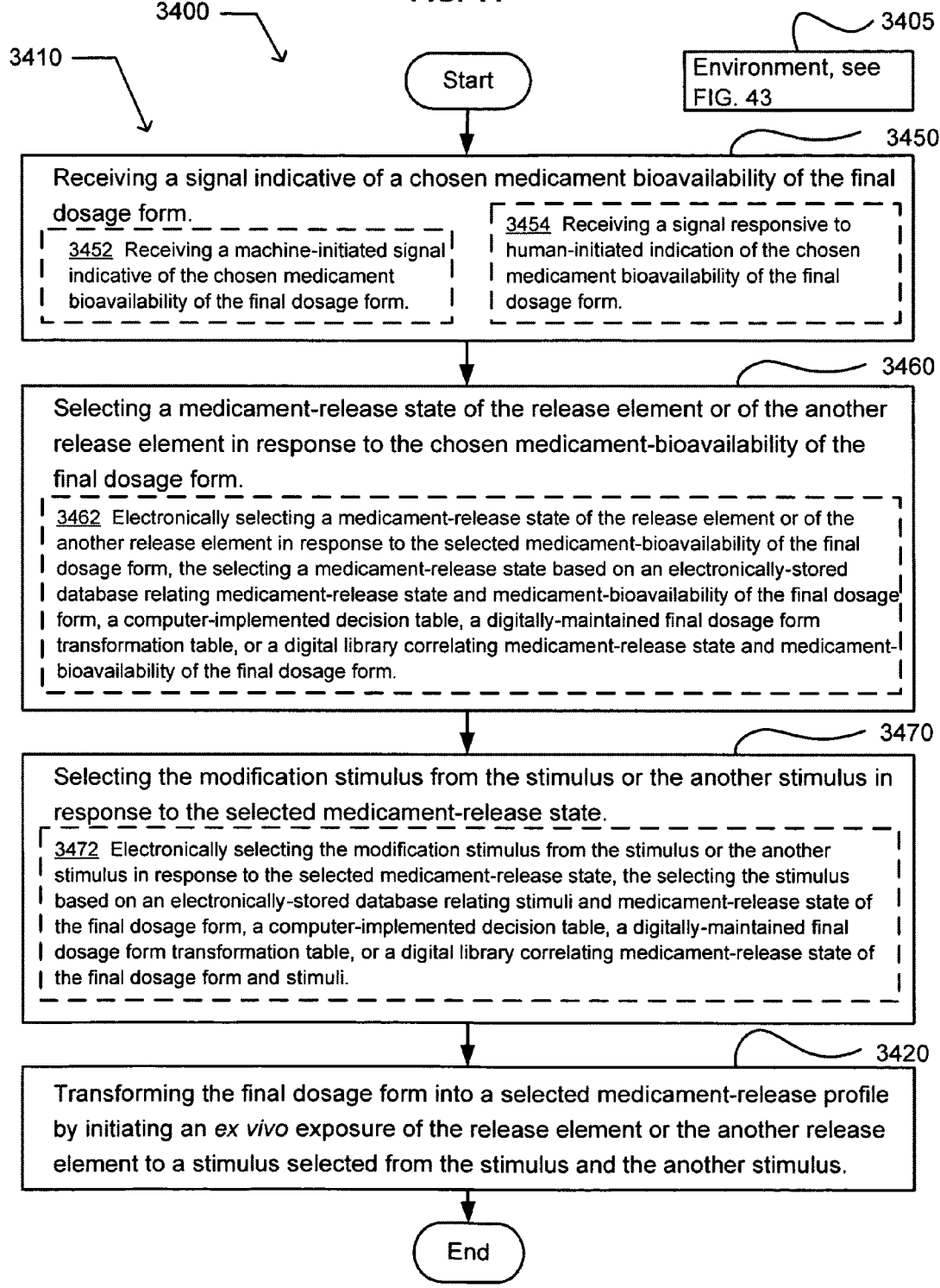
FIG. 44 illustrates an alternative embodiment of the operational flow of FIG. 43.

FIG. 44 illustrates an alternative embodiment of the operational flow 3410 of FIG. 43. The operational flow may include at least one additional operation. The at least one additional operation may include a treatment-order operation 3450, a release-state selection operation 3460, or a stimulus selection operation 3470. The treatment-order operation includes receiving a signal indicative of a chosen medicament bioavailability of the final dosage form 3405. In an embodiment, the treatment-order operation may include a medicament bioavailability indicated by a physician's prescription, a request by a person to receive the final dosage form, or a table. In an embodiment, the treatment-order operation may be implemented using the system 2100 described in conjunction with FIG. 21. The treatment-order operation may include at least one additional operation. The at least one additional operation may include an operation 3452 or an operation 3454. The operation 3452 includes receiving a machine-initiated signal indicative of the chosen medicament bioavailability of the final dosage form. In an embodiment, the operation 3452 may be implemented using the other circuit(s) 2190 to receive data or an email indicative of the chosen medicament bioavailability of the final dosage form. The operation 3454 includes receiving a signal responsive to human-initiated indication of the chosen medicament bioavailability of the final dosage form. In an embodiment, the operation 3454 may be implemented using the user interface 2195 to receive a human-initiated input by the person 2199.

The release-state selection operation 3460 includes selecting a medicament-release state of the release element or of the another release element in response to the chosen medicament-bioavailability of the final dosage form. In an embodiment, the release-state selection operation may be implemented using the system 2100 described in conjunction with FIG. 21. The release-state selection operation may include at least one additional operation, such as an operation 3462. The operation 3462 includes electronically selecting a medicament-release state of the release element or of the another release element in response to the selected medicament-bioavailability of the final dosage form. The selecting a medicament-release state is based on an electronically-stored database relating medicament-release state and medicament-bioavailability of the final dosage form, a computer-implemented decision table, a digitally-maintained final dosage form transformation table, or a digital library correlating medicament-release state and medicament-bioavailability of the final dosage form. In an embodiment, the operation 3462 may be implemented using the release-state selection circuit 2165 described in conjunction with FIG. 21. In another embodiment, the operation 3462 may be implemented using a combination of the release-state selection circuit 2165, the computing device 2175, and/or the final dosage form and stimulus exposure database 2182 described in conjunction with FIG. 21.

The stimulus selection operation 3470 includes selecting the modification stimulus from the stimulus or the another stimulus in response to the selected medicament-release state. In an embodiment, the stimulus selection operation may be implemented using the system 2100 described in conjunction with FIG. 21. The stimulus selection operation may include at least one additional operation, such as an operation 3472. The operation 3472 includes electronically selecting the modification stimulus from the stimulus or the another stimulus in response to the selected medicament-release state, the selecting the stimulus based on an electronically-stored database relating stimuli and medicament-release state of the final dosage form, a computer-implemented decision table, a digitally-maintained final dosage form transformation table, or a digital library correlating medicament-release state of the final dosage form and stimuli. In an embodiment, the operation 3472 may be implemented using the stimulus selection circuit 2170 described in conjunction with FIG. 21. In another embodiment, the operation 3472 may be implemented using a combination of the stimulus selection circuit 2170, the computing device 2175, and/or the final dosage form and stimulus exposure database 2182 described in conjunction with FIG. 21. The modification operation 3420 is described in conjunction with FIG. 43.

FIG. 45 illustrates an example environment 3500. The environment includes an article of manufacture 3501. The article of manufacture includes a final dosage form 502 for administering medicament to an animal. The final dosage form is described in conjunction with FIG. 5. In another embodiment, the final dosage form 502 is substantially similar to the final dosage 3310 described in conjunction with FIG. 42.

The article of manufacture 3501 also includes instructions 3570 specifying an ex vivo exposure of the release element 530A to the stimulus 192A (not shown) of the stimulus 192, or an ex vivo exposure of the another release element 530B to the another stimulus 192B (not shown) of the stimulus 190. The instructions when implemented transform the release element to the second medicament-release state or the another release element to the another second medicament-release state. In an embodiment, the instructions may be implemented using the system 2100 described in conjunction with FIG. 27.

FIG. 46 illustrates an example article of manufacture 3602 for administering medicament to an animal. The article of manufacture includes a first portion 3610 and a second portion 3650. The first portion includes means 3620 for carrying a medicament 190A. In an embodiment, the means 3620 includes means for releasably holding a medicament. The first portion also includes means 3624 for medicament release control in a first state wherein the medicament has a first bioavailability to the animal if the article of manufacture is administered to the animal. The means for medicament release control is modifiable ex vivo to a second state by an exposure to a stimulus, wherein the medicament has a second bioavailability to the animal if the article of manufacture is administered to the animal. The first portion further includes the medicament 190A. In an embodiment, the first portion includes means 3628 for indicating an exposure of the means for medicament release control to the stimulus.

The second portion 3650 includes another means 3660 for carrying another medicament 190B. The second portion also includes another means 3664 for medicament release control in another first state wherein the another medicament has another first bioavailability to the animal if the article of manufacture is administered to the animal. The another means for medicament release control is modifiable ex vivo to another second state by an exposure to another stimulus, wherein the another medicament has another second bioavailability to the animal if the article of manufacture is administered to the animal. The second portion further includes the another medicament. In an embodiment, the second portion includes another means 3668 for indicating an exposure of the another means for medicament release control to the another stimulus.

FIG. 47 illustrates an environment 3700. The environment includes a final dosage form 3702 for administering medicament to the animal 198. The final dosage form includes a dosage portion, illustrated as "A Dosage Portion." The dosage portion includes a medicament 190A. The dosage portion also include a release element 3730A in a first medicament-release state wherein the medicament has a first bioavailability to the animal if the final dosage form is administered to the animal in the first medicament-release state. The release element is modifiable ex vivo to a second medicament-release state by an exposure to a stimulus, wherein the medicament has a second bioavailability to the animal if the final dosage form is administered to the animal in the second medicament-release state.

The final dosage form 3702 also includes another dosage portion, illustrated as "Another Dosage Portion." The another dosage portion includes a medicament 190B. The another dosage portion also includes another release element 3730B in another first medicament-release state wherein the another medicament has another first bioavailability to the animal if the final dosage form is administered to the animal in the another first medicament-release state. The another release element is modifiable ex vivo to another second medicament-release state by an exposure to another stimulus, wherein the another medicament has another second bioavailability to the animal if the final dosage form is administered to the animal in the another second medicament-release state.

In an embodiment, the first medicament-release state wherein the medicament has a first bioavailability to the animal includes a first medicament-release state wherein the medicament is not bioavailable to the animal. In an embodiment, the first medicament-release state wherein the medicament has a first bioavailability to the animal includes a first medicament-release state wherein the medicament is bioavailable to the animal. In an embodiment, the second medicament-release state wherein the medicament has a second bioavailability to the animal includes a second medicament-release state wherein the medicament is not bioavailable to the animal. In an embodiment, the second medicament-release state wherein the medicament has a second bioavailability to the animal includes a second medicament-release state wherein the medicament is bioavailable to the animal. In an embodiment, the first bioavailability to the animal includes a first bioavailability characteristic and the second bioavailability to the animal includes a second bioavailability characteristic.

In an embodiment, the another first medicament-release state wherein the another medicament has another first bioavailability to the animal includes another first medicament-release state wherein the another medicament is not bioavailable to the animal. In an embodiment, the another first medicament-release state wherein the another medicament has another first bioavailability to the animal includes another first medicament-release state wherein the another medicament is bioavailable to the animal. In an embodiment, the another second medicament-release state wherein the another medicament has another second bioavailability to the animal includes another second medicament-release state wherein the another medicament is not bioavailable to the animal. In an embodiment, the another second medicament-release state wherein the another medicament has another second bioavailability to the animal includes another second medicament-release state wherein the another medicament is bioavailable to the animal.

In an embodiment, the stimulus includes at least one of a mechanical stimulus, a non-ionizing radiation stimulus, an ionizing radiation stimulus, a chemical stimulus, an acoustic stimulus, an ultrasound stimulus, a radio wave stimulus, a microwave stimulus, a light wave stimulus, or a thermal stimulus.

FIG. 47 also illustrates another embodiment of the example environment 3700. The environment includes a final dosage form 3702 for administering a medicament to the animal. The final dosage form includes a dosage portion, illustrated as "A" Dosage Portion. The dosage portion includes a medicament 190A. The dosage portion also include a release element 3730A. The release element is in a medicament-holding state wherein the medicament is substantially not bioavailable to the animal if the final dosage form is administered to the animal in the medicament-holding state. The release element is modifiable ex vivo to a medicament-discharging state by an exposure to a stimulus wherein the medicament is bioavailable to the animal if the final dosage form is administered to the animal in the medicament-discharging state.

The final dosage form 3702 also includes another dosage portion, illustrated as "B" Dosage Portion. The another dosage portion includes a medicament 190B. The another dosage portion also includes another release element 3730B in another medicament-holding state wherein the another medicament is substantially not bioavailable to the animal if the final dosage form is administered to the animal in the another medicament-holding state. The another release element is modifiable ex vivo to another medicament-discharge state by an exposure to another stimulus wherein the another medicament is bioavailable to the animal if the final dosage form is administered to the animal in the another medicament-discharge state. In an embodiment, the final dosage form 3702 further includes an outer layer 3710 carrying the dosage portion and the another dosage portion.

The following table illustrates several states of example embodiments of the final dosage form 2610:

TABLE 3

Example bioavailability configurations

| State of | Example Configuration #1 Bioavailability Profile | | Example Configuration #2 Bioavailability Profile | |
|---|---|---|---|---|
| | RE 1 | RE 2 | RE 1 | RE 2 |
| release element (RE) | RE 1 (100 mg) | RE 2 (200 mg TR) | (100 mg Medicament A) | (200 mg medicament B) |
| State 1 (initial) | 0 | 0 | 0 | 0 |
| State 2 (stimulus to first RE) | 1 | 0 | 1 | 0 |
| State 3 (stimulus to second RE) | 0 | 1 | 0 | 1 |
| State 4 (stimuli to both REs) | 1 | 1 | 1 | 1 |

0 = medicament is substantially not bioavailable
1 = medicament is bioavailable

FIG. 48 illustrates an example environment 3800. The example environment includes a final dosage form 3810 for administering medicament to an animal. The final dosage form includes a dosage portion 3804A, and is illustrated in an embodiment as including two molecules. In another embodiment, the dosage portion may include a large number of molecules. A molecule of the dosage portion includes a release element; the molecule is generally illustrated as including a release element 3802 having a medicament (not shown). In an embodiment, a small molecule includes the release element. In an embodiment, a particle or polymer material includes the release element. In an embodiment, an intelligent molecule includes the release element. In an embodiment, a gel, illustrated as a hydrogel 3802A, includes the release element having an associated medicament 190A. In an embodiment, a liposome, illustrated as a liposome 3802B, includes the release element having an associated medicament 190B. In an embodiment, a nanoparticle includes the release element, illustrated as a nanosphere 3802C having an associated medicament 190C.

The release element 3802 is in a first medicament-release state wherein the medicament has a first bioavailability to the animal 198 if the final dosage form is administered to the animal in the first medicament-release state. The release element is modifiable ex vivo to a second medicament-release state by an exposure to a stimulus, wherein the medicament has a second bioavailability to the animal if the final dosage form is administered to the animal in the second medicament-release state.

The final dosage form also includes another dosage portion, illustrated as a dosage portion 3804B, illustrated in an embodiment as including two molecules. In another embodiment, the another dosage portion may include a large number of molecules. A molecule of the another dosage portion includes another release element, generally also illustrated as release element 3802 having another medicament (not shown). In an embodiment, another small molecule includes the another release element. In an embodiment, another particle or polymer material includes the another release element. In an embodiment, another intelligent molecule includes the another release element. In an embodiment, another gel, illustrated as the hydrogel 3802A, includes the another release element having an associated medicament 190A. In an embodiment, another liposome, illustrated as the liposome 3802B, includes the another release element having an associated medicament 190B. In an embodiment, another nanoparticle, illustrated as the nanosphere 3802C, includes the another release element having an associated medicament 190C.

The another release element is in another first medicament-release state wherein the another medicament has another first bioavailability to the animal if the final dosage form is administered to the animal in the another first medicament-release state. The another release element is modifiable ex vivo to another second medicament-release state by an exposure to another stimulus, wherein the another medicament has another second bioavailability to the animal if the final dosage form is administered to the animal in the another second medicament-release state.

While FIG. 48 illustrates the molecules comprising release elements dosage portion 3804A in a proximity, in an embodiment, the molecules comprising release elements dosage portion 3804A may be distributed in any manner throughout the final dosage form 3810. Likewise, in an embodiment, the molecules comprising release elements dosage portion 3804B may be distributed in any manner throughout the final dosage form 3810. Further, the molecules comprising release elements dosage portion 3804A and the molecules comprising release elements dosage portion 3804B may be intermingled in any manner throughout the final dosage form 3810. In an embodiment, the molecules that comprise the dosage portion 3804A and 3804B may be substantially a same type of molecule, or may be substantially different types of molecules.

FIG. 48 also illustrates another embodiment of the example environment 3800. The another embodiment of the example environment includes a final dosage form 3810 for administering medicament to an animal. The final dosage form includes a dosage portion 3804A, illustrated in an embodiment as including two molecules. A molecule of the dosage portion includes a release element, generally illustrated as release element 3802, having a medicament (not shown). In an embodiment, a small molecule includes the release element. In an embodiment, a particle or polymer material includes the release element. In an embodiment, an intelligent molecule includes the release element. In an embodiment, a gel, illustrated as a hydrogel 3802A, includes the release element having a medicament 190A. In an embodiment, a liposome, illustrated as a liposome 3802B, includes the release element having a medicament 190B. In an embodiment, a nanoparticle includes the release element, illustrated as a nanosphere 2202C having a medicament 190C.

The release element 3802 is in a medicament-holding state wherein the medicament is substantially not bioavailable to the animal 198 if the final dosage form 3810 is administered to the animal in the medicament-holding state. The release element is modifiable ex vivo to a medicament-discharging state by an exposure to a stimulus wherein the medicament is bioavailable to the animal if the final dosage form is administered to the animal in the medicament-discharging state.

The final dosage form also includes another dosage portion 3804B, illustrated in an embodiment, as including two molecules. A molecule of the another dosage portion includes another release element, generally also illustrated as release element 3802 having another medicament (not shown). In an embodiment, another small molecule includes the another release element. In an embodiment, another particle or polymer material includes the another release element. In an embodiment, another intelligent molecule includes the another release element. In an embodiment, another gel, illustrated as the hydrogel 3802A, includes the another release element having a medicament 190A. In an embodiment, another liposome, illustrated as the liposome 3802B, includes the another release element having a medicament 190B. In an embodiment, another nanoparticle, illustrated as the nanosphere 3802C, includes the another release element having a medicament 190C.

The another release element is in another medicament-holding state wherein the another medicament is substantially not bioavailable to the animal 198 if the final dosage form 3810 is administered to the animal in the another medicament-holding state. The another release element is modifiable ex vivo to another medicament-discharge state by an exposure to another stimulus wherein the another medicament is bioavailable to the animal if the final dosage form is administered to the animal in the another medicament-discharge state.

FIG. 49 illustrates an example environment 3900 that includes a final dosage form 3905 and an operational flow 3910. The final dosage form includes a dosage portion having a medicament. The dosage portion includes a release element in a first medicament-release state wherein the medicament has a first bioavailability to the animal if the final dosage form is administered to the animal in the first medicament-release state. The release element is modifiable ex vivo to a second medicament-release state by an exposure to a stimulus, wherein the medicament has a second bioavailability to the animal if the final dosage form is administered to the animal in the second medicament-release state. The final dosage form also includes another dosage portion having another medicament. The another dosage portion includes another release element in another first medicament-release state wherein the another medicament has another first bioavailability to the animal if the final dosage form is administered to the animal in the another first medicament-release state. The another release element is modifiable ex vivo to another second medicament-release state by an exposure to another stimulus, wherein the another medicament has another second bioavailability to the animal if the final dosage form is administered to the animal in the another second medicament-release state. In an embodiment, the final dosage form 3905 is substantially similar to the final dosage form 3702 described in conjunction with FIG. 47, or the final dosage form 3810 described in conjunction with FIG. 48.

After a start operation, the operational flow 3910 includes a customization operation 3920. The customization operation includes transforming the final dosage form 3905 into a selected medicament release profile by initiating an ex vivo exposure of the release element or the another release element to a modification stimulus respectfully selected from the stimulus or the another stimulus. The operational flow includes an end operation. In an embodiment, the customization operation may include at least one additional operation, such as the operation 3922. The operation 3922 includes transforming the final dosage form into a selected medicament release profile by initiating an ex vivo exposure of the release element and the another release element to the stimulus and the another stimulus. In an embodiment, the operational flow 3910 may be implemented using the system 2100 described in conjunction with FIG. 27.

FIG. 50 illustrates an example alternative embodiment of the operational flow 3910 of FIG. 49. The operational flow may include at least one additional operation. The at least one additional operation may include a treatment-order operation 3950, a release-state selection operation 3960, or a stimulus selection operation 3970. The treatment-order operation includes receiving a signal indicative of a chosen medicament bioavailability of the final dosage form 3905. In an embodiment, the treatment-order operation may be implemented using the system 2100 described in conjunction with FIG. 21. The treatment-order operation may include at least one additional operation. The at least one additional operation may include an operation 3952 or an operation 3954. The operation 3952 includes receiving a machine-initiated signal indicative of the chosen medicament bioavailability of the final dosage form. In an embodiment, the operation 3952 may be implemented using the other circuit(s) 2190 to receive data or an email indicative of the chosen medicament bioavailability of the final dosage form. The operation 3954 includes receiving a signal responsive to human-initiated indication of the chosen medicament bioavailability of the final dosage form. In an embodiment, the operation 3954 may be implemented using the user interface 2195 to receive a human-initiated input by the person 2199 described in conjunction with FIG. 27.

The release-state selection operation 3960 includes selecting a medicament-release state of the release element or of the another release element in response to the chosen medicament-bioavailability of the final dosage form. In an embodiment, the release-state selection operation may be implemented using the system 2100 described in conjunction with FIG. 21. The release-state selection operation may include at least one additional operation, such as an operation 3962. The operation 3962 includes electronically selecting a medicament-release state of the release element or of the another release element in response to the selected medicament-bioavailability of the final dosage form. The selecting a medicament-release state is based on an electronically-stored database relating medicament-release state and medicament-bioavailability of the final dosage form, a computer-implemented decision table, a digitally-maintained final dosage form transformation table, or a digital library correlating medicament-release state and medicament-bioavailability of the final dosage form. In an embodiment, the operation 3962 may be implemented using the release-state selection circuit 2165 described in conjunction with FIG. 21. In another embodiment, the operation 3962 may be implemented using a combination of the release-state selection circuit 2165, the computing device 2175, and/or the final dosage form and stimulus exposure database 2182 described in conjunction with FIG. 21.

The stimulus selection operation 3970 includes selecting the modification stimulus from the stimulus or the another stimulus in response to the selected medicament-release state. In an embodiment, the stimulus selection operation may be implemented using the system 2100 described in conjunction with FIG. 21. The stimulus selection operation may include at least one additional operation, such as an operation 3972. The operation 3972 includes electronically selecting the modification stimulus from the stimulus or the another stimulus in response to the selected medicament-release state, the selecting the stimulus based on an electronically-stored database relating stimuli and medicament-release state of the final dosage form, a computer-implemented decision table, a digitally-maintained final dosage form transformation table, or a digital library correlating medicament-release state of the final dosage form and stimuli. In an embodiment, the operation 3972 may be implemented using the stimulus selection circuit 2170 described in conjunction with FIG. 21. In another embodiment, the operation 3972 may be implemented using a combination of the stimulus selection circuit 2170, the computing device 2175, and/or the final dosage form and stimulus exposure database 2182 described in conjunction with FIG. 21. The modification operation 3920 is described in conjunction with FIG. 49.

Figure 51:
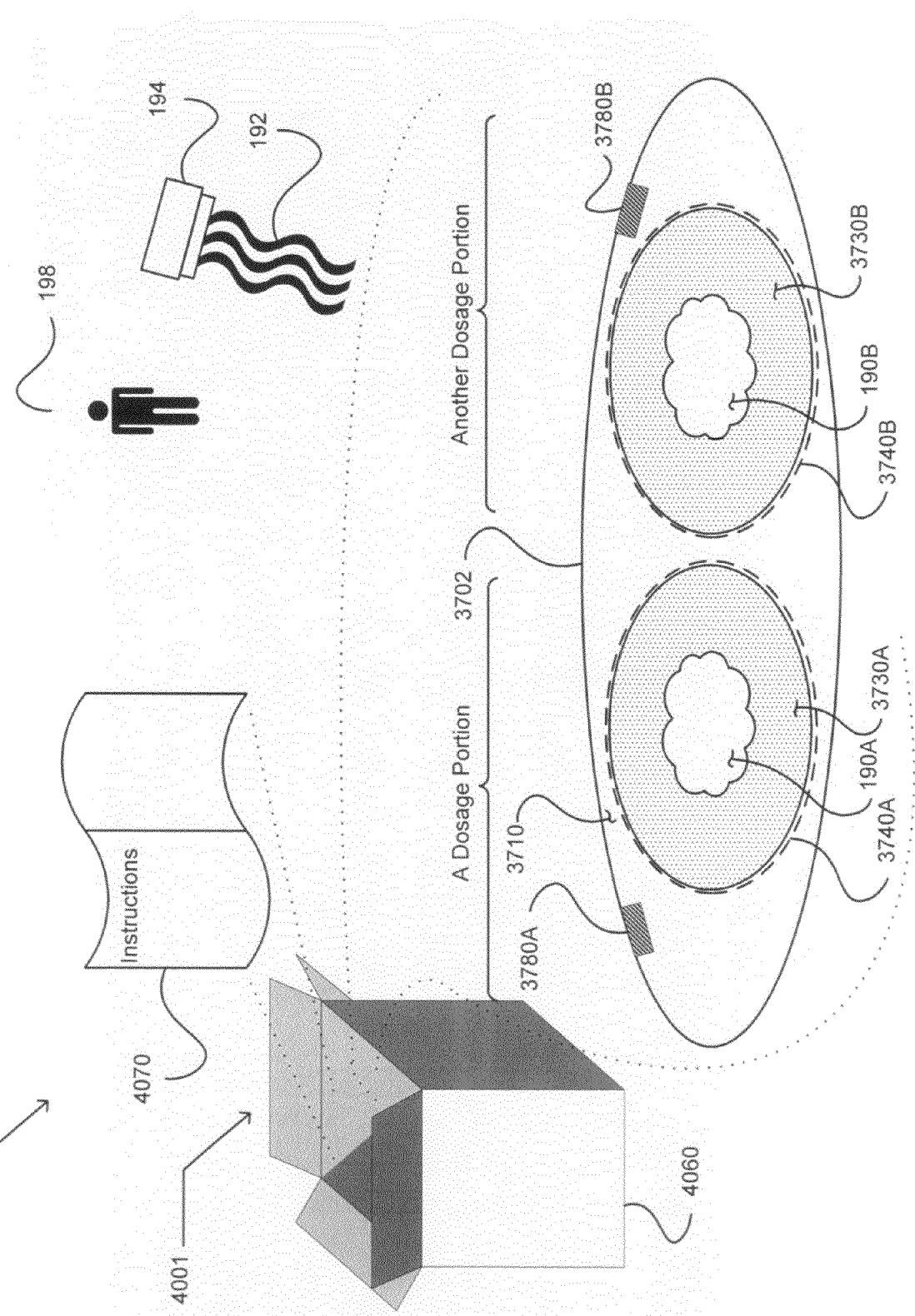
FIG. 51 illustrates an example environment that includes an article of manufacture 4001.

FIG. 51 illustrates an example environment 4000 that includes an article of manufacture 4001. In an embodiment, the article of manufacture includes the final dosage form 3702 described in conjunction with FIG. 47. The article of manufacture also includes instructions 4070. The instructions specify an ex vivo exposure of the release element of the final dosage form to the stimulus or an ex vivo exposure of the another release element of the final dosage form to the another stimulus. The instructions when implemented transform the release element to the second medicament-release state or the another release element to the another second medicament-release state.

FIG. 52 illustrates an example environment 4100 that includes an article of manufacture 4101. In an embodiment, the article of manufacture includes the final dosage form 3810 described in conjunction with FIG. 48. The article of manufacture also includes instructions 4170. The instructions specify an ex vivo exposure of the release element of the final dosage form to the stimulus or an ex vivo exposure of the another release element of the final dosage form to the another stimulus. The instructions when implemented transform the release element to the second medicament-release state or the another release element to the another second medicament-release state.

FIG. 53 illustrates an example article of manufacture 4202 for administering medicament to an animal. The article includes the medicament 190A. The article also includes means 4224 for medicament release control in a first state wherein the medicament has a first bioavailability to the animal if the article of manufacture is administered to the animal. The means for medicament release control is modifiable ex vivo to a second state by an exposure to a stimulus, wherein the medicament has a second bioavailability to the animal if the article of manufacture is administered to the animal. The article includes another medicament 190B. The article also includes another means 4264 for medicament release control in another first state wherein the another medicament has another first bioavailability to the animal if the article of manufacture is administered to the animal. The another means for medicament release control is modifiable ex vivo to another second state by an exposure to another stimulus, wherein the another medicament has another second bioavailability to the animal if the article of manufacture is administered to the animal.

In an embodiment, the article 4202 includes means 4228 for indicating an exposure of the means 4224 for medicament release control to the stimulus 190A. In an embodiment, the article includes another means 4268 for indicating an exposure of the another means 4264 for medicament release control to the another stimulus 190B. In an embodiment, the article includes means 4280 for protecting the article of manufacture against an ex vivo environment. In an embodiment, the article includes means 4290 for carrying the article of manufacture into the animal.

Figure 54:
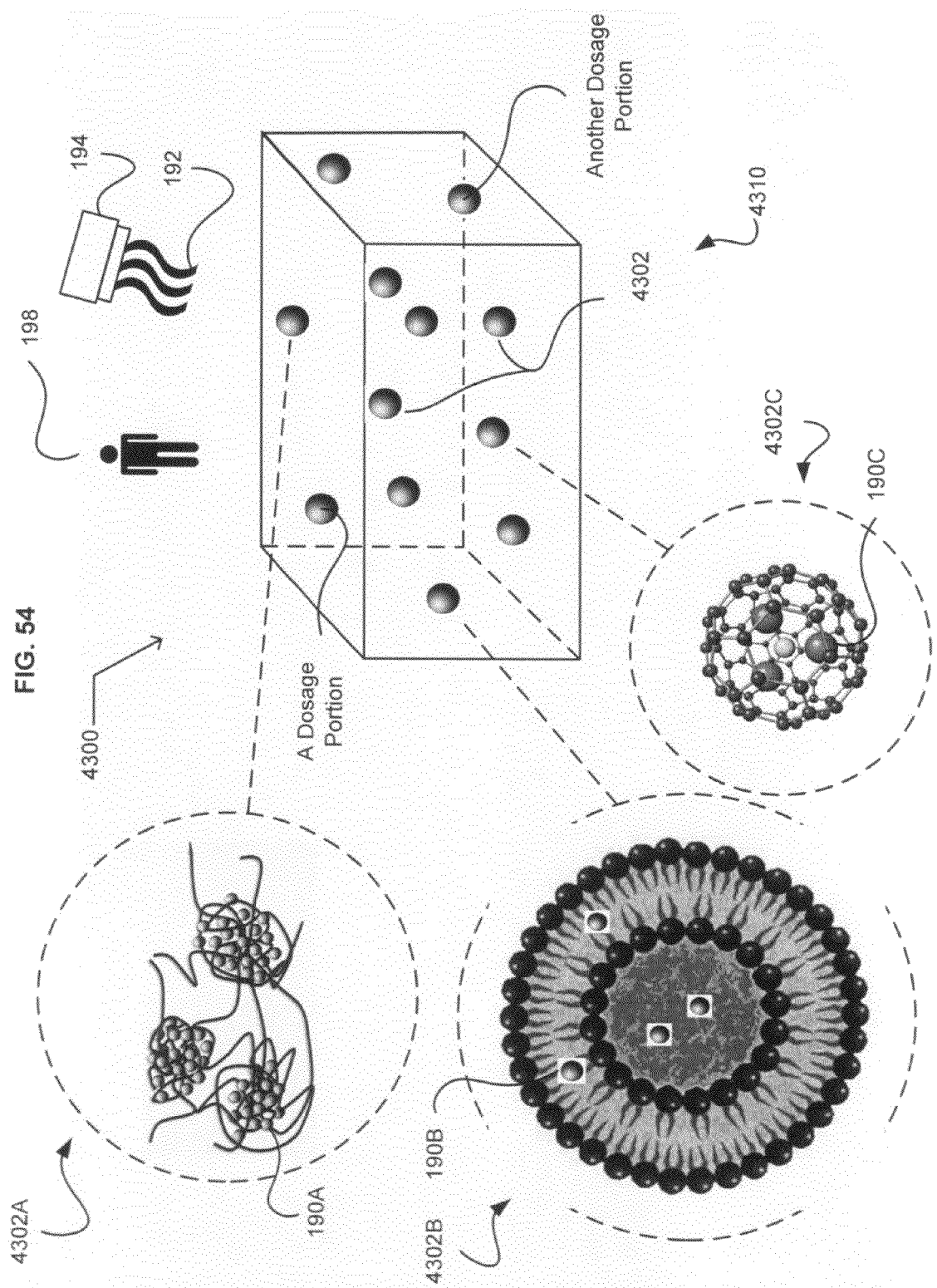
FIG. 54 illustrates an example environment that includes a final dosage form for administering medicament to an animal.

FIG. 54 illustrates an example environment 4300. The environment includes a final dosage form 4310 for administering medicament to the animal 198. The final dosage form includes a dosage portion having a site and a medicament in a first association. The dosage portion is illustrated as "A Dosage Portion," and illustrates a molecule having a site and the medicament (illustrated below as medicaments 190A, 190B, and 190C) in a first association. In another embodiment, the "A Dosage Portion" may include a large number of molecules each respectfully having a site and an instance of the medicament in a first association. In an embodiment, the site is provided by a gel, illustrated as a hydrogel 4302A, and the medicament 190A is in a first association with the site. In an embodiment, the site of the dosage portion is provided by a liposome, illustrated as a liposome 4302B, and the medicament 190B is in a first association with the site. In an embodiment, the site of the dosage portion is provided by a nanoparticle, illustrated as nanosphere 4302C and the medicament 190C is in a first association with the site. In an embodiment, the site of the dosage portion includes an active site of a molecule. In an embodiment, the site of the dosage portion includes a binding site of a molecule. In an embodiment, the site of the dosage portion includes a site of an intelligent molecule.

In the first association, the medicament has a first bioavailability to the animal if the final dosage form is administered to the animal. The first association of the site and the medicament is modifiable ex vivo to a second association of the site and the medicament by an exposure to a stimulus, wherein the medicament has a second bioavailability to the animal if the final dosage form is administered to the animal.

The final dosage form 4310 includes another dosage portion having another site and another medicament in another first association. The another dosage portion is illustrated as "Another Dosage Portion," and illustrates another molecule having another site and the another medicament (illustrated below as medicaments 190A, 190B, and 190C) in another first association. In another embodiment, the "Another Dosage Portion" may include a large number of another molecules each respectfully having another site and an instance of the medicament in another first association. In an embodiment, the another site is provided by a gel, illustrated as a hydrogel 4302A, and the medicament 190A is in a first association with the another site. In an embodiment, the another site of the another dosage portion is provided by a liposome, illustrated as a liposome 4302B, and the medicament 190B is in another first association with the another site. In an embodiment, the another site of the another dosage portion is provided by a nanoparticle, illustrated as nanosphere 4302C and the medicament 190C is in another first association with the another site. In an embodiment, the another site of the another dosage portion includes an active site of another molecule. In an embodiment, the another site of the another dosage portion includes another binding site of another molecule. In an embodiment, the another site of the another dosage portion includes another site of another intelligent molecule.

In the another first association, the another medicament has another first bioavailability to the animal if the final dosage form is administered to the animal. The another first association of the another site and the another medicament is modifiable ex vivo to another second association of the another site and the another medicament by an exposure to another stimulus, wherein the another medicament has another second bioavailability to the animal if the final dosage form is administered to the animal.

In an embodiment, the dosage portion and the another dosage portion may be in an unstructured proximity. For example, the dosage portion and the another dosage portion may be dispersed or suspended in a solid transport medium, a liquid transport medium, a gel transport medium, or a solid transport medium. In another embodiment, the dosage portion and the another dosage portion may be in a structured relationship in a solid transport medium, a liquid transport medium, a gel transport medium, or a solid transport medium.

In an embodiment, the dosage portion includes a particle. In an embodiment, the dosage portion includes a polymeric material. In an embodiment, the another dosage portion includes another particle. In an embodiment, the site and the medicament in a first association includes a site of a particle or polymeric material in a first association with the medicament. In an embodiment, the site and the medicament in a first association includes a site of a particle or polymeric material encapsulating the medicament and in a first association with the medicament. In an embodiment, the site and the medicament in a first association includes a particle or polymeric material site that at least one of engages, retains, or binds the medicament in a first association. In an embodiment, the another dosage portion includes another polymeric material.

In an embodiment, the first bioavailability to the animal 198 includes the medicament is not bioavailable to the animal. In an embodiment, the first bioavailability to the animal includes the medicament is bioavailable to the animal. In an embodiment, the second bioavailability to the animal includes the medicament is not bioavailable to the animal. In an embodiment, the second bioavailability to the animal includes the medicament is bioavailable to the animal. In an embodiment, the another first bioavailability to the animal includes the another medicament is not bioavailable to the animal. In an embodiment, the another first bioavailability to the animal includes the another medicament is bioavailable to the animal. In an embodiment, the another second bioavailability to the animal includes the another medicament is not bioavailable to the animal. In an embodiment, the another second bioavailability to the animal includes the another second medicament is bioavailable to the animal.

In an embodiment, the first bioavailability to the animal includes a first bioavailability characteristic and the second bioavailability to the animal includes a second bioavailability characteristic. In an embodiment, the another first bioavailability to the animal includes another first bioavailability characteristic and the another second bioavailability to the animal includes another second bioavailability characteristic.

In an embodiment, the stimulus includes at least one of a mechanical stimulus, a non-ionizing radiation stimulus, an ionizing radiation stimulus, a chemical stimulus, an acoustic stimulus, an ultrasound stimulus, a radio wave stimulus, a microwave stimulus, a light wave stimulus, or a thermal stimulus. In an embodiment, the another stimulus includes at least one of a mechanical stimulus, a non-ionizing radiation stimulus, an ionizing radiation stimulus, a chemical stimulus, an acoustic stimulus, an ultrasound stimulus, a radio wave stimulus, a microwave stimulus, a light wave stimulus, or a thermal stimulus.

FIG. 54 illustrates another embodiment of the final dosage form 4130 for administering medicament to the animal 198. In this another embodiment, in the first association of site and the medicament, the medicament is substantially not bioavailable to the animal 198 if the final dosage form 4130 is administered to the animal. The first association of the site and the medicament is modifiable ex vivo to a second association by an exposure to a stimulus of the stimulus 192, wherein the medicament is substantially bioavailable to the animal if the final dosage form is administered to the animal.

In this another embodiment, in the another first association of the another site and the another medicament, the another medicament is substantially not bioavailable to the animal 198 if the final dosage form 4130 is administered to the animal. The another first association of the another site and the another medicament is modifiable ex vivo to another second association by an exposure to another stimulus, wherein the another medicament is substantially bioavailable to the animal if the final dosage form is administered to the animal.

FIG. 55 illustrates an example environment 4400 that includes a final dosage form 4405 and an operational flow 4420. The final dosage form 4405 is substantially similar to the final dosage form 4310 described in conjunction with FIG. 54.

After a start operation, the operational flow includes a customization operation 4420. The customization operation includes transforming the final dosage form into a selected medicament release state by initiating an ex vivo exposure of the first association of the site and the medicament or the another first association of the another site and the another medicament to a modification stimulus respectfully selected from the stimulus or the another stimulus. The operational flow includes an end operation.

In an embodiment, the customization operation 4420 may include at least one additional operation, such as an operation 4422. The operation 4422 includes transforming the final dosage form into a selected medicament release state by initiating an ex vivo exposure of the first association of the site and the medicament and the another first association of the another site and the another medicament to the stimulus and the another stimulus. In an embodiment, the operational flow 4420 may be implemented using the system 2100 described in conjunction with FIG. 27.

FIG. 56 illustrates an alternative embodiment of the operational flow 4420 described in FIG. 55. In an embodiment, the operational flow may include at least one additional operation. The at least one additional operation may include a treatment-order operation 4450, a release-state selection operation 4460, or a modification-stimulus selection operation 4470. The treatment-order operation includes receiving a signal indicative of a chosen medicament bioavailability of the final dosage form 4405. The treatment-order operation may be implemented using the system 2100 described in conjunction with FIG. 27. In an embodiment, the treatment-order operation may include at least one additional operation. The at least one additional operation may include an operation 4452 or an operation 4454. The operation 4452 includes receiving a machine-initiated signal indicative of the chosen medicament bioavailability of the final dosage form. In an embodiment, the operation 4452 may be implemented using the other circuit(s) 2190 to receive data, an email or fax indicative of the chosen medicament bioavailability of the final dosage form. The operation 4454 includes receiving a signal responsive to human-initiated indication of the chosen medicament bioavailability of the final dosage form. In an embodiment, the operation 4454 may be implemented using the user interface 2195 of FIG. 27 to receive a human-initiated input by the person 2199.

The release-state selection operation 4460 includes selecting a medicament-release state of the site and the medicament or of the another site and the another medicament in response to the chosen medicament-bioavailability of the final dosage form. In an embodiment, the release-state selection operation may be implemented using the release-state selection circuit 2165 of FIG. 27. In an embodiment, the release-state selection operation may be implemented using the release-state selection circuit 2165 and a human 2199 initiated input entered into the user interface 2195. The release-state selection operation may include at least one additional operation, such as an operation 4462. The operation 4462 includes electronically selecting a medicament-release state of the site and the medicament or of the another site and the another medicament in response to the chosen medicament-bioavailability of the final dosage form, the selecting a medicament-release state based on an electronically-stored database relating medicament-release state and medicament-bioavailability of the final dosage form, a computer-implemented decision table, a digitally-maintained final dosage form transformation table, or a digital library correlating medicament-release state and medicament-bioavailability of the final dosage form. In an embodiment, the operation 4462 may be implemented using the release-state selection circuit 2165. In an embodiment, the operation 4462 may be implemented using the release-state selection circuit, the computing device 2175, and/or the final dosage form and stimulus exposure database 2182 (saved on the computer-readable storage medium 2180).

The modification-stimulus selection operation 4470 includes selecting the modification-stimulus from the stimulus or the another stimulus in response to the selected medicament-release state. In an embodiment, modification-stimulus selection operation may be implemented using the stimulus selection circuit 2170 described in conjunction with FIG. 27. The modification-stimulus selection operation may include at least one additional operation, such as the operation 4472. The operation 4472 electronically selecting the modification-stimulus from the stimulus or the another stimulus in response to the selected medicament-release state, the selecting the modification-stimulus based on an electronically-stored database relating stimuli and medicament-release state of the final dosage form, a computer-implemented decision table, a digitally-maintained final dosage form transformation table, or a digital library correlating medicament-release state of the final dosage form and stimuli. In an embodiment, the stimulus selection circuit, the computing device 2175, and/or the final dosage form and stimulus exposure database 2182 may cooperatively implement the operation 4472.

FIG. 57 illustrates an example environment 4500. The environment includes an article of manufacture 4501. In an embodiment, the article of manufacture includes the final dosage form 4310 described in conjunction with FIG. 54. The article of manufacture includes instructions 4570 specifying an ex vivo exposure of the first association of the site and the medicament to the stimulus or an ex vivo exposure of the another first association of the another site and the another medicament to the another stimulus. The ex vivo exposure if implemented transforms the first association of the site and the medicament to the second association or the another first association of the another site and the another medicament to the another second association.

FIG. 58 illustrates an example article of manufacture 4602 for administering medicament to an animal. The article includes means 4624 for encapsulating a medicament 190A in a first medicament-release state. In the first medicament-release state, medicament has a first bioavailability to the animal if the article of manufacture is administered to the animal in the first medicament-release state. The means for encapsulating a medicament in a first medicament-release state is modifiable ex vivo to a second medicament-release state by an exposure to a stimulus, wherein the medicament has a second bioavailability to the animal if the article of manufacture is administered to the animal in the second medicament-release state. The article of manufacture also includes the medicament 190A.

The article of manufacture 4602 includes another means 4664 for encapsulating another medicament 190B in another first medicament-release state. In the another first medicament-release state, the another medicament has another first bioavailability to the animal if the article of manufacture is administered to the animal in the another first medicament-release state. The another means for encapsulating another medicament is modifiable ex vivo to another second medicament-release state by an exposure to another stimulus, wherein the another medicament has another second bioavailability to the animal if the article of manufacture is administered to the animal in the another second medicament-release state. The article of manufacture also includes the medicament 190B.

In an embodiment, the article of manufacture may include means 4628 for indicating an exposure of the means for encapsulating a medicament in a first medicament-release state to the stimulus. In an embodiment, the article of manufacture may include another means 4668 for indicating an exposure of the another means for encapsulating another medicament in another first medicament-release state to the another stimulus. In an embodiment, the article of manufacture may include means 4680 for protecting the article of manufacture against an ex vivo environment. In an embodiment, the article of manufacture may include means 4590 for carrying the article of manufacture into the animal.

FIG. 59 illustrates an example environment 4700. The environment includes a final dosage form 4710 for administering medicament to the animal 198. The final dosage form includes a dosage portion, illustrated as "A Dosage Portion," that includes a substance associated with a medicament (illustrated and described below as medicaments 190A, 190B, and 190C) in a first release-control state. In an embodiment, the "A Dosage Portion" may include a large number of substances each respectfully associated with an instance of the medicament in a first release-control state.

In an embodiment, the substance includes a gel, illustrated as a hydrogel 4702A, associated with the medicament 190A in a first release-control state. In an embodiment, the substance includes a liposome, illustrated as a liposome 4702B, associated with the medicament 190B in a first release-control state. In an embodiment, the substance includes a nanoparticle, illustrated as nanosphere 4702C associated with the medicament 190C in a first release-control state. In an embodiment, the substance includes an active site of a molecule associated with the medicament in a first release-control state. In an embodiment, the substance includes a molecule associated with the medicament in a first release-control state. In an embodiment, the substance includes an intelligent molecule associated with the medicament in a first release-control state.

In the first release control state, the medicament has a first bioavailability to the animal 198 if the final dosage form 4710 is administered to the animal. The substance associated with the medicament in a first release-control state is modifiable ex vivo by an exposure to a stimulus to associate with the medicament in a second release-control state. In the second release-control state, the medicament has a second bioavailability to the animal if the final dosage form is administered to the animal.

The final dosage form 4710 includes another dosage portion, illustrated as "Another Dosage Portion," that includes another substance associated with another medicament (illustrated and described as medicaments 190A, 190B, and 190C) in another first release-control state. In an embodiment, the "Another Dosage Portion" may include a large number of another substances each respectfully associated with an instance of the another medicament in another first release-control state.

In an embodiment, the another substance includes another gel, illustrated as a hydrogel 4702A, associated with the another medicament 190A in another first release-control state. In an embodiment, the another substance includes another liposome, illustrated as a liposome 4702B, associated with the another medicament 190B in another first release-control state. In an embodiment, the another substance includes another nanoparticle, illustrated as nanosphere 4702C associated with the another medicament 190C in another first release-control state. In an embodiment, the another substance includes an active site of another molecule associated with the another medicament in another first release-control state. In an embodiment, the another substance includes another molecule associated with the medicament in a first release-control state. In an embodiment, the another substance includes another intelligent molecule associated with the another medicament in another first release-control state.

In the another first release control state, the another medicament has another first bioavailability to the animal 198 if the final dosage form 4710 is administered to the animal. The another substance associated with the another medicament in a first release-control state is modifiable ex vivo by an exposure to another stimulus to associate with the another medicament in another second release-control state. In the second release-control state, the another medicament has another second bioavailability to the animal if the final dosage form is administered to the animal.

In an embodiment, the dosage portion and the another dosage portion may be in an unstructured proximity, and not necessarily physically distinct structures. For example, the dosage portion and the another dosage portion may be dispersed or suspended in a solid transport medium, a liquid transport medium, a gel transport medium, or a solid transport medium. In another embodiment, the dosage portion and the another dosage portion may be in a structured relationship in a solid transport medium, a liquid transport medium, a gel transport medium, or a solid transport medium.

In an embodiment, the substance associated with the medicament in a first release-control state includes a particle associated with the medicament in a first release-control state. In an embodiment, the substance associated with the medicament in a first release-control state includes a polymeric material associated with the medicament in a first release-control state. In an embodiment, the substance associated with the medicament in a first release-control state includes a small molecule associated with the medicament in a first release-control state. In an embodiment, the substance associated with the medicament in a first release-control state includes an intelligent molecule associated with the medicament in a first release-control state. In an embodiment, the substance associated with the medicament in a first release-control state includes an encapsulating substance associated with the medicament in a first release-control state. In an embodiment, the substance associated with the medicament in a first release-control state includes a conjugating substance joined with the medicament in a first release-control state. In an embodiment, the substance associated with the medicament in a first release-control state includes a binding substance bound with the medicament in a first release-control state. In an embodiment, the substance associated with the medicament in a first release-control state includes a substance at least one of engaging, or retaining the medicament in a first release-control state.

In an embodiment, the first bioavailability includes a first bioavailability characteristic and the second bioavailability includes a second bioavailability characteristic. In an embodiment, the first bioavailability to the animal includes the medicament being substantially not bioavailable to the animal. In an embodiment, the first bioavailability to the animal includes the medicament being substantially bioavailable to the animal. In an embodiment, the second bioavailability to the animal includes the medicament being substantially not bioavailable to the animal. In an embodiment, the second bioavailability to the animal includes the medicament being substantially bioavailable to the animal. In an embodiment, the second bioavailability to the animal includes the medicament being substantially bioavailable to the animal, wherein the second bioavailability to the animal is substantially different than the first bioavailability to the animal.

FIG. 59 also illustrates an alternative embodiment of the example environment 4700. The alternative embodiment of environment includes an alternative embodiment of the final dosage form 4710 for administering medicament to the animal 198. The final dosage form includes a dosage portion, illustrated as "A Dosage Portion," that includes a substance associated with a medicament (illustrated and described below as medicaments 190A, 190B, and 190C) in a first state. In an embodiment, the "A Dosage Portion" may include a large number of substances each respectfully associated with an instance of the medicament in a first state.

In an embodiment, the substance includes a gel, illustrated as a hydrogel 4702A, associated with the medicament 190A in a first state. In an embodiment, the substance includes a liposome, illustrated as a liposome 4702B, associated with the medicament 190B in a first state. In an embodiment, the substance includes a nanoparticle, illustrated as nanosphere 4702C associated with the medicament 190C in a first state. In an embodiment, the substance includes an active site of a molecule associated with the medicament in a first state. In an embodiment, the substance includes a molecule associated with the medicament in a first state. In an embodiment, the substance includes an intelligent molecule associated with the medicament in a first state.

In the first state, the medicament has a first bioavailability to the animal 198 if the final dosage form 4710 is administered to the animal. The substance associated with the medicament in a first state is modifiable ex vivo by an exposure to a stimulus to associate with the medicament in a second state. In the second state, the medicament has a second bioavailability to the animal if the final dosage form is administered to the animal.

The final dosage form 4710 includes another dosage portion, illustrated as "Another Dosage Portion," that includes another substance associated with another medicament (illustrated and described as medicaments 190A, 190B, and 190C) in another first state. In an embodiment, the "Another Dosage Portion" may include a large number of another substances each respectfully associated with an instance of the another medicament in another first state.

In an embodiment, the another substance includes another gel, illustrated as a hydrogel 4702A, associated with the another medicament 190A in another first state. In an embodiment, the another substance includes another liposome, illustrated as a liposome 4702B, associated with the another medicament 190B in another first state. In an embodiment, the another substance includes another nanoparticle, illustrated as nanosphere 4702C associated with the another medicament 190C in another first state. In an embodiment, the another substance includes an active site of another molecule associated with the another medicament in another first state. In an embodiment, the another substance includes another molecule associated with the medicament in a first state. In an embodiment, the another substance includes another intelligent molecule associated with the another medicament in another first state.

In the another first state, the another medicament has another first bioavailability to the animal 198 if the final dosage form 4710 is administered to the animal. The another substance associated with the another medicament in a first state is modifiable ex vivo by an exposure to another stimulus to associate with the another medicament in another second state. In the second state, the another medicament has another second bioavailability to the animal if the final dosage form is administered to the animal.

FIG. 60 illustrates an example environment 4800 that includes a final dosage form 4805 for administering medicament to an animal and an operational flow 4820. The final dosage form includes a medicament. The final dosage form also includes a substance associated with the medicament in a first release-control state. In the first release-control state, the medicament has a first bioavailability to the animal if the final dosage form is administered to the animal. The substance is modifiable ex vivo by an exposure to a stimulus to associate with the medicament in a second release-control state. In the second release-control state, the medicament has a second bioavailability to the animal if the final dosage form is administered to the animal. The final dosage form also includes another medicament. The final dosage form includes another substance associated with the another medicament in another first release-control state. In the another first release-control state, the another medicament has another first bioavailability to the animal if the final dosage form is administered to the animal. The another substance is modifiable ex vivo by an exposure to another stimulus to associate with the another medicament in another second release-control state, wherein the another medicament has another second bioavailability to the animal if the final dosage form is administered to the animal. In an embodiment, the final dosage form 4805 is substantially similar to the final dosage form 4710 previously described in conjunction with FIG. 59.

After a start operation, the operational flow 4810 includes a customization operation 4820. The customization operation includes transforming the final dosage form 4805 into a selected medicament release state by initiating an ex vivo exposure of the substance associated with the medicament in a first release-control state or an ex vivo exposure of the another substance associated with the another medicament in another first release-control state to a modification stimulus respectfully selected from the stimulus or the another stimulus. The operational flow includes an end operation. In an embodiment, the operational flow 4810 may be implemented using the system 2100 described in conjunction with FIG. 27.

In an alternative embodiment, the operational flow 4810 may include at least one additional operation, such as an operation 4822. The operation 4822 includes transforming the final dosage form into a selected medicament release state by initiating an ex vivo exposure of the substance associated with the medicament in a first release-control state and an ex vivo exposure of the another substance associated with the another medicament in another first release-control state to the stimulus and the another stimulus.

FIG. 61 illustrates an alternative embodiment of the operational flow 4805 described in conjunction with FIG. 60. In an embodiment, the operational flow may include at least one additional operation. The at least one additional operation may include a treatment-order operation 4850, a release-state selection operation 4860, or a modification-stimulus selection operation 4870. The treatment-order operation includes receiving a signal indicative of a chosen medicament bioavailability of the final dosage form. The treatment-order operation may be implemented using the system 2100 described in conjunction with FIG. 27. The treatment-order operation may include at least one additional operation. The at least one additional operation may include an operation 4852 or an operation 4854. The operation 4852 includes receiving a machine-initiated signal indicative of a chosen medicament bioavailability of the final dosage form. In an embodiment, the operation 4852 may be implemented using the other circuit(s) 2190 to receive data, an email or fax indicative of the chosen medicament bioavailability of the final dosage form. The operation 4854 includes receiving a human-initiated a signal indicative of a chosen medicament bioavailability of the final dosage form. In an embodiment, the operation 4854 may be implemented using the user interface 2195 of FIG. 27 to receive a human-initiated input by the person 2199.

The release-state selection operation 4860 includes selecting the medicament-release state of the substance associated with the medicament or of the another substance associated with the another medicament in response to the chosen medicament-bioavailability of the final dosage form. In an embodiment, the release-state selection operation may be implemented using the release-state selection circuit 2165 of FIG. 27. In an embodiment, the release-state selection operation may be implemented using the release-state selection circuit 2165 and a human 2199 initiated input entered into the user interface 2195. In an embodiment, the release-state selection operation may include at least one additional operation, such as an operation 4862. The operation 4862 includes electronically selecting the medicament-release state of the substance associated with the medicament or of the another substance associated with the another medicament in response to the chosen medicament-bioavailability of the final dosage form. The selecting a medicament-release state is based on an electronically-stored database relating medicament-release state and medicament-bioavailability of the final dosage form, a computer-implemented decision table, a digitally-maintained final dosage form transformation table, or a digital library correlating medicament-release state and medicament-bioavailability of the final dosage form. In an embodiment, the operation 4862 may be implemented using the release-state selection circuit 2165. In an embodiment, the operation 4862 may be implemented using the release-state selection circuit, the computing device 2175, and/or the final dosage form and stimulus exposure database 2182 (saved on the computer-readable storage medium 2180).

The modification-stimulus selection operation 4870 includes selecting the modification-stimulus from the stimulus or the another stimulus in response to the selected medicament-release state. In an embodiment, modification-stimulus selection operation may be implemented using the stimulus selection circuit 2170 described in conjunction with FIG. 27. The modification-stimulus selecting operation may include at least one additional operation, such as the operation 4872. The operation 4872 includes electronically selecting the modification-stimulus from the stimulus or the another stimulus in response to the selected medicament-release state, the selecting the stimulus based on an electronically-stored database relating stimuli and medicament-release state of the final dosage form, a computer-implemented decision table, a digitally-maintained final dosage form transformation table, or a digital library correlating medicament-release state of the final dosage form and stimuli. In an embodiment, the stimulus selection circuit, the computing device 2175, and/or the final dosage form and stimulus exposure database 2182 may cooperatively implement the operation 4872. The customization operation 4820 is described in conjunction with FIG. 60.

FIG. 62 illustrates an example article of manufacture 4902 for administering medicament to an animal. The article of manufacture includes the medicament 190A. The article of manufacture also includes an intelligent molecular means 4924 associated with the medicament in a first release-control state. In the first release-control state, the medicament has a first bioavailability to the animal if the article of manufacture is administered to the animal. The intelligent molecular means is modifiable ex vivo by an exposure to a stimulus to associate with the medicament in a second release-control state. In the second release-control state, the medicament has a second bioavailability to the animal if the article of manufacture is administered to the animal.

The article of manufacture 4902 includes the another medicament 190B. The article of manufacture also include another intelligent molecular means 4964 associated with the another medicament in another first release-control state. In the another first release-control state, the another medicament has another first bioavailability to the animal if the article of manufacture is administered to the animal. The another intelligent molecular means is modifiable ex vivo by an exposure to another stimulus to associate with the another medicament in another second release-control state. In the another second release-control state, the another medicament has another second bioavailability to the animal if the article of manufacture is administered to the animal.

In an embodiment, the article of manufacture 4902 includes means 4928 for indicating an exposure to the stimulus of the intelligent molecular means associated with a medicament in a first medicament-release state. In an embodiment, the article of manufacture includes another means 4968 for indicating an exposure to the another stimulus of the another intelligent molecular means associated with another medicament in another first medicament-release state. In an embodiment, the article of manufacture includes means 4980 for protecting the article of manufacture against an ex vivo environment. In an embodiment, the article of manufacture includes means 4990 for carrying the article of manufacture into the animal.

FIG. 63 illustrates an example environment 5000. The environment includes a final dosage form 5010 for administering medicament to the animal 198. The final dosage form includes at least two respective instances of a medicament and a substance, illustrated as instances 5002.

The final dosage form 5010 includes an instance 5002.1 of a substance carrying a medicament in a first medicament-release state. In an embodiment, the instance 5002.1 may include a large number of substances each respectfully carrying the medicament in a first medicament-release state. In an embodiment, the substance includes a gel, illustrated as a hydrogel 5002A, carrying the medicament 190A in a first medicament-release state. In an embodiment, the substance includes a liposome, illustrated as a liposome 5002B, carrying the medicament 190B in a first medicament-release state. In an embodiment, the substance includes a nanoparticle, illustrated as nanosphere 5002C carrying the medicament 190C in a first medicament-release state. In an embodiment, the substance includes an active site of a molecule carrying the medicament in a first medicament-release state. In an embodiment, the substance includes a molecule carrying the medicament in a first medicament-release state. In an embodiment, the substance includes an intelligent molecule carrying the medicament in a first medicament-release state.

The medicament has a first bioavailability to the animal 198 if the final dosage form 5010 is administered to the animal. The substance is modifiable ex vivo by an exposure to a first stimulus to carry the medicament in a second medicament-release state. In the second medicament-release state, the medicament has a second bioavailability to the animal if the final dosage form is administered to the animal. The substance is modifiable ex vivo by an exposure to a second stimulus to carry the medicament in a third medicament-release state. In the third medicament-release state, the medicament has a third bioavailability to the animal if the final dosage form is administered to the animal.

The final dosage form 5010 includes another instance 5002.2 of another substance carrying another medicament in another first medicament-release state. In an embodiment, the another instance 5002.2 may include a large number of another substances each respectfully carrying the another medicament in another first medicament-release state. In an embodiment, the another substance includes a gel, illustrated as a hydrogel 5002A, carrying the another medicament 190A in another first medicament-release state. In an embodiment, the another substance includes a liposome, illustrated as a liposome 5002B, carrying the another medicament 190B in another first medicament-release state. In an embodiment, the another substance includes another nanoparticle, illustrated as nanosphere 5002C carrying the another medicament 190C in another first medicament-release state. In an embodiment, the another substance includes another active site of another molecule carrying the another medicament in another first medicament-release state. In an embodiment, the another substance includes another molecule carrying the another medicament in another first medicament-release state. In an embodiment, the another substance includes another intelligent molecule carrying the another medicament in another first medicament-release state.

The another medicament has another first bioavailability to the animal if the final dosage form is administered to the animal. The another substance is modifiable ex vivo by an exposure to another first stimulus to carry the another medicament in another second medicament-release state. In the another second medicament-release state, the another medicament has another second bioavailability to the animal if the final dosage form is administered to the animal. The another substance is modifiable ex vivo by an exposure to another second stimulus to carry the another medicament in another third medicament-release state. In the another third medicament-release state, the another medicament has another third bioavailability to the animal if the final dosage form is administered to the animal.

In an embodiment, the substance 5002 carrying the medicament in a first medicament-release state includes a substance having a modifiable medicament release characteristic and carrying the medicament in a first medicament-release state. In an embodiment, the substance carrying the medicament in a first medicament-release state includes a substance carrying the medicament in an initial medicament-retention state. In an embodiment, the substance carrying the medicament in a first medicament-release state includes a particle carrying the medicament in a first medicament-release state. In an embodiment, the substance carrying the medicament in a first medicament-release state includes a polymeric material carrying the medicament in a first medicament-release state. In an embodiment, the substance carrying the medicament in a first medicament-release state includes a small molecule carrying the medicament in a first medicament-release state. In an embodiment, the substance carrying the medicament in a first medicament-release state includes a capsule structure carrying the medicament in a first medicament-release state.

In an embodiment, the medicament has a first bioavailability to the animal includes the medicament is not bioavailable to the animal. In an embodiment, the medicament has a first bioavailability to the animal includes the medicament is bioavailable to the animal. In an embodiment, the medicament has a second bioavailability to the animal includes the medicament is not bioavailable to the animal. In an embodiment, the medicament has a second bioavailability to the animal includes the medicament is bioavailable to the animal. In an embodiment, the medicament has a third bioavailability to the animal includes the medicament is not bioavailable to the animal. In an embodiment, the medicament has a third bioavailability to the animal includes the medicament is bioavailable to the animal.

In an embodiment, the another medicament has another first bioavailability to the animal includes the another medicament is not bioavailable to the animal. In an embodiment, the another medicament has another first bioavailability to the animal includes the another medicament is bioavailable to the animal. In an embodiment, the another medicament has another second bioavailability to the animal includes wherein the another medicament is not bioavailable to the animal. In an embodiment, the another medicament has another second bioavailability to the animal includes the another medicament is bioavailable to the animal. In an embodiment, the another medicament has another third bioavailability to the animal includes the another medicament is not bioavailable to the animal. In an embodiment, the another medicament has another third bioavailability to the animal includes the another medicament is bioavailable to the animal. In an embodiment, the first bioavailability includes a first bioavailability characteristic, the second bioavailability includes a second bioavailability characteristic, and the third bioavailability includes a third bioavailability characteristic.

The example environment 5000 of FIG. 63 illustrates another embodiment of the final dosage form 5010 for administering medicament to the animal 198. The final dosage form includes at least two instances of a medicament and a substance, illustrated as instances 5002.

The final dosage form 5010 includes an instance 5002.1 of a substance carrying a medicament in a medicament-retention state. The medicament is substantially not bioavailable to the animal if the final dosage form is administered to the animal. The substance is modifiable ex vivo by an exposure to a first stimulus to carry the medicament in a first medicament-release state. In the first medicament-release state, the medicament has a first bioavailability to the animal if the final dosage form is administered to the animal. The substance is modifiable ex vivo by an exposure to a second stimulus to carry the medicament in a second medicament-release state. In the second medicament-release state, the medicament has a second bioavailability to the animal if the final dosage form is administered to the animal.

The final dosage form 5010 includes another instance 5002.2 of another substance carrying another medicament in another medicament-retention state. The another medicament is substantially not bioavailable to the animal if the final dosage form is administered to the animal 198. The another substance is modifiable ex vivo by an exposure to another first stimulus to carry the another medicament in another first medicament-release state. In the another first medicament-release state, the another medicament has another first bioavailability to the animal if the final dosage form is administered to the animal. The another substance is modifiable ex vivo by an exposure to another second stimulus to carry the another medicament in another second medicament-release state. In the another second medicament-release state, the another medicament has another second bioavailability to the animal if the final dosage form is administered to the animal.

The following table illustrates several states of example embodiments of the final dosage form 5010:

TABLE 4

Example bioavailability configurations

| | Example Configuration #1 Bioavailability | | Example Configuration #2 Bioavailability | |
|---|---|---|---|---|
| | Substance 1 | Substance 2 | Substance 1 | Substance 2 |
| State of substance | (100 mg medicament A) | (200 mg TR medicament A) | (100 mg medicament A) | (200 mg medicament B) |
| State 1 (initial) | 0 | 0 | 1 | 0 |
| State 2 (first stimulus to Substance 1) | 1 | 0 | 0 | 0 |
| State 3 (second stimulus to Substance 1) | 2 | 0 | 2 | 0 |
| State 4 (another first stimulus to Substance 2) | 0 | 1 | 1 | 1 |
| State 4 (another second stimulus to Substance 2) | 0 | 2 | 1 | 2 |
| State 5 (first stimulus to Substance 1, and another first stimulus to Substance 2) | 1 | 1 | 0 | 1 |
| State 6 (second stimulus to Substance 1, and another first stimulus to Substance 2) | 2 | 1 | 2 | 1 |
| State 7 (first stimulus to Substance 1, and another second stimulus to Substance 2) | 1 | 2 | 0 | 2 |
| State 8 (second stimulus to Substance 1, and another second stimulus to Substance 2) | 2 | 2 | 1 | 2 |

0 = medicament is substantially not bioavailable
1 = medicament is bioavailable
2 = medicament is bioavailable in a substantially different characteristic than in bioavailability 1

FIG. 64 illustrates an example environment 5100. The environment includes a final dosage form 5110 for administering medicament to the animal 198. An element of the final dosage form is illustrated as an element 5102.1. Another element of the final dosage includes another element 5102.2 (not shown). The element and the another element may be included in a transport medium (not shown) of the final dosage form. The transport medium may include a carrier, admixture, diluent, or excipient.

In an embodiment, the element 5102.1 of the final dosage form 5110 includes an "A Dosage Portion" that is substantially similar to final dosage form 102 described in conjunction with FIG. 1, and a "Another Dosage Portion" that is substantially similar to final dosage form 302 described in conjunction with FIG. 3. The element 5102.1 of the final dosage form 5110 includes a medicament, illustrated in "A Dosage Portion" as the medicament 190A, and a medicament, illustrated in "Another Dosage Portion" as the medicament 190B. The element 5102.1 carries the medicament 190A in a first medicament-release state. In the first medicament-release state, the medicament 190A has a first bioavailability to the animal 198 if the final dosage form is administered to the animal. The element 5102.1 is modifiable ex vivo by an exposure to a first stimulus to carry the medicament 190A in a second medicament-release state. In the second medicament-release state, the medicament 190A has a second bioavailability to the animal if the final dosage form is administered to the animal.

The element 5102.1 carries the medicament 190B in the "B Dosage Portion" in the first medicament-release state. In the first medicament-release state, the medicament 190B has a first bioavailability to the animal 198 if the final dosage form is administered to the animal. The "Another Dosage Portion" of element 5102.1 is modifiable ex vivo by an exposure to a second stimulus to carry the medicament 190B in a third medicament-release state. In the third medicament-release state, the medicament has a third bioavailability to the animal if the final dosage form is administered to the animal.

In an embodiment, the element 5102.2 includes another medicament having release states modifiable ex vivo in a manner substantially similar to the element 5102.1.

FIG. 65 illustrates an example environment 5200. The environment includes a final dosage form 5205 and an operational flow 5220. In an embodiment, the final dosage form is substantially similar to the final dosage form 5010 described in conjunction with FIG. 63. In another embodiment, the final dosage form is substantially similar to the final dosage form 5110 described in conjunction with FIG. 64.

After a start operation, the operational flow 5210 includes a customization operation 5220. The customization operation includes transforming the final dosage form 5205 into a selected medicament-release state by initiating an ex vivo exposure to a modification stimulus of the substance carrying the medicament in a first medicament-release state or the another substance carrying the another medicament in another first medicament-release state. The modification stimulus is respectfully selected from the first stimulus or the second stimulus for the substance, or from the another first stimulus or the another second stimulus for the another substance. The operational flow includes an end operation. In an embodiment, the operational flow 5210 may be implemented using the system 2100 described in conjunction with FIG. 27.

In an embodiment, the customization operation 5220 may include at least one additional operation, such as an operation 5222. The operation 5222 includes transforming the final dosage form 5205 into a selected medicament-release state by initiating an ex vivo exposure to a modification stimulus of the substance carrying the medicament in a first medicament-release state and the another substance carrying the another medicament in another first medicament-release state. The modification stimulus includes a stimulus selected from the first stimulus or the second stimulus for the substance, and another stimulus selected from the another first stimulus or the another second stimulus for the another substance.

FIG. 66 illustrates an alternative embodiment of the operational flow 5210 described in conjunction with FIG. 65. In an embodiment, the operational flow may include at least one additional operation. The at least one additional operation may include a treatment-order operation 5250, a release-state selection operation 5260, or a modification-stimulus selection operation 5270. The treatment order operation includes receiving a signal indicative of a chosen medicament bioavailability of the final dosage form. The treatment-order operation may be implemented using the system 2100 described in conjunction with FIG. 27. The treatment-order operation may include at least one additional operation. The at least one additional operation may include an operation 5252 or an operation 5254. The operation 5252 includes receiving a machine-initiated signal indicative of a chosen medicament bioavailability of the final dosage form. In an embodiment, the operation 5252 may be implemented using the other circuit(s) 2190 to receive data or an email or fax indicative of the chosen medicament bioavailability of the final dosage form. The operation 5254 includes receiving a human-initiated signal indicative of the chosen medicament bioavailability of the final dosage form. In an embodiment, the operation 5254 may be implemented using the user interface 2195 of FIG. 27 to receive a human-initiated input by the person 2199.

The release-state selection operation 5260 includes selecting the medicament-release state of the substance or of the another substance in response to the chosen medicament-bioavailability of the final dosage form. In an embodiment, the release-state selection operation may be implemented using the release-state selection circuit 2165 of FIG. 27. In an embodiment, the release-state selection operation may be implemented using the release-state selection circuit 2165 and a human 2199 initiated input entered into the user interface 2195. In an embodiment, the release-state selection operation may include at least one additional operation, such as an operation 5262. The operation 5262 includes electronically selecting the medicament-release state of the substance or of the another substance in response to the chosen medicament-bioavailability of the final dosage form. The selecting a medicament-release state is based on an electronically-stored database relating medicament-release state and medicament-bioavailability of the final dosage form, a computer-implemented decision table, a digitally-maintained final dosage form transformation table, or a digital library correlating medicament-release state and medicament-bioavailability of the final dosage form. In an embodiment, the operation 5262 may be implemented using the release-state selection circuit 2165. In an embodiment, the operation 5262 may be implemented using the release-state selection circuit, the computing device 2175, and/or the final dosage form and stimulus exposure database 2182 (saved on the computer-readable storage medium 2180).

The modification-stimulus selection operation 5270 includes selecting the modification-stimulus from the first stimulus, the second stimulus, the another first stimulus or the another second stimulus in response to the selected medicament-release state. In an embodiment, modification-stimulus selection operation may be implemented using the stimulus selection circuit 2170 described in conjunction with FIG. 27. In an embodiment, the stimulus selection circuit, the computing device 2175, and/or the final dosage form and stimulus exposure database 2182 may cooperatively implement the operation 5270. The modification-stimulus selecting operation may include at least one additional operation, such as the operation 5272. The operation 5272 includes electronically selecting the modification stimulus in response to the selected medicament-release state. The selecting the modification stimulus is based on an electronically-stored database relating stimuli and medicament-release state of the final dosage form, a computer-implemented decision table, a digitally-maintained final dosage form transformation table, or a digital library correlating medicament-release state of the final dosage form and stimuli. The customization operation 5220 is described in conjunction with FIG. 65.

FIG. 67 illustrates an example article of manufacture 5702 for administering medicament to an animal. The article of manufacture includes a medicament 190A. The article of manufacture also includes intelligent molecular 5724 means associated with the medicament in a first medicament-release state wherein the medicament has a first bioavailability to the animal if the article of manufacture is administered to the animal. The intelligent molecular means is modifiable ex vivo by an exposure to a first stimulus to carry the medicament in a second medicament-release state. In the second medicament-release state, the medicament has a second bioavailability to the animal if the article of manufacture is administered to the animal. The intelligent molecular means is modifiable ex vivo by an exposure to a second stimulus to carry the medicament in a third medicament-release state. In the third medicament-release state, the medicament has a third bioavailability to the animal if the article of manufacture is administered to the animal.

The article of manufacture includes another medicament 190B. The article of manufacture also includes another intelligent molecular means 5764 associated with the another medicament in another first medicament-release state wherein the another medicament has another first bioavailability to the animal if the article of manufacture is administered to the animal. The another intelligent molecular means is modifiable ex vivo by an exposure to another first stimulus to carry the another medicament in another second medicament-release state. In another second medicament-release state, the another medicament has another second bioavailability to the animal if the article of manufacture is administered to the animal. The another intelligent molecular means is modifiable ex vivo by an exposure to another second stimulus to carry the another medicament in another third medicament-release state. In another third medicament-release state, the another medicament has another third bioavailability to the animal if the article of manufacture is administered to the animal.

All references cited herein are hereby incorporated by reference in their entirety or to the extent their subject matter is not inconsistent herewith.

In some embodiments, "configured" includes at least one of designed, set up, shaped, implemented, constructed, or adapted for at least one of a particular purpose, application, or function.

It will be understood that, in general, terms used herein, and especially in the appended claims, are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of introductory phrases such as "at least one" or "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a receiver" should typically be interpreted to mean "at least one receiver"); the same holds true for the use of definite articles used to introduce claim recitations. In addition, even if a specific number of an introduced claim recitation is explicitly recited, it will be recognized that such recitation should typically be interpreted to mean at least the recited number (e.g., the bare recitation of "at least two chambers," or "a plurality of chambers," without other modifiers, typically means at least two chambers).

Use of "Start," "End" or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application.

In those instances where a phrase such as "at least one of A, B, and C," "at least one of A, B, or C," or "an [item] selected from the group consisting of A, B, and C," is used, in general such a construction is intended to be disjunctive (e.g., any of these phrases would include but not be limited to systems that have A alone, B alone, C alone, A and B together, A and C together, B and C together, or A, B, and C together, and may further include more than one of A, B, or C, such as $A_1$, $A_2$, and C together, A, $B_1$, $B_2$, $C_1$, and $C_2$ together, or $B_1$ and $B_2$ together). It will be further understood that virtually any disjunctive word or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The herein described aspects depict different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable or physically interacting components or wirelessly interactable or wirelessly interacting components.

With respect to the appended claims the recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, the various aspects and embodiments are for purposes of illustration and are not intended to be limiting, with the true scope and spirit being indicated by the following claims.

What is claimed is:

1. A final dosage form for administering medicament to an animal, the final dosage form comprises:
   a dosage portion having
      a medicament; and
      a release element in a first medicament-release state wherein the medicament has a first bioavailability to the animal,
         wherein, when the release element is exposed ex vivo to a particular stimulus, an alteration occurs in a structure of the release element switching the release element from the first medicament-release state to a second medicament-release state wherein the medicament has a second bioavailability to the animal;
   another dosage portion having
      another medicament; and
      another release element in another first medicament-release state wherein the another medicament has another first bioavailability to the animal,
         wherein, when the release element is exposed ex vivo to another particular stimulus, an alteration occurs in a structure of the another release element switching the release element from the another first medicament-release state to another second medicament-release state wherein the medicament has another second bioavailability to the animal;
   a capsule structure including an outer layer and enclosing the dosage portion and the another dosage portion;
   an electronically detectable indicator element including a material that polymerizes responsive to the particular stimulus to thereby indicate exposure to the particular stimulus, the responsive polymerization inducing a change in a conductive property of the electronically detectable indicator element, the electronically detectable indicator element at least partially embedded in the outer layer of the capsule structure; and
   another electronically detectable indicator element including a material that polymerizes responsive to the another particular stimulus to thereby indicate exposure to the another particular stimulus, the responsive polymerization inducing a change in a conductive property of the another electronically detectable indicator element, the another electronically detectable indicator element at least partially embedded in the outer layer of the capsule structure.

2. The final dosage form of claim 1, wherein the first medicament-release state wherein the medicament has a first bioavailability to the animal includes:
a first medicament-release state wherein the medicament is not bioavailable to the animal.

3. The final dosage form of claim 1, wherein the first medicament-release state wherein the medicament has a first bioavailability to the animal includes:
a first medicament-release state wherein the medicament is bioavailable to the animal.

4. The final dosage form of claim 1, wherein the second medicament-release state wherein the medicament has a second bioavailability to the animal includes:
a second medicament-release state wherein the medicament is not bioavailable to the animal.

5. The final dosage form of claim 1, wherein the second medicament-release state wherein the medicament has a second bioavailability to the animal includes:
a second medicament-release state wherein the medicament is bioavailable to the animal.

6. The final dosage form of claim 1, wherein the another first medicament-release state wherein the another medicament has another first bioavailability to the animal includes:
another first medicament-release state wherein the another medicament is not bioavailable to the animal.

7. The final dosage form of claim 1, wherein the another first medicament-release state wherein the another medicament has another first bioavailability to the animal includes:
another first medicament-release state wherein the another medicament is bioavailable to the animal.

8. The final dosage form of claim 1, wherein the another second medicament-release state wherein the another medicament has another second bioavailability to the animal includes:
another second medicament-release state wherein the another medicament is not bioavailable to the animal.

9. The final dosage form of claim 1, wherein the another second medicament-release state wherein the another medicament has another second bioavailability to the animal includes:
another second medicament-release state wherein the another medicament is bioavailable to the animal.

10. The final dosage form of claim 1, wherein the first bioavailability to the animal includes a first bioavailability characteristic and the second bioavailability to the animal includes a second bioavailability characteristic.

11. The final dosage form of claim 1, wherein the particular stimulus includes:
at least one of a particular non-ionizing radiation stimulus, a particular ionizing radiation stimulus, a particular chemical stimulus, a particular acoustic stimulus, a particular ultrasound stimulus, a particular radio wave stimulus, a particular microwave stimulus, or a particular light wave stimulus.

12. A final dosage form for administering a medicament to an animal, the final dosage form comprises:
a dosage portion having:
a medicament;
a release element in a medicament-holding state wherein the medicament is substantially not bioavailable to the animal,
wherein, when the release element is exposed ex vivo to a particular stimulus, an alteration occurs in a structure of the release element switching the release element from the medicament-holding state to a medicament-discharging state wherein the medicament is substantially bioavailable to the animal; and
wherein the particular stimulus includes at least one of a particular non-ionizing radiation stimulus, a particular ionizing radiation stimulus, a particular chemical stimulus, a particular acoustic stimulus, a particular ultrasound stimulus, a particular radio wave stimulus, a particular microwave stimulus, or a particular light wave stimulus;
another dosage portion having
another medicament;
another release element in another medicament-holding state wherein the another medicament is substantially not bioavailable to the animal,
wherein, when the another release element is exposed ex vivo to another particular stimulus, an alteration occurs in a structure of the another release element switching the another release element from the another medicament-holding state to another medicament-discharging state wherein the medicament is substantially bioavailable to the animal; and
wherein the another particular stimulus includes at least one of a particular non-ionizing radiation stimulus, a particular ionizing radiation stimulus, a particular chemical stimulus, a particular acoustic stimulus, a particular ultrasound stimulus, a particular radio wave stimulus, a particular microwave stimulus, or a particular light wave stimulus;
a capsule structure including an outer layer and enclosing the dosage portion and the another dosage portion; and
a plurality of electronically detectable indicator elements different than the release element and the another release element and exhibiting a physical property that changes responsive to exposure to the particular stimulus or the another particular stimulus to thereby indicate exposure to the particular stimulus or the another particular stimulus, the plurality of electronically detectable indicator elements at least partially embedded in the outer layer of the capsule structure.

13. An article of manufacture comprising:
a final dosage form for administering medicament to an animal, the final dosage form including:
a dosage portion having
a medicament;
a release element in a first medicament-release state wherein the medicament has a first bioavailability to the animal,
wherein, when the release element is exposed ex vivo to a particular stimulus, an alteration occurs in a structure of the release element switching the release element from the first medicament-release state to a second medicament-release state wherein the medicament has a second bioavailability to the animal;
wherein the particular stimulus includes at least a particular ultrasound stimulus;
another dosage portion having:
another medicament
another release element in another first medicament-release state wherein the another medicament has another first bioavailability to the animal, wherein, when the release element is exposed ex vivo to another particular stimulus, an alteration occurs in a structure of the another release element switching the release element from the another first medicament-release state to another second medicament-release state wherein the medicament has another second bio-availability to the animal;

a capsule structure including an outer layer enclosing the dosage portion and the another dosage portion;

an electronically detectable indicator element including a material that polymerizes in response to exposure to the particular stimulus, the polymerization inducing a change in a conductivity property of the electronically detectable indicator element, the electronically detectable indicator element at least partially embedded in the outer layer of the capsule structure;

another electronically detectable indicator element including a material that polymerizes in response to exposure to the another particular stimulus, the polymerization inducing a change in a conductivity property of the another electronically detectable indicator element, the another electronically detectable indicator element at least partially embedded in the outer layer of the capsule structure; and instructions specifying an ex vivo exposure of the release element to the particular stimulus or an ex vivo exposure of the another release element to the another particular stimulus, which when implemented respectfully switches the release element to the second medicament-release state or the another release element to the another second medicament-release state.

14. The final dosage form of claim 1, wherein the final dosage form has completed a manufacturing or production process and is suitable for direct administration to the animal.

15. The final dosage form of claim 12, wherein the final dosage form is a tablet, a capsule, a suppository, or a structure carryable or transportable by a liquid or other fluid carrier, has completed a manufacturing or production process, and is suitable for direct administration to the animal.

16. The final dosage form of claim 13, wherein the final dosage form is a tablet, a capsule, a suppository, or a structure carryable or transportable by a liquid or other fluid carrier, has completed a manufacturing or production process, and is suitable for direct administration to the animal.

* * * * *